(12) United States Patent
Devlin et al.

(10) Patent No.: US 12,419,897 B2
(45) Date of Patent: Sep. 23, 2025

(54) SYNTHETIC DERIVATIVES OF CHOLIC ACID 7-SULFATE AND USES THEREOF

(71) Applicants: President and Fellows of Harvard College, Cambridge, MA (US); The Brigham and Women's Hospital, Inc., Boston, MA (US)

(72) Inventors: Abigail Sloan Devlin, Cambridge, MA (US); Snehal N. Chaudhari, Cambridge, MA (US); Eric Garland Sheu, Brookline, MA (US); David A. Harris, Arlington, MA (US); Jinbo Lee, Cambridge, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1059 days.

(21) Appl. No.: 17/309,520

(22) PCT Filed: Dec. 4, 2019

(86) PCT No.: PCT/US2019/064488
§ 371 (c)(1),
(2) Date: Jun. 3, 2021

(87) PCT Pub. No.: WO2020/117945
PCT Pub. Date: Jun. 11, 2020

(65) Prior Publication Data
US 2022/0016138 A1  Jan. 20, 2022

Related U.S. Application Data

(60) Provisional application No. 62/775,029, filed on Dec. 4, 2018.

(51) Int. Cl.
*A61K 31/664* (2006.01)
*A61K 31/575* (2006.01)
(Continued)

(52) U.S. Cl.
CPC .......... *A61K 31/664* (2013.01); *A61K 31/575* (2013.01); *A61P 3/04* (2018.01); *A61P 3/10* (2018.01)

(58) Field of Classification Search
None
See application file for complete search history.

(56) References Cited

U.S. PATENT DOCUMENTS 5,210,272 A    5/1993  Palmer
5,695,738 A   12/1997  Anderson et al.
(Continued)

FOREIGN PATENT DOCUMENTS

CN    106478759 A    3/2017
DE    19941764 A1    3/2001
(Continued)

OTHER PUBLICATIONS

Iguchi et al., Biological and Pharmaceutical Bulletin, 2011, vol. 34, Issue 1, p. 1-7 (Year: 2011).*
(Continued)

*Primary Examiner* — Jeffrey S Lundgren
*Assistant Examiner* — Anthony Joseph Seitz
(74) *Attorney, Agent, or Firm* — Wolf, Greenfield & Sacks, P.C.

(57) ABSTRACT

The compositions and methods provided herein are related, in part, to the discovery of cholic acid 7-sulfate as a treatment for diabetes. Provided herein is a method for treating a metabolic disorder (e.g., diabetes, obesity), or an inflammatory disease (e.g., Crohn's disease, inflammatory bowel disease, ulcerative colitis, pancreatitis, hepatitis,
(Continued)

appendicitis, gastritis, diverticulitis, celiac disease, food intolerance, enteritis, ulcer, gastroesophageal reflux disease (GERD), psoriatic arthritis, psoriasis, and rheumatoid arthritis) in a subject in need thereof comprising administering to a subject a compound of Formulae (I)-(XVII).

19 Claims, 34 Drawing Sheets

Specification includes a Sequence Listing.

(51) Int. Cl.
*A61P 3/04* (2006.01)
*A61P 3/10* (2006.01)

(56) References Cited

U.S. PATENT DOCUMENTS

| | | | |
|---|---|---|---|
| 5,733,566 | A | 3/1998 | Lewis |
| 6,451,355 | B1 | 9/2002 | Reisner et al. |
| 9,345,715 | B2 | 5/2016 | Young et al. |
| 9,580,459 | B2 | 2/2017 | Dosa et al. |
| 2007/0032464 | A1 | 2/2007 | Liao et al. |
| 2009/0118306 | A1 | 5/2009 | Husson et al. |
| 2010/0130426 | A1 | 5/2010 | Yung et al. |
| 2011/0059932 | A1 | 3/2011 | Peng et al. |
| 2012/0277198 | A1 | 11/2012 | Ling et al. |
| 2014/0206657 | A1* | 7/2014 | Yu .................. C07J 41/0061 514/182 |
| 2014/0234256 | A1 | 8/2014 | March et al. |
| 2014/0323748 | A1 | 10/2014 | Dosa et al. |
| 2016/0184266 | A9 | 6/2016 | Szewczyk |
| 2018/0319836 | A1 | 11/2018 | Yu et al. |
| 2018/0340006 | A1 | 11/2018 | Weymouth-Wilson et al. |
| 2021/0315908 | A1* | 10/2021 | Devlin ............... A61K 45/06 |
| 2022/0204548 | A1 | 6/2022 | Devlin et al. |
| 2023/0174988 | A1* | 6/2023 | Devlin ............. A61K 31/575 514/44 A |

FOREIGN PATENT DOCUMENTS

| | | | | |
|---|---|---|---|---|
| EP | 0117570 | A1 | 9/1986 | |
| EP | 548793 | A2 | 6/1993 | |
| EP | 624593 | A2 | 11/1994 | |
| EP | 2221313 | A1 * | 8/2010 | ............... C07J 1/00 |
| GB | 1360354 | A | 7/1974 | |
| JP | S49-095955 | A | 9/1974 | |
| JP | S51-26870 | A | 3/1976 | |
| JP | H07-017997 | A | 1/1995 | |
| RU | 2665685 | C1 | 9/2018 | |
| TW | 201700447 | A | 1/2017 | |
| WO | WO 94/00126 | A1 | 1/1994 | |
| WO | WO 95/07089 | A1 | 3/1995 | |
| WO | WO 97/18816 | A1 | 5/1997 | |
| WO | WO 98/52585 | A1 | 11/1998 | |
| WO | WO 2000/024761 | A1 | 5/2000 | |
| WO | WO 2000/066611 | A1 | 11/2000 | |
| WO | WO 2001/021642 | A1 | 3/2001 | |
| WO | WO 2003/066657 | A1 | 8/2003 | |
| WO | WO 2004/092193 | A1 | 10/2004 | |
| WO | WO 2011/022838 | A1 | 3/2011 | |
| WO | WO 2013/096771 | A1 | 6/2013 | |
| WO | WO 2013/113680 | A1 | 8/2013 | |
| WO | WO 2016/100619 | A2 | 6/2016 | |
| WO | WO 2016/205475 | A2 | 12/2016 | |
| WO | WO 2017/035501 | A1 | 3/2017 | |
| WO | WO 2017/106818 | A1 | 6/2017 | |
| WO | WO 2017/142895 | A1 | 8/2017 | |
| WO | WO 2019/075365 | A1 | 4/2019 | |
| WO | WO 2019/191637 | A1 | 10/2019 | |
| WO | WO 2020/041673 | A1 | 2/2020 | |
| WO | WO 2020/117945 | A1 | 6/2020 | |

OTHER PUBLICATIONS

Extended European Search Report for Application No. 20805532.7, mailed Jan. 5, 2023.
International Preliminary Report on Patentability for Application No. PCT/US2020/032016, mailed Nov. 25, 2021.
International Preliminary Report on Patentability for Application No. PCT/US2021/031277, mailed Nov. 17, 2022.
Adhikari et al., Development of a covalent inhibitor of gut bacterial bile salt hydrolases. Nat Chem Biol. Mar. 2020;16(3):318-326. doi: 10.1038/s41589-020-0467-3. Epub Feb. 10, 2020.
Adhikari et al., Development of a covalent inhibitor of gut bacterial bile salt hydrolases. bioRxiv. May 17, 2019. URL: https://www.biorxiv.org/content/10.1101/640086v1.full/ [retrieved from the internet: Dec. 14, 2022].
Fader et al., 2,3,7,8-Tetrachlorodibenzo-p-dioxin (TCDD)-elicited effects on bile acid homeostasis: Alterations in biosynthesis, enterohepatic circulation, and microbial metabolism. Sci Rep. Jul. 19, 2017;7(1):5921. doi: 10.1038/s41598-017-05656-8.
Fried et al., The synthesis of diazo, halo, and sulfoxy bile acid derivatives: potential affinity labels. Steroids. Aug. 1979;34(2):171-87. doi: 10.1016/0039-128x(79)90046-1.
Ishihara et al., Uber Den Systematischen Abbau Der Chenodeoxycholsaure. Journal of Biochemistry. 1938; 27(2):265-277. DOI: 10.1093/oxfordjournals.jbchem.a125715.
Lööf, Enzymatic sulphation of bile salts in man. Bile salt sulphotransferase activity in human adrenal. Digestion. 1981;21(6):297-303. doi: 10.1159/000198580.
Skyler et al., Differentiation of Diabetes by Pathophysiology, Natural History, and Prognosis. Diabetes. Feb. 2017;66(2):241-255. doi: 10.2337/db16-0806. Epub Dec. 15, 2016.
International Search Report and Written Opinion for Application No. PCT/US2019/047856, mailed Dec. 10, 2019.
International Preliminary Report on Patentability for Application No. PCT/US2019/047856, mailed Mar. 4, 2021.
Invitation to Pay Additional Fees for Application No. PCT/US2020/032016, mailed Jul. 16, 2020.
International Search Report and Written Opinion for Application No. PCT/US2020/032016, mailed Sep. 22, 2020.
International Search Report and Written Opinion for Application No. PCT/US2019/064488, mailed Apr. 9, 2020.
International Preliminary Report on Patentability for Application No. PCT/US2019/064488, mailed Jun. 17, 2021.
Genbank Submission. NCBI; Accession No. ABC26911, version ABC26911.1. bile salt hydrolase [*Bifidobacterium breve* DSM 20213 = JCM 1192]. Goswami et al.; Dec. 19, 2005.
Genbank Submission. NCBI; Accession No. ABC26910, version ABC26910.1. bile salt hydrolase [*Bifidobacterium bifidum*]. Goswami et al.; Dec. 19, 2005.
Genbank Submission. NCBI; Accession No. ACL98203, version ACL98203.1; bile salt hydrolase (plasmid) [*Ligilactobacillus salivarius*]. Fang et al.; Jul. 24, 2016.
Genbank Submission. NCBI; Accession No. AAS98803, version AAS98803.1; bile salt hydrolase [*Bifidobacterium animalis*]. Kim et al.; Aug. 25, 2008.
Genbank Submission. NCBI; Accession No. AKI55714, version AKI55714.1; bile salt hydrolase [*Listeria monocytogenes*]. Bergholz et al.; Jun. 3, 2015.
Genbank Submission. NCBI; Accession No. Accession: AAP20760, version AAP20760.1; bile salt hydrolase [*Enterococcus faecium*]. Wijaya et al.; Apr. 28, 2003.
Genbank Submission. NCBI; Accession No. Accession: NM_006143, version NM_006143.2; *Homo sapiens* G protein-coupled receptor 19 (GPR19), mRNA. Rao et al.; Nov. 11, 2018.
Genbank Submission. NCBI; Accession No. Accession: NP_006134, version NP_006134.1; probable G-protein coupled receptor 19 [*Homo sapiens*]. Yang et al.; Nov. 11, 2018.
Genbank Submission. NCBI; Accession No. Accession: NG_008731, version NG_008731.1; *Homo sapiens* vitamin D receptor (VDR), RefSeqGene on chromosome 12. Loughran et al.; Feb. 15, 2021.
Genbank Submission. NCBI; Accession No. Accession: NP_001017535, version NP_001017535.1; vitamin D3 receptor isoform VDRA [*Homo sapiens*]. Moosavi et al.; Apr. 19, 2021.

(56) References Cited

OTHER PUBLICATIONS

Genbank Submission. NCBI; Accession No. Accession: NP¬_001017536, version NP_001017536.1; vitamin D3 receptor isoform VDRB1 [*Homo sapiens*]. Moosavi et al.; Apr. 18, 2021.
Genbank Submission. NCBI; Accession No. Accession: NM_000376, version NM_000376.2; *Homo sapiens* vitamin D receptor (VDR), transcript variant 1, mRNA. Kirac et al.; May 28, 2019.
Genbank Submission. NCBI; Accession No. Accession: NG_016745, version NG_016745.1; *Homo sapiens* sulfotransferase family 2A member 1 (SULT2A1), RefSeqGene on chromosome 19. No Author Listed; Dec. 14, 2020.
Genbank Submission. NCBI; Accession No. Accession: NP_003158, version NP_003158.2; sulfotransferase 2A1 [*Homo sapiens*]. Luck et al.; Apr. 15, 2021.
Genbank Submission. NCBI; Accession No. Accession: NM_003167, version NM_003167.4; *Homo sapiens* sulfotransferase family 2A member 1 (SULT2A1), mRNA. Luck et al.; Apr. 15, 2021.
[No Author Listed] Chemical Abstracts STN Database Record for RN 1240039-42-2. Entered Sep. 7, 2020. 4 pages.
[No Author Listed], Pubchem Compound for CID 129820655. Sep. 13, 2017. 9 pages.
[No Author Listed], Pubchem Compound for CID 126738689. Apr. 22, 2017. 8 pages.
[No Author Listed], Supplementary Information. Harvard University. Dec. 2019. 62 pages.
Abbasi, Unveiling the "Magic" of Diabetes Remission After Weight-Loss Surgery. JAMA. Feb. 14, 2017;317(6):571-574. doi: 10.1001/jama.2017.0020.
Adachi et al., Selective activation of vitamin D receptor by lithocholic acid acetate, a bile acid derivative. J Lipid Res. Jan. 2005;46(1):46-57. doi: 10.1194/jlr.M400294-JLR200. Epub Oct. 16, 2004.
Afonine et al., Towards automated crystallographic structure refinement with phenix.refine. Acta Crystallogr D Biol Crystallogr. Apr. 2012;68(Pt 4):352-67. doi: 10.1107/S0907444912001308. Epub Mar. 16, 2012.
Alexander et al., multiplierz v2.0: A Python-based ecosystem for shared access and analysis of native mass spectrometry data. Proteomics. Aug. 2017;17(15-16). doi: 10.1002/pmic.201700091.
Alnouti, Bile Acid sulfation: a pathway of bile acid elimination and detoxification. Toxicol Sci. Apr. 2009;108(2):225-46. doi: 10.1093/toxsci/kfn268. Epub Jan. 8, 2009.
Angliker et al., The Synthesis of Lysylfluoromethanes and Their Properties as Inhibitors of Trypsin, Plasmin and Cathepsin B. Biochem. J. 1987; 241(3): 871-875.
Assimakopoulos et al., Altered intestinal tight junctions' expression in patients with liver cirrhosis: a pathogenetic mechanism of intestinal hyperpermeability. Eur J Clin Invest. Apr. 2012;42(4):439-46. doi: 10.1111/j.1365-2362.2011.02609.x. Epub Oct. 24, 2011.
Atarashi et al., Treg Induction by a Rationally Selected Mixture of Clostridia Strains From the Human Microbiota. Nature. Aug. 8, 2013; 500 (7461): 232-236.
Baba et al., Selective activity of several cholic acid derivatives against human immunodeficiency virus replication in vitro. J Acquir Immune Defic Syndr (1988). 1989;2(3):264-71.
Bäckhed et al., Mechanisms Underlying the Resistance to Diet-Induced Obesity in Germ-Free Mice. PNAS. 2007; 104(3):979-84.
Bandiera et al., A convenient procedure for the synthesis of ursodeoxycholic acid sulfated derivatives. Synthetic Communications. 1987; 17(9): 1111-17.
Barnes et al., Renal mechanisms influencing the bile acid composition of cholestatic urine. Bile Acid Metab. Health Dis., Proc. Bile Acid Meeting. 1977; 89-92.
Barnes et al., The role of tubular reabsorption in the renal excretion of bile acids. Biochem J. Jul. 15, 1977;166(1):65-73. doi: 10.1042/bj1660065.
Batterham et al., Mechanisms of Diabetes Improvement Following Bariatric/Metabolic Surgery. Diabetes Care. Jun. 2016;39(6):893-901. doi: 10.2337/dc16-0145.
Begley et al., Bile Salt Hydrolase Activity in Probiotics. Appl. Environ. Microbiol. 2006; 72(3): 1729-1738.

Bernier-Latmani et al., Intestinal lymphatic vasculature: structure, mechanisms and functions. Nat Rev Gastroenterol Hepatol. Sep. 2017;14(9):510-526. doi: 10.1038/nrgastro.2017.79. Epub Jun. 28, 2017.
Besnard et al., Is the ileal bile acid-binding protein (I-BABP) gene involved in cholesterol homeostasis?. Med Sci (Paris). Jan. 2004;20(1):73-7. doi: 10.1051/medsci/200420173.
Bhutta et al., Effect of Roux-en-Y gastric bypass surgery on bile acid metabolism in normal and obese diabetic rats. PLoS One. Mar. 23, 2015;10(3):e0122273. doi: 10.1371/journal.pone.0122273. eCollection 2015.
Blosser et al., A method to assess target gene involvement in angiogenesis in vitro and in vivo using lentiviral vectors expressing shRNA. PLoS One. Apr. 23, 2014;9(4):e96036. doi: 10.1371/journal.pone.0096036. eCollection 2014.
Brighton et al., Bile Acids Trigger GLP-1 Release Predominantly by Accessing Basolaterally Located G Protein-Coupled Bile Acid Receptors. Endocrinology. Nov. 2015;156(11):3961-70. doi: 10.1210/en.2015-1321. Epub Aug. 17, 2015.
Bureeva et al., Selective inhibition of the interaction of C1q with immunoglobulins and the classical pathway of complement activation by steroids and triterpenoids sulfates. Bioorg Med Chem. May 15, 2007;15(10):3489-98. doi: 10.1016/j.bmc.2007.03.002. Epub Mar. 6, 2007.
Callahan et al., DADA2: High-resolution sample inference from Illumina amplicon data. Nat Methods. Jul. 2016;13(7):581-3. doi: 10.1038/nmeth.3869. Epub May 23, 2016.
Cao et al., Intestinally-targeted TGR5 agonists equipped with quaternary ammonium have an improved hypoglycemic effect and reduced gallbladder filling effect. Sci Rep. Jun. 24, 2016;6:28676. doi: 10.1038/srep28676.
Cao et al., Liposomes Coated with Isolated Macrophage Membrane Can Target Lung Metastasis of Breast Cancer. ACS Nano. Aug. 23, 2016;10(8):7738-48. doi: 10.1021/acsnano.6b03148. Epub Jul. 27, 2016.
Caporaso et al., QIIME allows analysis of high-throughput community sequencing data. Nat Methods. May 2010;7(5):335-6. doi: 10.1038/nmeth.f.303. Epub Apr. 11, 2010.
Castro-Perez et al., Attenuation of Slc27a5 gene expression followed by LC-MS measurement of bile acid reconjugation using metabolomics and a stable isotope tracer strategy. J Proteome Res. Oct. 7, 2011;10(10):4683-91. doi: 10.1021/pr200475g. Epub Aug. 26, 2011.
Chand et al., Structure and Function of a Highly Active Bile Salt Hydrolase (BSH) From Enterococcus Faecalis and Post-Translational Processing of BSH Enzymes. Biochim Biophys Acta Proteins Proteom. 2018; 1866(4): 507-518.
Chaudhari et al., A microbial metabolite remodels the gut-liver axis following bariatric surgery. Cell Host Microbe. Mar. 10, 2021;29(3):408-424.e7. doi: 10.1016/j.chom.2020.12.004. Epub Jan. 11, 2021.
Chaudhari et al., Bariatric surgery reveals a gut-restricted TGR5 agonist with anti-diabetic effects. Nat Chem Biol. Jan. 2021;17(1):20-29. doi: 10.1038/s41589-020-0604-z. Epub Aug. 3, 2020.
Chen et al., Design of Gut-Restricted Thiazolidine Agonists of G Protein-Coupled Bile Acid Receptor 1 (GPBAR1, TGR5). J Med Chem. Sep. 13, 2018;61(17):7589-7613. doi: 10.1021/acs.jmedchem.8b00308. Epub Aug. 24, 2018.
Chen et al., MolProbity: all-atom structure validation for macromolecular crystallography. Acta Crystallogr D Biol Crystallogr. Jan. 2010;66(Pt 1):12-21. doi: 10.1107/S0907444909042073. Epub Dec. 21, 2009.
Chiang, Recent Advances in Understanding Bile Acid Homeostasis. F1000Res. Nov. 20, 2017;6:2029. doi: 10.12688/f1000research.12449.1. eCollection 2017.
Cohen et al., Differing effects of nor-ursodeoxycholic or ursodeoxycholic acid on hepatic histology and bile acid metabolism in the rabbit. Gastroenterology. Jul. 1986;91(1):189-97. doi: 10.1016/0016-5085(86)90457-9.
Cohen et al., Solvolysis of chenodeoxycholic acid sulfates. Steroids. Jun. 1981;37(6):621-6. doi: 10.1016/s0039-128x(81)90149-5.
Cohen et al., Structural Bioinformatics-Based Design of Selective, Irreversible Kinase Inhibitors. Science. 2005; 308(5726):1318-1321.

(56) References Cited

OTHER PUBLICATIONS

Coleman et al., Cloning and Characterization of a Conjugated Bile Acid Hydrolase Gene From Clostridium Perfringens. Appl Environ Microbiol. 1995; 61(7): 2514-2520.

Compher et al., Vitamin D and the bariatric surgical patient: a review. Obes Surg. Feb. 2008;18(2):220-4. doi: 10.1007/s11695-007-9289-6. Epub Jan. 5, 2008.

Craddock et al., Expression and transport properties of the human ileal and renal sodiumdependent bile acid transporter. Am J Physiol. Jan. 1998;274(1):G157-69. doi: 10.1152/ajpgi.1998.274.1.G157.

Cross et al., The Isothiocyanate Class of Bioactive Nutrients Covalently Inhibit the MEKK1 Protein Kinase. BMC Cancer. 2007; 7(1): 183.

Czygan et al., Synthesis and excretion of bile acid sulfate esters in the isolated perfused rat kidney. Bile Acid Metab. Health Dis., Proc. Bile Acid Meet., 4th (1977), Meeting Date 1976, 83-7.

Dawson et al., Targeted deletion of the ileal bile acid transporter eliminates enterohepatic cycling of bile acids in mice. J Biol Chem. Sep. 5, 2003;278(36):33920-7. doi: 10.1074/jbc.M306370200. Epub Jun. 20, 2003.

Dawson, Roles of Ileal ASBT and OSTalpha-OSTbeta in Regulating Bile Acid Signaling. Dig Dis. 2017;35(3):261-266. doi: 10.1159/000450987. Epub Mar. 1, 2017.

De Witt et al., Effects of sulfation patterns on intestinal transport of bile salt sulfate esters. Am J Physiol. Jan. 1980;238(1):G34-9. doi: 10.1152/ajpgi.1980.238.1.G34.

Devlin, Gut Bacterial Modification of Bile Acids Alters Host Physiology. Harvard Chan Microbiome in Public Health Center Symposium. May 8, 2020. 55 pages.

Diaz et al., Normal Gut Microbiota Modulates Brain Development and Behavior. Proc. Natl. Acad. Sci. U.S.A. 2011; 108(7):3047-3052.

Ding et al., Vertical sleeve gastrectomy activates GPBAR-1/TGR5 to sustain weight loss, improve fatty liver, and remit insulin resistance in mice. Hepatology. Sep. 2016;64(3):760-73. doi: 10.1002/hep.28689. Epub Jul. 25, 2016.

Disibio et al., Metastatic patterns of cancers: results from a large autopsy study. Arch Pathol Lab Med. Jun. 2008;132(6):931-9. doi: 10.5858/2008-132-931-MPOCRF.

Dong et al., Bile Salt Hydrolases: Structure and Function, Substrate Preference, and Inhibitor Development. Protein Sci. 2018; 27(10): 1742-1754.

Donia et al., Human Microbiota. Small Molecules From the Human Microbiota. Science. 2015; 349(6246): 1254766.

Dosa et al., Synthesis and evaluation of water-soluble prodrugs of ursodeoxycholic acid (UDCA), an anti-apoptotic bile acid. ChemMedChem. Jun. 2013;8(6):1002-11. doi: 10.1002/cmdc.201300059. Epub May 2, 2013.

Duboc et al., The bile acid TGR5 membrane receptor: from basic research to clinical application. Dig Liver Dis. Apr. 2014;46(4):302-12. doi: 10.1016/j.dld.2013.10.021. Epub Jan. 9, 2014.

Eissele et al., Glucagon-like peptide-1 cells in the gastrointestinal tract and pancreas of rat, pig and man. Eur J Clin Invest. Apr. 1992;22(4):283-91. doi: 10.1111/j.1365-2362.1992.tb01464.x.

Eriksson et al., Occurrence of sulfated 5alpha-cholanoates in rat bile. J Lipid Res. Feb. 1978;19(2):177-86.

Eyssen et al., Sulfate bile acids in germ-free and conventional mice. Eur J Biochem. Jul. 15, 1976;66(3):507-14. doi: 10.1111/j.1432-1033.1976.tb10576.x.

Ferruzza et al., A protocol for differentiation of human intestinal Caco-2 cells in asymmetric serum-containing medium. Toxicol In Vitro. Dec. 2012;26(8):1252-5. doi: 10.1016/j.tiv.2012.01.008. Epub Jan. 15, 2012.

Ficarro et al., Improved electrospray ionization efficiency compensates for diminished chromatographic resolution and enables proteomics analysis of tyrosine signaling in embryonic stem cells. Anal Chem. May 1, 2009;81(9):3440-7. doi: 10.1021/ac802720e.

Ficarro et al., mzStudio: A Dynamic Digital Canvas for User-Driven Interrogation of Mass Spectrometry Data. Proteomes. Aug. 1, 2017;5(3):20. doi: 10.3390/proteomes5030020.

Fiorucci et al., Bile Acid-Activated Receptors, Intestinal Microbiota, and the Treatment of Metabolic Disorders. Trends Mol Med. 2015; 21(11): 702-714.

Frank et al., Molecular-Phylogenetic Characterization of Microbial Community Imbalances in Human Inflammatory Bowel Diseases. PNAS. 2007; 104 (34):13780-13785.

Franzone et al., [Pharmacokinetics and hepatic metabolism of ursulcholic acid (a soluble form of ursodeoxycholic acid in the rat]. Boll Chim Farm. Jul. 1987;126(7):289-93.

Franzone et al., [The pharmacologic activity of ursulcholic acid, a soluble form of ursodeoxycholic acid]. Boll Chim Farm. Jul. 1987;126(7):282-8.

Fukui, Gut-liver axis in liver cirrhosis: How to manage leaky gut and endotoxemia. World J Hepatol. Mar. 27, 2015;7(3):425-42. doi: 10.4254/wjh.v7.i3.425.

Garland et al., Covalent Modifiers of Botulinum Neurotoxin Counteract Toxin Persistence. ACS Chem Biol. 2019; 14(1): 76-87.

Gartner et al., Transport of chenodeoxycholic acid and its 3-alpha- and 7-alpha-sulfates by isolated perfused rat liver. Hepatology. Oct. 1990; 12(4 Pt 1):738-42. doi: 10.1002/hep.1840120419.

Gehringer et al., Emerging and Re-Emerging Warheads for Targeted Covalent Inhibitors: Applications in Medicinal Chemistry and Chemical Biology. J Med Chem. 2019; 62:5673-5724.

Gehringer et al., Solution-Phase Parallel Synthesis of Ruxolitinib-Derived Janus Kinase Inhibitors via Copper-Catalyzed Azide-Alkyne Cycloaddition. ACS Comb Sci. 2015; 17(1): 5-10.

Ghosh et al., c-Fos mediates repression of the apical sodium-dependent bile acid transporter by fibroblast growth factor-19 in mice. Am J Physiol Gastrointest Liver Physiol. Jan. 2014;306(2):G163-71. doi: 10.1152/ajpgi.00276.2013. Epub Dec. 5, 2013.

Gloy et al., Bariatric surgery versus non-surgical treatment for obesity: a systematic review and meta-analysis of randomised controlled trials. BMJ. Oct. 22, 2013;347:f5934. doi: 10.1136/bmj.f5934.

Gonzalez et al., Putative irreversible inhibitors of the human sodium-dependent bile acid transporter (hASBT; SLC10A2) support the role of transmembrane domain 7 in substrate binding/translocation. Pharm Res. Jul. 2012;29(7):1821-31. doi: 10.1007/s11095-012-0706-8. Epub Feb. 22, 2012.

Goto et al., Separation of monosulfated bile acids by high-performance liquid chromatography. J Chromatogr. 1980;3(5): 645-55.

Goto et al., Studies on steroids. Part CCXXXII. Synthesis of disulfates of unconjugated and conjugated bile acids. Chem Pharm Bull (Tokyo). Nov. 1987;35(11):4562-7. doi: 10.1248/cpb.35.4562.

Goto et al., Studies on steroids. CCXXVII. Separation and determination of bile acid 7- and 12-sulphates in urine by high-performance liquid chromatography with fluorescence labelling. J Chromatogr. Mar. 20, 1987;415(1):45-52.

Goto et al., Studies on steroids. CCXXXIII. Separation and characterization of bile acid disulphates in human urine by high-performance liquid chromatography. J Chromatogr. Mar. 4, 1988;425(1):59-66. doi: 10.1016/0378-4347(88)80006-9.

Goto et al., Studies on steroids. CLXIII. Synthesis of monosulfates of cholic acid derivatives. Chem Pharm Bull. 1980; 28(11):3389-94.

Goto et al., Studies on steroids. CLXX. Separation and determination of bile acid 3-sulfates in human bile by high-performance liquid chromatography. J Chromatogr. Nov. 13, 1981;226(1):13-24.

Goto et al., Synthesis of monosulfates of unconjugated and conjugated bile acids. Chem Pharm Bull (Tokyo). Jun. 1979;27(6):1402-11. doi: 10.1248/cpb.27.1402.

Goto, [Chromatographic determination of bile acids in biological fluids with sensitive and selective detection]. Yakugaku Zasshi. Nov. 1990;110(11):807-21. doi: 10.1248/yakushi1947.110.11_807.

Goudarzi et al., An Integrated Multi-Omic Approach to Assess Radiation Injury on the Host-Microbiome Axis. Radiat Res. Sep. 2016;186(3):219-34. doi: 10.1667/RR14306.1. Epub Aug. 11, 2016.

Griffiths et al., Charge-remote fragmentation of sulfated and glucuronidated bile acids and their 2-aminoethanesulfonic acid derivatives. Rapid Commun Mass Spectrom. 1994; 8(3): 227-36.

Hamilton et al., Human Cecal Bile Acids: Concentration and Spectrum. Am. J. Physiol. Gastrointest. Liver Physiol. 2007; 293(1): G256-G263.

(56) References Cited

OTHER PUBLICATIONS

Harach et al., TGR5 potentiates GLP-1 secretion in response to anionic exchange resins. Sci Rep. 2012;2:430. doi: 10.1038/srep00430. Epub May 30, 2012.
Hasegawa et al., Effect of ursodeoxycholate-3,7-disulfate on biliary excretion of lithocholate-3-O-glucuronide in Eisai hyperbilirubinemic rat (EHBR). Hepatol Res. Aug. 2002;23(4):296-300. doi: 10.1016/s1386-6346(01)00188-7.
He et al., Gut microbiota as a potential target of metabolic syndrome: the role of probiotics and prebiotics. Cell Biosci. Oct. 25, 2017;7:54. doi: 10.1186/s13578-017-0183-1. eCollection 2017.
Henise et al., Irreversible Nek2 Kinase Inhibitors with Cellular Activity. Journal of Medicinal Chemistry. 2011; 54(12):4133-4146.
Hodge et al., Therapeutic potential of Takeda-G-protein-receptor-5 (TGR5) agonists. Hope or hype? Diabetes Obes Metab. May 2016;18(5):439-43. doi: 10.1111/dom.12636. Epub Mar. 17, 2016.
Hofmann, The Function of Bile Salts in Fat Absorption. the Solvent Properties of Dilute Micellar Solutions of Conjugated Bile Acids. Biochem J. 1963; 89(1): 57-68.
Huijghebaert et al., Influence of the Amino Acid Moiety on Deconjugation of Bile Acid Amidates by Cholylglycine Hydrolase or Human Fecal Cultures. J Lipid Res. 1986; 27(7): 742-752.
Huijghebaert et al., Specificity of bile salt sulfatase activity from *Clostridium* sp. strains S1. Appl Environ Microbiol. Nov. 1982;44(5):1030-4. doi: 10.1128/AEM.44.5.1030-1034.1982.
Iguchi et al., Effects of chemical modification of ursodeoxycholic acid on TGR5 activation. Biol Pharm Bull. 2011;34(1):1-7. doi: 10.1248/bpb.34.1.
Ivanov et al., Induction of Intestinal Th17 Cells by Segmented Filamentous Bacteria. Cell. 2009; 139(3): 485-98.
Jacobs et al., A Disease-Associated Microbial and Metabolomics State in Relatives of Pediatric Inflammatory Bowel Disease Patients. Cell Mol Gastroenterol Hepatol. Jul. 2, 2016;2(6):750-766. doi: 10.1016/j.jcmgh.2016.06.004. eCollection Nov. 2016.
Jahansouz et al., Antibiotic-induced Disruption of Intestinal Microbiota Contributes to Failure of Vertical Sleeve Gastrectomy. Ann Surg. Jun. 2019;269(6):1092-1100. doi: 10.1097/SLA.0000000000002729.
Jarocki et al., A New Insight into the Physiological Role of Bile Salt Hydrolase among Intestinal Bacteria from the Genus Bifidobacterium. PLoS One. Dec. 3, 2014;9(12):e114379. doi: 10.1371/journal.pone.0114379. eCollection 2014.
Joyce et al., Bacterial bile salt hydrolase in host metabolism: Potential for influencing gastrointestinal microbe-host crosstalk. Gut Microbes. 2014;5(5):669-74. doi: 10.4161/19490976.2014.969986.
Joyce et al., Regulation of Host Weight Gain and Lipid Metabolism by Bacterial Bile Acid Modification in the Gut. Proc. Natl. Acad. Sci. U.S.A. 2014; 111(20): 7421-7426.
Kakizaki et al., Xenobiotic-sensing nuclear receptors CAR and PXR as drug targets in cholestatic liver disease. Curr Drug Targets. Nov. 2009;10(11):1156-1163. doi: 10.2174/138945009789735174.
Kaplan et al., Monitoring dynamic changes in lymph metabolome of fasting and fed rats by electrospray ionization-ion mobility mass spectrometry (ESI-IMMS). Anal Chem. Oct. 1, 2009;81(19):7944-53. doi: 10.1021/ac901030k.
Kaska et al., Improved glucose metabolism following bariatric surgery is associated with increased circulating bile acid concentrations and remodeling of the gut microbiome. World J Gastroenterol. Oct. 21, 2016;22(39):8698-8719. doi: 10.3748/wjg.v22.i39.8698.
Katsuma et al., Bile acids promote glucagon-like peptide-1 secretion through TGR5 in a murine enteroendocrine cell line STC-1. Biochem Biophys Res Commun. Apr. 1, 2005;329(1):386-90. doi: 10.1016/j.bbrc.2005.01.139.
Kawamoto et al., Purification and Characterization of a New Hydrolase for Conjugated Bile Acids, Chenodeoxycholyltaurine Hydrolase, From Bacteroides Vulgatus. J. Biochem. 1989; 106(6): 1049-1053.

Khorgami et al., Trends in utilization of bariatric surgery, 2010-2014: sleeve gastrectomy dominates. Surg Obes Relat Dis. May 2017;13(5):774-778. doi: 10.1016/j.soard.2017.01.031. Epub Jan. 25, 2017.
Kraal et al., The Prevalence of Species and Strains in the Human Microbiome: a Resource for Experimental Efforts. PLOS ONE. 2014; 9(5): e97279.
Kuhre et al., Peptide production and secretion in GLUTag, NCI-H716, and STC-1 cells: a comparison to native L-cells. J Mol Endocrinol. Apr. 2016;56(3):201-11. doi: 10.1530/JME-15-0293. Epub Jan. 27, 2016.
Larraufie et al., Important Role of the GLP-1 Axis for Glucose Homeostasis after Bariatric Surgery. Cell Rep. Feb. 5, 2019;26(6):1399-1408.e6. doi: 10.1016/j.celrep.2019.01.047.
Lastya et al., The low level of glucagon-like peptide-1 (glp-1) is a risk factor of type 2 diabetes mellitus. BMC Res Notes. Nov. 26, 2014;7:849. doi: 10.1186/1756-0500-7-849.
Lebel et al., Boc-Protected Amines via a Mild and Efficient One-Pot Curtius Rearrangement. Org Lett. 2005; 7(19): 4107-4110.
Lepage et al., Separation of sulfated from non-sulfated serum bile acids without the use of Sephadex columns. J Lipid Res. May 1981;22(4):705-11.
Lespessailles et al., Vitamin D alteration associated with obesity and bariatric surgery. Exp Biol Med (Maywood). May 2017;242(10):1086-1094. doi: 10.1177/1535370216688567. Epub Jan. 1, 2017.
Lewis et al., Inactivation of Protein Tyrosine Phosphatases by Dietary Isothiocyanates. Bioorganic & Medicinal Chemistry Letters. 2015; 25(20):4549-52.
Li et al., Bile acids as metabolic regulators. Curr Opin Gastroenterol. Mar. 2015 ; 31(2): 159-165. doi:10.1097/MOG.0000000000000156.
Li et al., Microbiome Remodelling Leads to Inhibition of Intestinal Farnesoid X Receptor Signalling and Decreased Obesity. Nat Commun. 2013;4:2384. doi: 10.1038/ncomms3384.
Lianidou et al., Enzymic fluorimetric determination of sulphated and non-sulphated primary bile acids in urine using a rapid solvolysis technique. Analyst. Sep. 1988;113(9):1459-63. doi: 10.1039/an9881301459.
Liu et al., Developing Irreversible Inhibitors of the Protein Kinase Cysteinome. Chemistry & Biology. 2013; 20(2): 146-159.
Liu et al., Role of gut microbiota, bile acids and their cross-talk in the effects of bariatric surgery on obesity and type 2 diabetes. J Diabetes Investig. Jan. 2018;9(1):13-20. doi: 10.1111/jdi.12687. Epub Jun. 12, 2017.
Lutz et al., M. The Use of Rat and Mouse Models in Bariatric Surgery Experiments. Front Nutr. Aug. 5, 2016;3:25. doi: 10.3389/fnut.2016.00025. eCollection 2016.
Ma et al., Gut Microbiome-Mediated Bile Acid Metabolism Regulates Liver Cancer via NKT Cells. Science. 2018; 360 (6391): eaan5931.
Madsbad, The role of glucagon-like peptide-1 impairment in obesity and potential therapeutic implications. Diabetes Obes Metab. Jan. 2014;16(1):9-21. doi: 10.1111/dom.12119. Epub May 26, 2013.
Magouliotis et al., Impact of Bariatric Surgery on Metabolic and Gut Microbiota Profile: a Systematic Review and Meta-analysis. Obes Surg. May 2017;27(5):1345-1357. doi: 10.1007/s11695-017-2595-8.
Mahowald et al., Characterizing a model human gut microbiota composed of members of its two dominant bacterial phyla. Proc Natl Acad Sci U S A. Apr. 7, 2009;106(14):5859-64. doi: 10.1073/pnas.0901529106. Epub Mar. 24, 2009.
Makishima et al., Vitamin D Receptor as an Intestinal Bile Acid Sensor. Science. May 17, 2002; 296 (5571): 1313-1316.
Manchanda et al., Vitamin D receptor and type 2 diabetes mellitus: Growing therapeutic opportunities. Indian J Hum Genet. Sep. 2012;18(3):274-5. doi: 10.4103/0971-6866.107975.
Marschall et al., The major metabolites of ursodeoxycholic acid in human urine are conjugated with N-acetylglucosamine. Hepatology. Oct. 1994;20(4 Pt 1):845-53. doi: 10.1002/hep.1840200412.
Martinez-Augustin et al., Intestinal bile acid physiology and pathophysiology. World J Gastroenterol. Oct. 7, 2008;14(37):5630-40. doi: 10.3748/wjg.14.5630.

(56) References Cited

OTHER PUBLICATIONS

Mccoy et al., Phaser crystallographic software. J Appl Crystallogr. Aug. 1, 2007;40(Pt 4):658-674. doi: 10.1107/S0021889807021206. Epub Jul. 13, 2007.
Mcdonald et al., Partitioning of polar fatty acids into lymph and portal vein after intestinal absorption in the rat. Q J Exp Physiol. Apr. 1987;72(2):153-9. doi: 10.1113/expphysiol.1987.sp003059.
Mcdonald et al., Portal venous transport of long-chain fatty acids absorbed from rat intestine. Am J Physiol. Sep. 1980;239(3):G141-50. doi: 10.1152/ajpgi.1980.239.3.G141.
Mcgavigan et al., TGR5 contributes to glucoregulatory improvements after vertical sleeve gastrectomy in mice. Gut. Feb. 2017;66(2):226-234. doi: 10.1136/gutjnl-2015-309871. Epub Oct. 28, 2015.
Medina et al., Distinct patterns in the gut microbiota after surgical or medical therapy in obese patients. PeerJ. Jun. 20, 2017;5:e3443. doi: 10.7717/peerj.3443. eCollection 2017.
Mertens et al., Bile Acid Signaling Pathways from the Enterohepatic Circulation to the Central Nervous System. Front Neurosci. Nov. 7, 2017;11:617. doi: 10.3389/fnins.2017.00617. eCollection 2017.
Mi et al., Covalent Binding to Tubulin by Isothiocyanates. a Mechanism of Cell Growth Arrest and Apoptosis. J Biol Chem. 2008; 283(32): 22136-22146.
Miller et al., Targeting Protein Kinases with Selective and Semipromiscuous Covalent Inhibitors. Meth Enzymol. 2014; 548: 93-116.
Miyata et al., Enterobacteria modulate intestinal bile acid transport and homeostasis through apical sodium-dependent bile acid transporter (SLC10A2) expression. J Pharmacol Exp Ther. Jan. 2011;336(1):188-96. doi: 10.1124/jpet.110.171736. Epub Sep. 30, 2010.
Modica et al., Deciphering the Nuclear Bile Acid Receptor FXR Paradigm. Nucl Recept Signal. 2010; 8:e005.
Moore et al., Intestinal Floras of Populations That Have a High Risk of Colon Cancer. Appl Environ Microbiol. 1995; 61(9): 3202-7.
Morin et al., Collaboration gets the most out of software. Elife. Sep. 10, 2013;2:e01456. doi: 10.7554/eLife.01456.
Moser et al., Bile Salt Hydrolase Activity and Resistance to Toxicity of Conjugated Bile Salts Are Unrelated Properties in Lactobacilli. Appl Environ Microbiol. Aug. 2001;67(8):3476-80. doi: 10.1128/AEM.67.8.3476-3480.2001.
Myronovych et al., Vertical sleeve gastrectomy reduces hepatic steatosis while increasing serum bile acids in a weight-loss-independent manner. Obesity (Silver Spring). Feb. 2014;22(2):390-400. doi: 10.1002/oby.20548. Epub Sep. 5, 2013.
Nair et al., The enzymatic cleavage of the carbon-nitrogen bond in 3-alpha, 7-alpha, 12-alpha-trihydroxy-5-beta-cholan-24-oylglycine. J Biol Chem. Jan. 10, 1967;242(1):7-11.
Nemati et al., Increased Bile Acids and FGF19 After Sleeve Gastrectomy and Roux-en-Y Gastric Bypass Correlate with Improvement in Type 2 Diabetes in a Randomized Trial. Obes Surg. Sep. 2018;28(9):2672-2686. doi: 10.1007/s11695-018-3216-x.
Nishida et al., Modulation of bile acid metabolism by 1alphahydroxyvitamin D3 administration in mice. Drug Metab Dispos. Oct. 2009;37(10):2037-44. doi: 10.1124/dmd.109.027334. Epub Jul. 6, 2009.
Ogasawara et al., Biliary excretion of phenolphthalein glucuronide in the rat. Hepatol Res. Jun. 2001;20(2):221-231. doi: 10.1016/s1386-6346(00)00143-1.
Pageaux et al., Bile acid sulfates in serum bile acids determination. Steroids. Jul. 1979;34(1):73-88. doi: 10.1016/0039-128x(79)90127-2.
Park et al., Metabolism of fluorine-containing drugs. Annu Rev Pharmacol Toxicol. 2001;41:443-70. doi: 10.1146/annurev.pharmtox.41.1.443.
Parmentier et al., Cholic acid-7-sulfate, a major bile acid in the large intestine of the mouse. Adv. Bile Acid Res., Bile Acid Meet., 3rd (1975), Meeting Date 1974, 139-44.
Parmentier et al., Synthesis and characteristics of the specific monosulfates of chenodeoxycholate, deoxycholate and their taurine or glycine conjugates. Steroids. Nov. 1977;30(5):583-90. doi: 10.1016/0039-128x(77)90049-6.
Parmentier et al., Synthesis of the specific monosulfates of cholic acid. Steroids. Dec. 1975;26(6):721-9. doi: 10.1016/0039-128x(75)90105-1.
Parmentier et al., Thin-layer chromatography of bile salt sulfates. Journal of Chromatography. 1978; 152(1):285-9.
Patti et al., Serum bile acids are higher in humans with prior gastric bypass: potential contribution to improved glucose and lipid metabolism. Obesity (Silver Spring). Sep. 2009;17(9):1671-7. doi: 10.1038/oby.2009.102. Epub Apr. 9, 2009.
Peng et al., Liquid-liquid extraction combined with differential isotope dimethylaminophenacyl labeling for improved metabolomic profiling of organic acids. Anal Chim Acta. Nov. 25, 2013;803:97-105. doi: 10.1016/j.aca.2013.07.045. Epub Jul. 27, 2013.
Pols et al., Lithocholic Acid Controls Adaptive Immune Responses by Inhibition of Th1 Activation Through the Vitamin D Receptor. PLOS ONE. 2017; 12(5): e0176715.
Princen et al., One-step solvolysis of 3-, 7- and 12-sulfated free and conjugated bile acids. Clin Chim Acta. Nov. 15, 1990;192(1):77-83. doi: 10.1016/0009-8981(90)90274-v.
Quintás-Cardama et al., Kinase Inhibitors for the Treatment of Myeloproliferative Neoplasias and Beyond. Nature Reviews Drug Discovery. 2011; 10(2): 127-140.
Raedsch et al., Separation of individual sulfated bile acid conjugates as calcium complexes using reversed-phase partition thin-layer chromatography. J Lipid Res. Aug. 1979;20(6):789-95.
Ridaura et al., Gut Microbiota From Twins Discordant for Obesity Modulate Metabolism in Mice. Science. 2013; 341(6150): 1241214.
Ridlon et al., Bile Salt Biotransformations by Human Intestinal Bacteria. J Lipid Res. 2006; 47(2): 241-259.
Rizzo et al., Functional characterization of the semisynthetic bile acid derivative INT-767, a dual farnesoid X receptor and TGR5 agonist. Mol Pharmacol. Oct. 2010;78(4):617-30. doi: 10.1124/mol.110.064501. Epub Jul. 14, 2010.
Robben et al., Formation of delta 2- and delta 3-cholenoic acids from bile acid 3-sulfates by a human intestinal Fusobacterium strain. Appl Environ Microbiol. Nov. 1989;55(11):2954-9. doi: 10.1128/AEM.55.11.2954-2959.1989.
Roberts et al., Development of a Gut Microbe-Targeted Nonlethal Therapeutic to Inhibit Thrombosis Potential. Nat. Med. 2018; 24(9): 1407-1417.
Roda et al., Quantitative aspects of the interaction of bile acids with human serum albumin. J Lipid Res. Mar. 1982;23(3):490-5.
Rodrigues et al., The site-specific delivery of ursodeoxycholic acid to the rat colon by sulfate conjugation. Gastroenterology. Dec. 1995; 109(6):1835-44. doi: 10.1016/0016-5085(95)90750-5.
Rossocha et al., Conjugated Bile Acid Hydrolase Is a Tetrameric N-Terminal Thiol Hydrolase with Specific Recognition of Its Cholyl but Not of Its Tauryl Product. Biochem. 2005; 44(15): 5739-5748.
Runge-Morris et al., Regulation of the cytosolic sulfotransferases by nuclear receptors. Drug Metab Rev. Feb. 2013;45(1):15-33. doi: 10.3109/03602532.2012.748794.
Ryan et al., FXR is a molecular target for the effects of vertical sleeve gastrectomy. Nature. May 8, 2014;509(7499):183-8. doi: 10.1038/nature13135. Epub Mar. 26, 2014.
Sampson et al., Gut Microbiota Regulate Motor Deficits and Neuroinflammation in a Model of Parkinson's Disease. Cell. 2016; 167(6): 1469-80.
Sandler et al., Short-Term Benefit From Oral Vancomycin Treatment of Regressive-Onset Autism. Journal of Child Neurology. 2016; 15(7): 429-435.
Sano et al., Estradiol-17 beta-glucuronide-induced cholestasis. Effects of ursodeoxycholate-3-O-glucuronide and 3,7-disulfate. J Hepatol. Feb. 1993;17(2):241-6. doi: 10.1016/s0168-8278(05)80045-5.
Santhekadur et al., Preclinical models of non-alcoholic fatty liver disease. J Hepatol. Feb. 2018;68(2):230-237. doi: 10.1016/j.jhep.2017.10.031. Epub Nov. 9, 2017.
Sasaki et al., Separation of double conjugates of bile acids by two-dimensional high-performance thin-layer chromatography with

(56) References Cited

OTHER PUBLICATIONS tetra-n-butylammonium phosphate and methyl β-cyclodextrin. Chromatographia. 1999; 49(11/12): 681-685.
Sato et al., Novel Potent and Selective Bile Acid Derivatives as TGR5 Agonists: Biological Screening, Structure-Activity Relationships, and Molecular Modeling Studies. J Med Chem. Mar. 27, 2008;51(6):1831-41. doi: 10.1021/jm7015864. Epub Feb. 29, 2008.
Sayin et al., Gut Microbiota Regulates Bile Acid Metabolism by Reducing the Levels of Tauro-Beta-Muricholic Acid, a Naturally Occurring FXR Antagonist. Cell Metab. 2013; 17(2): 225-235.
Schloss et al., Introducing mothur: open-source, platform-independent, community-supported software for describing and comparing microbial communities. Appl Environ Microbiol. Dec. 2009;75(23):7537-41. doi: 10.1128/AEM.01541-09. Epub Oct. 2, 2009.
Serafimova et al., Reversible Targeting of Noncatalytic Cysteines with Chemically Tuned Electrophiles. Nature Chemical Biology. 2012; 8(5): 471-476.
Setchell et al., General methods for the analysis of metabolic profiles of bile acids and related compounds in feces. J Lipid Res. 1983; 24: 1085-1100.
Setchell et al., Serum bile acid analysis. Clin Chim Acta. Jan. 7, 1983;127(1):1-17. doi: 10.1016/0009-8981(83)90070-0.
Setchell et al., Ursodeoxycholic acid-disulphate (SUDCA)—a potent chemopreventive agent against colon cancer in: Bile Acids: Biological Actions and Clinical Relevance. Falk Symposium 155. 2007; 194-200.
Shang et al., Colesevelam improves insulin resistance in a diet-induced obesity (F-DIO) rat model by increasing the release of GLP-1. Am J Physiol Gastrointest Liver Physiol. Mar. 2010;298(3):G419-24. doi: 10.1152/ajpgi.00362.2009. Epub Dec. 31, 2009.
Sisley et al., Hypothalamic Vitamin D Improves Glucose Homeostasis and Reduces Weight. Diabetes. Sep. 2016;65(9):2732-41. doi: 10.2337/db16-0309. Epub May 23, 2016.
Smith et al., Discovery of Bile Salt Hydrolase Inhibitors Using an Efficient High-Throughput Screening System. PLOS ONE. 2014; 9(1): e85344.
Solbach et al., BaiCD gene cluster abundance is negatively correlated with Clostridium difficile infection. PLoS One. May 8, 2018;13(5):e0196977. doi: 10.1371/journal.pone.0196977. eCollection 2018.
Song et al., Selective Activation of Liver X Receptor Alpha by 6alpha-Hydroxy Bile Acids and Analogs. Steroids. 2000; 65(8): 423-427.
Song et al., Taxonomic Profiling and Populational Patterns of Bacterial Bile Salt Hydrolase (BSH) Genes Based on Worldwide Human Gut Microbiome. Microbiome. 2019; 7(1): 9.
Spiljar et al., The Immune System Bridges the Gut Microbiota with Systemic Energy Homeostasis: Focus on TLRs, Mucosal Barrier, and SCFAs. Front Immunol. 2017; 8: 1353.
Staudinger et al., The Nuclear Receptor PXR Is a Lithocholic Acid Sensor That Protects Against Liver Toxicity. PNAS. 2001; 98(6):3369-3374.
Steinert et al., Intestinal GLP-1 and satiation: from man to rodents and back. Int J Obes (Lond). Feb. 2016;40(2):198-205. doi: 10.1038/ijo.2015.172. Epub Aug. 28, 2015.
Stellwag et al., Purification and Characterization of Bile Salt Hydrolase From *Bacteroides fragilis* Subsp. *Fragilis*. Biochim Biophys Acta. Nov. 8, 1976;452(1):165-76. doi: 10.1016/0005-2744(76)90068-1.
Stoltz et al., Synthesis and Biological Evaluation of Bile Acid Analogues Inhibitory to Clostridium difficile Spore Germination. J Med Chem. Apr. 27, 2017;60(8):3451-3471. doi: 10.1021/acs.jmedchem.7b00295. Epub Apr. 12, 2017.
Strelow, A Perspective on the Kinetics of Covalent and Irreversible Inhibition. SLAS Discov. 2017; 22(1): 3-20.
Summerfield et al., Renal synthesis of bile acid sulphates: evidence from man and the isolated perfused rat kidney. Clinical Science and Molecular Medicine. 1976; 50(2): 25P-26P.
Summerfield et al., Synthesis of bile acid monosulphates by the isolated perfused rat kidney. Biochem J. May 15, 1976;156(2):339-45. doi: 10.1042/bj1560339.
Sun et al., Gut Microbiota and Intestinal FXR Mediate the Clinical Benefits of Metformin. Nat. Med. 2018; 24(12): 1919-1929.
Sun et al., Identification of functionally relevant residues of the rat ileal apical sodium-dependent bile acid cotransporter. J Biol Chem. Jun. 16, 2006;281(24):16410-8. doi: 10.1074/jbc.M600034200. Epub Apr. 11, 2006.
Takikawa et al., Binding of bile acids by glutathione S-transferases from rat liver. J Lipid Res. Sep. 1986;27(9):955-66.
Takikawa et al., Comparison of the affinities of newly identified human bile acid binder and cationic glutathione S-transferase for bile acids. J Lipid Res. Jun. 1986;27(6):652-7.
Takikawa et al., Effects of organic anions and bile acids on biliary lipid excretion in hyperbilirubinemic mutant Sprague-Dawley rats. J Hepatol. Feb. 1993;17(2):247-52. doi: 10.1016/s0168-8278(05)80046-7.
Takikawa et al., Effects of ursodeoxycholate and its conjugates on biliary glutathione excretion in rats. Dig Dis Sci. Oct. 1996;41(10):1953-8. doi: 10.1007/BF02093595.
Takikawa et al., Effects of ursodeoxycholate, its glucuronide and disulfate and beta-muricholate on biliary bicarbonate concentration and biliary lipid excretion. J Hepatol. May 1992;15(1-2):77-84. doi: 10.1016/0168-8278(92)90015-h.
Takikawa et al., Enhanced biliary excretion of lithocholate-3-sulfate by ursodeoxycholate-3,7-disulfate infusion in Eisai hyperbilirubinemic rat (EHBR). Dig Dis Sci. Jan. 1998;43(1):188-92. doi: 10.1023/a:1018809028425.
Tan et al., A multi-chamber microfluidic intestinal barrier model using Caco-2 cells for drug transport studies. PLoS One. May 10, 2018;13(5):e0197101. doi: 10.1371/journal.pone.0197101. eCollection 2018.
Tanaka et al., Bile Salt Hydrolase of Bifidobacterium Longum-Biochemical and Genetic Characterization. Appl Environ Microbiol. 2000; 66(6): 2502-2512.
Thaiss et al., The Microbiome and Innate Immunity. Nature. 2016; 535 (7610): 65-74.
Tiscornia et al., A general method for gene knockdown in mice by using lentiviral vectors expressing small interfering RNA. Proc Natl Acad Sci U S A. Feb. 18, 2003;100(4):1844-8. doi: 10.1073/pnas.0437912100. Epub Jan. 27, 2003.
Tremaroli et al., Roux-en-Y Gastric Bypass and Vertical Banded Gastroplasty Induce Long-Term Changes on the Human Gut Microbiome Contributing to Fat Mass Regulation. Cell Metab. Aug. 4, 2015;22(2):228-38. doi: 10.1016/j.cmet.2015.07.009.
Tserng et al., Bile acid sulfates. III. Synthesis of 7- and 12-monosulfates of bile acids and their conjugates using a sulfur trioxide-triethylamine complex. Steroids. Feb. 1979;33(2):167-82. doi: 10.1016/0039-128x(79)90024-2.
Turnbaugh et al., An Obesity-Associated Gut Microbiome with Increased Capacity for Energy Harvest. Nature. 2006; 444(7122): 1027-31.
Uegaki et al., Effect of organic anions and bile acid conjugates on biliary excretion of taurine-conjugated bile acid sulfates in the rat. Steroids. Nov. 1999;64(11):790-5. doi: 10.1016/s0039-128x(99)00071-9.
Van De Laarschot et al., The role of bile salts in liver regeneration. Hepatol Int. Sep. 2016;10(5):733-40. doi: 10.1007/s12072-016-9723-8. Epub Apr. 5, 2016.
Vavassori et al., The Bile Acid Receptor FXR Is a Modulator of Intestinal Innate Immunity. J. Immunol. 2009; 183(10): 6251-6261.
Verhoeckx et al., Caco-2 Cell Line. The Impact of Food Bioactives on Health. 2015; 175:103-111.
Wahlstrom et al., Intestinal Crosstalk between Bile Acids and Microbiota and Its Impact on Host Metabolism. Cell Metab. Jul. 12, 2016;24(1):41-50. doi: 10.1016/j.cmet.2016.05.005. Epub Jun. 16, 2016.
Walker et al., Importance of sulfur-containing metabolites in discriminating fecal extracts between normal and type-2 diabetic mice. J Proteome Res. Oct. 3, 2014;13(10):4220-31. doi: 10.1021/pr500046b. Epub Sep. 2, 2014.

(56) References Cited

OTHER PUBLICATIONS

Wallace et al., Alleviating Cancer Drug Toxicity by Inhibiting a Bacterial Enzyme. Science. 2010; 330(6005): 831-835.
Wang et al., Identification and Characterization of a Bile Salt Hydrolase From Lactobacillus Salivarius for Development of Novel Alternatives to Antibiotic Growth Promoters. Appl. Environ. Microbiol. 2012; 78(24): 8795-8802.
Weber et al., Nephele: a cloud platform for simplified, standardized and reproducible microbiome data analysis. Bioinformatics. Apr. 15, 2018;34(8):1411-1413. doi: 10.1093/bioinformatics/btx617.
Weerapana et al., Tandem orthogonal proteolysis-activity-based protein profiling (TOP-ABPP)—a general method for mapping sites of probe modification in proteomes. Nat Protoc. 2007;2(6):1414-25. doi: 10.1038/nprot.2007.194.
Wilson et al., Keap Calm, and Carry on Covalently. J Med Chem. Oct. 10, 2013;56(19):7463-76. doi: 10.1021/jm400224q. Epub Jul. 25, 2013.
Wrzosek et al. Transplantation of human microbiota into conventional mice durably reshapes the gut microbiota. Sci Rep. May 1, 2018;8(1):6854. doi: 10.1038/s41598-018-25300-3.
Xie et al., An Intestinal Farnesoid X Receptor-Ceramide Signaling Axis Modulates Hepatic Gluconeogenesis in Mice. Diabetes. 2017; 66 (3): 613-626.
Xie et al., Pharmacological Targeting of the Pseudokinase Her3. Nature Chemical Biology. 2014; 10(12): 1006-1012.
Yang et al., MX1013, a Dipeptide Caspase Inhibitor with Potent in Vivo Antiapoptotic Activity. Br. J. Pharmacol. 2003; 140(2): 402-412.
Yao et al., A selective gut bacterial bile salt hydrolase alters host metabolism. Elife. Jul. 17, 2018;7:e37182. doi: 10.7554/eLife.37182.
Yao et al., Nontargeted analysis of the urine nonpolar sulfateome: a pathway to the nonpolar xenobiotic exposome. Rapid Commun Mass Spectrom. Nov. 15, 2016;30(21):2341-2350. doi: 10.1002/rcm.7726.
Yousef et al., Effect of complete sulfation of bile acids on bile formation: role of conjugation and number of sulfate groups. Hepatology. Mar. 1992;15(3):438-45. doi: 10.1002/hep.1840150314.
Zhang et al., Effects of feeding bile acids and a bile acid sequestrant on hepatic bile acid composition in mice. J Lipid Res. Nov. 2010;51(11):3230-42. doi: 10.1194/jlr.M007641. Epub Jul. 29, 2010.
Zhang et al., Lake char (*Salvelinus namaycush*) olfactory neurons are highly sensitive and specific to bile acids. J Comp Physiol A Neuroethol Sens Neural Behav Physiol. Feb. 2009;195(2):203-15. doi: 10.1007/s00359-008-0399-y. Epub Jan. 10, 2009.
Zybailov et al., Statistical analysis of membrane proteome expression changes in *Saccharomyces cerevisiae*. J Proteome. Sep. 2006;5(9):2339-47. doi: 10.1021/pr060161n.

Extended European Search Report for Application No. 19892790.7, mailed Aug. 18, 2022.
D'Amore et al., Design, synthesis, and biological evaluation of potent dual agonists of nuclear and membrane bile acid receptors. J Med Chem. Feb. 13, 2014;57(3):937-54. doi: 10.1021/jm401873d. Epub Jan. 17, 2014.
Festa et al., Exploitation of cholane scaffold for the discovery of potent and selective farnesoid X receptor (FXR) and G-protein coupled bile acid receptor 1 (GP-BAR1) ligands. J Med Chem. Oct. 23, 2014;57(20):8477-95. doi: 10.1021/jm501273r. Epub Oct. 9, 2014.
Nakhi et al., 7-Methylation of Chenodeoxycholic Acid Derivatives Yields a Substantial Increase in TGR5 Receptor Potency. J Med Chem. Jul. 25, 2019;62(14):6824-6830. doi: 10.1021/acs.jmedchem.9b00770. Epub Jul. 3, 2019.
Sepe et al., Modification on ursodeoxycholic acid (UDCA) scaffold. discovery of bile acid derivatives as selective agonists of cell-surface G-protein coupled bile acid receptor 1 (GP-BAR1). J Med Chem. Sep. 25, 2014;57(18):7687-701. doi: 10.1021/jm500889f. Epub Sep. 7, 2014.
Invitation to Pay Additional Fees for Application No. PCT/US2021/031277, mailed Aug. 11, 2021.
International Search Report and Written Opinion for Application No. PCT/US2021/031277, mailed Oct. 14, 2021.
Ferrell et al., Understanding Bile Acid Signaling in Diabetes: From Pathophysiology to Therapeutic Targets. Diabetes Metab J. Jun. 2019;43(3):257-272. doi: 10.4093/dmj.2019.0043.
Rearick et al., Increase in cholesterol sulfotransferase activity during in vitro squamous differentiation of rabbit tracheal epithelial cells and its inhibition by retinoic acid. J Biol Chem. Sep. 25, 1987;262(27):13069-74.
Wu et al., Vitamin D receptor negatively regulates bacterial-stimulated NF-kappaB activity in intestine. Am J Pathol. Aug. 2010;177(2):686-97. doi: 10.2353/ajpath.2010.090998. Epub Jun. 21, 2010.
Adhikari et al., A Gut-Restricted Lithocholic Acid Analog as an Inhibitor of Gut Bacterial Bile Salt Hydrolases. ACS Chem Biol. Aug. 20, 2021;16(8):1401-1412. doi: 10.1021/acschembio.1c00192. Epub Jul. 19, 2021.
Kurosawa et al., Synthesis of 3α,7α, 12α-trihydroxy- and 3α, 7α-dihydroxy-5β-cholestan-26-oic acids by the use of β-ketosulfoxide. Steroids. Jul. 1995;60(7):439-44. doi: 10.1016/0039-128x(95)00033-m.
Kurosawa et al., Synthesis of diastereomers of 3 alpha,7 alpha, 12 alpha, 24-tetrahydroxy- and 3 alpha, 7 alpha,24-trihydroxy-5 beta-cholestan-26-oic acids and their structures. Steroids. Jul. 1996;61(7):421-8. doi: 10.1016/0039-128x(96)00062-1.

\* cited by examiner

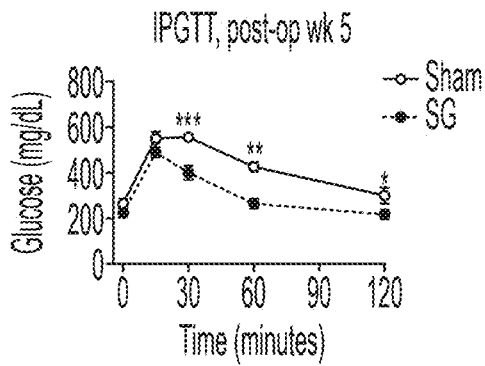
Fig. 16A
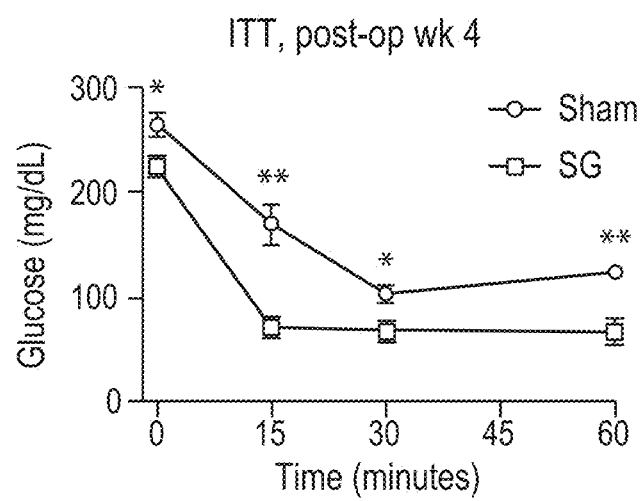
Fig. 16B
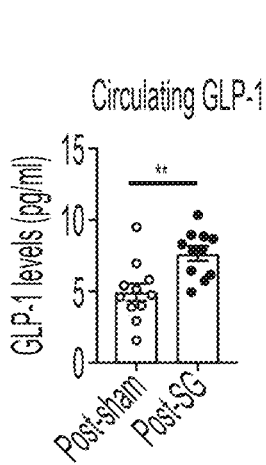
Fig. 16C
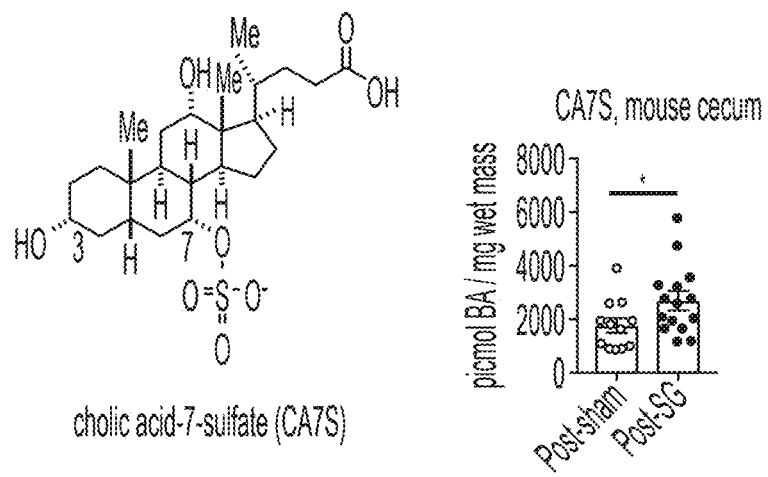
cholic acid-7-sulfate (CA7S)
Fig. 16D
Fig. 16E

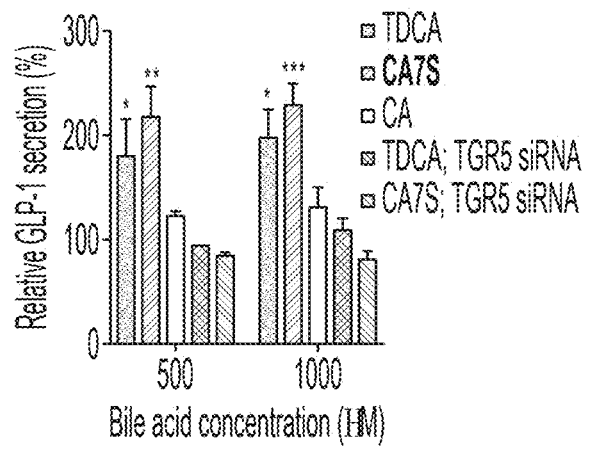
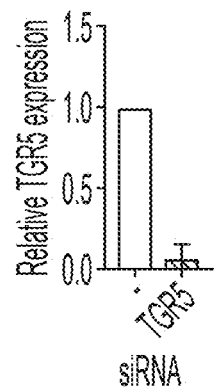
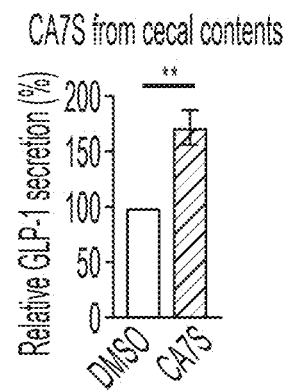
Fig. 20A    Fig. 20B    Fig. 20C
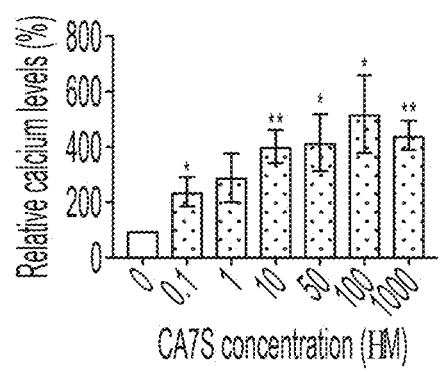
Fig. 20D
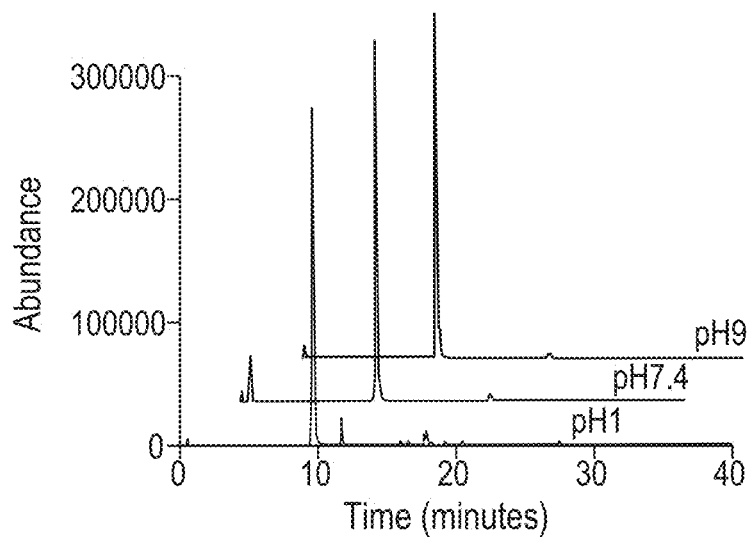
Fig. 20E R=H or OH

SYNTHETIC DERIVATIVES OF CHOLIC ACID 7-SULFATE AND USES THEREOF

RELATED APPLICATIONS

This application is a national stage filing under 35 U.S.C. § 371 of International PCT Application PCT/US2019/064488, filed Dec. 4, 2019, which claims priority under 35 U.S.C. § 119 (e) to U.S. Provisional Application, U.S. Ser. No. 62/775,029, filed Dec. 4, 2018, each of which is incorporated herein by reference.

GOVERNMENT SUPPORT

This invention was made with government support under GM128618, and DK057521 awarded by the National Institutes of Health. The government has certain rights in the invention.

FIELD OF THE INVENTION

The present disclosure relates to the treatment of metabolic disorders (e.g., diabetes, obesity) and inflammatory diseases.

BACKGROUND OF THE INVENTION

Obesity and type 2 diabetes (T2D) are medical pandemics. Bariatric surgery, in the form of Roux-en-Y gastric bypass or sleeve gastrectomy (SG), is currently the most effective and lasting treatment for obesity and related comorbidities (Batterham, R. L., et al. Diabetes Care 2016 39, 893-901; Gloy, V. L. et al., BMJ 2013, 347, f5934-f5934). While maximal weight-loss occurs at 1 year, remarkably, many patients see resolution of their T2D within hours to days of surgery (Abbasi, J. JAMA, 2017, 317, 571-574). For a majority of patients, remission is durable and lasts for years after surgery.

Two changes consistently observed following bariatric surgery are increased levels of Glucagon-like peptide-1 (GLP-1), a circulating incretin hormone, and changes in the systemic repertoire of bile acids (BAs) (Kaska, L., et al. J. World J. Gastroenterol. 2016, 22, 8698-8719). BAs are cholesterol-derived metabolites that play crucial roles in host metabolism by acting as detergents that aid in absorption of lipids and vitamins, and as ligands for host receptors (Fiorucci, S., et al., Trends Mol Med. 2015, 21, 702-714). BAs have been implicated in post-SG therapeutic benefits due to their ability to mediate farnesoid X receptor (FXR) signaling (Ryan, K. K. et al. Nature 2014, 509, 183-188). However, the causal role of BAs in eliciting beneficial metabolic changes post-surgery remains unclear. Thus far, research efforts have focused on overall changes in the total BA pool or in levels of BAs conjugated to amino acids (Patti, M.-E. et al. Obesity (Silver Spring) 2009, 17, 1671-1677). Individual BAs, however, have different binding affinities for nuclear hormone receptors (NhRs) and GPCRs, and thus unique abilities to modulate glucose homeostasis, lipid accumulation, and energy expenditure (Patti, M.-E. et al. Obesity (Silver Spring) 2009, 17, 1671-1677; Sayin, S. I. et al. Cell Metab., 2013, 17, 225-235).

Diabetes mellitus is a disease that is characterized by a lack of insulin production (e.g., type 1 diabetes) by the pancreas or a lack of insulin sensitivity (e.g., type II diabetes). Patients with diabetes mellitus are diagnosed by a glucose tolerance test. The plasma glucose levels are elevated in patients diagnosed with diabetes compared with healthy patients. Diabetes can result in a number of long term complications including diabetic ketoacidosis, hyperosmolar hyperglycemic state, or death. Serious long-term complications include cardiovascular disease, stroke, chronic kidney disease, foot ulcers, and damage to the eyes. Current treatments, such as insulin injections, manage the symptoms but do not prevent the long term complications of the disease and require constant monitoring of blood glucose levels. New treatments for diabetes are needed to improve the quality of life and prevent future complications of the disease.

Obesity and type 2 diabetes (T2D or type-II diabetes) are medical pandemics. Bariatric surgery, in the form of Roux-en-Y gastric bypass or sleeve gastrectomy (SG), is currently the most effective and durable treatment for obesity and related comorbidities[1,2]. Owing to robust post-surgical metabolic benefits and favorable side-effect profile, SG is the most common bariatric surgery performed in the US[3]. While maximal weight loss occurs at 1 year, many patients see resolution of their T2D within days of surgery[4]. For a majority of patients, remission is durable, lasting for at least 7 years[1,4]. The molecular mechanisms underlying T2D remission, however, remain largely unknown[5].

Two consistently observed post-surgical changes are increased levels of GLP-1, a circulating incretin hormone, and changes in the systemic repertoire of bile acids (BAs). BAs are cholesterol-derived metabolites that play crucial roles in host metabolism by acting as detergents that aid in the absorption of lipids and vitamins and as ligands for host receptors[6]. The therapeutic benefits of GLP-1 and the causal role of bile acids in mediating beneficial metabolic changes post-surgery are provided herein.

The compounds, compositions, and methods provided herein are related, in part, to the discovery that cholic acid 7-sulfate is increased in subjects following bariatric surgery and ameliorates the symptoms of diabetes. Also provided herein is evidence that cholic acid 7-sulfate is a TGR5 agonist and induces GLP-1 secretion in vitro.

SUMMARY OF THE INVENTION

The compositions and methods provided herein are related, in part, to the discovery of cholic acid 7-sulfate as a treatment for diabetes, obesity, or an inflammatory disease, for example, see: PCT Application, Application No.: PCT/US2019/047856, the entire contents of which are incorporated herein by reference.

In one aspect, provided herein is a method for treating diabetes, obesity, or an inflammatory disease in a subject, the method comprising administering to a subject in need thereof a compound of Formula (I):

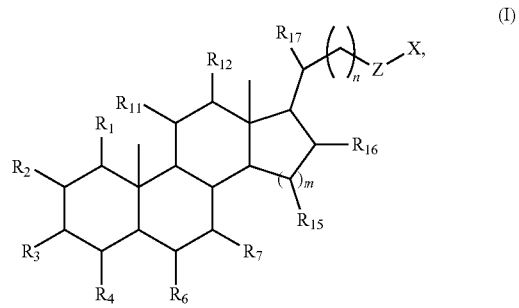

wherein:
n is 1, 2, 3, 4, 5, 6, 7, 8, 9, or 10;
m is 1, 2, 3, or 4;
Z is —C(O)—, —C(O)O—, —C(O)NR$_{18}$—, or —CH$_2$—;

X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, —$NHC(O)NHNH_2$, or a polar amino acid (e.g., taurine);

each $R_1$, $R_2$, $R_3$, $R_4$, $R_{11}$, $R_{12}$, $R_{15}$, $R_{16}$ and $R_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, each $R_3$, $R_6$, $R_7$ and $R_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, —CN, —CHO, —$CO_2H$, —$CO_2R_{18}$, —$NO_2$, —$ONO_2$, —$SO_2Cl$, —$SO_3^-$; —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, provided that at least one of $R_3$, $R_6$, $R_7$ and $R_{12}$ is a polar group;

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

or a pharmaceutically acceptable salt thereof.

In another aspect, provided herein is a method for treating metabolic disorders (e.g., diabetes, obesity) or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, gastroesophageal reflux disease (GERD), psoriatic arthritis, psoriasis, and rheumatoid arthritis) in a subject, the method comprising administering to a subject in need thereof a compound of Formula (I) as defined herein.

In another aspect, provided herein is a compound of Formula (I):

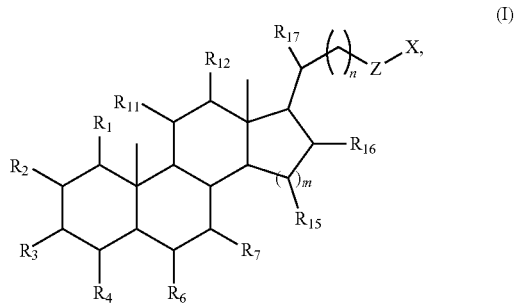

(I)

wherein:
n is 1, 2, 3, 4, 5, 6, 7, 8, 9 or 10;
m is 1, 2, 3 or 4;
Z is —C(O)—, —C(O)O—, —$C(O)NR_{18}$— or —$CH_2$—;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, —$NHC(O)NHNH_2$, or a polar amino acid (e.g., taurine);

each $R_1$, $R_2$, $R_3$, $R_4$, $R_{11}$, $R_{12}$, $R_{15}$, $R_{16}$ and $R_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

each $R_3$, $R_6$, $R_7$ and $R_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, provided that at least one of $R_3$, $R_6$, $R_7$ and $R_{12}$ is a polar group;

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

or a pharmaceutically acceptable salt thereof.

In another aspect, provided herein is a pharmaceutical composition comprising a compound of Formula (I) and a pharmaceutically acceptable carrier or excipient, wherein the compound of Formula (I) has the structure:

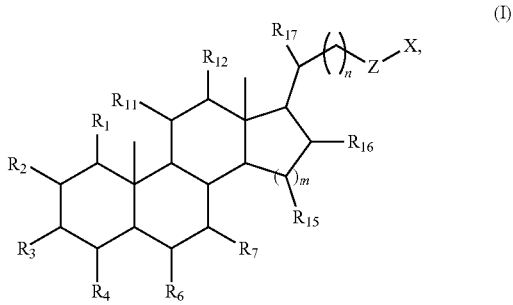

wherein:
n is 1, 2, 3, 4, 5, 6, 7, 8, 9 or 10;
m is 1, 2, 3 or 4;
Z is —C(O)—, —C(O)O—, —C(O)NR$_{18}$— or —CH$_2$—;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, —NHC(O)NHNH$_2$, or a polar amino acid (e.g., taurine);
each R$_1$, R$_2$, R$_3$, R$_4$, R$_{11}$, R$_{12}$, R$_{15}$, R$_{16}$ and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;
each R$_3$, R$_6$, R$_7$ and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$, provided that at least one of R$_3$, R$_6$, R$_7$ and R$_{12}$ is a polar group;
each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;
or a pharmaceutically acceptable salt thereof.

In another aspect, provided herein is a method for treating a metabolic disorder (e.g., diabetes, obesity), or an inflammatory disease, the method comprising: administering to a subject in need thereof a compound of Formulae (I)-(XVII).

In another aspect, provided are compounds of Formulae (I)-XVII), or pharmaceutically acceptable salts thereof, or pharmaceutical compositions comprising a compound of Formulae (I)-(XVII), for use in treating a metabolic disorder (e.g., diabetes, obesity), or an inflammatory disease in a subject in need thereof.

In another aspect, provided are kits comprising a compound of Formulae (I)-(XVII), or a pharmaceutically acceptable salt thereof, or a pharmaceutical composition comprising a compound of Formulae (I)-(XVII). In certain embodiments, the kit further comprises instructions for administration (e.g., human administration) and/or use.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

FIG. 1A shows the glucose levels from sham and SG mice before surgery. FIG. 1B shows sham and SG mice glucose levels following bariatric surgery. High fat diet (HFD) mice post-sleeve show improved glucose tolerance and insulin sensitivity.

FIG. 2A shows that mice 6 weeks post-sleeve have higher levels of cholic acid 7-sulfate in their cecum compared to sham-operated mice. FIG. 2B shows that sleeve mice livers also showed increased cholic acid 7-sulfate, and reduced levels of CDCA, and TCDCA.

FIG. 3A shows that sleeve mice show an increase in GLP-1 in systemic circulation. FIG. 3B shows that cholic acid 7-sulfate induces GLP-1 secretion in vitro better than the known GLP-1 inducer TDCA, while cholic acid had no effect. FIG. 3C shows that cholic acid 7-sulfate extracted from cecum of mice also has activity in inducing GLP-1 secretion in vitro. FIG. 3D shows that cholic acid 7-sulfate activates TGR5 in L-cells. The dose response curve shows an EC$_{50}$ of 0.013 micromolar (µM).

FIG. 4A shows that cholic acid 7-sulfate is stable in a wide range of pHs. FIG. 4B shows that cholic acid 7-sulfate is not toxic to intestinal Caco cells in vitro. FIG. 4C-D shows that treatment of HFD-fed mice with cholic acid 7-sulfate in vivo reduced blood glucose levels and induced GLP-1 levels within 15 minute of treatment.

FIG. 4E shows that dosing with 1 mg cholic acid 7-sulfate resulted in ~2500 µM cholic acid 7-sulfate in the cecum, similar to the amounts were observed in sleeve-operated mice. FIG. 4F-G shows that ectopic introduction of cholic acid 7-sulfate allowed only minor amounts to leak into systemic circulation and into the portal vein. This did not significantly affect other bile acids in the cecum, blood, or the portal vein. FIG. 4H shows that feces from human patients pre- and post-sleeve gastrectomy also have an increase in cholic acid 7-sulfate.

FIG. 5A shows that livers from mice exhibit an increase in SULT2A enzyme isoform 1, previously shown to sulfate bile acids. FIG. 5B shows that the portal vein has a different repertoire of bile acids compared to circulating blood. FIG. 5C shows that the bile acid pool in the portal vein of sleeve-operated mice significantly induced SULT2A1 compared to the portal vein bile acid pool in sham-operated mice. FIG. 5D-E show that there was no difference in induction of SULT2A1 between the pools of bile acids mimicking those observed in the antibiotic-treated sleeve- and sham-operated mouse portal veins. FIG. 5D also shows that LCA, TDCA, CA, and CDCA were absent in the antibiotic-treated mouse portal veins. FIG. 5F shows that LCA induced SULT2A1 in HepG2, while others did not in all concentrations tested. FIG. 5G shows the relative expression of SULT2A of siRNA treated groups. FIG. 5H shows the relative expression of PXR in the liver of Sham and SG mice.

FIG. 8A shows that knockdown of TGR5 abolished GLP-1 secretion. FIG. 8B shows that cholic acid 7-sulfate increases calcium levels in L-cells in vitro. FIG. 8C shows that cholic acid 7-sulfate induces TGR5 activation in HEK293T cells.

FIG. 16A-I shows cholic acid 7-sulfate (CA7S), a bile acid metabolite increased in mice and humans following sleeve gastrectomy and that cholic acid 7-sulfate is a TGR5 agonist that induces GLP-1 secretion in vivo. FIG. 16A shows intraperitoneal glucose tolerance test (IPGTT; AUC [95% CI], sham 51422 [46838-56006] vs SG 37251 [33735-40768]). FIG. 16B shows insulin tolerance test (ITT) performed on mice 5-weeks and 4-weeks post-surgery, respectively (SG, n=7; sham, n=6; t test, *p<0.05, p<0.01). FIG. 16C shows GLP-1 levels were increased in mice post-SG compared to post-sham (n=1 per group, p<0.01, Welch's t test). FIG. 16D shows the structure of CA7S. FIG. 16E shows CA7S was increased in cecal contents of SG mice (sham, n=12, SG, n=15, *p<0.05, Welch's t test). FIG. 16F shows CA7S was increased in livers of SG mice (n=12 per group, *p<0.05, Welch's t test). FIG. 16G shows CA7S in human feces was increased post-SG compared to pre-surgery (n=17 patients, *p<0.05, paired t test). FIG. 16H shows dose response curves for human TGR5 activation in HEK293T cells overexpressing human TGR5 for CA7S, TDCA, CA (≥3 biological replicates per condition). FIG. 16I shows CA7S induced secretion of GLP-1 in NCI-H716 cells compared to both CA and the known TGR5 agonist, TDCA. SiRNA-mediated knockdown of TGR5 abolished GLP-1 secretion (≥3 biological replicates per condition, one-way ANOVA followed by multiple comparisons test, *p<0.05, **p<0.01). All data are presented as mean±SEM.

FIG. 17A shows a schematic of the acute treatment experiment wherein anesthetized DIO mice were treated with PBS or CA7S via duodenal and rectal catheters. FIG. 17B shows the concentration of CA7S in mouse cecum 15 minutes after treatment with PBS or CA7S (PBS, n=7; CA7S, n=8 mice per group, **p<0.01, Welch's t test). FIG. 17C-D shows CA7S-treated mice displayed increased GLP-1 (c, *p<0.05, Welch's t test) and reduced blood glucose levels (d, **p<0.01, Welch's t test) compared to PBS-treated mice. FIG. 17E shows the percentage cell viability upon treatment of Caco-2 cells with CA7S in vitro (3 biological replicates per condition, one-way ANOVA followed by multiple comparisons test; not significant). All data are presented as mean±SEM.

FIG. 18A shows structure of CA7S and the 1H NMR of authentic sample of cholic acid 7-sulfate (Cayman Chemical). FIG. 18B shows the 1H NMR of CA7S purified from the cecal contents of SG mice using UPLC-MS.

FIG. 19A shows commercially available cholic acid 7-sulfate (Cayman Chemical) and FIG. 19B shows CA7S purified from the cecal contents of SG mice have the same mass (487.2 m/z) and elute at 9.2 minutes.

FIG. 20A-E shows CA7S activates TGR5 and induces GLP-1 secretion. FIG. 20A shows CA7S induced secretion of GLP-1 in NCI-H716 cells compared to both CA and the known TGR5 agonist, TDCA. SiRNA-mediated knockdown of TGR5 abolished GLP-1 secretion (3 biological replicates per condition, one-way ANOVA followed by multiple comparisons test *p<0.05, p<0.01, *p<0.001). FIG. 20B shows quantitative real time PCR analysis of expression of human TGR5 in TGR5 siRNA and negative (−) siRNA-treated NCI-H716 cells for FIG. 16I and FIG. 19A. FIG. 20C shows CA7S (500 μM) purified from SG mouse cecal contents induced secretion of GLP-1 in NCI-H716 cells compared to DMSO control (**p<0.01, Welch's t test). FIG. 20D shows CA7S induced an increase in intracellular calcium levels in NCI-H716 cells (3 biological replicates per condition *p<0.05, **p<0.01, t test). FIG. 20E shows UPLC-MS traces of CA7S after incubation at 37° C. in buffer at the indicated physiological pHs.

DEFINITIONS

Chemical Definitions

Figure 1A:
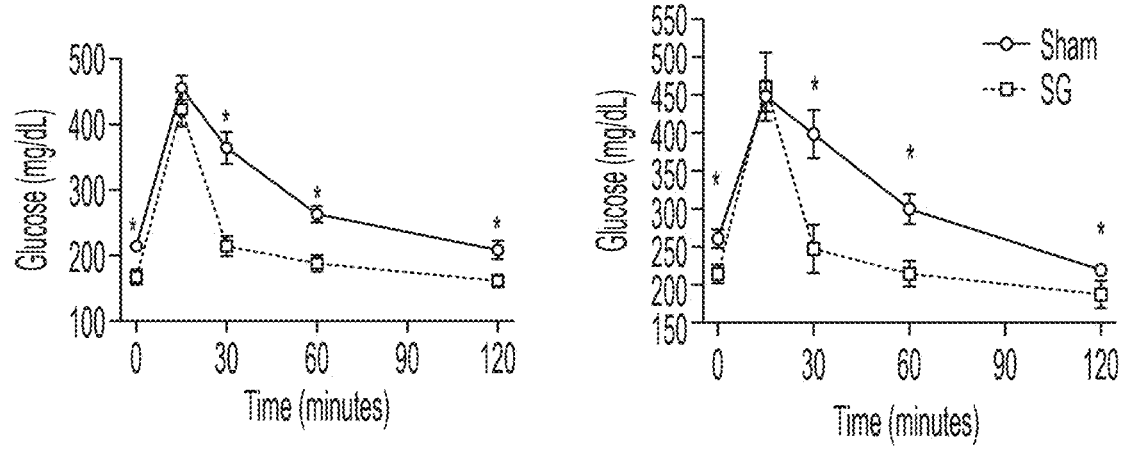
FIG. 1A-B shows that mice are a suitable model for bariatric surgery-induced amelioration of diabetic phenotypes.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in *The Merck Manual of Diagnosis and Therapy*, 19th Edition, published by Merck Sharp & Dohme Corp., 2011 (ISBN 978-O-911910-19-3); Robert S. Porter et al. (eds.), *The Encyclopedia of Molecular Cell Biology and Molecular Medicine*, published by Blackwell Science Ltd., 1999-2012 (ISBN 9783527600908); and Robert A. Meyers (ed.), *Molecular Biology and Biotechnology: a Comprehensive Desk Reference*, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); *Lewin's Genes XI*, published by Jones & Bartlett Publishers, 2014 (ISBN-1449659055); Michael Richard Green and Joseph Sambrook, *Molecular Cloning: A Laboratory Manual*, 4th ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); *Current Protocols in Molecular Biology* (CPMB), Frederick M. Ausubel (ed.), John Wiley and Sons, 2014 (ISBN 047150338X, 9780471503385), *Current Protocols in Protein Science* (CPPS), John E. Coligan (ed.), John Wiley and Sons, Inc., 2005; and *Current Protocols in Immunology* (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry*, $7^{th}$ Edition, John Wiley & Sons, Inc., New York, 2013; Richard C. Larock, *Comprehensive Organic Transformations*, John Wiley & Sons, Inc., New York, 2018; and Carruthers, Some Modern Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, *Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). An alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3(1,4-pentadienyl), ethynyl, 1- and 3propynyl, ibutynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present disclosure. An alkylene is au uncyclized chain. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. A heteroalkyl is an uncyclized chain. The heteroatom(s) O, N, P, S, B, As, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

The term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. A heteroalkylene is an uncyclized chain. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. A cycloalkyl or heteroalkyl is not aromatic. Examples of cycloalkyl include, but are not limited to, cyclopropyl, cyclobutyl, cyclopentyl, cyclohexyl, 1-cyclohexenyl, icyclohexenyl, cycloheptyl, and the like. Examples of heterocycloalkyl include, but are not limited to, 1-(1,2,5,6-tetrahydropyridyl), 1-piperidinyl, 2-piperidinyl, ipiperidinyl, 4-morpholinyl, imorpholinyl, tetrahydrofuran-2-yl, tetrahydrofuran-3yl, tetrahydrothien-2-yl, tetrahydrothien-3yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, ibromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3pyrrolyl, 3pyrazolyl, 2-imidazolyl, 4-imidazolyl, pyrazinyl, 2-oxazolyl, 4-oxazolyl, 2-phenyl-4-oxazolyl, 5-oxazolyl, 3isoxazolyl, 4-isoxazolyl, 5-isoxazolyl, 2-thiazolyl, 4-thiazolyl, 5-thiazolyl, 2-furyl, $_3$furyl, 2-thienyl, thienyl, 2-pyridyl, 3pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A "fused ring aryl-heterocycloalkyl" is an aryl fused to a heterocycloalkyl. A "fused ring heteroaryl-heterocycloalkyl" is a heteroaryl fused to a heterocycloalkyl. A "fused ring heterocycloalkyl-cycloalkyl" is a heterocycloalkyl fused to a cycloalkyl. A "fused ring heterocycloalkyl-heterocycloalkyl" is a heterocycloalkyl fused to another heterocycloalkyl.

Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be unsubstituted or substituted with one or more of the substitutents described herein. Fused ring aryl-heterocycloalkyl, fused ring heteroaryl-heterocycloalkyl, fused ring heterocycloalkyl-cycloalkyl, or fused ring heterocycloalkyl-heterocycloalkyl may each independently be named according to the size of each of the fused rings. Thus, for example, 6,5 aryl-heterocycloalkyl fused ring describes a 6 membered aryl moiety fused to a 5 membered heterocycloalkyl. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Figure 27:
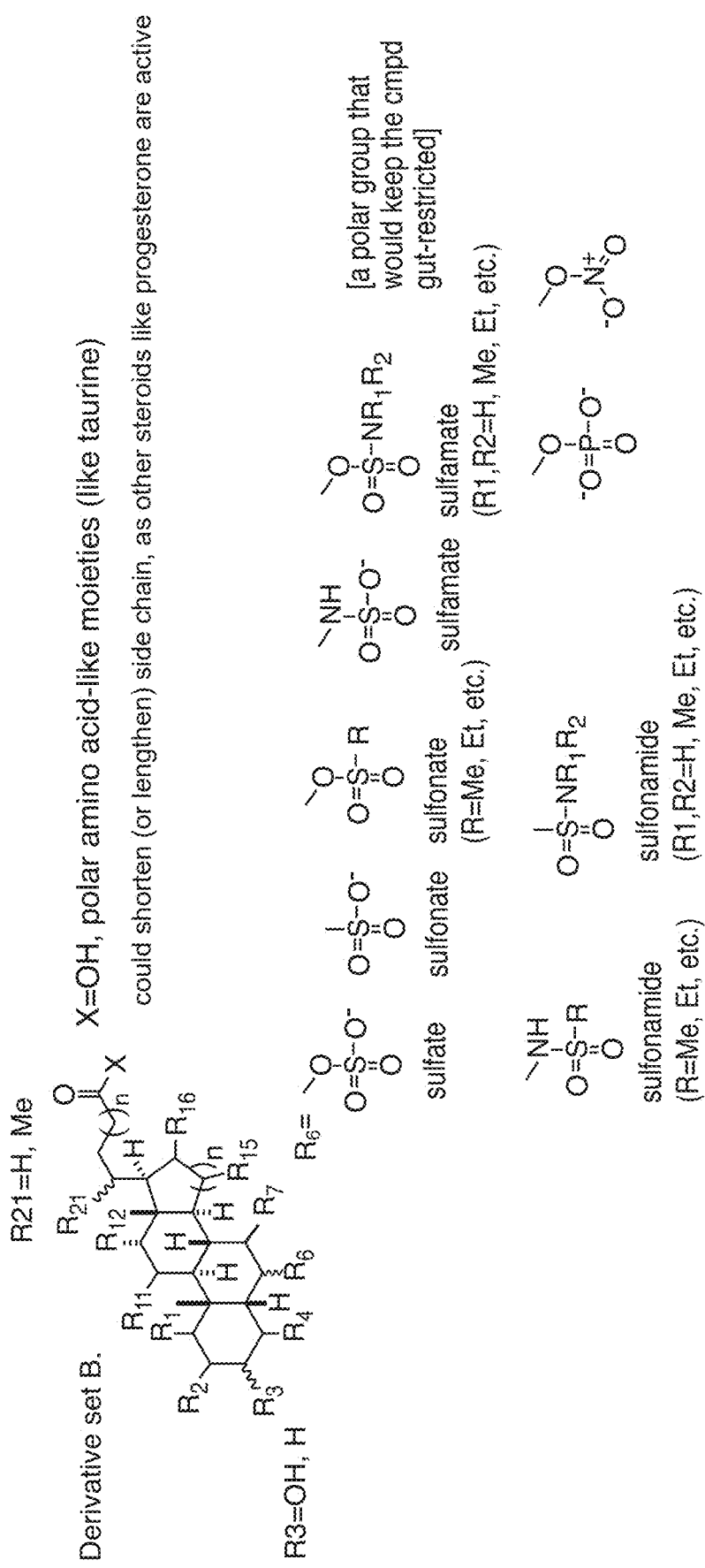
FIG. 27 shows several moieties that can be added to the $R_6$ position of cholic acid 7-sulfate and include modifications (e.g. polar groups) that can restrict the compound to the gut.

The term "polar group" refers to chemical moieties that increase the polarity of the compound. FIG. 27 shows several polar groups that can be added to the $R_7$ position of a cholic acid derivative. Polar groups include but are not limited to $OR_{18}$, $N(R_{18})_2$, $SR_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$, wherein each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$. In certain embodiments, a polar group is —NR$_{18}$SO$_3^-$. In certain embodiments, a polar group is CH$_2$SO$_3^-$. In certain embodiments, a polar group is —SO$_3$. In certain embodiments, a polar group is —SO$_2$N(R$_{18}$)$_2$. In certain embodiments, a polar group is —OSO$_2$N(R$_{18}$)$_2$.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R'", —ONR'R", —NR'C═(O)NR"NR'"R"", —CN, —NO$_2$, —NR'SO$_2$R", —NR'C═(O)R", —NR'C(O)—OR", —NR'OR", in a number ranging from zero to (2m'+1), where m' is the total number of carbon atoms in such radical. R', R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the disclosure includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —NR'NR"R'", —ONR'R", —NR'C═

(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T—C(O)—(CRR')$_q$—U—, wherein T and U are independently —NR—, —O—, —CRR'—, or a single bond, and q is an integer of from 0 to 3.

Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R', R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=

(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, and unsubstituted heteroaryl.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

The term "silyl ether" as used herein, refers to a chemical compound containing a silicon atom covalently bonded to an alkoxy group generally having the structure $R^wR^xR^ySi$—O—$R^z$, wherein $R^w$, $R^x$, $R^y$, and $R^z$ are independently alkyl or aryl groups.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts. In certain embodiments, the pharmaceutically acceptable sat is an ammonium salt. In certain embodiments, the pharmaceutically acceptable salt is a sodium salt.

As used herein, the term "salt" refers to acid or base salts of the compounds used in the methods of the present invention. Illustrative examples of salts include mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. The term salt also refers to formation of a salt between two compounds.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) Am J Clin Nutr 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g. with age, gender, ethnicity, fitness, and body type, amongst other factors. In some embodiments, a subject with obesity can be a subject with a body mass index of at least about 25 kg/m² prior to administration of a treatment as described herein. In some embodiments, a subject with obesity can be a subject with a body mass index of at least about 30 kg/m² prior to administration of a treatment, compound, or agent as described herein.

As used herein, the term "inflammation" or "inflamed" or "inflammatory" refers to activation or recruitment of the immune system or immune cells (e.g. T cells, B cells, macrophages). A tissue that has inflammation can become reddened, white, swollen, hot, painful, exhibit a loss of function, or have a film or mucus. Methods of identifying inflammation are well known in the art. Inflammation generally occurs following injury or infection by a microorganism.

As used herein the term "an inflammatory disease" refers to any disease that affects the immune system. The inflammatory disease can cause at least one symptom of the disease. These symptoms can include but are not limited to, diarrhea, vomiting, nausea, upset stomach, pain, swollen joints, malaise, fever, weight loss, weight gain, bleeding, any change in the consistency or frequency of a bowel movement or stool, or any other symptom associated with an inflammatory disease in a subject. In some embodiments, the inflammatory disease is an autoimmune disease.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with diabetes, e.g., type II diabetes. The term "treating" includes reducing or alleviating at least one adverse effect or symptom of diabetes. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "small molecule" refers to an organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" *J. Am. Chem. Soc.* 120:8565, 1998; incorporated herein by reference). In certain other preferred embodiments, natural-product-like small molecules are utilized.

As used herein, a "compound" refers to any chemical, test chemical, drug, new chemical entity (NCE) or other moiety. For example, a compound can be any foreign chemical not normally present in a subject such as mammals including humans. A compound can also be an endogenous chemical that is normally present and synthesized in biological systems, such as mammals including humans. For example, a compound, such as a test compound, such as a drug, can induce the secretion of GLP-1 in a subject by activation of TGR5 as provided herein.

The term "derivative" as used herein means any chemical, conservative substitution, or structural modification of an agent. The derivative can improve characteristics of the agent or small molecule such as pharmacodynamics, pharmacokinetics, absorption, distribution, delivery, targeting to a specific receptor, or efficacy. For example, for a small molecule, the derivative can consist essentially of at least one chemical modification to about ten modifications. The derivative can also be the corresponding salt of the agent. The derivative can be the pro-drug of the small molecule as provided herein.

In another embodiment, the agent is a derivative of cholic acid 7-sulfate as provided herein. In another embodiment, the agent is a bile acid or derivative thereof.

As used herein, the term "bile acid" refers to a steroid acid that aids digestion as emulsifiers of fat, and may also play a role in various systemic endocrine hormone-like functions. Bile acids in mammals are synthesized from cholesterol in the liver as primary bile acids and are metabolized by particular mammalian gut microbes to secondary bile acids.

Bile acids in mammals regulate metabolic pathways by activation of Farnesoid X receptor as well as the G-protein-coupled receptor (GPCRs) such as TGR5. Non-limiting examples of bile acids include cholic acid, glycocholic acid, taurocholic acid, deoxycholic acid, chenodeoxycholic acid, glycochenodeoxycholic acid, taurochenodeoxycholic acid (TCDA), lithocholic acid (LCA), ursodeoxycholic acid (UDCA), muricholic acids, obeticholic acid, and any other bile acid known in the art. The term "bile acid" can further refer to salt forms of bile acids, sulfated bile acids, and other metabolites.

As used herein, the term "cholic acid 7-sulfate," or "CA7S" or "7-sulfocholic acid" refers to the sulfated form of cholic acid. The structure of cholic acid 7-sulfate is as follows:

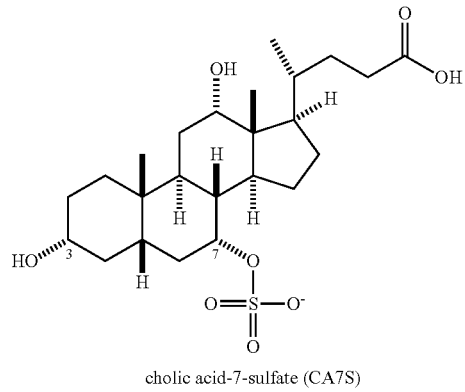

cholic acid-7-sulfate (CA7S)

As used herein, the term "TGR5" or "G protein-coupled bile acid receptor 1" or GPBAR1" or "G-protein coupled receptor 19" or "GPCR19" or "membrane-type receptor for bile acids" or "M-BAR" refers to a receptor for bile acids encoded by the GPBAR1 gene (NCBI Gene ID: 2842). Sequences for TGR5 are known in the art, e.g., the human mRNA transcript (e.g. NM_006143.2, SEQ ID NO: 1), and polypeptide sequence (e.g. NP_006134.1, SEQ ID NO: 2).

As used herein, the term "glucagon-like peptide-1" or "GLP-1" refers to a peptide hormone that is 30 amino acids long that is derived from the pro-glucagon peptide. GLP-1 is produced primarily by enteroendocrine cells in the gut (e.g. L-cells). However, other cell types such as neurons can produce GLP-1. GLP-1 has the ability to decrease blood glucose levels in a glucose-dependent manner by enhancing insulin secretion from the pancreas.

GLP-1 has also been shown in enhance the insulin gene transcription, replenish insulin stores in the pancreas, and promote pancreatic beta cell growth. GLP-1 further inhibits gastric emptying, acid secretion, motility, and decreases appetite. The polypeptide sequence of GLP-1 can be found in SEQ ID NO: 3.

As used herein, the terms "TGR 5 activity" or "activity of TGR5" refers to the cellular functions of the TGR5 receptor, for example, activation of TGR5 results in the secretion of GLP-1 from a cell (e.g. L-cells in the gut). As provided herein, an increase in TGR5 levels and activity results in an increase in GLP-1. TGR5 activity can further refer to the sensing of bile acids, metabolites, and regulation of glucose homeostasis. The activation of TGR 5 or an increase in TGR5 activity as provided herein can also refer to an increase in the production of intracellular cAMP, activation of MAP kinase signaling pathways, internalization of the receptor, suppression of macrophage function or immune functions, and regulation of bile acid synthesis, degradation, or function. While the activation of TGR5 in macrophages decreases pro-inflammatory cytokine production, the stimulation of TGR5 by bile acids in adipocytes and myocytes enhances energy expenditure.

As used herein, an "appropriate control" refers to an untreated, otherwise identical cell or population (e.g., a subject who was not administered an agent provided herein, or was administered by only a subset of agents provided herein, as compared to a non-control cell).

As used herein, the term "pharmaceutical composition" can include any material or substance that, when combined with an active ingredient (e.g. a compound of Formulae (I)-(XVII) or a cholic acid derivative derivative), allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

As used herein, the term "restricts delivery of the composition to the gastrointestinal tract" refers to a formulation that permits or facilitates the delivery of the agent or pharmaceutical composition described herein to the colon, large intestine, or small intestine in viable form. Enteric coating or micro- or nano-particle formulations can facilitate such delivery as can, for example, buffer or other protective formulations.

The term "effective amount" is used interchangeably with the term "therapeutically effective amount" or "amount sufficient" and refers to the amount of at least one agonist of TGR5, e.g., a compound of formulae (I)-(XVII), at dosages and for periods of time necessary to achieve the desired therapeutic result, for example, to "attenuate", reduce or stop at least one symptom of diabetes. For example, an effective amount using the methods as disclosed herein would be considered as the amount sufficient to reduce one or more symptoms of diabetes, obesity, or an inflammatory disease by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from diabetes, prediabetes, hyperglycemia, obesity, or an inflammatory disease. Accordingly, the term "effective amount" or "therapeutically effective amount" as used herein refers to the amount of therapeutic agent (e.g. cholic acid 7-sulfate) of a pharmaceutical composition to alleviate at least one symptom of a disease. Stated another way, "therapeutically effective amount" of an agonist of TGR5 as disclosed herein is the amount of an agonist which exerts a beneficial effect on, for example, the symptoms of the disease (e.g. diabetes). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of a diabetes, obesity, or an inflammatory disease or at one related symptom thereof.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another embodiment, more than one unit dosage form can be administered simultaneously.

The terms "administered" and "subjected" are used interchangeably in the context of treatment of a disease or disorder.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. Without limitations, oral administration can be in the form of solutions, suspensions, tablets, pills, capsules, sustained-release formulations, oral rinses, powders and the like. As used herein, the term "modulates" refers to an effect including increasing or decreasing a given parameter as those terms are defined herein.

As used herein, the term "contacting" when used in reference to a cell or organ, encompasses both introducing or administering an agent, surface, hormone, etc. to the cell, tissue, or organ in a manner that permits physical contact of the cell with the agent, surface, hormone etc., and introducing an element, such as a genetic construct or vector, that permits the expression of an agent, such as a miRNA, polypeptide, or other expression product in the cell. It should be understood that a cell genetically modified to express an agent, is "contacted" with the agent, as are the cell's progeny that express the agent.

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

DETAILED DESCRIPTION OF CERTAIN EMBODIMENTS OF THE INVENTION

Generally, diabetes is characterized and diagnosed by high blood glucose levels in a subject's serum (e.g. hyperglycemia). The diagnosis can be carried out by a physician with a glucose challenge test and/or a glucose tolerance test. For an oral glucose tolerance test in humans, a blood sugar level less than about 140 mg/dL (7.8 mmol/L) is normal. A reading of more than about 200 mg/dL (11.1 mmol/L) after two hours indicates that the subject has diabetes. A reading between about 140 and about 199 mg/dL (7.8 mmol/L and 11.0 mmol/L) can indicate prediabetes.

Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), inflammatory diseases, chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation.

Compounds

In one aspect, provided herein is a compound of Formula (I):

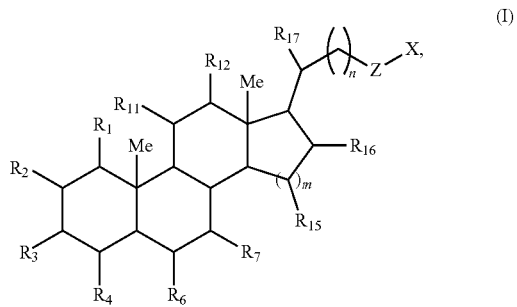

wherein:

n is 1, 2, 3, 4, 5, 6, 7, 8, 9 or 10;

m is 1, 2, 3 or 4;

Z is —C(O)—, —C(O)O—, —C(O)NR$_{18}$— or —CH$_2$—;

X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$—OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, —NHC(O)NHNH$_2$, or a polar amino acid (e.g., taurine);

each R$_1$, R$_2$, R$_3$, R$_4$, R$_{11}$, R$_{12}$, R$_{15}$, R$_{16}$ and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

each R$_3$, R$_6$, R$_7$ and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$, provided that at least one of R$_3$, R$_6$, R$_7$ and R$_{12}$ is a polar group;

each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

or a pharmaceutically acceptable salt thereof.

In certain embodiments, a compound of Formula (I) is of the Formula (I'):

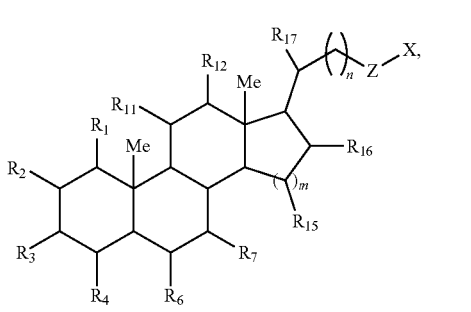

(I')

wherein:

n is 1, 2, 3, 4, 5, 6, 7, 8, 9 or 10;

m is 1, 2, 3 or 4;

Z is —C(O)—, —C(O)O—, —C(O)NR$_{18}$— or —CH$_2$—;

X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3$H, —OSO$_3$H, —NR$_{18}$SO$_3$H, —PO$_3$H$_2$, —OPO$_3$H$_2$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, —NHC(O)NHNH$_2$, or a polar amino acid (e.g., taurine);

each R$_1$, R$_2$, R$_3$, R$_4$, R$_{11}$, R$_{12}$, R$_{15}$, R$_{16}$ and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3$H, —OSO$_3$H, —NR$_{18}$SO$_3$H, —PO$_3$H$_2$, —OPO$_3$H$_2$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

each R$_3$, R$_6$, R$_7$ and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3$H, —OSO$_3$H, —NR$_{18}$SO$_3$H, —PO$_3$H$_2$, —OPO$_3$H$_2$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$, provided that at least one of R$_3$, R$_6$, R$_7$ and R$_{12}$ is a polar group;

each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3$H, —OSO$_3$H, —NR$_{18}$SO$_3$H, —PO$_3$H$_2$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

or a pharmaceutically acceptable salt thereof.

In certain embodiments, the compound of Formula (I) is of the formula:

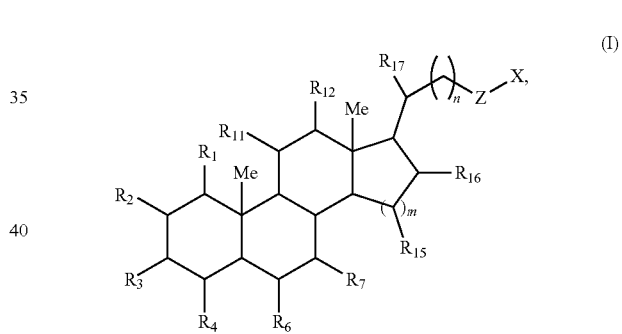

(I)

wherein:

n is 1, 2, 3, 4, 5, 6, 7, 8, 9 or 10;

m is 1, 2, 3 or 4;

Z is —C(O)—, —C(O)O—, —C(O)NR$_{18}$— or —CH$_2$—;

X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, —NHC(O)NHNH$_2$, or a polar amino acid;

each R$_1$, R$_2$, R$_3$, R$_4$, R$_{11}$, R$_{12}$, R$_{15}$, R$_{16}$ and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

each R$_3$, R$_6$, R$_7$ and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$, provided that at least one of R$_3$, R$_6$, R$_7$ and R$_{12}$ is a polar group;

each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$;

or a pharmaceutically acceptable salt thereof, provided that the compound is not a naturally occurring bile acid, and provided that the compound is not

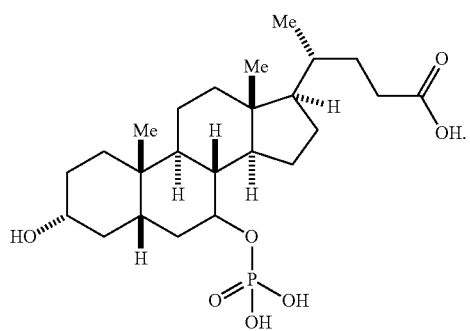

In certain embodiments, Z is —C(O)—, —C(O)O—, —C(O)NR$_{18}$— or —CH$_2$—. In certain embodiments, Z is —C(O)—. In certain embodiments, Z is —C(O)O—. In certain embodiments, Z is —C(O)NR$_{18}$—. In certain embodiments, Z is —CH$_2$—.

In certain embodiments, X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, —NHC(O)NHNH$_2$, or a polar amino acid (e.g., taurine). In certain embodiments, X is H. In certain embodiments, X is substituted or unsubstituted alkyl. In certain embodiments, X is substituted or unsubstituted heteroalkyl. In certain embodiments, X is substituted or unsubstituted cycloalkyl. In certain embodiments, X is substituted or unsubstituted heterocycloalkyl. In certain embodiments, X is substituted or unsubstituted aryl. In certain embodiments, X is substituted or unsubstituted heteroaryl. In certain embodiments, X is OR$_{18}$. In certain embodiments, X is N(R$_{18}$)$_2$. In certain embodiments, X is SR$_{18}$. In certain embodiments, X is halogen. In certain embodiments, X is CN. In certain embodiments, X is —CHO. In certain embodiments, X is —CO$_2$H. In certain embodiments, X is —CO$_2$R$_{18}$. In certain embodiments, X is —NO$_2$. In certain embodiments, X is —ONO$_2$. In certain embodiments, X is —SO$_2$Cl. In certain embodiments, X is —SO$_3^-$. In certain embodiments, X is —OSO$_3^-$. In certain embodiments, X is —NR$_{18}$SO$_3^-$. In certain embodiments, X is —PO$_3^{2+}$. In certain embodiments, X is —OPO$_3^{2+}$. In certain embodiments, X is —OSO$_2$R$_{18}$. In certain embodiments, X is —SO$_2$N(R$_{18}$)$_2$. In certain embodiments, X is —OSO$_2$N(R$_{18}$)$_2$. In certain embodiments, X is —NR$_{18}$SO$_2$R$_{18}$. In certain embodiments, X is —SO$_2$N(R$_{18}$)$_2$. In certain embodiments, X is —NHNH$_2$. In certain embodiments, X is —ONH$_2$. In certain embodiments, X is —NHC(O)NHNH$_2$. In certain embodiments, X is a polar amino acid (e.g., taurine).

In certain embodiments, each R$_1$, R$_2$, R$_3$, R$_4$, R$_{11}$, R$_{12}$, R$_{15}$, R$_{16}$ and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, OR$_{18}$, N(R$_{18}$)$_2$, SR$_{18}$, halogen, CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —SO$_2$N(R$_{18}$)$_2$, —OSO$_2$N(R$_{18}$)$_2$, —NR$_{18}$SO$_2$R$_{18}$, —SO$_2$N(R$_{18}$)$_2$, —NHNH$_2$, —ONH$_2$, or —NHC(O)NHNH$_2$. In certain embodiments, each R$_1$, R$_2$, R$_3$, R$_4$, R$_{11}$, R$_{12}$, R$_{15}$, R$_{16}$ and R$_{17}$ is independently H. In certain embodiments, each R$_1$, R$_2$, R$_3$, R$_4$, R$_{11}$, R$_{12}$, R$_{15}$, R$_{16}$ and R$_{17}$ is independently substituted or unsubstituted alkyl. In certain embodiments, each R$_1$, R$_2$, R$_3$, R$_4$, R$_{11}$, R$_{12}$, R$_{15}$, R$_{16}$ and R$_{17}$ is independently methyl. In certain embodiments, each R$_1$, R$_2$, R$_3$, R$_4$, R$_{11}$, R$_{12}$, R$_{15}$, R$_{16}$ and R$_{17}$ is independently unsubstituted methyl. In certain embodiments, each R$_1$, R$_2$, R$_3$, R$_4$, R$_{11}$, R$_{12}$, R$_{15}$, R$_{16}$ and R$_{17}$ is independently substituted or unsubstituted heteroalkyl. In certain embodiments, each R$_1$, R$_2$, R$_3$, R$_4$, R$_{11}$, R$_{12}$, R$_{15}$, R$_{16}$ and R$_{17}$ is independently substituted or unsubstituted cycloalkyl. In certain embodiments, each R$_1$, R$_2$, R$_3$, R$_4$, R$_{11}$, R$_{12}$, R$_{15}$, R$_{16}$ and R$_{17}$ is independently substituted or unsubstituted heterocycloalkyl. In certain embodiments, each R$_1$, R$_2$, R$_3$, R$_4$, R$_{11}$, R$_{12}$, R$_{15}$, R$_{16}$ and R$_{17}$ is independently substituted or unsubstituted aryl. In certain embodiments, each R$_1$, R$_2$, R$_3$, R$_4$, Rn, R$_{12}$, R$_{15}$, R$_{16}$ and R$_{17}$ is independently substituted or unsubstituted heteroaryl. In certain embodiments, each R$_1$, R$_2$, R$_3$, R$_4$, R$_{11}$, R$_{12}$, R$_{15}$, R$_{16}$ and R$_{17}$ is independently OR$_{18}$. In certain embodiments, each R$_1$, R$_2$, R$_3$, R$_4$, R$_{11}$, R$_{12}$, R$_{15}$, R$_{16}$ and R$_{17}$ is independently N(R$_{18}$)$_2$. In certain embodiments, each R$_1$, R$_2$, R$_3$, R$_4$, R$_{11}$, R$_{12}$, R$_{15}$, R$_{16}$ and R$_{17}$ is independently SR$_{18}$. In certain embodiments, each R$_1$, R$_2$, R$_3$, R$_4$, R$_{11}$, R$_{12}$, R$_{15}$, R$_{16}$ and R$_{17}$ is independently halogen. In certain embodiments, each R$_1$, R$_2$, R$_3$, R$_4$, R$_{11}$, R$_{12}$, R$_{15}$, R$_{16}$ and R$_{17}$ is independently CN. In certain embodiments, each R$_1$, R$_2$, R$_3$, R$_4$, R$_{11}$, R$_{12}$, R$_{15}$, R$_{16}$ and R$_{17}$ is independently —CHO. In certain embodiments, each R$_1$, R$_2$, R$_3$, R$_4$, R$_{11}$, R$_{12}$, R$_{15}$, R$_{16}$ and R$_{17}$ is independently —CO$_2$H. In certain embodiments, each R$_1$, R$_2$, R$_3$, R$_4$, R$_{11}$, R$_{12}$, R$_{15}$, R$_{16}$ and R$_{17}$ is independently —CO$_2$R$_{18}$. In certain embodiments, each R$_1$, R$_2$, R$_3$, R$_4$, R$_{11}$, R$_{12}$, R$_{15}$, R$_{16}$ and R$_{17}$ is independently —NO$_2$. In certain embodiments, each R$_1$, R$_2$, R$_3$, R$_4$, $R_{11}$, $R_{12}$, $R_{15}$, $R_{16}$ and $R_{17}$ is independently —$ONO_2$. In certain embodiments, each $R_1$, $R_2$, $R_3$, $R_4$, $R_{11}$, $R_{12}$, $R_{15}$, $R_{16}$ and $R_{17}$ is independently —$SO_2Cl$. In certain embodiments, each $R_1$, $R_2$, $R_3$, $R_4$, $R_{11}$, $R_{12}$, $R_{15}$, $R_{16}$ and $R_{17}$ is independently —$SO_3^-$. In certain embodiments, each $R_1$, $R_2$, $R_3$, $R_4$, $R_{11}$, $R_{12}$, $R_{15}$, $R_{16}$ and $R_{17}$ is independently —$OSO_3$. In certain embodiments, each $R_1$, $R_2$, $R_3$, $R_4$, $R_{11}$, $R_{12}$, $R_{15}$, $R_{16}$ and $R_{17}$ is independently —$NR_{18}SO_3^+$. In certain embodiments, each $R_1$, $R_2$, $R_3$, $R_4$, $R_{11}$, $R_{12}$, $R_{15}$, $R_{16}$ and $R_{17}$ is independently —$PO_3^{2-}$. In certain embodiments, each $R_1$, $R_2$, $R_3$, $R_4$, $R_{11}$, $R_{12}$, $R_{15}$, $R_{16}$ and $R_{17}$ is independently —$OPO_3^{2-}$. In certain embodiments, each $R_1$, $R_2$, $R_3$, $R_4$, $R_{11}$, $R_{12}$, $R_{15}$, $R_{16}$ and $R_{17}$ is independently —$OSO_2R_{18}$. In certain embodiments, each $R_1$, $R_2$, $R_3$, $R_4$, $R_{11}$, $R_{12}$, $R_{15}$, $R_{16}$ and $R_{17}$ is independently —$SO_2N(R_{18})_2$. In certain embodiments, each $R_1$, $R_2$, $R_3$, $R_4$, $R_{11}$, $R_{12}$, $R_{15}$, $R_{16}$ and $R_{17}$ is independently —$OSO_2N(R_{18})_2$. In certain embodiments, each $R_1$, $R_2$, $R_3$, $R_4$, $R_{11}$, $R_{12}$, $R_{15}$, $R_{16}$ and $R_{17}$ is independently —$NR_{18}SO_2R_{18}$. In certain embodiments, each $R_1$, $R_2$, $R_3$, $R_4$, $R_{11}$, $R_{12}$, $R_{15}$, $R_{16}$ and $R_{17}$ is independently —$SO_2N(R_{18})_2$. In certain embodiments, each $R_1$, $R_2$, $R_3$, $R_4$, $R_{11}$, $R_{12}$, $R_{15}$, $R_{16}$ and $R_{17}$ is independently —$NHNH_2$. In certain embodiments, each $R_1$, $R_2$, $R_3$, $R_4$, $R_{11}$, $R_{12}$, $R_{15}$, $R_{16}$ and $R_{17}$ is independently —$ONH_2$. In certain embodiments, each $R_1$, $R_2$, $R_3$, $R_4$, $R_{11}$, $R_{12}$, $R_{15}$, $R_{16}$ and $R_{17}$ is independently —$NHC(O)NHNH_2$. In certain embodiments, each $R_3$, $R_6$, $R_7$ and $R_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, provided that at least one of $R_3$, $R_6$, $R_7$ and $R_{12}$ is a polar group. In certain embodiments, each $R_3$, $R_6$, $R_7$ and $R_{12}$ is independently H. In certain embodiments, each $R_3$, $R_6$, $R_7$ and $R_{12}$ is independently substituted or unsubstituted alkyl. In certain embodiments, each $R_3$, $R_6$, $R_7$ and $R_{12}$ is independently $C(R_{18})_2SO_3^+$. In certain embodiments, each $R_3$, $R_6$, $R_7$ and $R_{12}$ is independently $C(H)_2SO_3^+$. In certain embodiments, each $R_3$, $R_6$, $R_7$ and $R_{12}$ is independently substituted or unsubstituted heteroalkyl. In certain embodiments, each $R_3$, $R_6$, $R_7$ and $R_{12}$ is independently substituted or unsubstituted cycloalkyl. In certain embodiments, each $R_3$, $R_6$, $R_7$ and $R_{12}$ is independently substituted or unsubstituted heterocycloalkyl. In certain embodiments, each $R_3$, $R_6$, $R_7$ and $R_{12}$ is independently substituted or unsubstituted aryl. In certain embodiments, each $R_3$, $R_6$, $R_7$ and $R_{12}$ is independently substituted or unsubstituted heteroaryl. In certain embodiments, each $R_3$, $R_6$, $R_7$ and $R_{12}$ is independently —$OR_{18}$. In certain embodiments, each $R_3$, $R_6$, $R_7$ and $R_{12}$ is independently —$N(R_{18})_2$. In certain embodiments, each $R_3$, $R_6$, $R_7$ and $R_{12}$ is independently —$SR_{18}$. In certain embodiments, each $R_3$, $R_6$, $R_7$ and $R_{12}$ is independently halogen. In certain embodiments, each $R_3$, $R_6$, $R_7$ and $R_{12}$ is independently —CN. In certain embodiments, each $R_3$, $R_6$, $R_7$ and $R_{12}$ is independently —CHO. In certain embodiments, each $R_3$, $R_6$, $R_7$ and $R_{12}$ is independently —$CO_2H$. In certain embodiments, each $R_3$, $R_6$, $R_7$ and $R_{12}$ is independently —$CO_2R_{18}$. In certain embodiments, each $R_3$, $R_6$, $R_7$ and $R_{12}$ is independently —$NO_2$. In certain embodiments, each $R_3$, $R_6$, $R_7$ and $R_{12}$ is independently —$ONO_2$. In certain embodiments, each $R_3$, $R_6$, $R_7$ and $R_{12}$ is independently —$SO_2Cl$. In certain embodiments, each $R_3$, $R_6$, $R_7$ and $R_{12}$ is independently —$SO_3^-$. In certain embodiments, each $R_3$, $R_6$, $R_7$ and $R_{12}$ is independently —OSO. In certain embodiments, each $R_3$, $R_6$, $R_7$ and $R_{12}$ is independently —$NR_{18}SO_3^-$. In certain embodiments, each $R_3$, $R_6$, $R_7$ and $R_{12}$ is independently —$PO_3^{2-}$. In certain embodiments, each $R_3$, $R_6$, $R_7$ and $R_{12}$ is independently —$OPO_3^{2-}$. In certain embodiments, each $R_3$, $R_6$, $R_7$ and $R_{12}$ is independently —$OSO_2R_{18}$. In certain embodiments, each $R_3$, $R_6$, $R_7$ and $R_{12}$ is independently —$SO_2N(R_{18})_2$. In certain embodiments, each $R_3$, $R_6$, $R_7$ and $R_{12}$ is independently —$OSO_2N(R_{18})_2$. In certain embodiments, each $R_3$, $R_6$, $R_7$ and $R_{12}$ is independently —$NR_{18}SO_2R_{18}$. In certain embodiments, each $R_3$, $R_6$, $R_7$ and $R_{12}$ is independently —$SO_2N(R_{18})_2$. In certain embodiments, each $R_3$, $R_6$, $R_7$ and $R_{12}$ is independently —$NHNH_2$. In certain embodiments, each $R_3$, $R_6$, $R_7$ and $R_{12}$ is independently —$ONH_2$. In certain embodiments, each $R_3$, $R_6$, $R_7$ and $R_{12}$ is independently or —$NHC(O)NHNH_2$.

In certain embodiments, $R_7$ is not —$PO_3^{2-}$. In certain embodiments, $R_7$ is not —$PO_3H_2$.

In certain embodiments, $R_7$ is substituted or unsubstituted alkyl. In certain embodiments, $R_7$ is $C(R_{18})_2SO_3^-$. In certain embodiments, $R_7$ is $C(H)_2SO_3^-$. In certain embodiments, $R_7$ is $C(R_{18})_2SO_3H$. In certain embodiments, $R_7$ is $C(H)_2SO_3H$. In certain embodiments, $R_7$ is substituted or unsubstituted alkyl. In certain embodiments, $R_7$ is $C(R_{18})_2SO_3^-$ and $R_3$ is —OH. In certain embodiments, $R_7$ is $C(H)_2SO_3$ and $R_3$ is —OH. In certain embodiments, $R_7$ is $C(R_{18})_2SO_3H$ and $R_3$ is —OH. In certain embodiments, $R_7$ is $C(H)_2SO_3H$ and $R_3$ is —OH.

In certain embodiments, $R_7$ is —$SO_3^-$. In certain embodiments, $R_7$ is —$SO_3H$. In certain embodiments, $R_7$ is —$SO_3^-$ and $R_3$ is —OH. In certain embodiments, $R_7$ is —$SO_3H$ and $R_3$ is —OH.

In certain embodiments, $R_7$ is —$SO_2N(R_{18})_2$. In certain embodiments, $R_7$ is —$SO_2NHMe$. In certain embodiments, $R_7$ is —$SO_2N(R_{18})_2$ and $R_3$ is —OH. In certain embodiments, $R_7$ is —$SO_2NHMe$ and $R_3$ is —OH.

In certain embodiments, $R_7$ is —$OSO_2N(R_{18})_2$. In certain embodiments, $R_7$ is —$OSO_2NHMe$. In certain embodiments, $R_7$ is —$OSO_2N(R_{18})_2$ and $R_3$ is —OH. In certain embodiments, $R_7$ is —$OSO_2NHMe$ and $R_3$ is —OH.

In certain embodiments, $R_7$ is —$NR_{18}SO_3^-$. In certain embodiments, $R_7$ is —$NHSO_3^-$. In certain embodiments, $R_7$ is —$NHPO_3^{2-}$. In certain embodiments, $R_7$ is —$NR_{18}SO_3H$. In certain embodiments, $R_7$ is —$NHSO_3H$. In certain embodiments, $R_7$ is —$NHPO_3H_2$. In certain embodiments, $R_7$ is —$NR_{18}SO_3^-$ and $R_3$ is —OH. In certain embodiments, $R_7$ is —$NHSO_3^-$ and $R_3$ is —OH. In certain embodiments, $R_7$ is —$NHPO_3^{2-}$ and $R_3$ is —OH. In certain embodiments, $R_7$ is —$NR_{18}SO_3H$ and $R_3$ is —OH. In certain embodiments, $R_7$ is —$NHSO_3H$ and $R_3$ is —OH. In certain embodiments, $R_7$ is —$NHPO_3H_2$ and $R_3$ is —OH.

In certain embodiments, each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$. In certain embodiments, each $R_{18}$ is independently H. In certain embodiments, each $R_{18}$ is independently substituted or unsubstituted alkyl. In certain embodiments, each $R_{18}$ is independently substituted or unsubstituted methyl. In certain embodiments, each $R_{18}$ is independently substituted or unsubstituted heteroalkyl. In certain embodiments, each $R_{18}$ is independently substituted or unsubstituted cycloalkyl. In certain embodiments, each $R_{18}$ is independently substituted or unsubstituted heterocycloalkyl. In certain embodiments, each $R_{18}$ is independently substituted or unsubstituted aryl. In certain embodiments, each $R_{18}$ is independently substituted or unsubstituted heteroaryl. In certain embodiments, each $R_{18}$ is independently $OR_{18}$. In certain embodiments, each $R_{18}$ is independently $N(R_{18})_2$. In certain embodiments, each $R_{18}$ is independently $SR_{18}$. In certain embodiments, each $R_{18}$ is independently halogen. In certain embodiments, each $R_{18}$ is independently CN. In certain embodiments, each $R_{18}$ is independently —CHO. In certain embodiments, each $R_{18}$ is independently —$CO_2H$. In certain embodiments, each $R_{18}$ is independently —$CO_2R_{18}$. In certain embodiments, each $R_{18}$ is independently —$NO_2$. In certain embodiments, each $R_{18}$ is independently —$ONO_2$. In certain embodiments, each $R_{18}$ is independently —$SO_2Cl$. In certain embodiments, each $R_{18}$ is independently —SO. In certain embodiments, each $R_{18}$ is independently —$OSO_3^-$. In certain embodiments, each $R_{18}$ is independently —$NR_{18}SO_3^-$. In certain embodiments, each $R_{18}$ is independently —$PO_3^{2-}$. In certain embodiments, each $R_{18}$ is independently —$OPO_3^{2-}$. In certain embodiments, each $R_{18}$ is independently —$OSO_2R_{18}$. In certain embodiments, each $R_{18}$ is independently —$SO_2N(R_{18})_2$. In certain embodiments, each $R_{18}$ is independently —$OSO_2N(R_{18})_2$. In certain embodiments, each $R_{18}$ is independently —$NR_{18}SO_2R_{18}$. In certain embodiments, each $R_{18}$ is independently —$SO_2N(R_{18})_2$. In certain embodiments, each $R_{18}$ is independently —$NHNH_2$. In certain embodiments, each $R_{18}$ is independently —$ONH_2$. In certain embodiments, each $R_{18}$ is independently —NHC(O)$NHNH_2$.

In some embodiments of the various aspects disclosed herein, $R_1$, $R_2$, $R_4$, $R_{15}$ and $R_{16}$ are H.

In some embodiments of the various aspects disclosed herein, $R_1$, $R_2$, $R_4$, $R_6$, $R_{11}$, $R_{15}$ and $R_{16}$ are H.

In some embodiments of the various aspects disclosed herein, $R_1$, $R_2$, $R_4$, $R_{11}$, $R_{15}$ and $R_{16}$ are H.

In some embodiments of the various aspects disclosed herein, $R_1$, $R_2$, $R_4$, $R_6$, $R_7$, $R_{11}$, $R_{15}$ and $R_{16}$ are H.

In some embodiments of the various aspects disclosed herein, $R_3$ and/or $R_{12}$ are —OH.

In some embodiments of the various aspects disclosed herein, $R_7$ and/or $R_{12}$ are —OH.

In some embodiments of the various aspects disclosed herein, $R_3$ and/or $R_7$ are —OH.

In some embodiments of the various aspects disclosed herein, $R_3$ and/or $R_6$ are —OH.

In some embodiments of the various aspects disclosed herein, $R_6$ and/or $R_7$ are —OH.

In some embodiments of the various aspects disclosed herein, $R_3$ and/or $R_7$ are —OH.

In some embodiments of the various aspects disclosed herein, $R_6$ and $R_7$ are H.

In some embodiments of the various aspects disclosed herein, $R_3$ is H or —OH.

In some embodiments of the various aspects disclosed herein, $R_{17}$ is $C_1$-$C_6$ alkyl.

For example, $R_{17}$ can be methyl, ethyl, propyl, isopropyl, butyl, pentyl.

In some embodiments of the various aspects disclosed herein, n is 2.

In some embodiments of the various aspects disclosed herein, n is 1.

In some embodiments of the various aspects disclosed herein, wherein at least one of $R_3$, $R_6$, $R_7$ and $R_{12}$ is —$OSO_3^-$, —$NR_{18}SO_3^-$, —$OPO_3^{2-}$.

In some embodiments of the various aspects disclosed herein, at least one of $R_6$, $R_7$ and $R_{12}$ is —$OSO_3^-$, —$NR_{18}SO_3^-$, or —$OPO_3^{2-}$.

In some embodiments of the various aspects disclosed herein, $R_6$ or $R_7$ is —$OSO_3^-$, —$NR_{18}SO_3^-$, or —$OPO_3^{2-}$.

In some embodiments of the various aspects disclosed herein, $R_6$ or $R_7$ is —$OSO_3^-$.

In some embodiments of the various aspects disclosed herein, $R_7$ and $R_{12}$ are independently —$OSO_3^-$.

In some embodiments of the various aspects disclosed herein, $R_3$, $R_6$, $R_7$ and $R_{12}$ are independently H, —OH, —$OSO_3^-$, —$NR_{18}SO_3^-$, or —$OPO_3^{2-}$, provided that at least one of $R_3$, $R_6$, $R_7$ and $R_{12}$ is —$OSO_3^-$, —$NR_{18}SO_3^-$, or —$OPO_3^{2-}$.

In some embodiments of the various aspects disclosed herein, $R_3$, $R_6$, $R_7$ and $R_{12}$ are independently H, —OH, —$OSO_3^-$, —$NR_{18}SO_3^-$, or —$OPO_3^{2-}$, provided that at least one of $R_6$, $R_7$ and $R_{12}$ is —$OSO_3^-$, —$NR_{18}SO_3^-$, or —$OPO_3^{2-}$.

In some embodiments of the various aspects disclosed herein, $R_3$, $R_6$, $R_7$ and $R_{12}$ are independently H, —OH, —$OSO_3^-$, —$NR_{18}SO_3^-$, or —$OPO_3^{2-}$, provided that $R_6$ or $R_7$ is —$OSO_3^-$, —$NR_{18}SO_3^-$, or —$OPO_3^{2-}$.

In some embodiments of the various aspects disclosed herein, $R_3$, $R_6$, $R_7$ and $R_{12}$ are independently H, —OH, —$OSO_3^-$, —$NR_{18}SO_3^-$, or —$OPO_3^{2-}$, provided that at least one of $R_6$ or $R_7$ is —$OSO_3^-$.

In some embodiments of the various aspects disclosed herein, $R_3$, and $R_6$ are independently H, —OH, —$OSO_3^-$, —$NR_{18}SO_3^-$, or —$OPO_3^{2-}$; and $R_7$ and $R_{12}$ are independently —$OSO_3$.

In some embodiments of the various aspects disclosed herein, the compound of Formula (I) can be a compound of any one of Formula (II)-(XV).

In certain embodiments, the compound of Formula (I) is of the Formula (II):

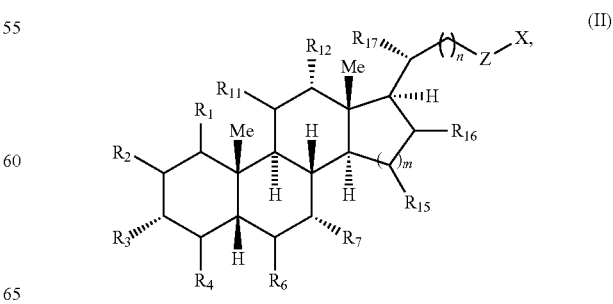

or a pharmaceutically acceptable salt thereof.

In certain embodiments, the compound of Formula (I) is of the Formula (III):

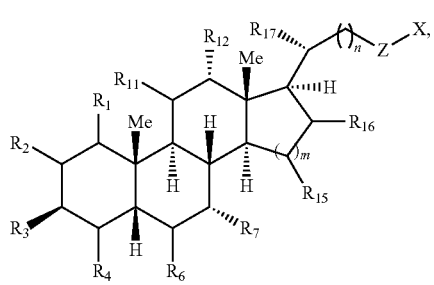

(III)

or a pharmaceutically acceptable salt thereof.

In certain embodiments, the compound of Formula (I) is of the Formula (IV):

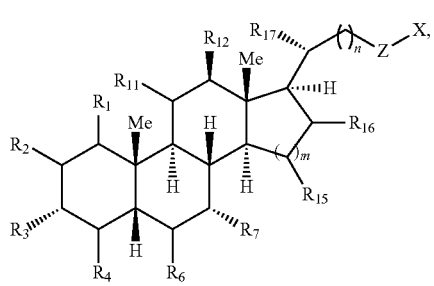

(IV)

or a pharmaceutically acceptable salt thereof.

In certain embodiments, the compound of Formula (I) is of the Formula (V):

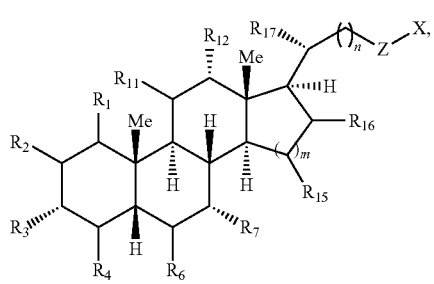

(V)

or a pharmaceutically acceptable salt thereof.

In certain embodiments, the compound of Formula (I) is of the Formula (VI):

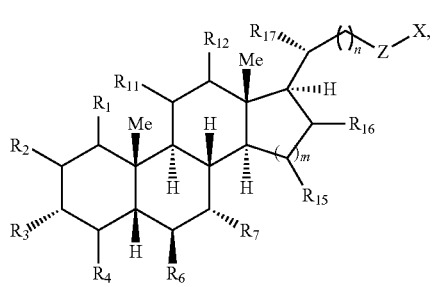

(VI)

or a pharmaceutically acceptable salt thereof.

In certain embodiments, the compound of Formula (I) is of the Formula (VII):

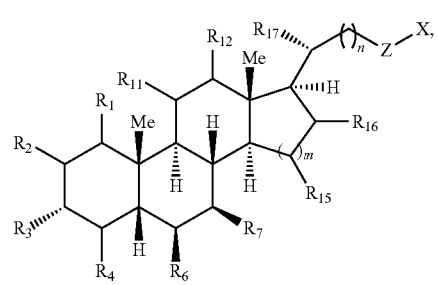

(VII)

or a pharmaceutically acceptable salt thereof.

In certain embodiments, the compound of Formula (I) is of the Formula (VIII):

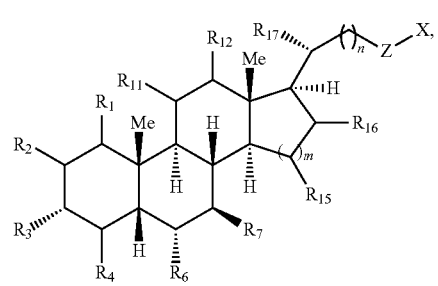

(VIII)

or a pharmaceutically acceptable salt thereof.

In certain embodiments, the compound of Formula (I) is of the Formula (IX):

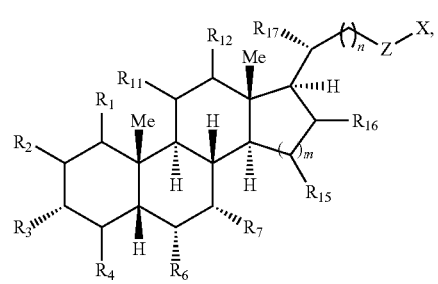

(IX)

or a pharmaceutically acceptable salt thereof.

In certain embodiments, the compound of Formula (I) is of the Formula (X):

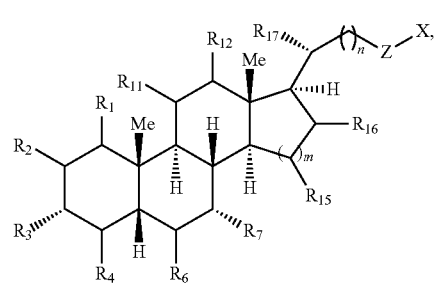

(X)

or a pharmaceutically acceptable salt thereof.

In certain embodiments, the compound of Formula (I) is of the Formula (XI):

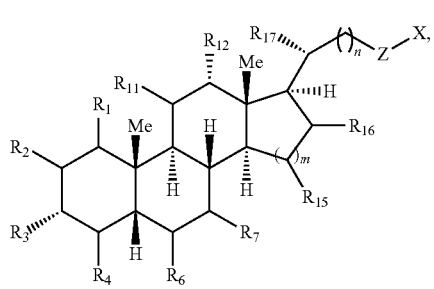

(XI)

or a pharmaceutically acceptable salt thereof.

In certain embodiments, the compound of Formula (I) is of the Formula (XII):

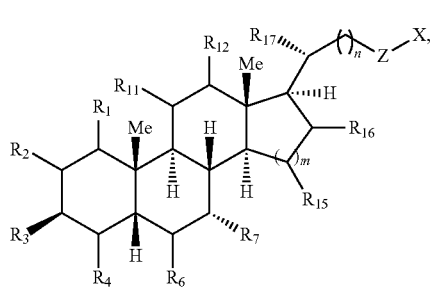

(XII)

or a pharmaceutically acceptable salt thereof.

In certain embodiments, the compound of Formula (I) is of the Formula (XIII):

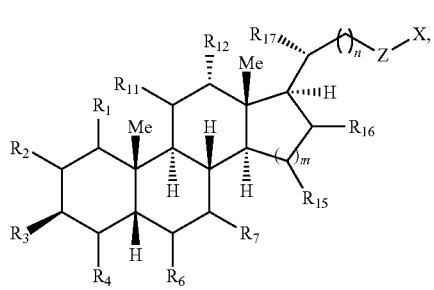

(XIII)

or a pharmaceutically acceptable salt thereof.

In certain embodiments, the compound of Formula (I) is of the Formula (XIV):

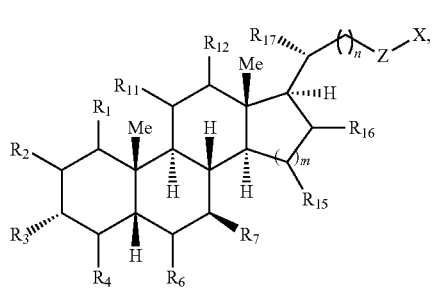

(XIV)

or a pharmaceutically acceptable salt thereof.

In certain embodiments, the compound of Formula (I) is of the Formula (XV):

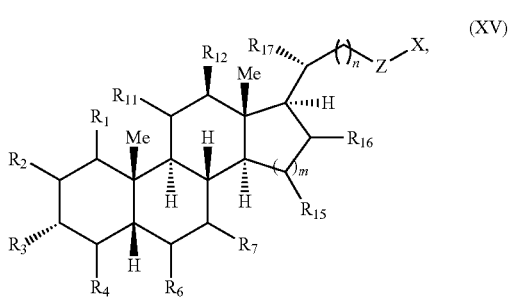

(XV)

or a pharmaceutically acceptable salt thereof.

In certain embodiments, the compound of Formula (I) is of the formula:

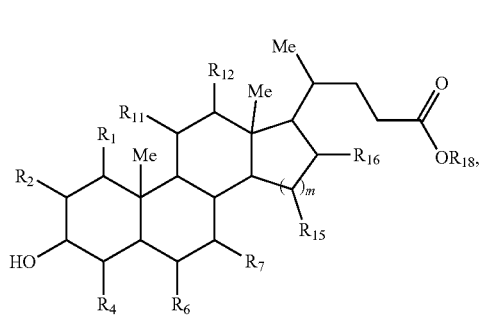

or a pharmaceutically acceptable salt thereof.

In certain embodiments, the compound of Formula (I) is of the formula:

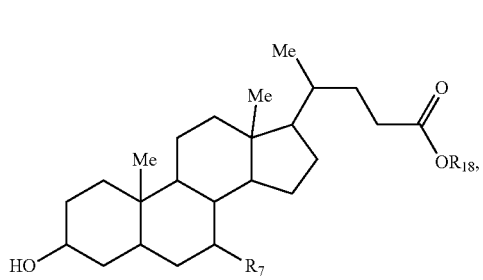

or a pharmaceutically acceptable salt thereof.

In certain embodiments, the compound of Formula (I) is of the formula:

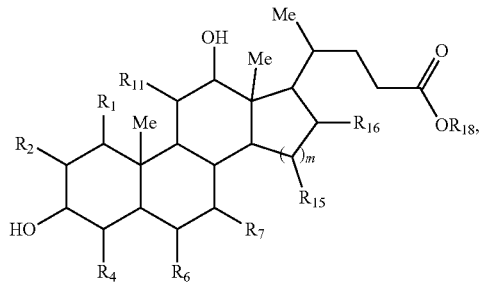

or a pharmaceutically acceptable salt thereof.

In certain embodiments, the compound of Formula (I) is of the formula:

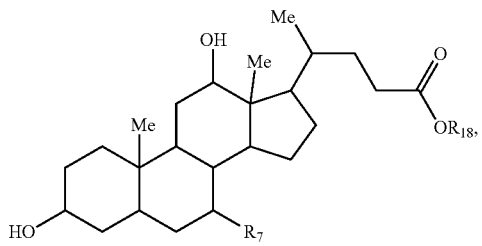

or a pharmaceutically acceptable salt thereof.

In certain embodiments, the compound of Formula (I) is of the formula:

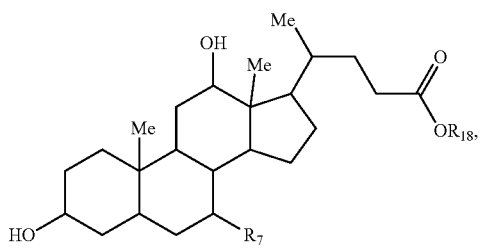

or a pharmaceutically acceptable salt thereof.

In certain embodiments, the compound of Formula (I) is of the formula:

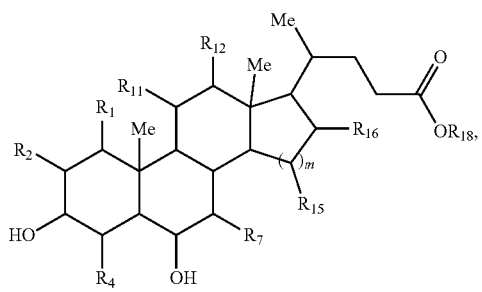

or a pharmaceutically acceptable salt thereof.

In certain embodiments, the compound of Formula (I) is of the formula:

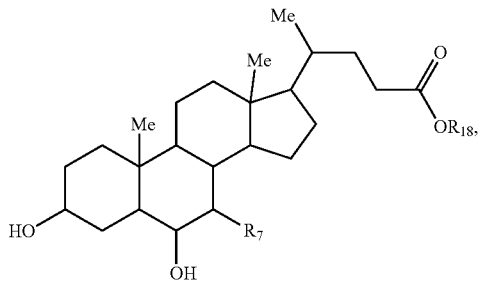

or a pharmaceutically acceptable salt thereof.

In certain embodiments, the compound of Formula (I) is of the formula:

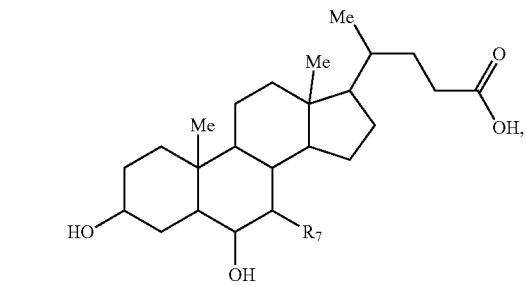

or a pharmaceutically acceptable salt thereof.

In certain embodiments, the compound of Formula (I) is of the formula:

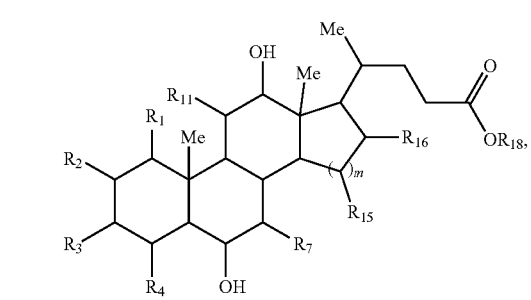

or a pharmaceutically acceptable salt thereof.

In certain embodiments, the compound of Formula (I) is of the formula:

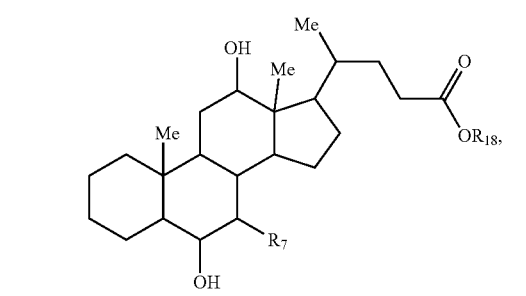

or a pharmaceutically acceptable salt thereof.

In certain embodiments, the compound of Formula (I) is of the formula:

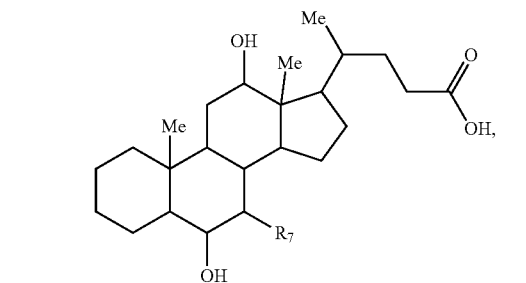

or a pharmaceutically acceptable salt thereof.

In certain embodiments, the compound of Formula (I) is of the formula:

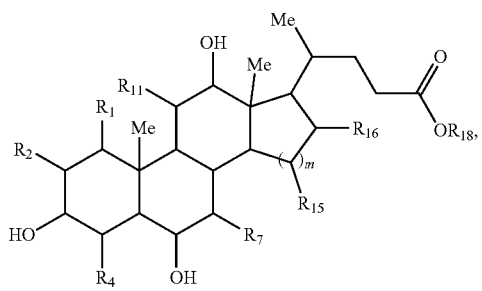

or a pharmaceutically acceptable salt thereof.

In certain embodiments, the compound of Formula (I) is of the formula:

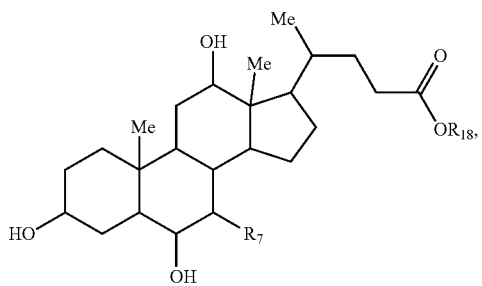

or a pharmaceutically acceptable salt thereof.

In certain embodiments, the compound of Formula (I) is of the formula:

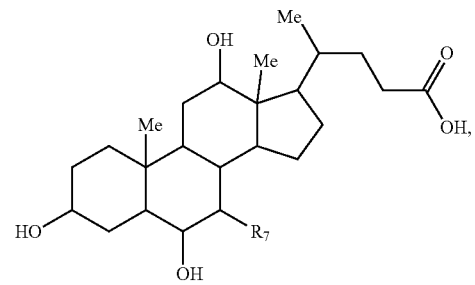

or a pharmaceutically acceptable salt thereof.

In certain embodiments, the compound of Formula (I) is of the formula:

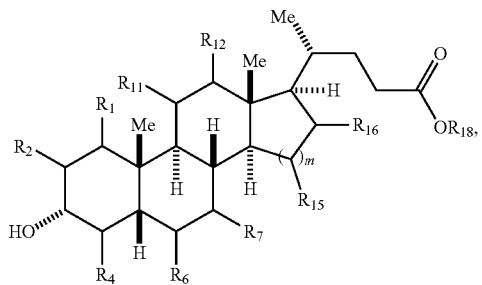

or a pharmaceutically acceptable salt thereof.

In certain embodiments, the compound of Formula (I) is of the formula:

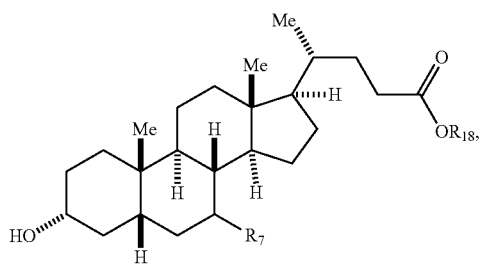

or a pharmaceutically acceptable salt thereof.

In certain embodiments, the compound of Formula (I) is of the formula:

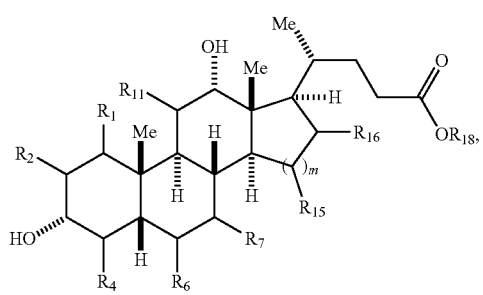

a pharmaceutically acceptable salt thereof.

In certain embodiments, the compound of Formula (I) is of the formula:

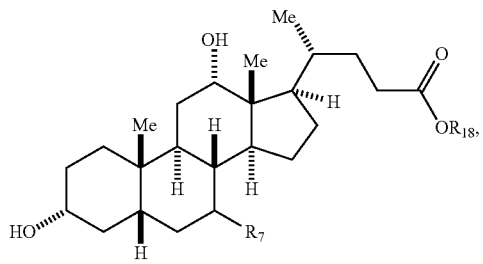

or a pharmaceutically acceptable salt thereof.

In certain embodiments, the compound of Formula (I) is of the formula:

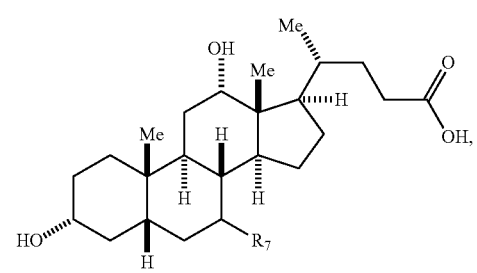

or a pharmaceutically acceptable salt thereof.

In certain embodiments, the compound of Formula (I) is of the formula:

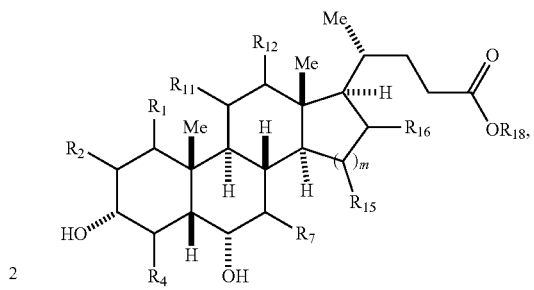

or a pharmaceutically acceptable salt thereof.

In certain embodiments, the compound of Formula (I) is of the formula:

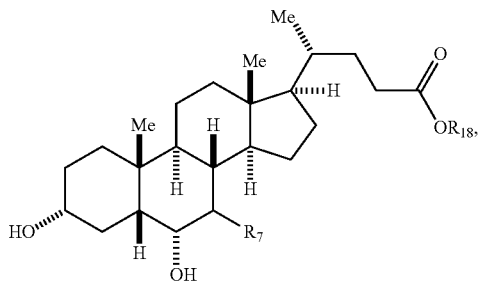

or a pharmaceutically acceptable salt thereof.

In certain embodiments, the compound of Formula (I) is of the formula:

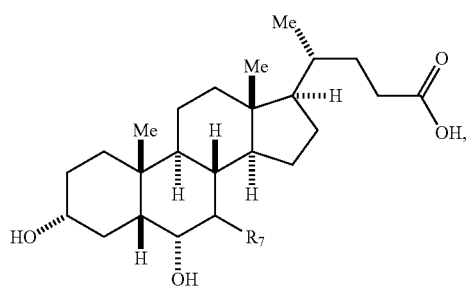

or a pharmaceutically acceptable salt thereof.

In certain embodiments, the compound of Formula (I) is of the formula:

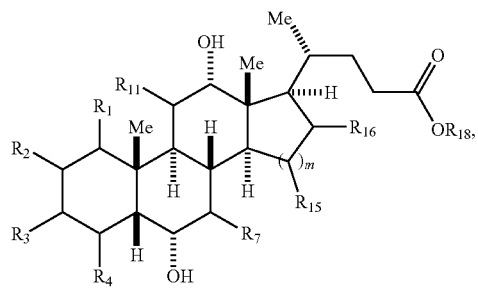

or a pharmaceutically acceptable salt thereof.

In certain embodiments, the compound of Formula (I) is of the formula:

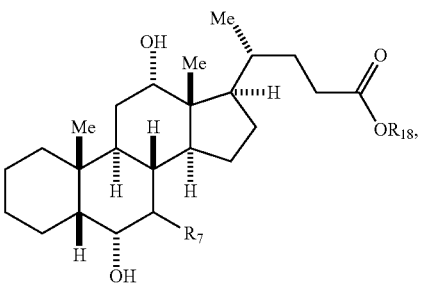

or a pharmaceutically acceptable salt thereof.

In certain embodiments, the compound of Formula (I) is of the formula:

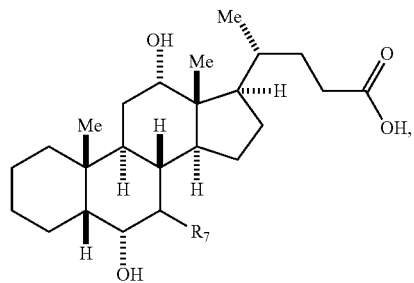

or a pharmaceutically acceptable salt thereof.

In certain embodiments, the compound of Formula (I) is of the formula:

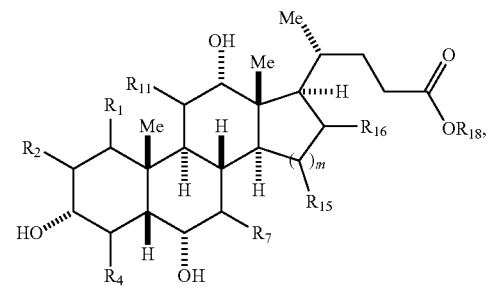

or a pharmaceutically acceptable salt thereof.

In certain embodiments, the compound of Formula (I) is of the formula:

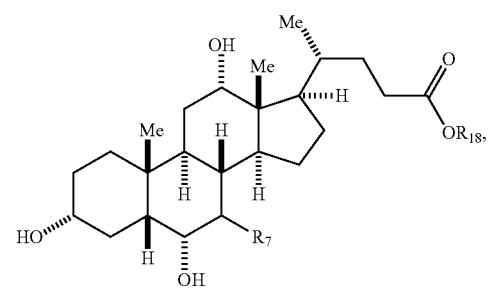

or a pharmaceutically acceptable salt thereof.

In certain embodiments, the compound of Formula (I) is of the formula:
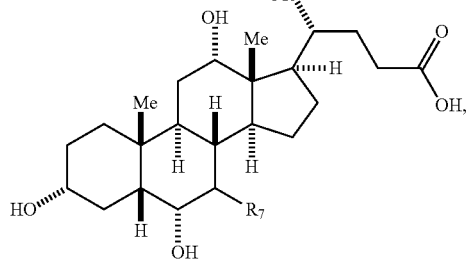
or a pharmaceutically acceptable salt thereof.
In certain embodiments, a compound of Formula (I) is of the formula:
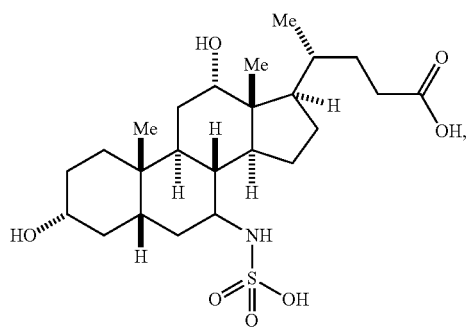
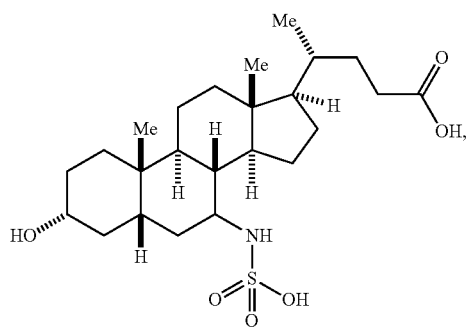
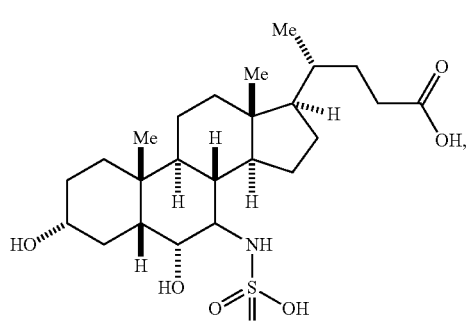
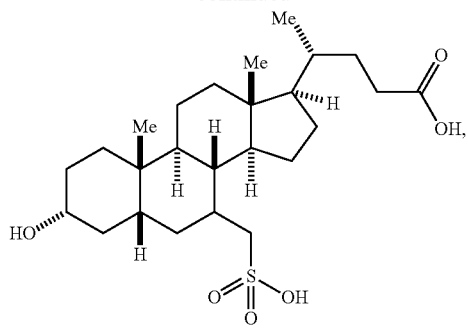
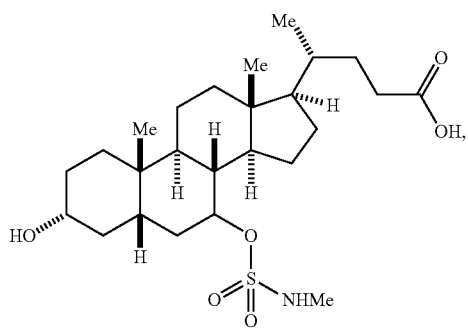
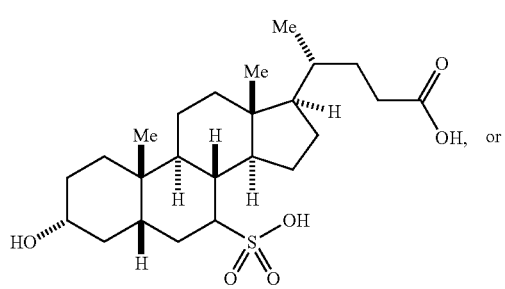
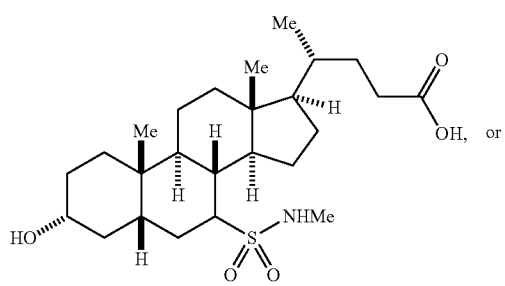
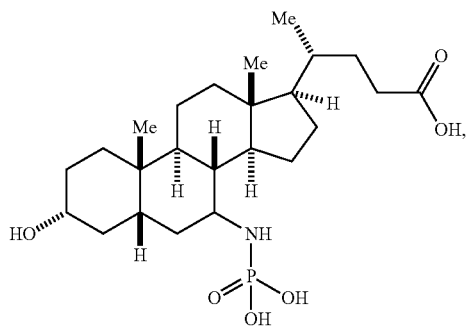
or a pharmaceutically acceptable salt thereof.

In certain embodiments, a compound of Formula (I) is not of the formula:

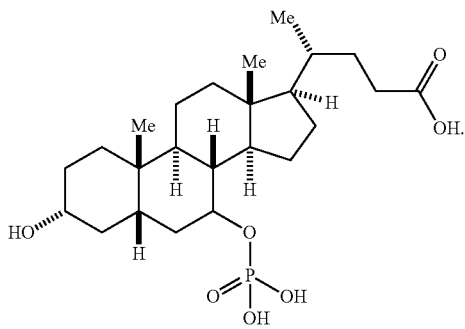

In certain embodiments, a compound of Formula (I) is of the formula:

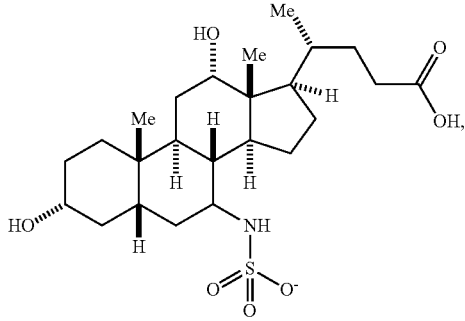

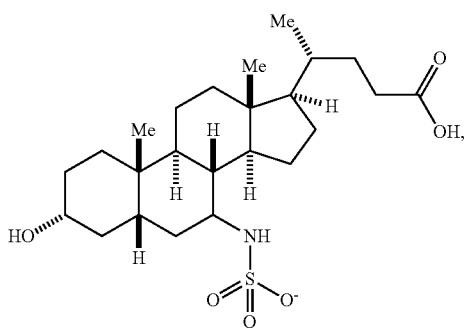

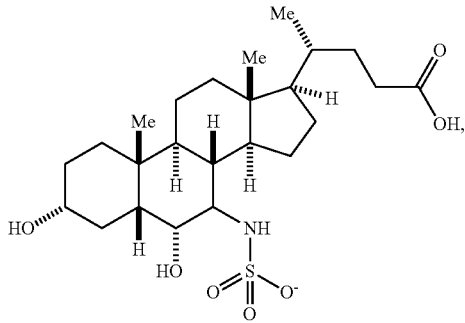

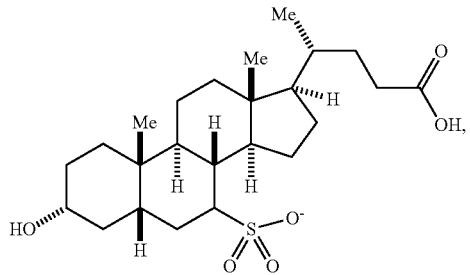

or an acid thereof.

In some embodiments of the various aspects described herein, the compound of Formula (I) is of Formula (XVI):

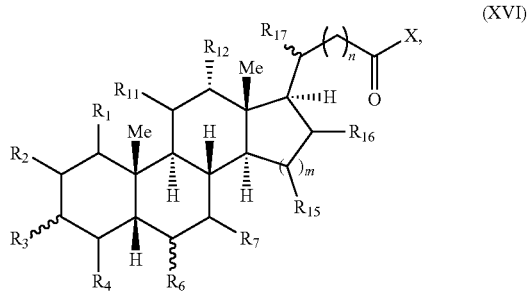

wherein: X is OH or a polar amino acid (e.g., taurine); $R_7$ is —$OSO_3H$, —$SO_3H$, $OSO_2R_{18}$, —$NHSO_3H$, $OSO_2N(R_{18})_2$, —$NHSO_2R_{18}$, —$SO_2N(R_{18})_2$, —$OPO_3H$, or —$ONO_2$; $R_1$, $R_2$, $R_4$, $R_6$, $R_{11}$, $R_{15}$, $R_{16}$, $R_{18}$, n and m are as defined for Formula (I); $R_3$ is H or —OH; and $R_{17}$ is H or methyl.

In some embodiments of the various aspects described herein, the compound of Formula (I) is of Formula (XVII):

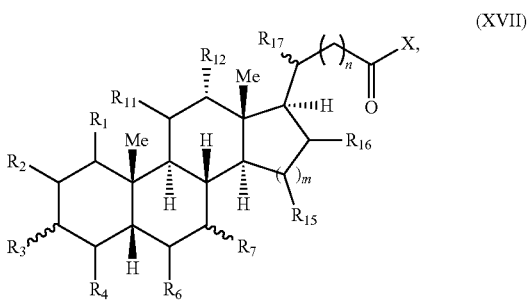

wherein: X is OH or a polar amino acid (e.g., taurine); $R_6$ is —$OSO_3H$, —$SO_3H$, $OSO_2R_{18}$, —$NHSO_3H$, $OSO_2N(R_{18})_2$, —$NHSO_2R_{18}$, —$SO_2N(R_{18})_2$, —$OPO_3H$, or —$ONO_2$; $R_1$, $R_2$, $R_4$, $R_7$, $R_{11}$, $R_{15}$, $R_{16}$, $R_{18}$, n and m are as defined for Formula (I); $R_3$ is H or OH; and $R_{17}$ is H or methyl.

In some embodiments, of the various aspects disclosed herein, the compound of Formula (I) is not a naturally occurring bile acid. For example, the compound of Formula (I) is not cholic acid 7-sulfate.

In certain embodiments, a compound of Formula (I) is not of the formula:

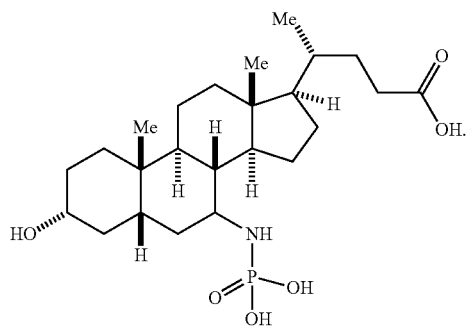

In some embodiments, of the various aspects disclosed herein, the compound of Formula (I) is not lithocholic acid 3-sulfate.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as, for example, tritium ($^3H$), iodine-125 ($^{125}I$), or carbon-14 ($^{14}C$). All isotopic variations of the compounds of the present disclosure, whether radioactive or not, are encompassed within the scope of the present disclosure.

Pharmaceutical Compositions, Kits, and Administration

In still another aspect, provided herein is a pharmaceutical composition comprising a compound of Formula (I) and a pharmaceutically acceptable carrier or excipient.

The present disclosure provides pharmaceutical compositions comprising a compound of Formulae (I)-(XVII), or a pharmaceutically acceptable salt thereof, and optionally a pharmaceutically acceptable excipient. In certain embodiments, the pharmaceutical composition described herein comprises a compound of Formulae (I)-(XVII), or a pharmaceutically acceptable salt thereof, and a pharmaceutically acceptable excipient.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups, and elixirs. In addition to the compound of any of Formulae (I)-(XVII), the liquid dosage forms can contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the compound of any of Formulae (I)-(XVII), are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The compound of any of Formulae (I)-(XVII) can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the compound of any of Formulae (I)-(XVII) can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

In some embodiments, the carrier or excipient restricts delivery of the composition to the gastrointestinal tract. In some embodiments, the composition provided herein is restricted to the gastrointestinal tract by the addition of a sulfate group or a polar group to the compounds.

In some embodiments, the carrier or excipient is an enteric coating or enteric-coated drug delivery device. As used herein, the terms "enteric coating" or "enteric-coated drug delivery device" refers to any drug delivery method that can be administered orally but is not degraded or activated until the device enters the intestines. Such methods can utilize a coating or encapsulation that is degraded using e.g., pH dependent means, permitting protection of the delivery device and the agent to be administered or transplanted throughout the gastrointestinal tract until the device reaches the alkaline pH of the intestines (e.g. cecum or colon).

An enteric coating can control the location of where an agent is released in the digestive system. Thus, an enteric coating can be used such that a pharmaceutical composition does not dissolve and release the agent in the stomach, but rather travels to the intestine, where it dissolves and releases the agent in an environment that is most beneficial for increasing GLP-1 secretion (e.g. targeting L-cells located in the cecum, ileum, large intestine, or colon). An enteric coating can be stable at low pH (such as in the stomach) and can dissolve at higher pH (for example, in the intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT™, AQUACOAT ECD™, SEPIFILM™ KLUCEL™, and METOLOSE™); polyvinylacetate phthalate (trade name SURETERIC™); and methacrylic acid (trade names EUDRAGIT™, EUDRAGIT L 100-55™ from Evonik Industries, Germany).

Another example of methods known in the art that allow for restriction of pharmaceutical compositions to the intestines, include enteric magnesium micromotors (EMgMs). EMgMs are described in the art, for example, in Li et al. *ACS NANO*, (2016).

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment compound of the present disclosure can be formulated for colonic or rectal administration.

In one aspect, provided herein is a composition comprising a compound that increases the level of cholic acid 7-sulfate in a subject. In one embodiment, the compound is not cholic acid 7-sulfate. In another embodiment, the compound is a derivative of cholic acid 7-sulfate. In another embodiment, the composition is formulated for treating diabetes, obesity, or an inflammatory disease. In another embodiment, the composition further comprises a pharmaceutically acceptable carrier or excipient.

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this disclosure can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the compound causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents, such as CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this disclosure. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound of formulae (I)-(XVII), or pharmaceutical composition described herein. In certain embodiments, the kits are useful for treating a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits are useful for preventing a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits are useful for reducing the risk of developing a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits and instructions provide for preventing a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. In certain embodiments, the kits and instructions provide for reducing the risk of developing a disease (e.g., a metabolic disorder (e.g., diabetes, obesity), inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof. A kit described herein may include one or more additional pharmaceutical compounds described herein in a separate composition.

Methods of Treatment

In one aspect, provided herein is a method for treating diabetes, the method comprising administering to a subject in need thereof a compound of Formula (I):

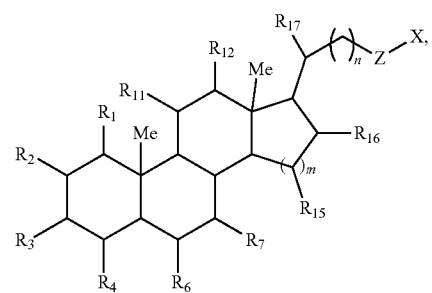

wherein:
n is 1, 2, 3, 4, 5, 6, 7, 8, 9 or 10;
m is 1, 2, 3 or 4;
Z is —C(O)—, —C(O)O—, —C(O)NR$_{18}$— or —CH$_2$—;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, CN, —CHO, —CO$_2$H, —CO$_2$R$_{18}$, —NO$_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, —$NHC(O)NHNH_2$, or a polar amino acid (e.g., taurine);

each $R_1$, $R_2$, $R_3$, $R_4$, $R_{11}$, $R_{12}$, $R_{15}$, $R_{16}$ and $R_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

each $R_3$, $R_6$, $R_7$ and $R_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, provided that at least one of $R_3$, $R_6$, $R_7$ and $R_{12}$ is a polar group;

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

or a pharmaceutically acceptable salt thereof.

In one aspect, provided herein is a method for treating a metabolic disorder (e.g., diabetes, obesity), the method comprising administering to a subject in need thereof a compound of Formula (I):

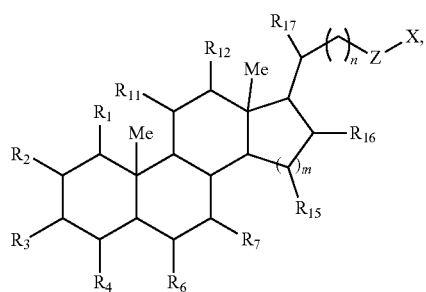

wherein:
n is 1, 2, 3, 4, 5, 6, 7, 8, 9 or 10;
m is 1, 2, 3 or 4;
Z is —C(O)—, —C(O)O—, —C(O)$NR_{18}$— or —$CH_2$—;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$OR_{18}$, —$N(R_{18})_2$, —$SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, —$NHC(O)NHNH_2$, or a polar amino acid (e.g., taurine);

each $R_1$, $R_2$, $R_3$, $R_4$, $R_{11}$, $R_{12}$, $R_{15}$, $R_{16}$ and $R_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

each $R_3$, $R_6$, $R_7$ and $R_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, —CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$, provided that at least one of $R_3$, $R_6$, $R_7$ and $R_{12}$ is a polar group;

each $R_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR_{18}$, $N(R_{18})_2$, $SR_{18}$, halogen, CN, —CHO, —$CO_2H$, —$CO_2R_{18}$, —$NO_2$, —$ONO_2$, —$SO_2Cl$, —$SO_3^-$, —$OSO_3^-$, —$NR_{18}SO_3^-$, —$PO_3^{2-}$, —$OPO_3^{2-}$, —$OSO_2R_{18}$, —$SO_2N(R_{18})_2$, —$OSO_2N(R_{18})_2$, —$NR_{18}SO_2R_{18}$, —$SO_2N(R_{18})_2$, —$NHNH_2$, —$ONH_2$, or —$NHC(O)NHNH_2$;

or a pharmaceutically acceptable salt thereof.

In another aspect, provided herein are methods of treating an inflammatory disease, the method comprising administering to a subject in need thereof a compound of Formula (I) as described herein, or a pharmaceutically acceptable salt thereof.

In certain embodiments, the compound of Formula (I) useful in the methods and uses of this disclosure is of the formula:

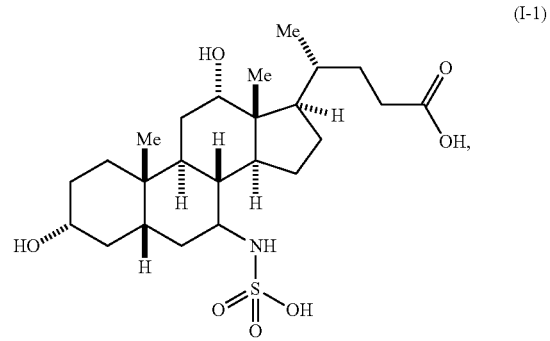

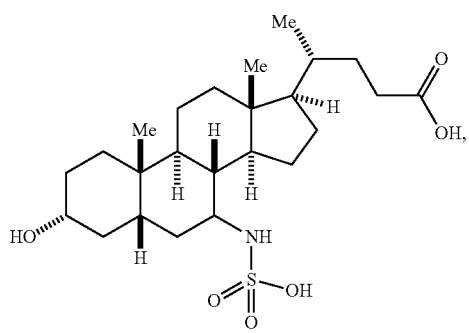
(I-2)

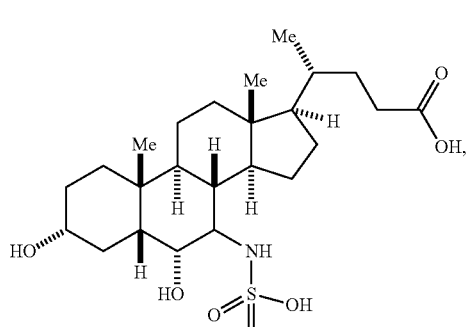
(I-3)

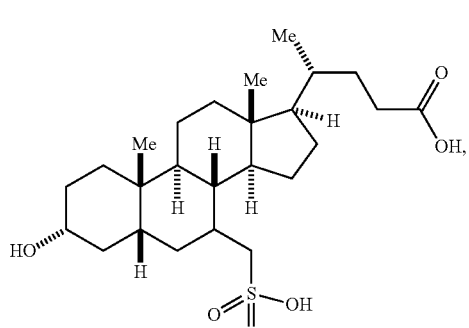
(I-4)

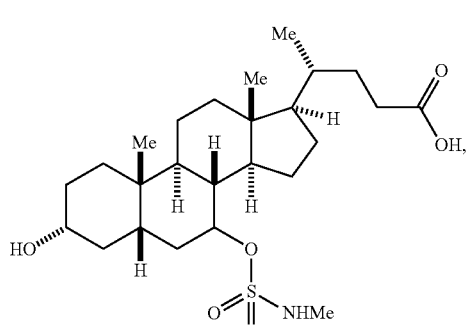
(I-5)

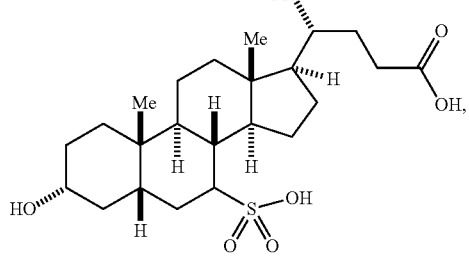
(I-6)

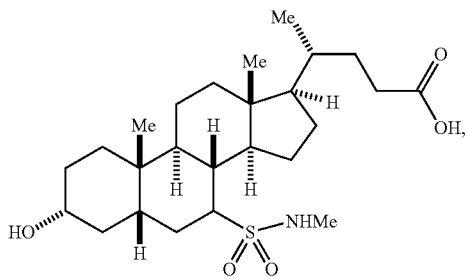
(I-7)

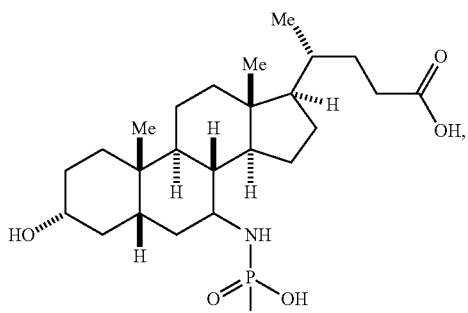
(I-8)

or a pharmaceutically acceptable salt thereof.

In certain embodiments, the compound of Formula (I) useful in the methods and uses of this disclosure is of the formula:

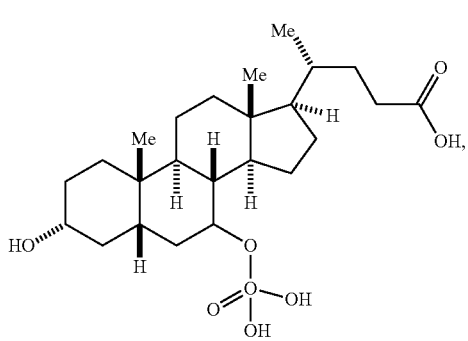
(I-9)

In one aspect, provided herein is a method of treating diabetes in a subject. As used herein the term "diabetes mellitus" or "diabetes" refers to any disease that affects the release of insulin from the pancreas (e.g., type I diabetes) or the sensitivity to insulin (e.g., type II diabetes). Diabetes can cause at least one symptom of the disease or patients can be asymptomatic. The symptoms associated with diabetes include but are not limited to, malaise, blurred vision, hunger, frequent urination, increased thirst, or any other symptom associated with the disease in a subject.

In some embodiments, the diabetes is type I diabetes, type II diabetes, neonatal diabetes, maturity onset diabetes in the young, or gestational diabetes.

In some embodiments, the diabetes is caused by obesity. In one aspect, provided herein is a method of treating obesity in a subject.

In some embodiments, the inflammatory disease is selected from the group consisting of: Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis.

In certain embodiments, the subject is an animal. The animal may be of either sex and may be at any stage of development. Preferably, the subject is a mammal. In certain embodiments, the subject described herein is a human. In certain embodiments, the subject is a non-human animal. The mammal can be a human, non-human primate, mouse, rat, dog, cat, horse, or cow, but is not limited to these examples. Mammals other than humans can be advantageously used as subjects that represent animal models of disease, e.g., diabetic or obesity model. A subject can be male or female.

A subject can be one who has been previously diagnosed with or identified as suffering from or having a disease or disorder in need of treatment (e.g., diabetes, obesity, or an inflammatory disease) or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

The methods and compositions provided herein can further be applied to treat or prevent prediabetes in a subject. A subject can also be one who is suffering from or at risk of developing diabetes or a pre-diabetic condition. The cause of diabetes can be due to a genetic mutation, inherited diabetes, obesity, lifestyle, or idiopathic.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of use or administration utilized.

The effective dose can be estimated initially from cell culture assays. A dose can be formulated in animals. Generally, the compositions are administered so that a compound of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the compound or composition is administered continuously (e.g., at constant levels over a period of time). Continuous administration of an compound can be achieved, e.g., by epidermal patches, continuous release formulations, or on-body injectors.

The compound can be administered as a single bolus or multiple boluses, as a continuous infusion, or a combination thereof. For example, the compound can be administered as a single bolus initially, and then administered as a continuous infusion following the bolus. The rate of the infusion can be any desired rate. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound in the bloodstream.

The dosage of the compound as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

In one embodiment of any of the aspects, the compound or compositions described herein are used as a monotherapy. In another embodiment of any of the aspects, the compounds described herein can be used in combination with other known agents and therapies for diabetes. Administered "in combination," as used herein, means that two (or more) different treatments are delivered to the subject during the course of the subject's affliction with the disorder, e.g., the two or more treatments are delivered after the subject has been diagnosed with the disorder (e.g. diabetes) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery."

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The compounds and agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

Therapeutics currently used to treat or prevent diabetes include, but are not limited to, insulin therapy, sulfonylureas (e.g. glyburide), meglitinides (e.g. nataglinide), SGLT2 inhibitors (e.g. canaglifozin), bile acid sequesterants (e.g. colesevelam), dopamine-2-agonists (e.g. bromocriptine), biguanides (e.g. metformin), DPP-4 inhibitors (e.g. alogliptin, linagliptin, etc.), alpha-glucosidase inhibitors (e.g. acarbose and miglitol), thiazolidinediones (e.g. rosiglitazone), and other treatments for diabetes known in the art.

When administered in combination, the agent or composition and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of diabetes) is lower (e.g., at least 20%, at least 30%, at least 40%, or at least 50% lower) than the amount or dosage of each agent individually required to achieve the same therapeutic effect.

Administration

In some embodiments of any of the aspects, the agent is administered by direct injection, subcutaneous injection, muscular injection, oral administration, or nasal administration. In some embodiments, administering of the agent or pharmaceutical composition provided herein reduces glucose levels in the serum of a subject.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In certain preferred embodiments, the compositions are administered orally.

Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, described herein is an agent or pharmaceutical composition that is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of Formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm&Haas, Spring House, Pa. USA).

Efficacy

The efficacy of an agents described herein, e.g., for the treatment of a metabolic disorder (e.g., diabetes, obesity) can be determined by the skilled practitioner. However, a treatment is considered "effective treatment," as the term is used herein, if one or more of the signs or symptoms of diabetes, obesity, or an inflammatory disease are altered in a beneficial manner, other clinically accepted symptoms are improved, or even ameliorated, or a desired response is induced, e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., glucose levels or glucose tolerance. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of diabetes, as the case may be. When using an experimental animal model, efficacy of treatment is evidenced when a statistically significant change in a marker is observed, e.g., reduced blood glucose levels.

In certain embodiments, provided herein are methods of treating a metabolic disorder (e.g., diabetes, obesity), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof.

In certain embodiments, provided herein are methods of preventing a metabolic disorder (e.g., diabetes, obesity), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis) in a subject in need thereof.

The present disclosure also provides compounds of Formulae (I)-(XVII), or a pharmaceutically acceptable salt thereof, for use in the treatment of a metabolic disorder (e.g., diabetes, obesity), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis).

The present disclosure also provides compounds of Formulae (I)-(XVII), or a pharmaceutically acceptable salt thereof, for use in the manufacture of a medicament for the treatment of a metabolic disorder (e.g., diabetes, obesity), or an inflammatory disease (e.g., Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis).

In certain embodiments, the disease is a metabolic disorder. In certain embodiments, the metabolic disorder is diabetes. In certain embodiments, the diabetes is type I diabetes. In certain embodiments, the diabetes is type II diabetes. In certain embodiments, the metabolic disorder is obesity.

In certain embodiments, the disease is an inflammatory disease. In certain embodiments, the inflammatory disease is Crohn's disease. In certain embodiments, the inflammatory disease is inflammatory bowel disease. In certain embodiments, the inflammatory disease is ulcerative colitis. In certain embodiments, the inflammatory disease is pancreatitis hepatitis. In certain embodiments, the inflammatory disease is appendicitis. In certain embodiments, the inflammatory disease is gastritis diverticulitis. In certain embodiments, the inflammatory disease is celiac disease. In certain embodiments, the inflammatory disease is food intolerance. In certain embodiments, the inflammatory disease is enteritis ulcer gastroesophageal reflux disease (GERD). In certain embodiments, the inflammatory disease is psoriatic arthritis. In certain embodiments, the inflammatory disease is psoriasis. In certain embodiments, the inflammatory disease is rheumatoid arthritis.

In certain embodiments, the methods of the disclosure comprise administering to the subject an effective amount of a compound of Formula I, or a pharmaceutically acceptable salt thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as a compound of Formulae (I)-(XVII), or at different times than the compound of Formulae (I)-(XVII). For example, the compound of Formulae (I)-(XVII) and any additional pharmaceutical agent(s) may be on the same dosing schedule or different dosing schedules. All or some doses of the compound of Formulae (I)-(XVII) may be administered before all or some doses of an additional pharmaceutical agent, after all or some does an additional pharmaceutical agent, within a dosing schedule of an additional pharmaceutical agent, or a combination thereof.

The timing of administration of the compound of Formulae (I)-(XVII) and additional pharmaceutical agents may be different for different additional pharmaceutical agents.

EXAMPLES

Example 1. Cholic Acid 7-Sulfate

Figure 1B:
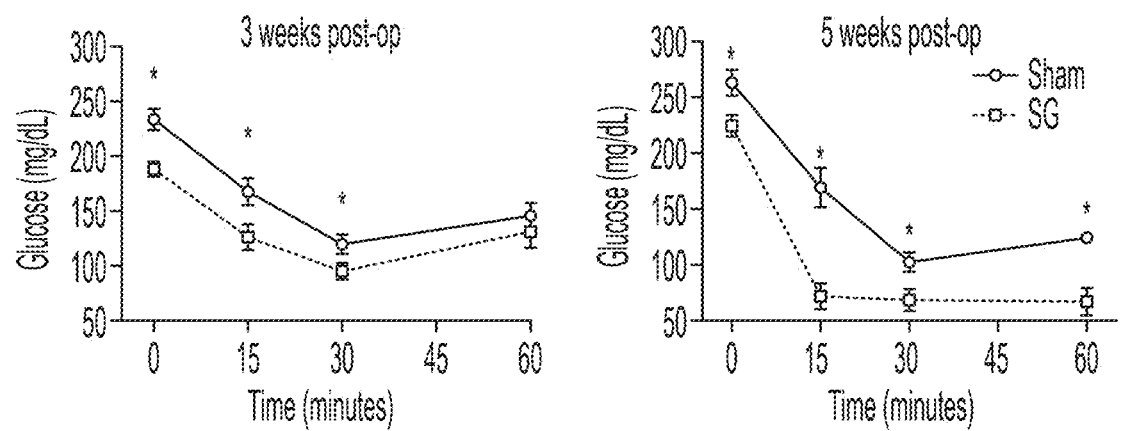

High fat diet-fed mice post-sleeve show improved glucose tolerance and insulin sensitivity (FIG. 1A-B) consistent with what has been observed before in humans. Therefore, the mouse model provided herein is used to study the amelioration of diabetic phenotypes post-sleeve surgery. Mice are suitable model for bariatric surgery-induced amelioration of diabetic phenotypes.

Figure 2A:
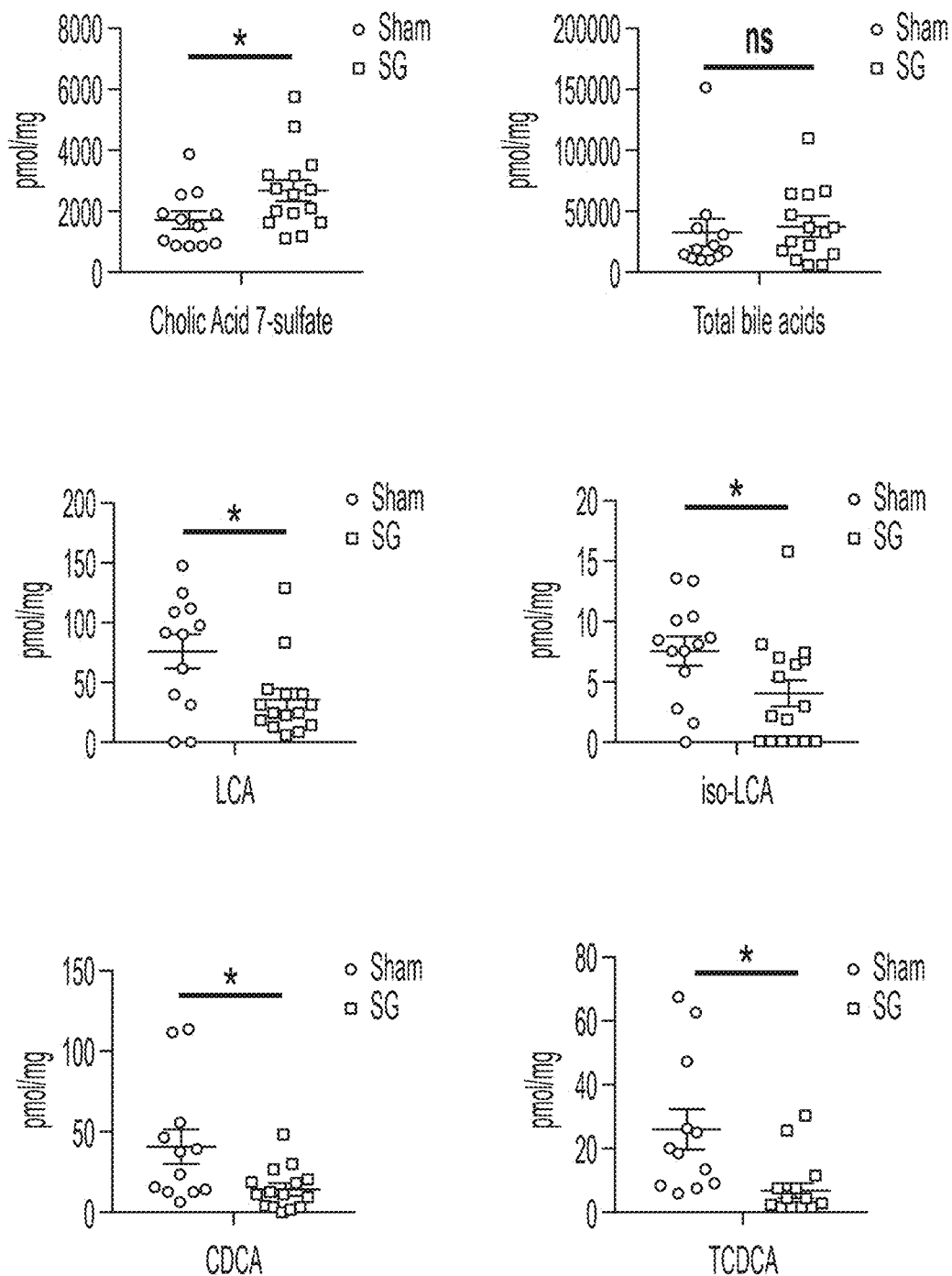
FIG. 2A-B shows that bile acid profiling reveals significant changes in individual bile acids including cholic acid 7-sulfate in mice post-sleeve.
Figure 18A:
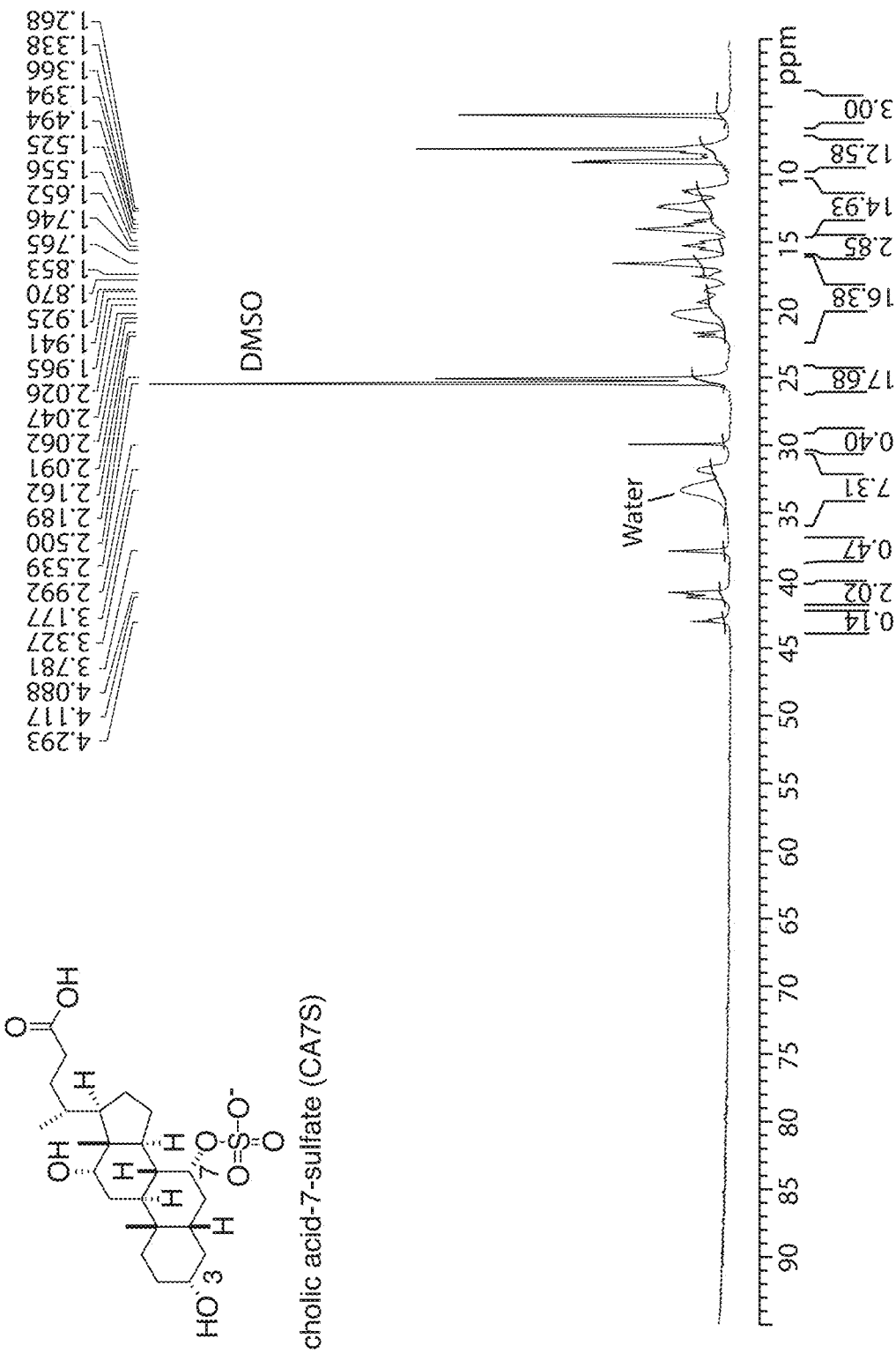
FIG. 18A-B shows the NMR spectroscopy and identification of cholic acid 7-sulfate (CA7S).
Figure 18B:
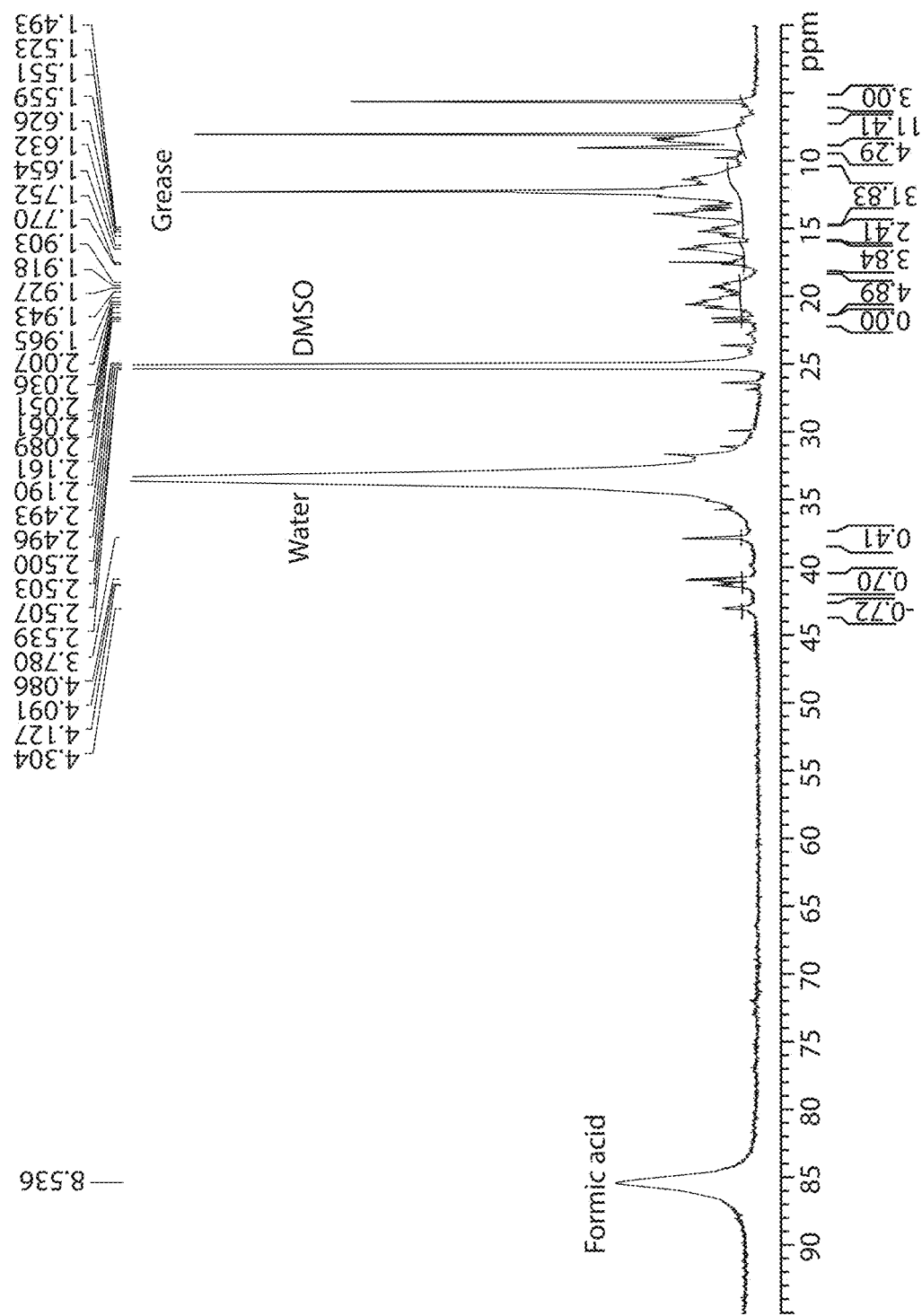
Figure 19A:
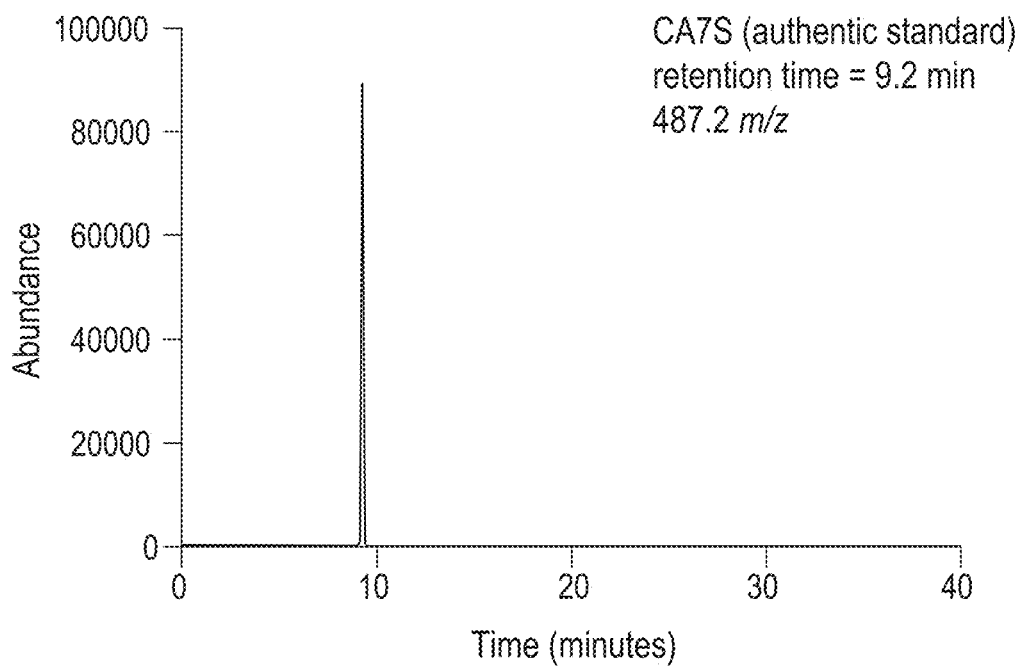
FIG. 19A-B shows UPLC-MS data.
Figure 19B:
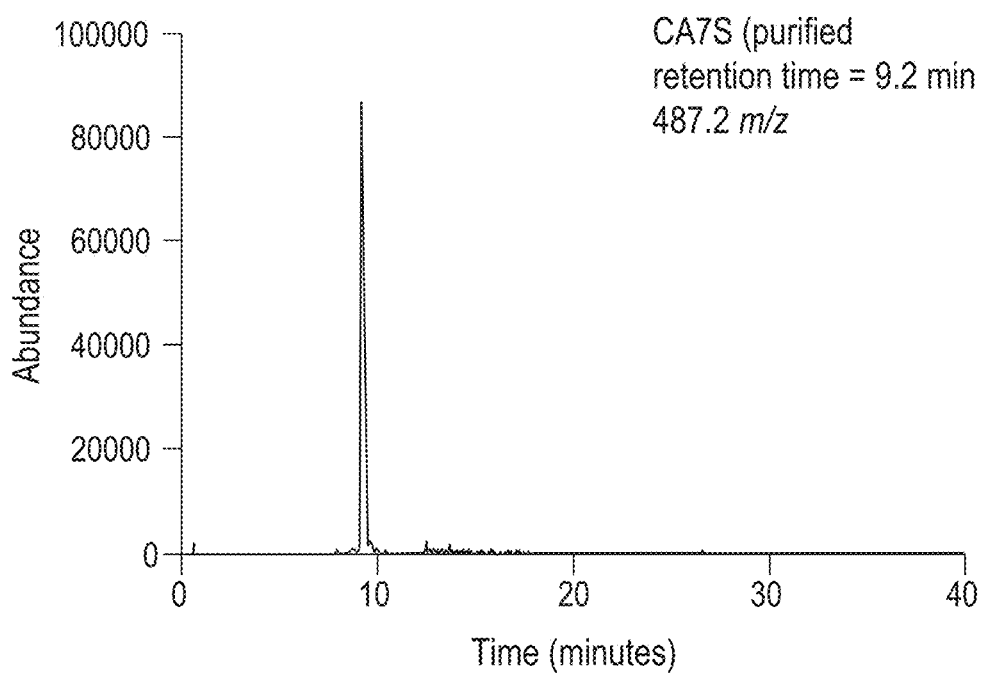

Bile acid profiling was performed and revealed significant changes in individual bile acids in mice post-sleeve. Interestingly, mice 6 weeks post-sleeve have higher levels of cholic acid 7-sulfate in their cecum compared to sham-operated mice (FIG. 2A). It was confirmed that the molecule in the bile acid was cholic acid 7-sulfate by NMR (FIG. 18A-B). Furthermore, mice post-sleeve have lower levels of secondary bile acid LCA and components of the "CDCA pathway" including CDCA, TCDCA, and iso-LCA in their cecum (FIG. 2A).

Figure 2B:
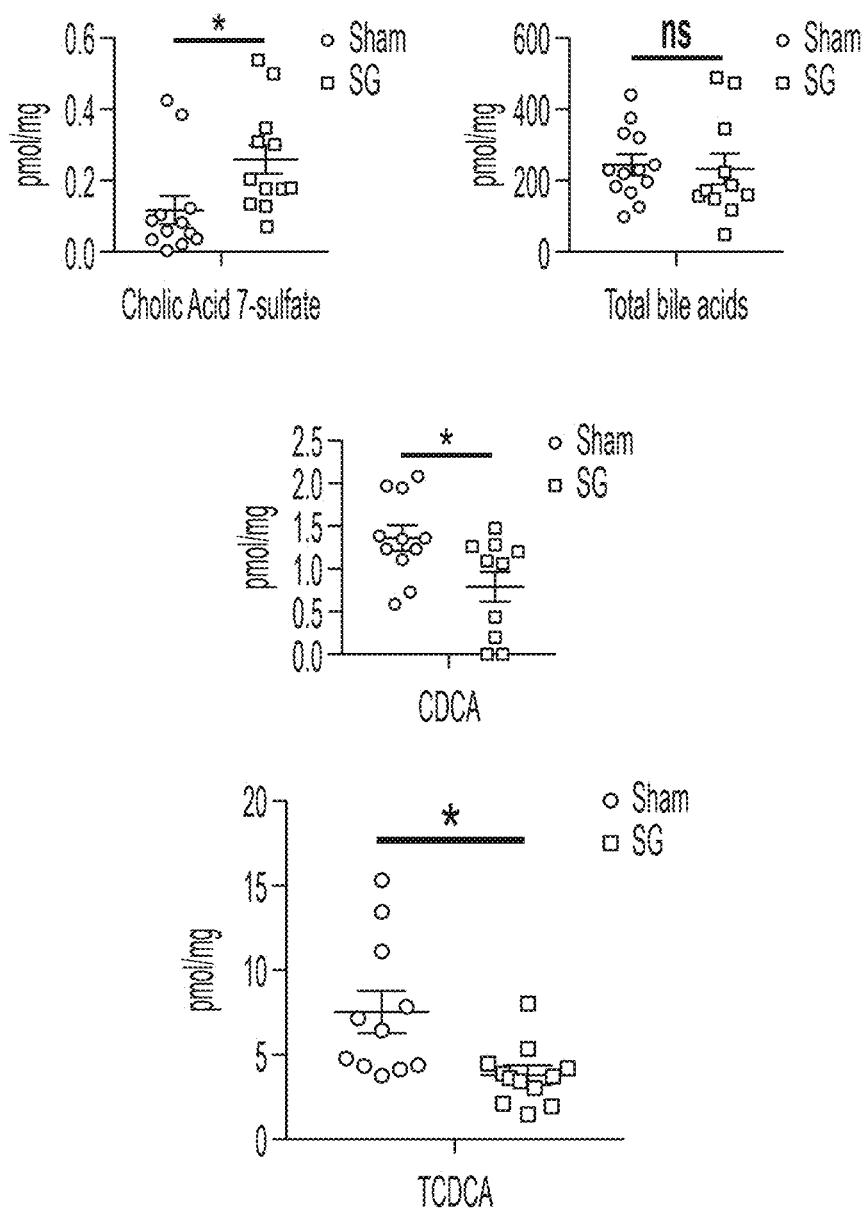
Figure 6:
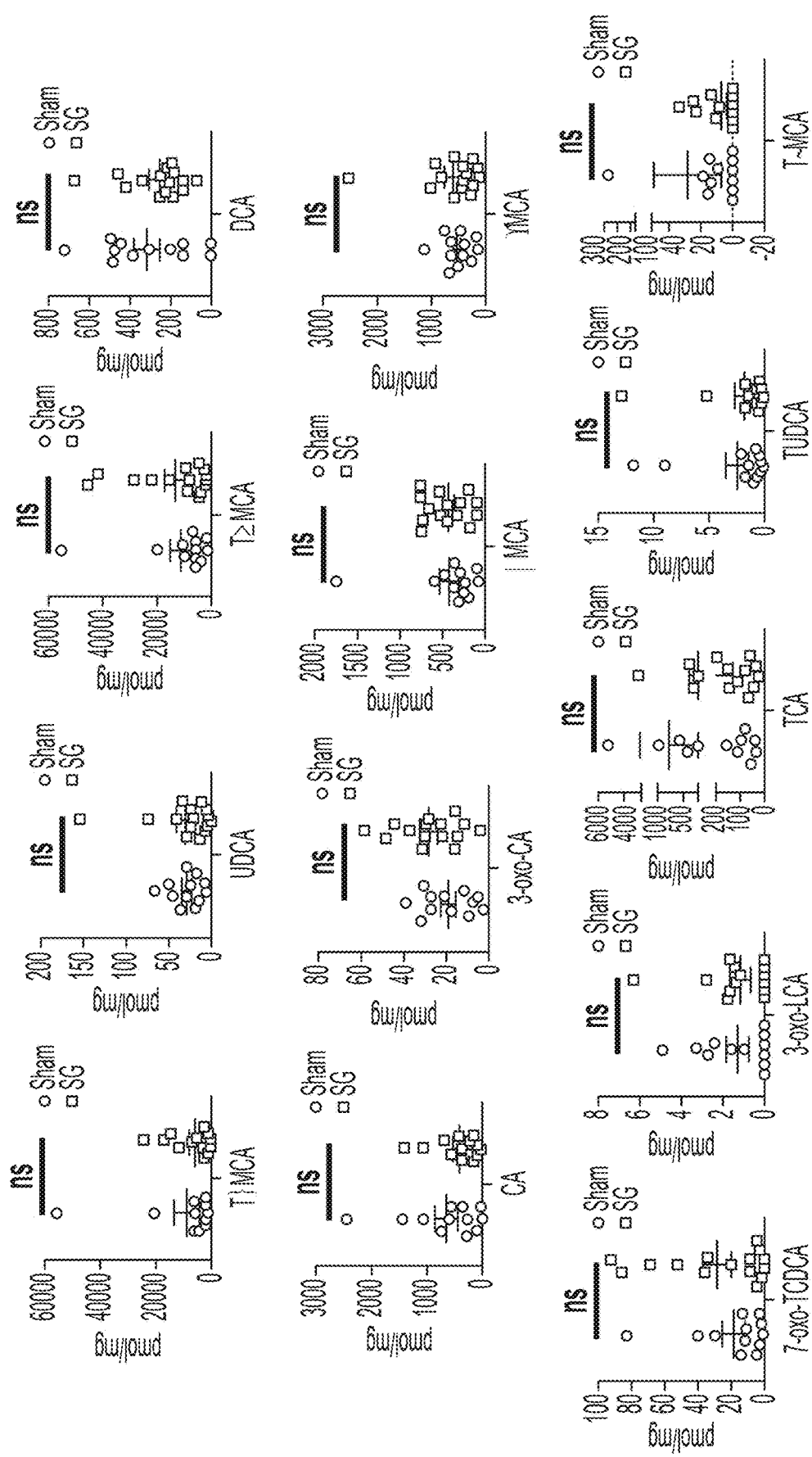
FIG. 6 shows that total bile acids and other bile acids did not differ significantly in the cecum of mice with sleeve or sham surgery.
Figure 7:
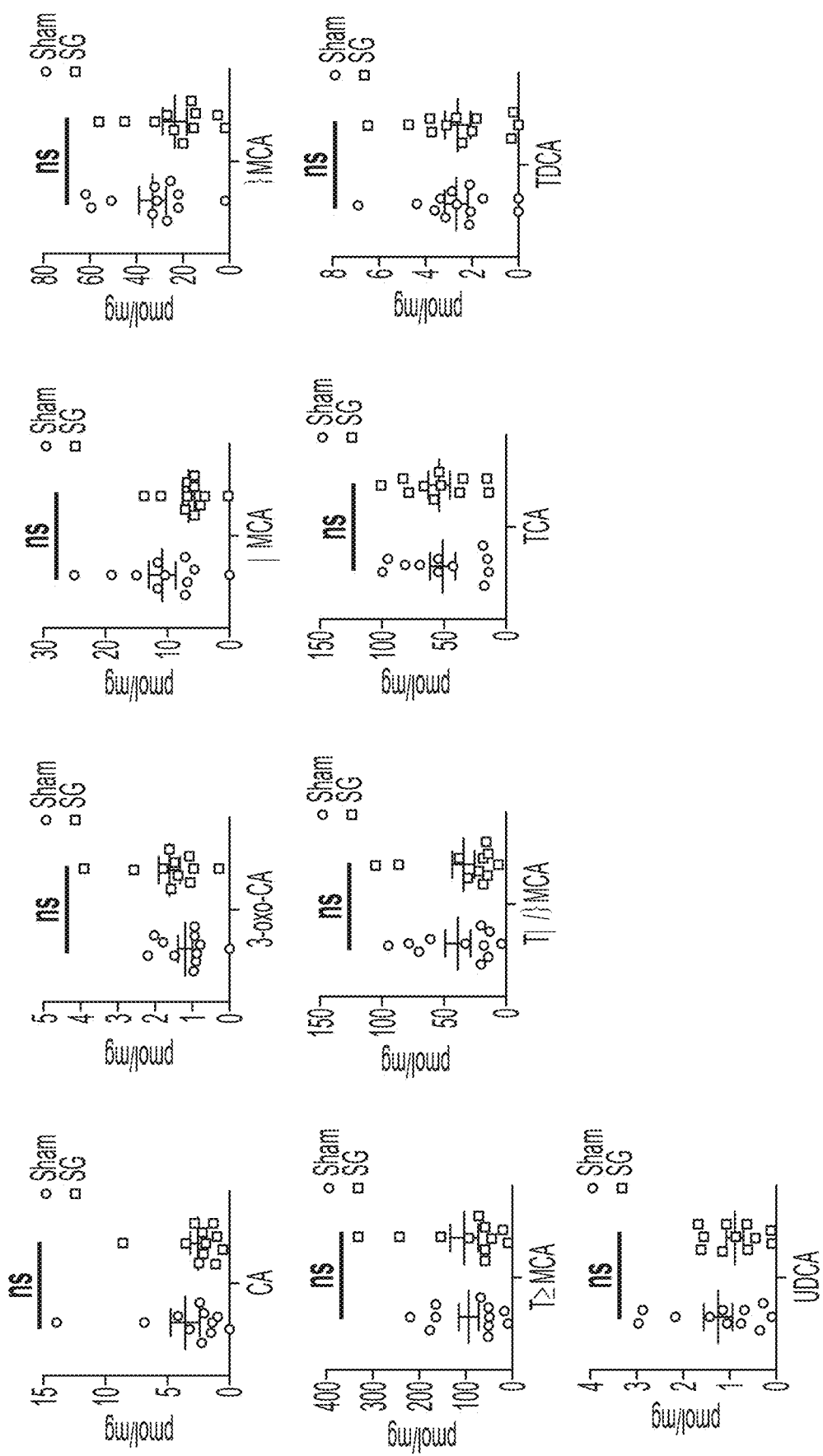
FIG. 7 shows that total bile acids and other bile acids did not differ significantly in the liver of mice operated with sleeve or sham surgery.

The total bile acids and other bile acids did not differ significantly in cecum of mice operated with sleeve or sham surgery (FIG. 6). Sleeve mice livers showed increased cholic acid 7-sulfate, CDCA, and TCDCA (FIG. 2B). However, total bile acids and other bile acids did not differ significantly in liver of mice operated with sleeve or sham surgery (FIG. 7).

Figure 3A:
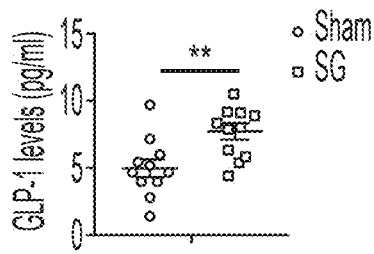
FIG. 3A-D shows that cholic acid 7-sulfate is a TGR5 agonist and induces GLP-1 secretion in vitro.
Figure 3B:
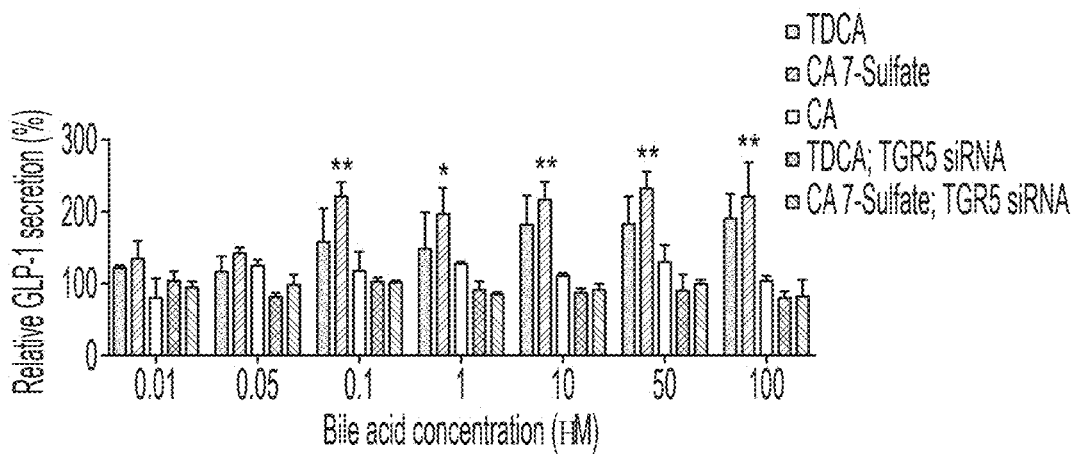

It was observed that sleeve mice show increase in GLP-1 in systemic circulation (FIG. 3A). Cholic acid 7-sulfate induces GLP-1 secretion in vitro better than the known GLP-1 inducer TDCA, while cholic acid had no effect (FIG. 3B and FIG. 8).

Figure 8A:
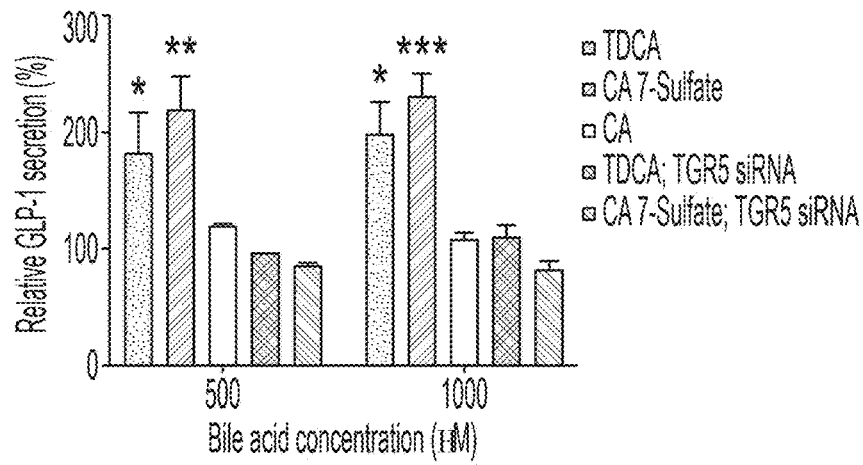
FIG. 8A-C shows that cholic acid 7-sulfate-mediated induction of GLP-1 requires TGR5.

To identify a particular target of cholic acid 7-sulfate, it was discovered that cholic acid 7-sulfate-mediated induction of GLP-1 and requires TGR5. This was confirmed when knockdown of TGR5 abolished GLP-1 secretion (FIG. 3B and FIG. 8A). Therefore, cholic acid 7-sulfate is a TGR5 agonist and induces GLP-1 secretion in vitro.

Figures 3C, 3D:
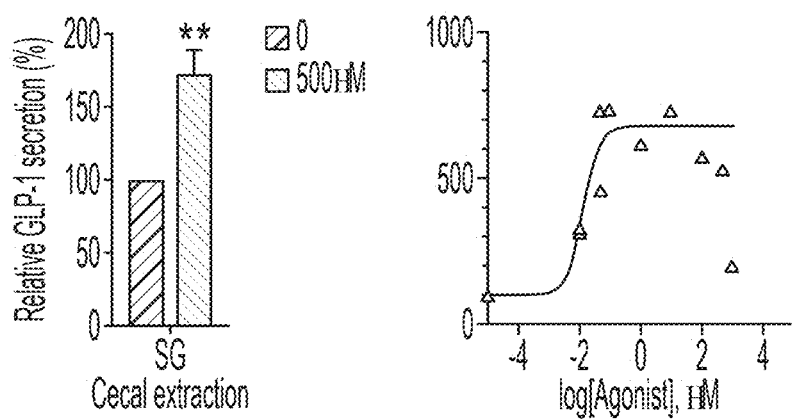
Figure 8B:
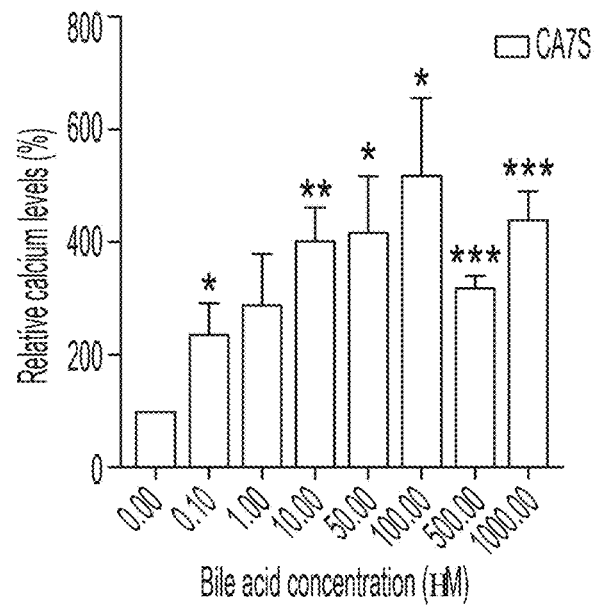
Figure 8C:
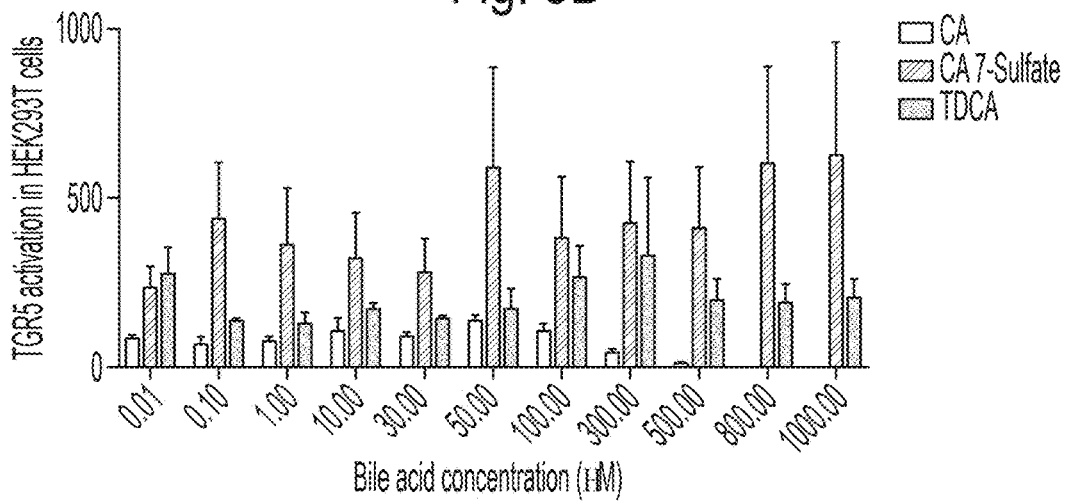
Figure 9:
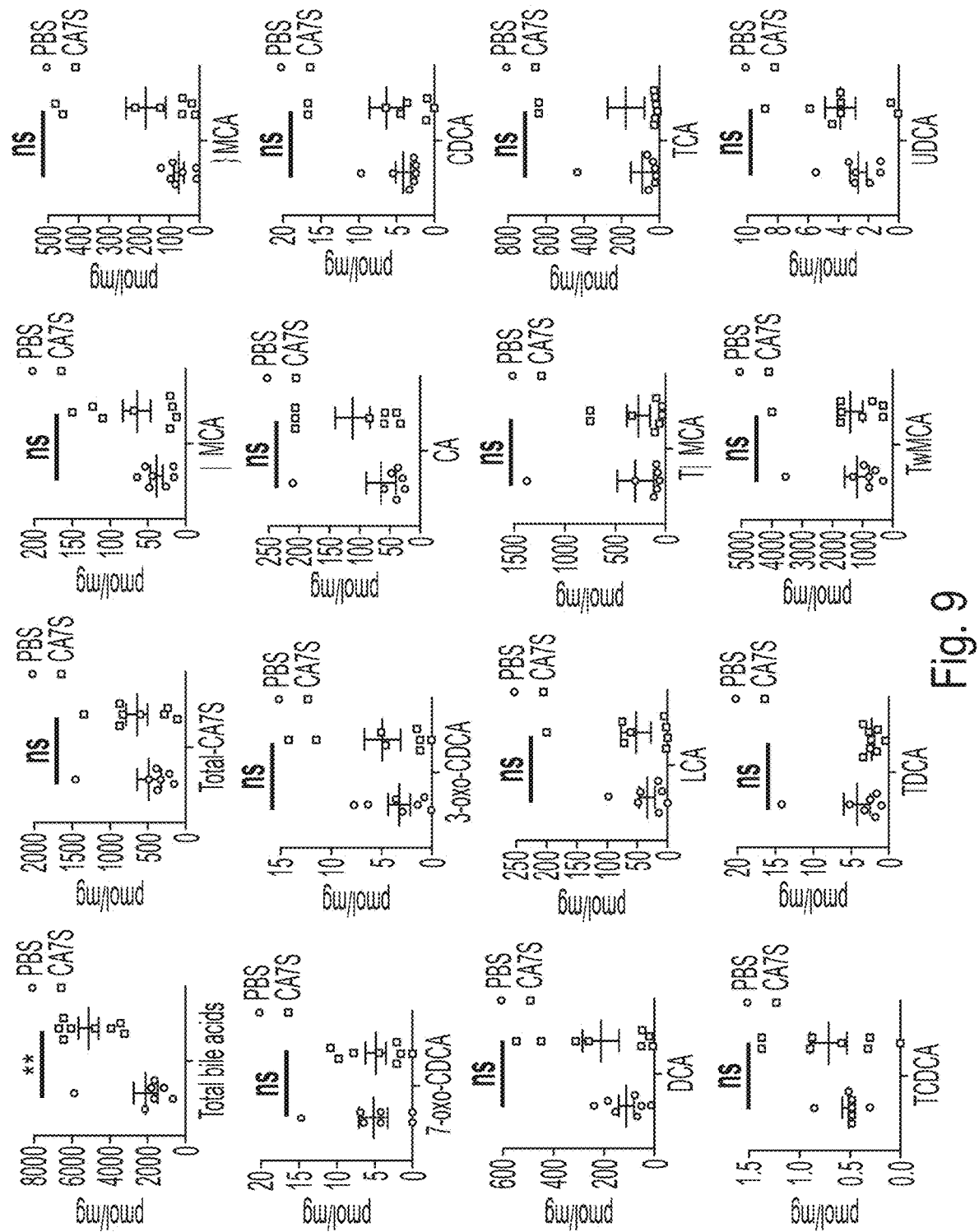
FIG. 9 shows that ectopic introduction of cholic acid 7-sulfate allowed only minor amounts to leak into systemic circulation and into the portal vein. This did not significantly affect other bile acids in the cecum, blood, or the portal vein.
Figure 10:
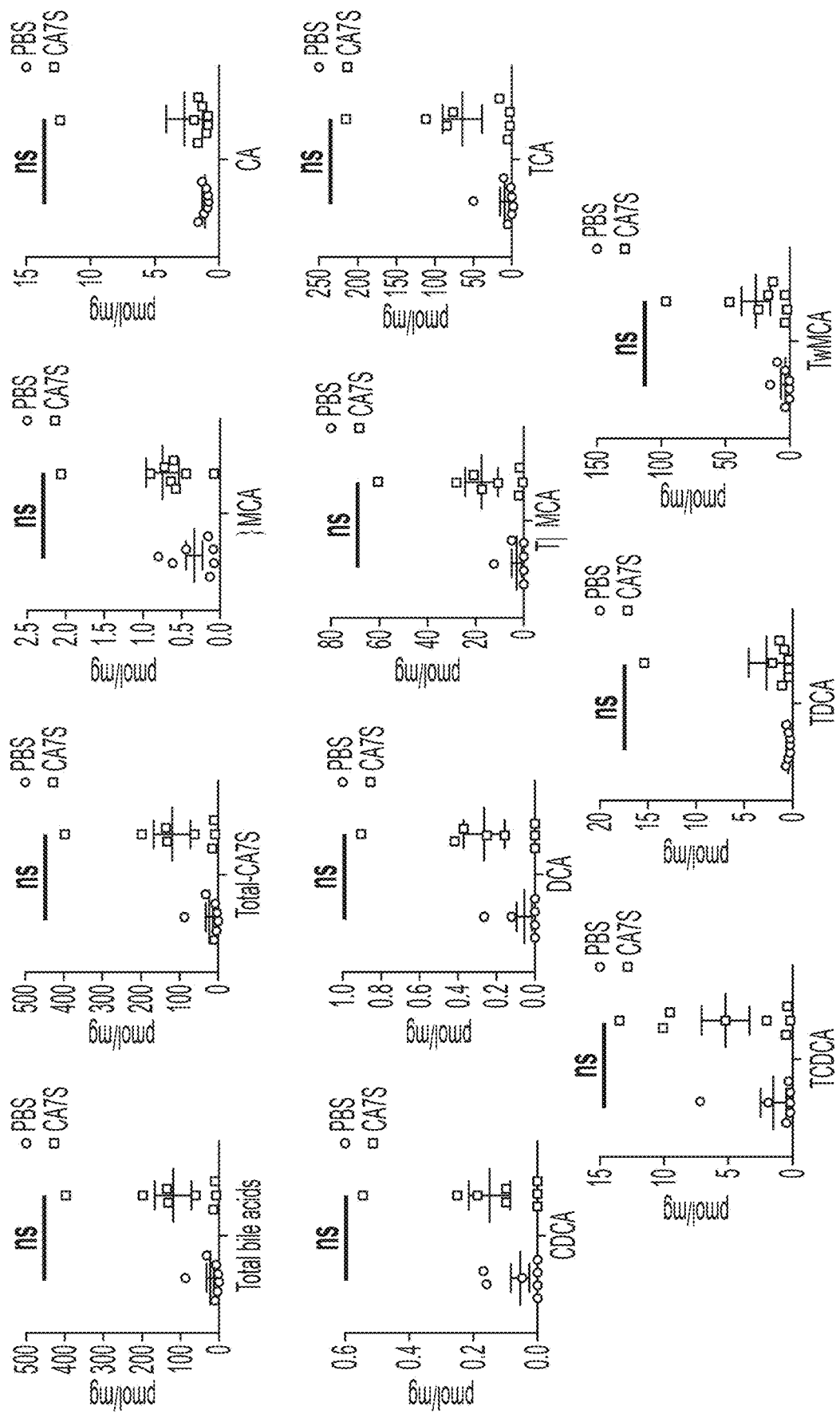
FIG. 10 shows that ectopic introduction of cholic acid 7-sulfate allowed only minor amounts to leak into systemic circulation and into the portal vein. This did not significantly affect other bile acids in the cecum, blood, or the portal vein.
Figure 11:
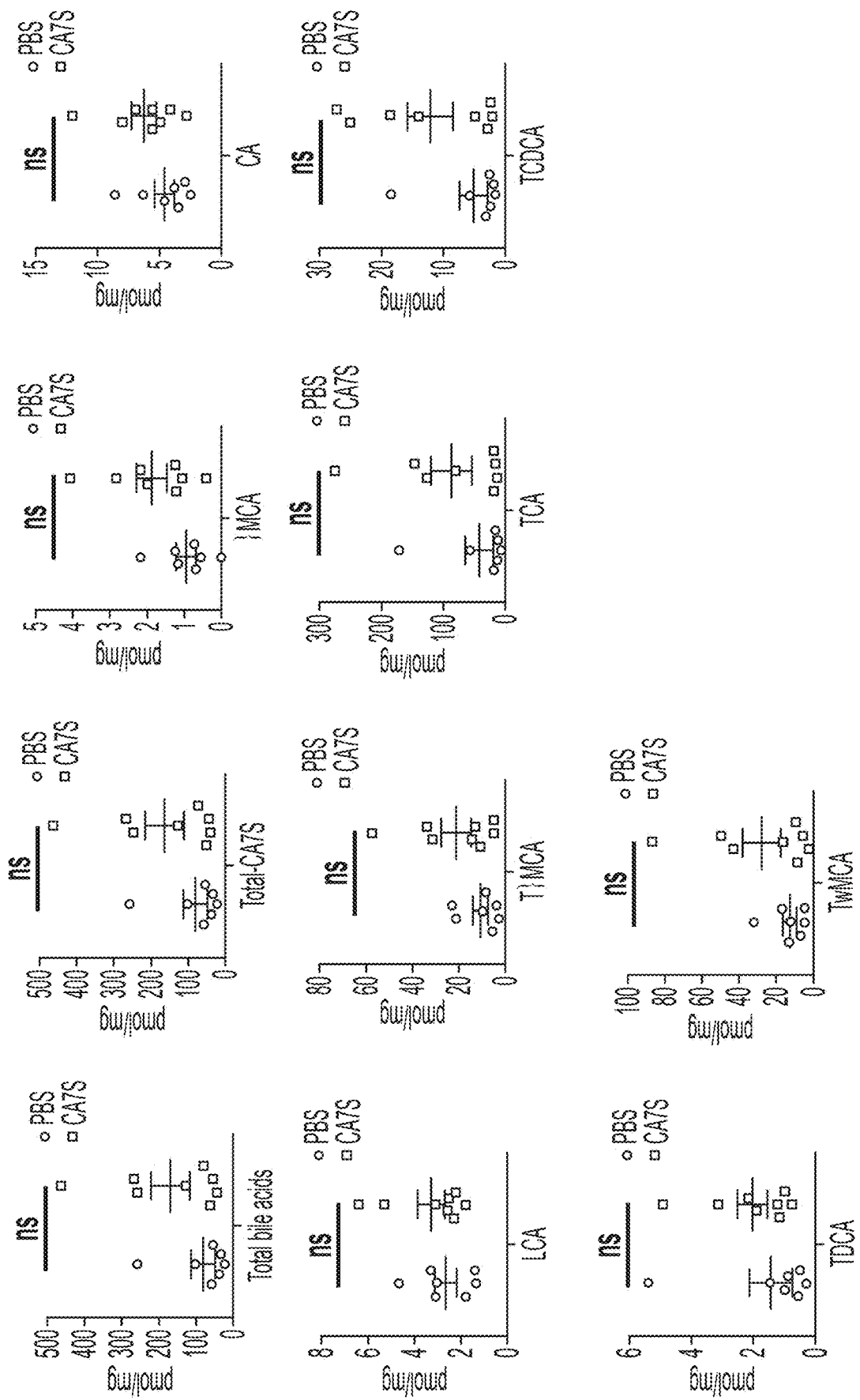
FIG. 11 also shows that ectopic introduction of cholic acid 7-sulfate allowed only minor amounts to leak into systemic circulation and in the portal vein. This did not significantly affect other bile acids in the cecum, blood, or the portal vein.

To further investigate this mechanism, cholic acid 7-sulfate was extracted from cecum of mice and found to also exhibit activity inducing GLP-1 secretion in vitro (FIG. 3C). Cholic acid 7-sulfate activates TGR5 in L-cells, dose response curve shows an EC50 of 0.013 µM (FIG. 3D). Cholic acid 7-sulfate increased calcium levels in L-cells in vitro (FIG. 8B). Cholic acid 7-sulfate induces TGR5 activation in HEK293T cells (FIG. 8C).

Figure 4A:
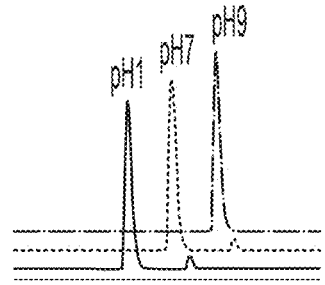
FIG. 4A-H shows that acute cholic acid 7-sulfate treatment induces GLP-1 and reduces serum glucose levels in vivo.
Figure 4B:
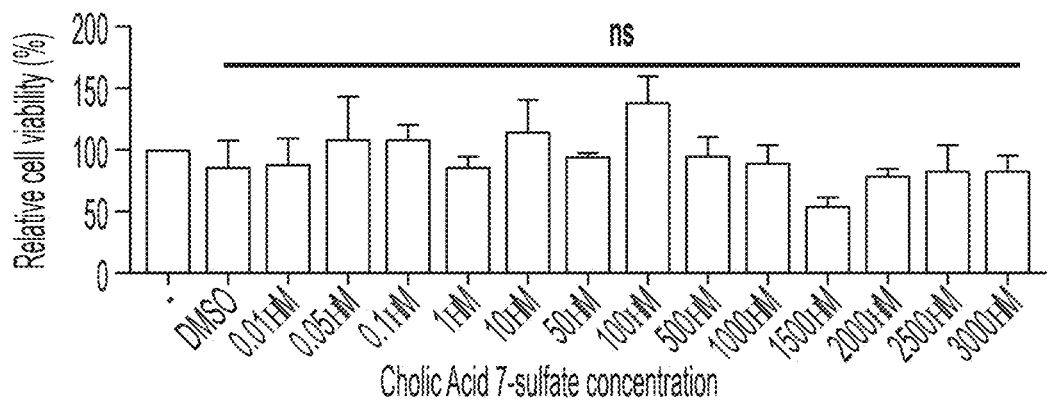
Figure 4C:
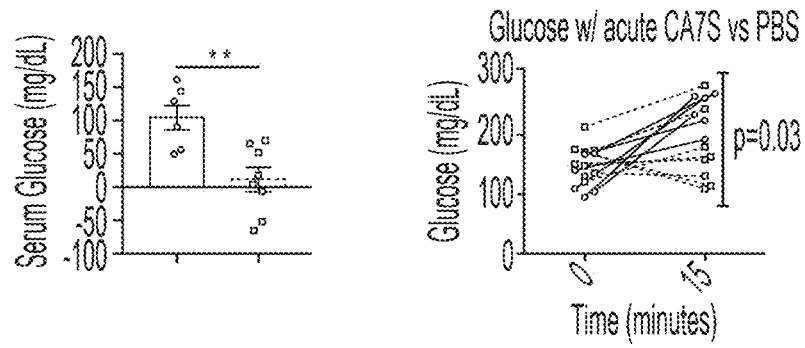
Figure 4D:
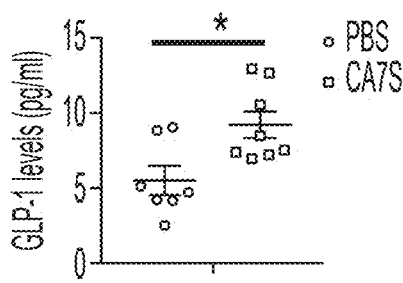
Figure 4E:
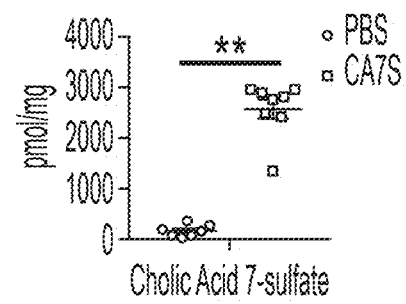
Figure 4F:
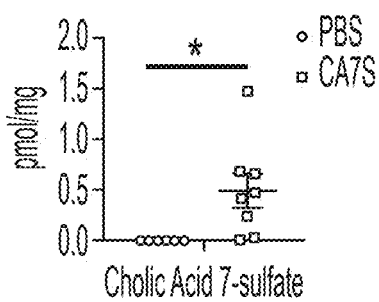
Figure 4G:
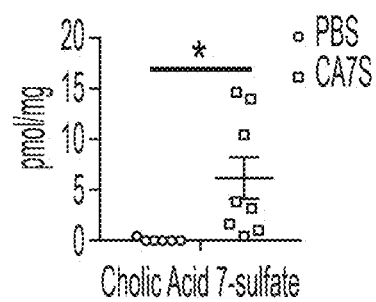
Figure 4H:
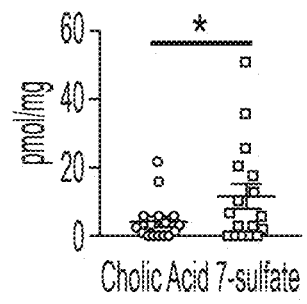

Cholic acid 7-sulfate is stable in a wide range of pHs, and has no toxicity in intestinal Caco cells in vitro (FIG. 4A-B). Treatment of HFD-fed mice with cholic acid 7-sulfate in vivo reduced blood glucose levels and induced GLP-1 levels within 15 min. of treatment (FIG. 4C-D). Therefore, acute cholic acid 7-sulfate treatment induces GLP-1 and reduces serum glucose levels in vivo. Dosing with 1 mg cholic acid 7-sulfate resulted in ~2500 µM cholic acid 7-sulfate in the cecum, similar to the amounts that were observed in sleeve-operated mice (FIG. 4E). Ectopic introduction of cholic acid 7-sulfate allowed only minor amounts to leak into systemic circulation and in the portal vein, and did not significantly affect other bile acids in the cecum, blood, or the portal vein (FIG. 4F-G, FIG. 9-11). Feces from human patients pre- and post-sleeve gastrectomy also have an increase in cholic acid 7-sulfate (FIG. 4H).

Figure 12:
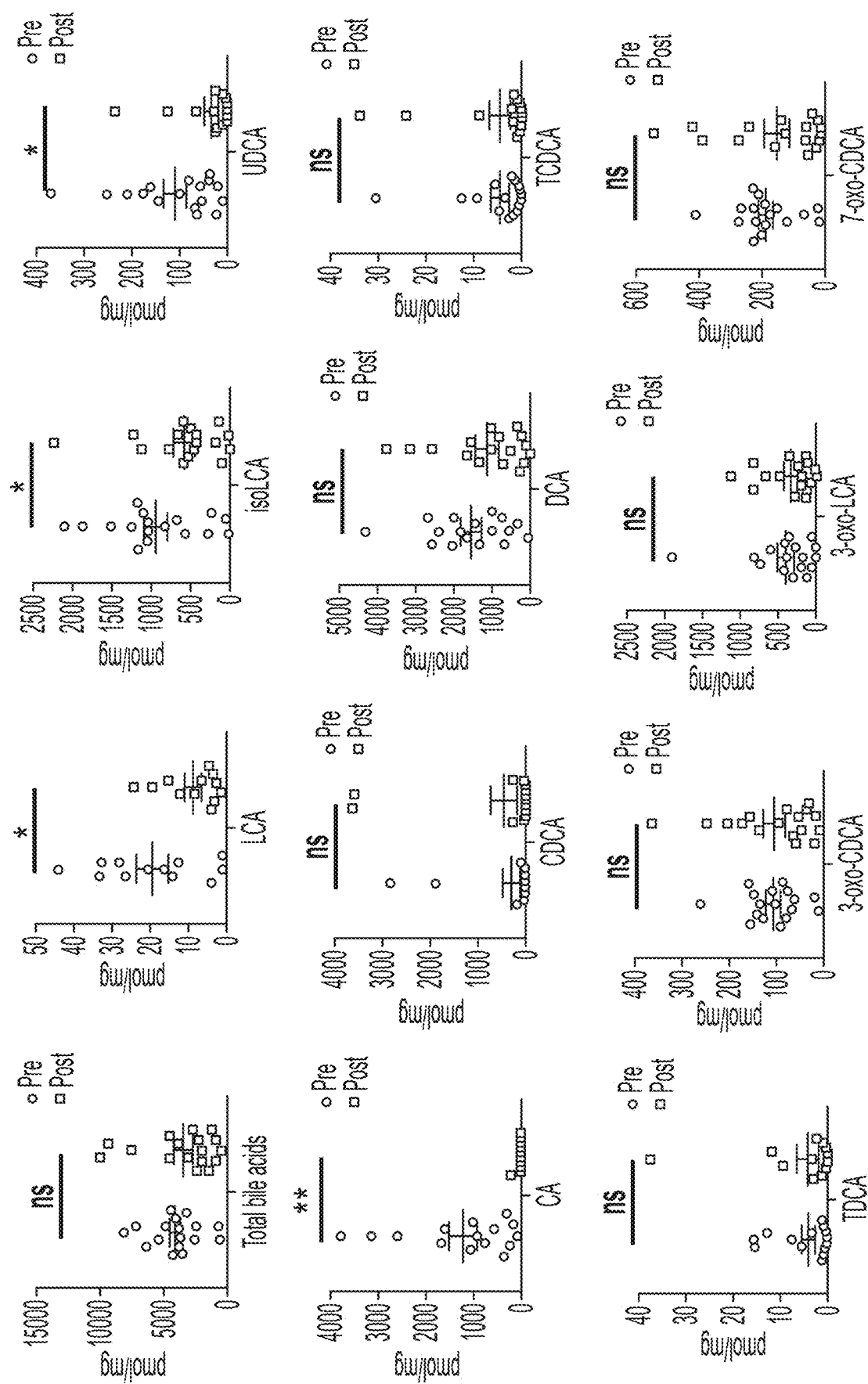
FIG. 12 shows that human fecal samples post-sleeve have a reduction in levels of secondary bile acids LCA, iso-LCA, and UDCA, similar to what was observed in mice post-sleeve. Other bile acids and total bile acids were not significantly affected, except for CA levels.

Interestingly, human fecal samples post-sleeve exhibit a reduction in levels of secondary bile acids LCA, iso-LCA, and UDCA, similar to what was observed in mice post-sleeve (FIG. 12). Other bile acids and total bile acids were not significantly affected, except for calcium levels. (FIG. 12).

Figure 5A:
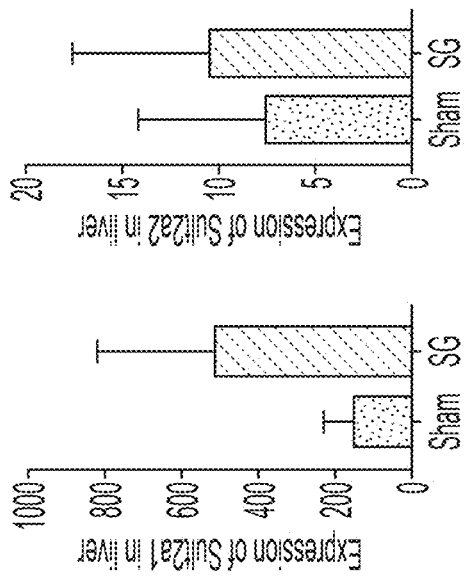
FIG. 5A-H shows that portal vein bile acids induce synthesis of cholic acid 7-sulfate via SULT2A1 enzyme.

Mice livers show an increase in SULT2A enzyme isoform 1, previously shown to sulfate bile acids (FIG. 5A).

Figure 5B:
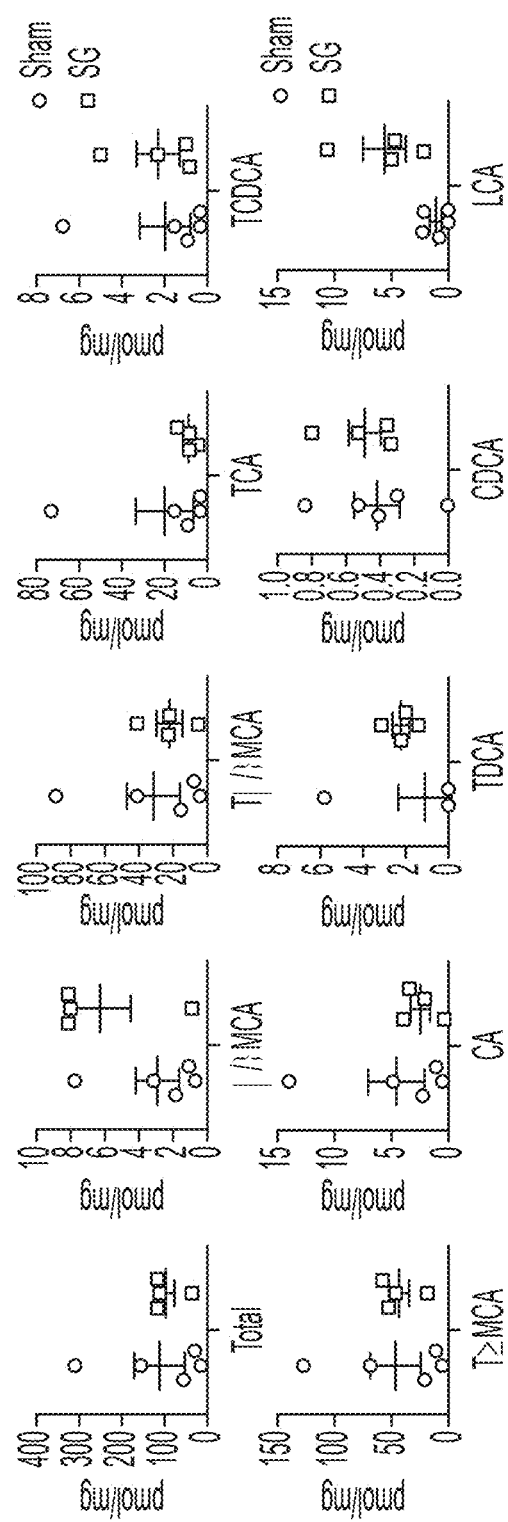
Figure 13:
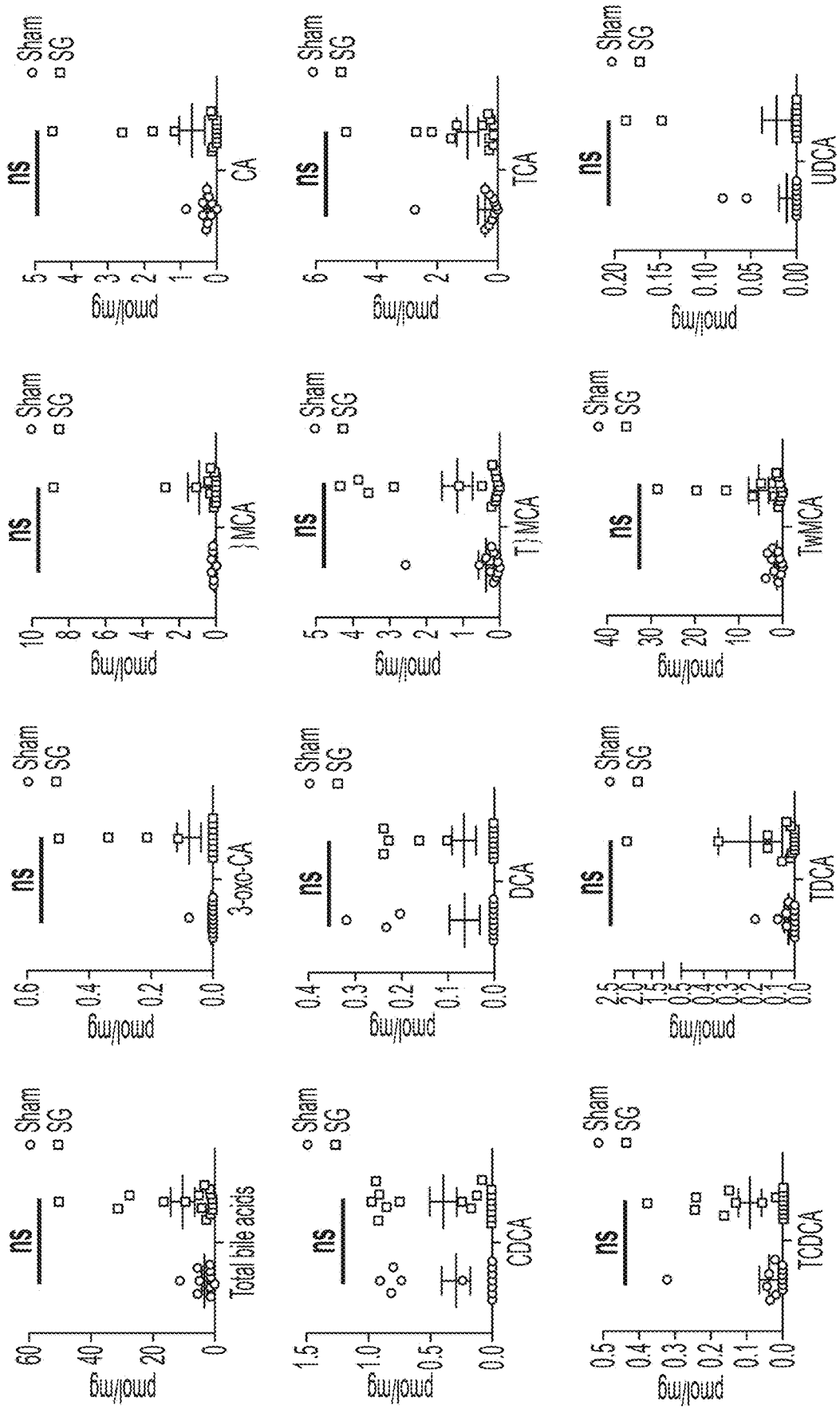
FIG. 13 shows that the portal vein had a very different repertoire of bile acids compared to circulating blood.

Sulfation is a detoxification method to excrete toxic bile acids. Bile acids have been shown to tightly regulate their own synthesis, conjugation, and sulfation. The liver is the major site for synthesis and sulfation of bile acids, therefore bile acids in the hepatic portal vein were analyzed to determine the origin of sulfated cholic acid and a mechanism for the increase in cholic acid 7-sulfate in sleeve mice. The hepatic portal vein is part of the enterohepatic circulation of bile acids. The liver receives 80% of its blood from the hepatic portal vein. The portal vein has a different repertoire of bile acids compared to circulating blood (FIG. 5B & FIG. 13).

Figure 5C:
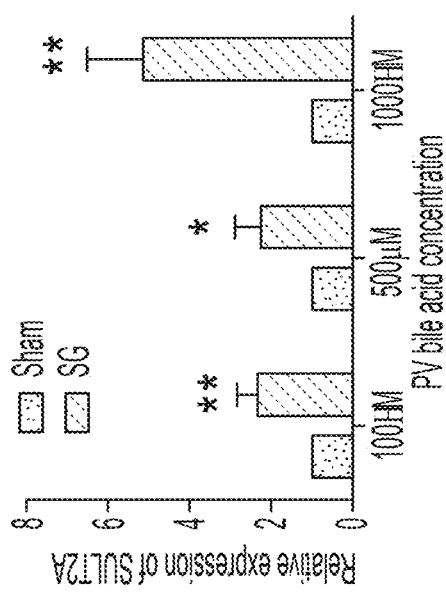

To not be bound by a particular theory, it was hypothesized that bile acids in the hepatic portal vein signal in the liver to induce sulfation of cholic acid. Pools of bile acids were tested mimicking those observed in the sleeve- and sham-operated mouse portal veins in inducing SULT2A1 in vitro. Using HepG2 cells, it was observed that the bile acid pool in the portal vein of sleeve-operated mice significantly induced SULT2A1 compared to the portal vein bile acid pool in sham-operated mice (FIG. 5C)

Figure 5D:
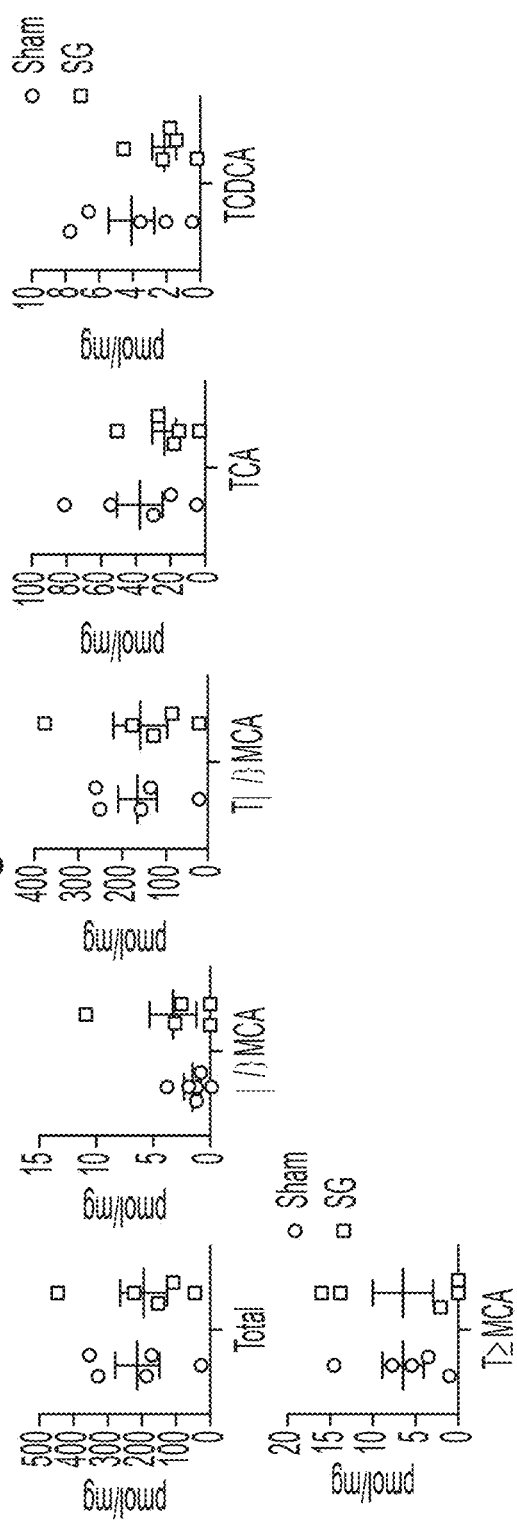
Figure 5E:
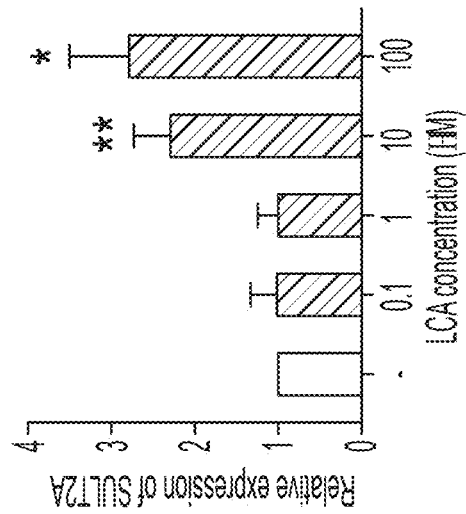

Bile acids are modified in the intestine by the microbiome. Therefore, the influence of the microbiome in inducing sulfation of bile acids in the liver was tested. Sleeve gastrectomy was performed and sham surgery on HFD-fed mice treated with antibiotics. Pools of bile acids mimicking those observed in the antibiotic-treated sleeve- and sham-operated mouse portal veins were tested inducing SULT2A1 in HepG2 cells. there was no difference in induction of SULT2A1 between the pools observed (FIG. 5D-E).

Figure 14:
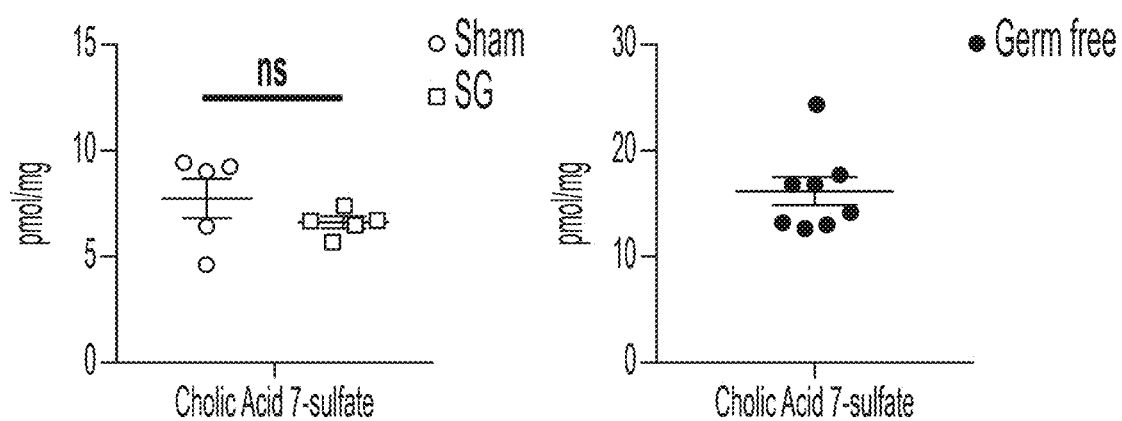
FIG. 14 shows that there is no cholic acid 7-sulfate in the liver and approximately 200-fold lower levels of cholic acid 7-sulfate in the cecum in antibiotic-treated mice compared to HFD-fed conventional mice.
Figure 15:
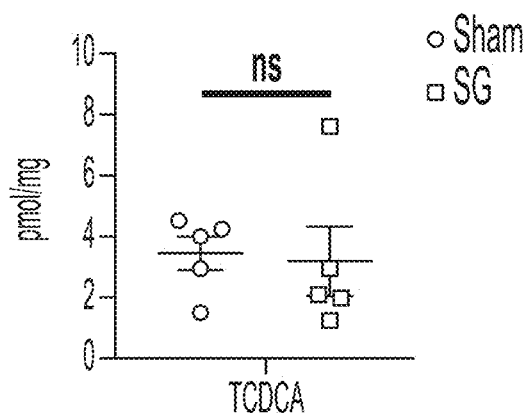
FIG. 15 shows TCDCA levels of Sham and SG mice.

Consistently, it was observed that there was not cholic acid 7-sulfate in the liver and approximately 200-fold lower levels of cholic acid 7-sulfate in the cecum in antibiotic-treated mice (FIG. 13 and FIG. 14) compared to HFD-fed conventional mice. Also, there was no significant difference in cholic acid 7-sulfate levels between antibiotic-treated sleeve- and sham-operated mouse cecum (FIG. 8). This suggests that a microbiome is required for sulfation of cholic acid. In support of this hypothesis, germ-free animals fed a high fat diet also show 200-fold lower cholic acid 7-sulfate in their cecum (FIG. 8).

To test which bile acid(s) may be involved in inducing SULT2A1 enzyme, the bile acids in the portal vein that were significantly different between HFD-fed conventional mice and HFD-fed mice treated with antibiotics were analyzed. It was observed that LCA, TDCA, CA, and CDCA were absent in the antibiotic-treated mouse portal veins (FIG. 5D).

Figure 5F:
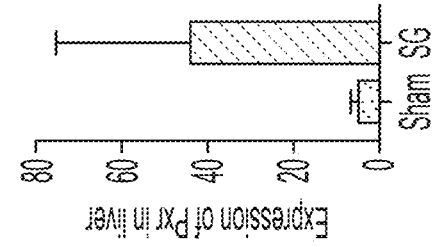
Figure 5G:
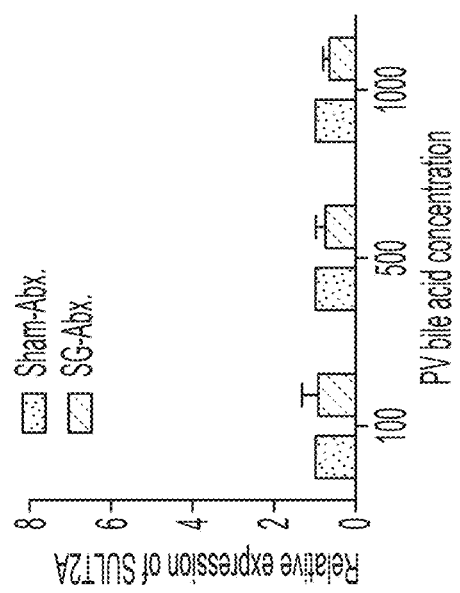
Figure 5H:
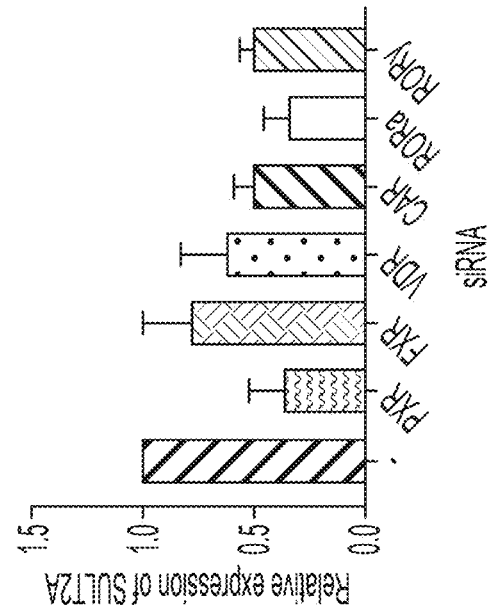

Amongst these, LCA induced SULT2A1 in HepG2, while others did not in all concentrations tested (FIG. 5F). LCA levels were also increased in sleeve mice compared to sham-operated, while the total bile acid levels did not differ significantly, suggesting that LCA is an inducer of SULT2A1 expression (FIG. 5B). To identify the receptor involved in LCA-mediated induction of SULT2A1 in liver cells, siRNA of known receptors was performed. The PXR receptor was consistently upregulated in mice post-sleeve in the liver (FIG. 5G-H).

Example 2. Bariatric Surgery Reveals a Gut-Restricted TGR5 Agonist and GLP-1 Secretagogue Summary The molecular mechanisms underlying the near-immediate resolution of diabetic phenotypes following bariatric surgery remain largely unknown. Here, the data show that sleeve gastrectomy leads to an increase in a naturally occurring bile acid metabolite, cholic acid 7-sulfate. This metabolite is a gut-restricted TGR5 agonist that induces GLP-1 secretion and reduces blood glucose levels in a mouse model. Thus these studies reveal a molecular link between bariatric surgery and amelioration of diabetic phenotypes.

Results

Obesity and type 2 diabetes (T2D) are medical pandemics. Bariatric surgery, in the form of Roux-en-Y gastric bypass or sleeve gastrectomy (SG), is currently the most effective and durable treatment for obesity and related comorbidities[1,2]. Owing to robust post-surgical metabolic benefits and favorable side-effect profile, SG is the most common bariatric surgery performed in the US[3]. While maximal weight loss occurs at 1 year, many patients see resolution of their T2D within days of surgery[4]. For a majority of patients, remission is durable, lasting for at least 7 years[1,4]. The molecular mechanisms underlying T2D remission, however, remain largely unknown[5].

Two consistently observed post-surgical changes are increased levels of GLP-1, a circulating incretin hormone, and changes in the systemic repertoire of bile acids (BAs). BAs are cholesterol-derived metabolites that play crucial roles in host metabolism by acting as detergents that aid in the absorption of lipids and vitamins and as ligands for host receptors[6]. While the potential therapeutic benefits of GLP-1 have been recently explored[7], the causal role of bile acids in mediating beneficial metabolic changes post-surgery remains unclear. Thus far, research efforts have focused on overall changes in the total BA pool or in conjugated and unconjugated BA forms following bariatric surgery[8,9]. Individual BAs, however, have different binding affinities for nuclear hormone receptors (NhRs) and GPCRs, and thus unique abilities to modulate glucose homeostasis, lipid accumulation, and energy expenditure[6,10]. It is not sufficient, therefore, to limit analyses to whole classes of BAs. Levels of individual BAs pre- and post-SG were identified to investigate whether specific BAs could be causally linked to changes in metabolic outcomes.

Rodent SG models mimic the positive metabolic outcomes observed in humans and are thus suitable for studying post-surgical outcomes[11]. In this study, SG or sham surgery was performed on insulin-resistant, diet-induced obese (DIO) mice. SG mice displayed improved glucose tolerance and insulin sensitivity 4-5 weeks post-surgery compared to shams (FIG. 16A-B). Mice were euthanized six weeks post SG or sham surgery and their tissues were harvested. Consistent with studies involving human patients[8], an increase in circulating GLP-1 in SG mice was observed (FIG. 16C). GLP-1 is secreted post-prandially by L-cells in the lower intestine and directly stimulates pancreatic insulin release[7]. Low levels of GLP-1 are associated with T2D, whereas increased levels post-SG correlate with weight-loss and T2D remission[12,13]. Activation of TGR5, a G-protein coupled receptor (GPCR) with a primary role in energy metabolism, stimulates GLP-1 secretion[14]. Notably, gluco-regulatory benefits of SG are attenuated in TGR5−/− mice, demonstrating the important role of this receptor in mediating the anti-diabetic effects of SG[15].

Figure 16F:
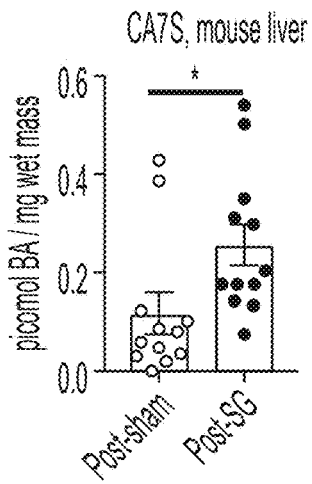

Individual BAs that are known agonists of TGR5 have been shown to induce GLP-1 secretion in lower-intestinal L-cells[8,14]. Next, individual Bas were assayed in cecal contents of SG and sham mice using UPLC-MS. A significant increase in a monosulfated, trihydroxy bile acid in cecal contents of SG mice were observed. Using NMR spectroscopy, this compound was identified as as cholic acid 7-sulfate (CA7S) (FIG. 16D-E, FIGS. 18-19). This molecule is a sulfated metabolite of cholic acid (CA), an abundant primary bile acid in both mice and humans. Sulfation of bile acids predominantly occurs in the liver[16]. Consistent with this observation, increased levels of CA7S were observed in the liver of SG mice (FIG. 16F). Notably, CA7S was the only bile acid detected whose levels were significantly higher in SG mouse cecal contents.

Figure 16G:
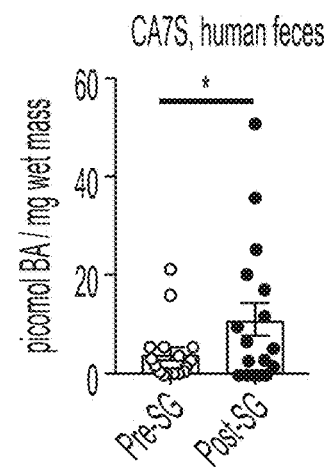

To determine the clinical relevance of this finding, BAs were assayed in stool from human patients who had undergone SG. Remarkably, fecal CA7S levels were also significantly increased in patients six months post-SG compared to their pre-surgery levels (FIG. 16G). This is the first report of a specific BA metabolite that is significantly increased following SG in both mice and human subjects.

Figure 16H:
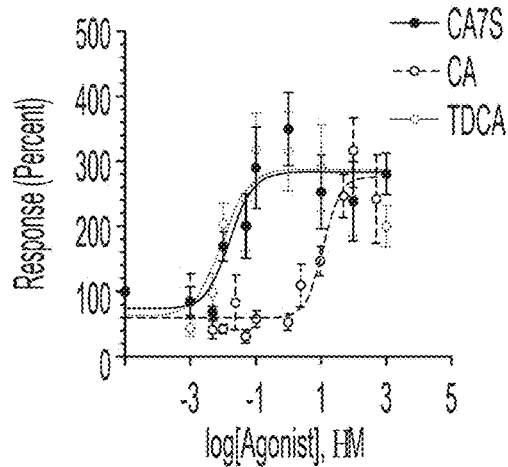

Next, it was assessed whether CA7S is causally involved in the development of post-SG metabolic phenotypes, and in particular, GLP-1 secretion. Previous work has shown that sulfation of both natural BAs and synthetic analogs significantly alters the TGR5 agonistic activity of these compounds[17]. To not be bound by a particular theory, it was hypothesized that CA7S might possess altered TGR5 agonism compared to CA. The activation of human TGR5 in HEK293T cells by CA7S, CA, or tauro-deoxycholic acid (TDCA), a naturally occurring BA and potent TGR5 agonist[18] were examined. CA7S activated human TGR5 in a dose-dependent manner and to a similar extent as TDCA. CA7S also displayed a lower EC50 (0.17 µM) than CA (12.22 µM) (FIG. 16H).

Figure 16I:
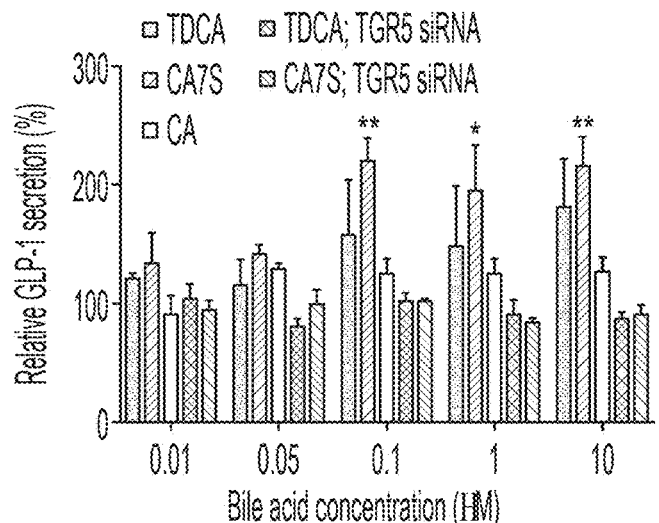

TDCA is currently one of the most potent naturally occurring GLP-1 secretagogue known[18]. It was observed that CA7S induced GLP-1 secretion to a similar degree as TDCA in a dose-dependent manner, while CA had no effect on GLP-1 secretion (FIG. 16I and FIG. 20A-B). CA7S extracted directly from cecal contents of SG mice also induced GLP-1 secretion in vitro (FIG. 20C). Furthermore, siRNA-mediated knockdown of TGR5 abolished both CA7S- and TDCA-mediated secretion of GLP-1 (FIG. 16I and FIG. 20A-B). This result indicates that induction of GLP-1 secretion by CA7S requires TGR5. TGR5 agonism also results in elevated intracellular calcium levels[19]. Consistent with this previous finding, a dose-dependent increase in calcium levels in NCI-H716 cells treated with CA7S was observed (FIG. 20D). Taken together, these results demonstrate that CA7S, a naturally occurring bile acid metabolite, is a potent TGR5 agonist and GLP-1 secretagogue.

Figure 17A:
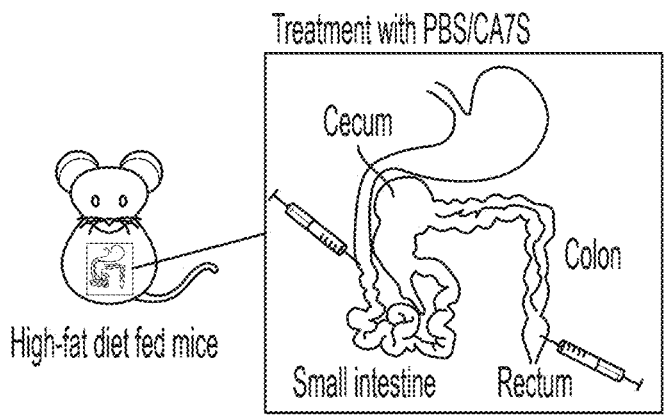
FIG. 17A-E shows acute CA7S treatment induces GLP-1 and reduces serum glucose levels in vivo.
Figure 17B:
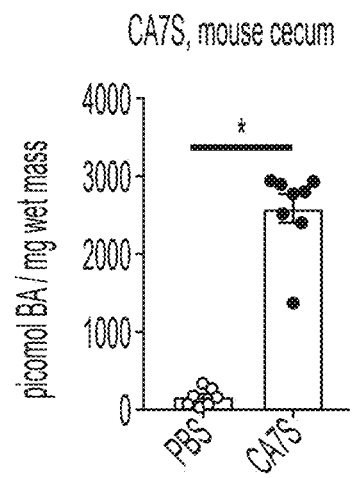
Figure 17C:
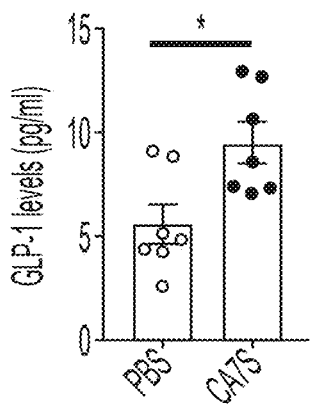
Figure 17D:
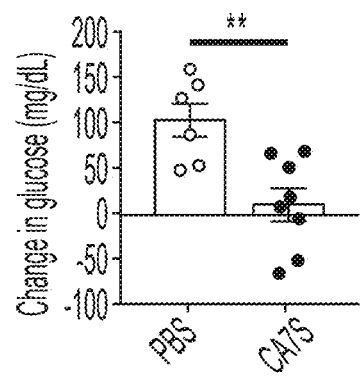
Figure 17E:
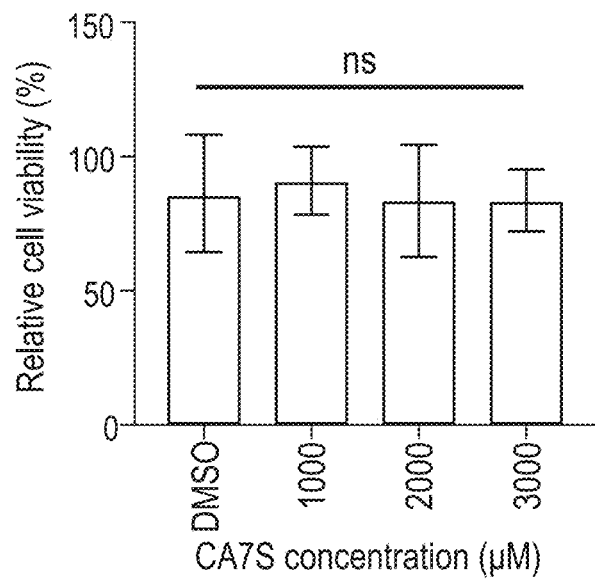

Next, the ability of CA7S to stimulate GLP-1 secretion and improve hyperglycemia in vivo was evaluated. DIO mice were treated with either CA7S or PBS via duodenal and rectal catheters (FIG. 17A). Administration of 1 mg of CA7S resulted in 2500 pmol/mg wet mass of CA7S on average in cecal contents, a concentration similar to observed post-SG levels (FIG. 17D, FIG. 17B, Table 1 below). Consistent with in vitro studies, CA7S-treated mice displayed increased systemic GLP-1 levels compared to PBS-treated mice within 15 minutes (FIG. 17C). Moreover, CA7S-treated mice exhibited reduced blood glucose levels compared to PBS-treated mice, suggesting that CA7S is protective against hyperglycemia (FIG. 17D).

TABLE 1

Cholic acid concentrations

| Treatment | Tissue | Cholic acid 7-sulfate concentration (mean ± SEM) |
|---|---|---|
| HFD-fed mice; sham surgery | Cecum | 1726 ± 267.1 pmol/mg |
|  | Liver | 0.116 ± 0.04 pmol/mg |
|  | Hepatic portal vein Blood | 0 ± 0 pmol/mg |
|  |  | 0 ± 0 pmol/µl |
| HFD-fed mice; sleeve gastrectomy | Cecum | 2661 ± 331.3 pmol/mg |
|  | Liver | 0.2575 ± 0.04 pmol/mg |
|  | Hepatic portal vein Blood | 0 ± 0 pmol/mg |
|  |  | 0 ± 0 pmol/µl |
| HFD-fed mice; acute PBS treatment | Cecum | 161.1 ± 46.41 pmol/mg |
|  | Hepatic portal vein Blood | 0.065 ± 0.056 pmol/mg |
|  |  | 0 ± 0 pmol/µl |
| HFD-fed mice; acute cholic acid 7-sulfate treatment | Cecum | 2577 ± 185.3 pmol/mg |
|  | Hepatic portal vein Blood | 6.128 ± 2.111 pmol/mg |
|  |  | 0.4954 ± 0.1673 pmol/µl |

CA7S was undetectable in both circulating and portal venous blood from SG and sham-operated mice (Table 1). This result suggests that CA7S is neither recycled via enterohepatic circulation nor absorbed into systemic circulation. Ectopic introduction of CA7S resulted in only minor amounts in circulating and portal venous blood (Table 1). These findings are consistent with previous observations that sulfated BAs, in particular 7α-sulfated BAs, are poorly absorbed in the intestine[16].

The results from this study may have clinical implications. While synthetic TGR5 agonists ameliorate diabetic phenotypes[20], their use as therapeutics is hampered by significant side effects. These compounds are absorbed into systemic circulation and can induce changes in the circulatory, digestive, and endocrine systems, causing changes in heart rate and blood pressure, induction of cholestasis, pancreatitis, and hepatic necrosis, and reduction in intestinal motility[20,21]. Owing to these significant off-target effects, it has been suggested that an ideal TGR5-based therapeutic for T2D would specifically activate intestinal TGR5[21]. CA7S remains gut-restricted and is stable at physiological pHs (FIG. 5E). Furthermore, CA7S does not affect the viability of human intestine-derived Caco-2 cells at concentrations up to 3 mM (FIG. 2E). As a result of its beneficial metabolic effects, gut restriction, and low toxicity, CA7S could be a candidate for the development of a new T2D therapeutic. Further studies are required, however, to assess the long-term effects of this metabolite on glucose tolerance, insulin sensitivity, and weight in vivo. Nonetheless, through the identification of the TGR5 agonist CA7S, this work has uncovered a molecular connection between SG and the beneficial effects of this surgical intervention on metabolism.

REFERENCES

1. Batterham, R. L. & Cummings, D. E. Mechanisms of Diabetes Improvement Following Bariatric/Metabolic Surgery. *Diabetes Care* 39, 893-901 (2016).
2. Gloy, V. L. et al. Bariatric surgery versus non-surgical treatment for obesity: a systematic review and meta-analysis of randomised controlled trials. *BMJ* 347, f5934-f5934 (2013).
3. Khorgami, Z. et al. Trends in utilization of bariatric surgery, 2010-2014: sleeve gastrectomy dominates. *Surg Obes Relat Dis* 13, 774-778 (2017).
4. Abbasi, J. Unveiling the 'Magic' of Diabetes Remission After Weight-Loss Surgery. *JAMA* 317, 571-574 (2017).
5. Ryan, K. K. et al. FXR is a molecular target for the effects of vertical sleeve gastrectomy. *Nature* 509, 183-188 (2014).
6. Fiorucci, S. & Distrutti, E. Bile Acid-Activated Receptors, Intestinal Microbiota, and the Treatment of Metabolic Disorders. *Trends Mol Med* 21, 702-714 (2015).
7. Madsbad, S. The role of glucagon-like peptide-1 impairment in obesity and potential therapeutic implications. *Diabetes Obes Metab* 16, 9-21 (2014).
8. Kaska, L., Sledzinski, T., Chomiczewska, A., Dettlaff-Pokora, A. & Swierczynski, J. Improved glucose metabolism following bariatric surgery is associated with increased circulating bile acid concentrations and remodeling of the gut microbiome. *World J. Gastroenterol.* 22, 8698-8719 (2016).
9. Patti, M.-E. et al. Serum bile acids are higher in humans with prior gastric bypass: potential contribution to improved glucose and lipid metabolism. *Obesity* (Silver Spring) 17, 1671-1677 (2009).
10. Sayin, S. I. et al. Gut microbiota regulates bile acid metabolism by reducing the levels of tauro-beta-muricholic acid, a naturally occurring FXR antagonist. *Cell Metab.* 17, 225-235 (2013).
11. Lutz, T. A. & Bueter, M. The Use of Rat and Mouse Models in Bariatric Surgery Experiments. *Front Nutr* 3, 25 (2016).
12. Steinert, R. E., Beglinger, C. & Langhans, W. Intestinal GLP-1 and satiation: from man to rodents and back. *Int J Obes* 40, 198-205 (2015).
13. Lastya, A., Saraswati, M. R. & Suastika, K. The low level of glucagon-like peptide-1 (glp-1) is a risk factor of type 2 diabetes mellitus. *BMC Res Notes* 7, 849 (2014).
14. Duboc, H., Taché, Y. & Hofmann, A. F. The bile acid TGR5 membrane receptor: from basic research to clinical application. *Dig Liver Dis* 46, 302-312 (2014).
15. McGavigan, A. K. et al. TGR5 contributes to glucoregulatory improvements after vertical sleeve gastrectomy in mice. *Gut* 66, 226-234 (2017).
16. Alnouti, Y. Bile Acid sulfation: a pathway of bile acid elimination and detoxification. *Toxicol. Sci.* 108, 225-246 (2009).
17. Sato, H. et al. Novel Potent and Selective Bile Acid Derivatives as TGR5 Agonists: Biological Screening, Structure-Activity Relationships, and Molecular Modeling Studies. *Journal of Medicinal Chemistry* 51, 1831-1841 (2008).
18. Brighton, C. A. et al. Bile Acids Trigger GLP-1 Release Predominantly by Accessing Basolaterally Located G Protein-Coupled Bile Acid Receptors. *Endocrinology* 156, 3961-3970 (2015).
19. Kuhre, R. E. et al. Peptide production and secretion in GLUTag, NCI-H716, and STC-1 cells: a comparison to native L-cells. *Journal of Molecular Endocrinology* 56, 201-211 (2016).
20. Hodge, R. J. & Nunez, D. J. Therapeutic potential of Takeda-G-protein-receptor -5 (TGR5) agonists. Hope or hype? *Diabetes Obes Metab* 18, 439-443 (2016).
21. Cao, H. et al. Intestinally-targeted TGR5 agonists equipped with quaternary ammonium have an improved hypoglycemic effect and reduced gallbladder filling effect. *Sci Rep* 6, 28676 (2016).

Example 3. SAR of Cholic Acid 7-Sulfate

Figure 21:
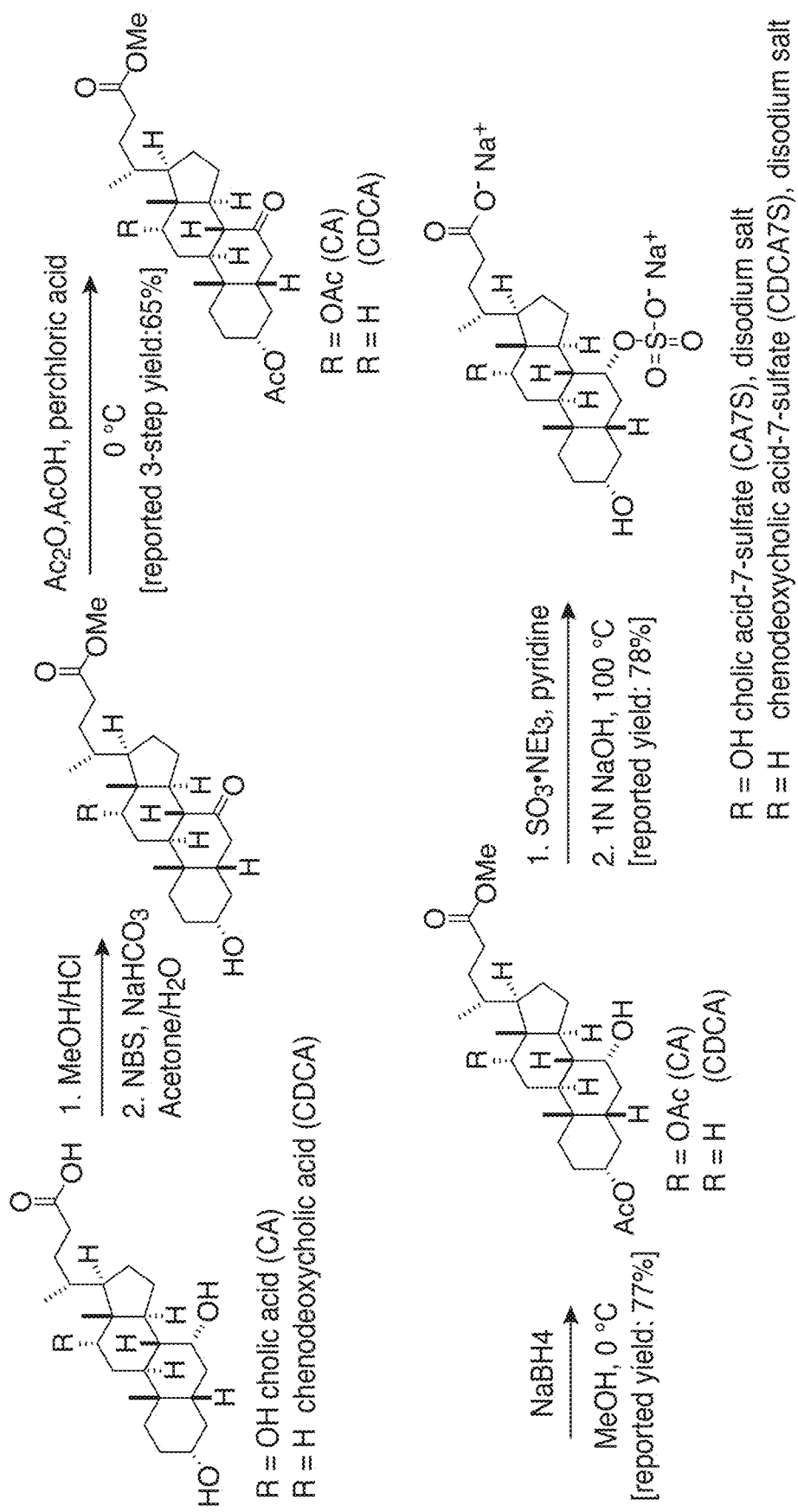
FIG. 21 shows synthesis of 7-sulfated bile acids. Synthesis of gram quantities (minimum of about 2 grams to about 10 grams) of cholic acid 7-sulfate (CA7S).

The synthesis of 7-sulfated bile acids are shown in FIG. 21. Synthesis of gram quantities (minimum of 2 grams, ideally to about 10 grams) of cholic acid 7-sulfate (CA7S) are shown.

Figure 22:
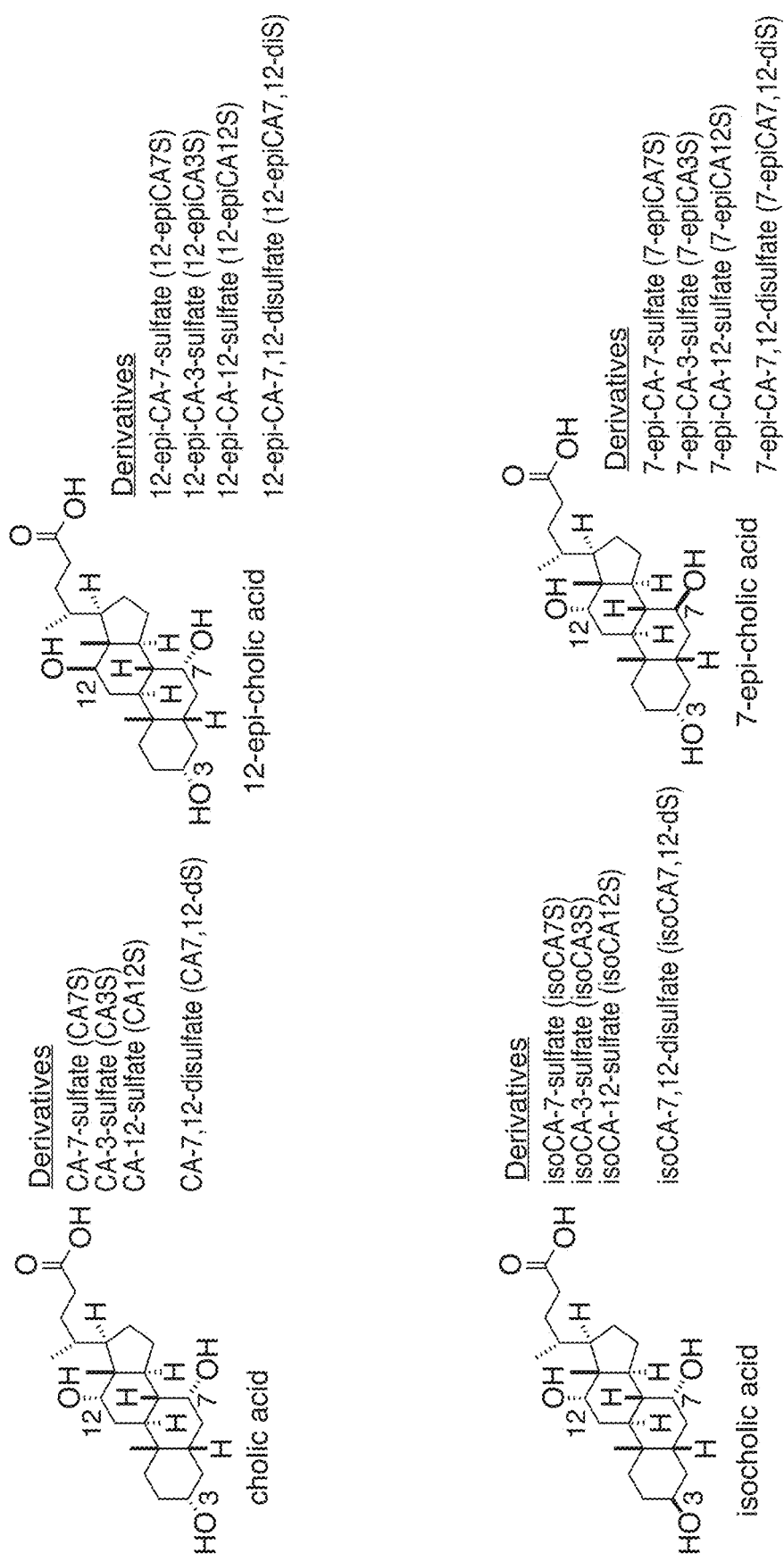
FIG. 22 shows synthesis of milligram quantities (about 100 mg each) of CA7S variants for structure-activity studies.

The synthesis of milligram quantities (about 100 mg each) of CA7S variants for structure-activity studies are shown in FIG. 22.

The goal of in vitro studies with these compounds is to determine the key structural elements that are necessary for TGR5 agonist activity (while attempting to maintain chemical properties that will GI-restrict the compound). The next step is the design and synthesis of non-natural derivatives. It is necessary to investigate the effect of combinations of bile acid cores and sulfate group(s) that can yield TGR5 agonists.

The syntheses of these compounds begin with the bile acid itself. One major limiting factor in which derivatives are accessible may be the availability and cost of the bile acid starting material. For example, cholic acid is cheap, but the muricholic acids are expensive.

Lithocholic acid-3-sulfate (LCA-3-S) and dehydroepiandrosterone-3-sulfate are likely not active ($EC_{50}$>100 uM), whereas their unsulfated parent compounds (i.e., LCA and dehydroepiandrosterone) are active ($EC_{50}$ of 0.58 uM and 3.33 uM, respectively). These data suggest that sulfation at the 3 position abolishes activity.

Figure 23:
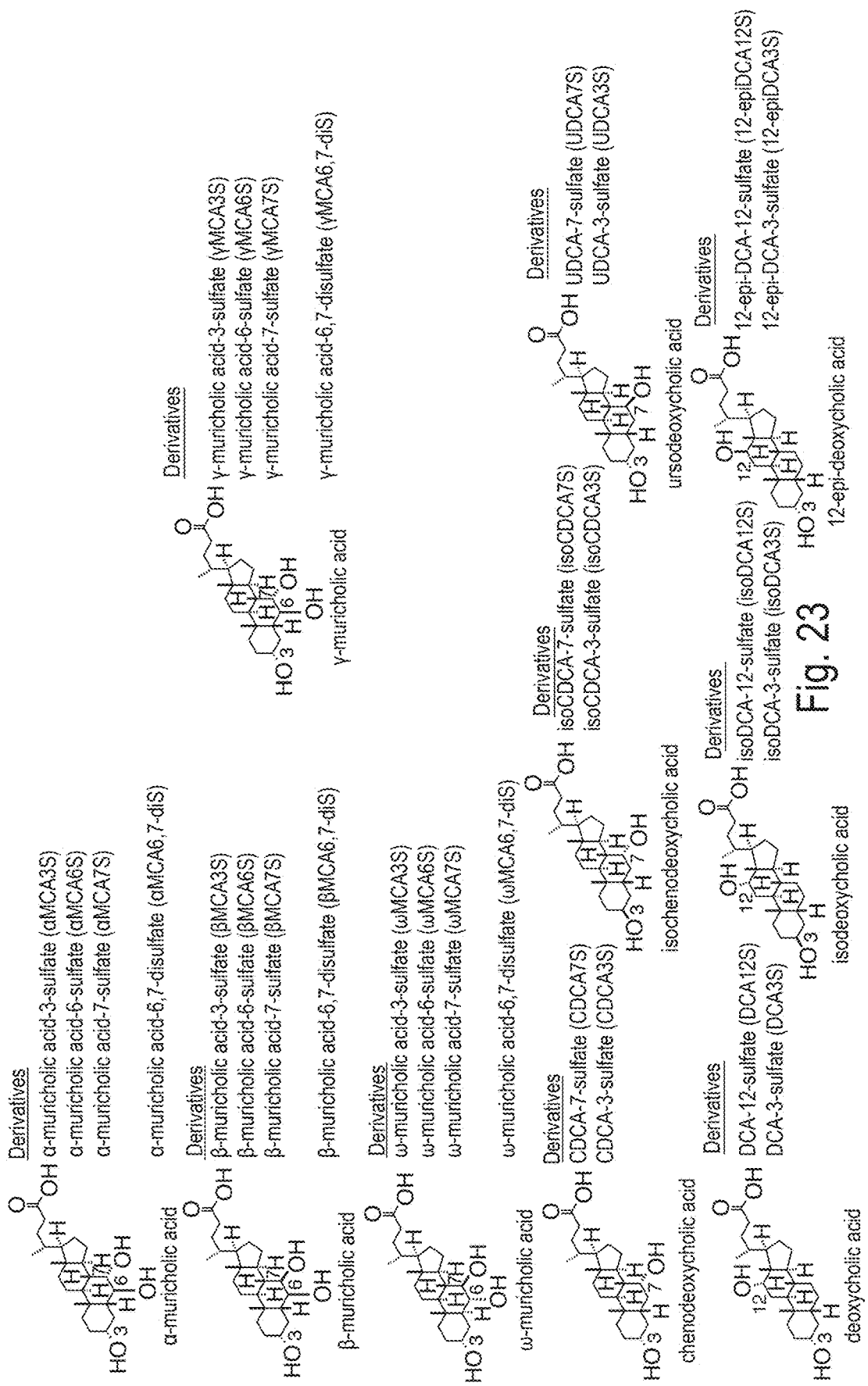
FIG. 23 shows structure activity relationships (SAR) for bile acids (BA). C6 β-OH BA have lower EC50s than C6 α-OH; C7 α-OH BA have lower EC50s than C6 β-OH; these data suggest that α-muricholic acid may be the preferred core on which to test sulfation due to its C6 β-OH and C7 α-OH.

The present data shows that there is a large pocket at C6-C7, but not that is hydrophobic. Testing the tolerance of sulfation at both $C_6$ and $C_7$ can involve synthesizing sulfated derivatives of muricholic acids, which are hydroxylated at C6 and C7 (FIG. 23).

Figure 24:
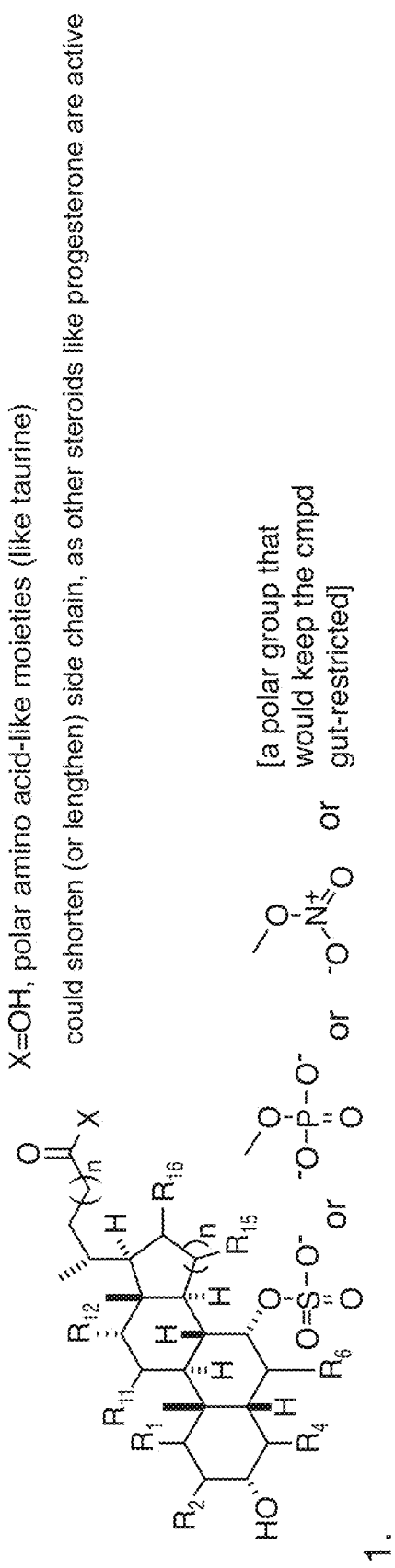
FIG. 24 shows the design and synthesis of milligram quantities synthetic/non-natural CA7S derivatives. These compounds maintain the potency of or are more potent than CA7S (i.e., lower EC50 values as TGR5 agonists), and remain gut-restricted (i.e., not absorbed into synthetic circulation).
Figure 24:
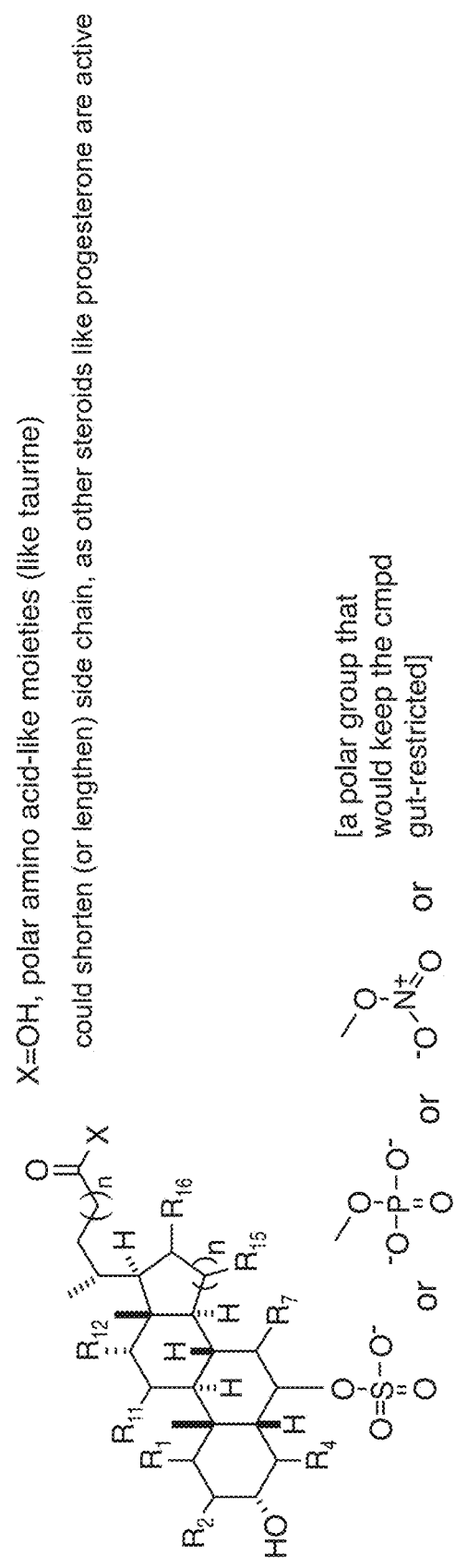
Figure 25:
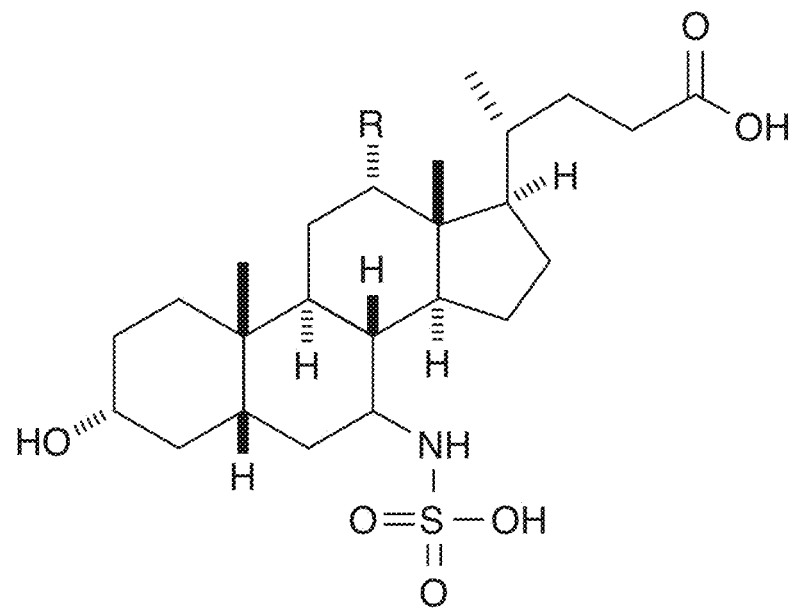
FIG. 25 shows additional derivatives of cholic acid 7-sulfate.
Figure 25:
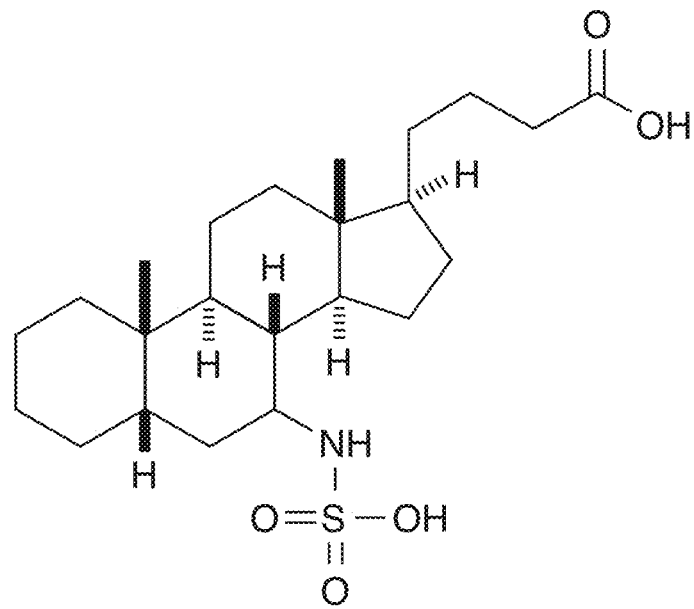
Figure 26:
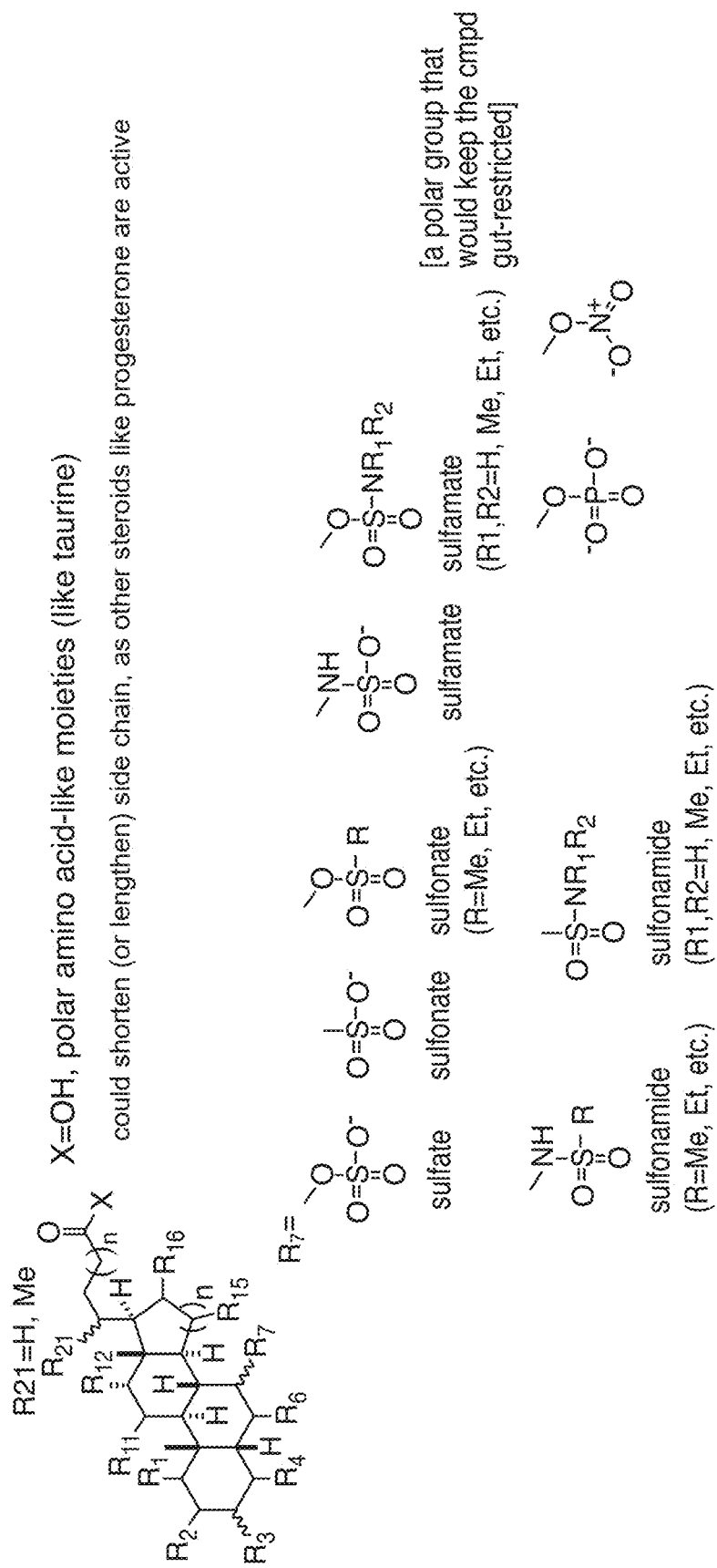
FIG. 26 shows several moieties that can replace the sulfate group at position 7 ($R_7$) of cholic acid 7-sulfate.

The design and synthesis of milligram quantities synthetic CA7S derivatives were considered (FIG. 24). The compounds in FIG. 24, maintain the potency of or be more potent than CA7S (i.e., lower $EC_{50}$ values as TGR5 agonists) and remain gut-restricted (i.e., not absorbed into synthetic circulation). To not be bound by a particular theory, it is hypothesized that the sulfate group at C7 (or C6) in addition to any further modifications will maintain activity. Additional examples of cholic acid 7-sulfate derivatives are shown in FIG. 25. Modifications can be made to the $R_7$ (FIG. 26) and $R_6$ (FIG. 27) positions of the compounds as described herein. A polar group can be added to keep the compounds gut-restricted.

```
SEQUENCES
(TGR5 mRNA transcript- Homo sapiens)
                                                                SEQ ID NO: 1
   1 ctttccgcct agtgagaggc ggtccgattt ggcccttggg gagtgtccgt cgcgttgatc 61 tgatggattc acgtacacaa caccacattc tatgagattt tgcaggcaaa agtccacaag 121 ctcgatatat gggacacctg caccggcatt ggatttggcc ccgcaacatc ttaaaggaag 181 caggctgtga gccaagggga aggcagagga cagaaatgaa tgtgtttcca ggctttcctg 241 gtggtttatg gcattctcca aactcctatg caagggctat tcctgaccaa gaagatctaa 301 agagaacgtc tctgaaatca agtccggatg aagaattaag agaaaaaaag tgaatatggt 361 ttttgctcac agaatggata acagcaagcc acatttgatt attcctacac ttctggtgcc 421 cctccaaaac cgcagctgca ctgaaacagc cacacctctg ccaagccaat acctgatgga 481 attaagtgag gagcacagtt ggatgagcaa ccaaacagac cttcactatg tgctgaaacc 541 cggggaagtg gccacagcca gcatcttctt tgggattctg tggttgtttt ctatcttcgg 601 caattccctg gtttgtttgg tcatccatag gagtaggagg actcagtcta ccaccaacta 661 ctttgtggtc tccatggcat gtgctgacct tctcatcagc gttgccagca cgcctttcgt 721 cctgctccag ttcaccactg gaaggtggac gctgggtagt gcaacgtgca aggttgtgcg 781 atattttcaa tatctcactc caggtgtcca gatctacgtt ctcctctcca tctgcataga 841 ccggttctac accatcgtct atcctctgag cttcaaggtg tccagagaaa aagccaagaa 901 aatgattgcg gcatcgtgga tctttgatgc aggctttgtg accctgtgc tcttttcta 961 tggctccaac tgggacagtc attgtaacta tttcctcccc tcctcttggg aaggcactgc 1021 ctacactgtc atccacttct tggtgggctt tgtgattcca tctgtcctca taatttatt 1081 ttaccaaaag gtcataaaat atatttggag aataggcaca gatggccgaa cggtgaggag 1141 gacaatgaac attgtccctc ggacaaaagt gaaaactatc aagatgttcc tcattttaaa 1201 tctgttgttt ttgctctcct ggctgccttt tcatgtagct cagctatggc accccatga 1261 acaagactat aagaaaagtt cccttgtttt cacagctatc acatggatat cctttagttc 1321 ttcagcctct aaacctactc tgtattcaat ttataatgcc aatttcggga gagggatgaa 1381 agagacttttt tgcatgtcct ctatgaaatg ttaccgaagc aatgcctata ctatcacaac
```

```
1441 aagttcaagg atggccaaaa aaaactacgt tggcatttca gaaatccctt ccatggccaa 1501 aactattacc aaagactcga tctatgactc atttgacaga gaagccaagg aaaaaaagct 1561 tgcttggccc attaactcaa atccaccaaa tactttgtc taagttctca ttctttcaat 1621 tgttatgcac cagagattaa aaagctttaa ctataaaaac agaagctatt tacatatttg 1681 ttttcactca actttccaag ggaaatgttt tattttgtaa aatgcattca tttgtttact 1741 gta
```

(TGR5 polypeptide- *Homo sapiens*)
SEQ ID NO: 2

```
  1 mvfahrmdns kphliiptll vplqnrscte tatplpsqyl melseehswm snqtdlhyvl 61 kpgevatasi ffgilwlfsi fgnslvclvi hrsrrtqstt nyfvvsmaca dllisvastp 121 fvllqfttgr wtlgsatckv vryfqyltpg vqiyvllsic idrfytivyp lsfkvsreka 181 kkmiaaswif dagfvtpvlf fygsnwdshc nyflpssweg taytvihflv gfvipsvlii 241 lfyqkvikyi wrigtdgrtv rrtmnivprt kvktikmfli lnllfllswl pfhvaqlwhp 301 heqdykkssl vftaitwisf sssaskptly siynanfrrg mketfcmssm kcyrsnayti 361 ttssrmakkn yvgiseipsm aktitkdsiy dsfdreakek klawpinsnp pntfv
```

(GLP-1- *Homo sapiens*)
SEQ ID NO: 3
His-Ala-Glu-Gly-Thr-Phe-Thr-Ser-Asp-Val-Ser-Ser-Tyr-Leu-Glu-Gly-Gln-
Ala-Ala-Lys-Glu-Phe-Ile-Ala-Trp-Leu-Val-Lys-Gly-Arg

Example 4. Compound Synthesis

Compounds of Formula (I) can be synthesized as shown in Scheme I below:

Synthesis of 7-sulfated bile acids

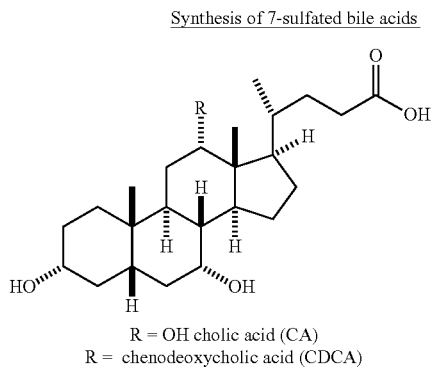

R = OH cholic acid (CA)
R = chenodeoxycholic acid (CDCA)

1. MeOH/HCl
2. NBS, NaHCO₃ Acetone/H₂O

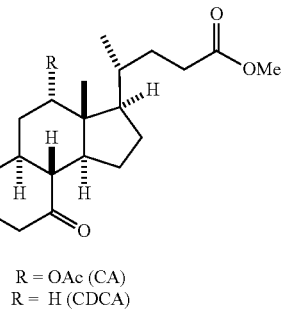

R = OAc (CA)
R = H (CDCA)

NaBH₄
MeOH,
0° C.
[reported yield: 77%]

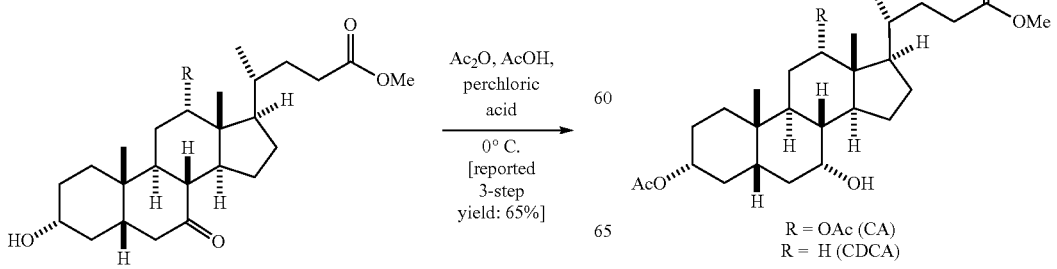

Ac₂O, AcOH, perchloric acid
0° C.
[reported 3-step yield: 65%]

R = OAc (CA)
R = H (CDCA)

1. SO₃·NEt₃, pyridine
2. 1N NaOH, 100° C.
[reported yield: 78%]

-continued

R = OH cholic acid-7-sulfate (CA7S), disodium salt
R = H chenodeoxycholic acid-7-sulfate (CDCA7S), disodium salt Ref: Tserng and Klein. Steroids 33:167-182, 1979.

Compound 1

1-1

$\xrightarrow{\text{NBS, acetone, H}_2\text{O, 25° C., 2 h}}$ 1-2

1) NaBH$_3$CN, NH$_4$OAc, MeOH, 25° C., 48 h
2) HCl, 25° C., 16 h 1-3

$\xrightarrow[\text{Et}_3\text{N, ACN, DMF, 25° C., 16 h}]{\text{HO-S(O)}_2\text{-Cl} \quad 1\text{-}4}$ Compound (I-1)

$\xrightarrow{\text{KOH, MeOH, 25° C., 16 h}}$

Compound 1

General procedure for preparation of Cpd.1-2

1-1

$\xrightarrow{\text{NBS, acetone, H}_2\text{O, 25° C., 2 h}}$ 1-2

A solution of Cpd.1-1 (15.0 g, 36.7 mmol, 1.00 eq) in acetone (240 mL) and H$_2$O (80.0 mL) was add NBS (9.47 g, 53.2 mmol, 1.45 eq) in portions at 25° C. The reaction was stirred at 25° C. for 2 h in dark condition. TLC (DCM/MeOH=10/1) shows Cpd.1-1 consumed, a new spot formed. H$_2$O (200 mL) and sat.NaHSO$_3$ (100 mL) were added to the mixture and stirred for 0.5 h. The mixture was extracted with DCM (200 mL, 100 mL) and the combined organic layer was washed with brine, dried with Na2SO$_4$ and concentrated in vacuo. The residue was purified by column chromatography (SiO$_2$, DCM/MeOH=100/1 to 20/1) to obtain Cpd.1-2

(10.0 g, 24.6 mmol, 67.0% yield) as white solid. $^1$H NMR: (400 MHz, CDCl$_3$) δ 4.00 (brs, 1H), 3.67-3.55 (m, 1H), 2.91-2.73 (m, 1H), 2.45-1.25 (m, 22H), 1.24 (s, 3H), 1.14-1.09 (m, 1H), 1.02-0.95 (m, 4H), 0.68 (s, 3H).

General Procedure for Preparation of Cpd.1-3

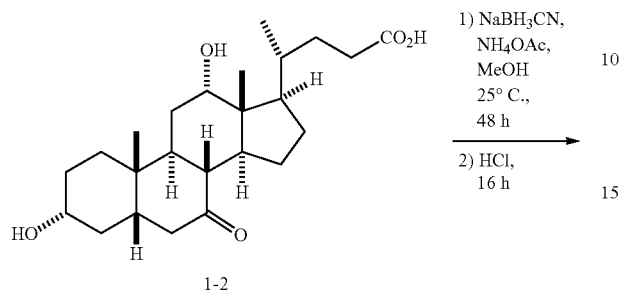

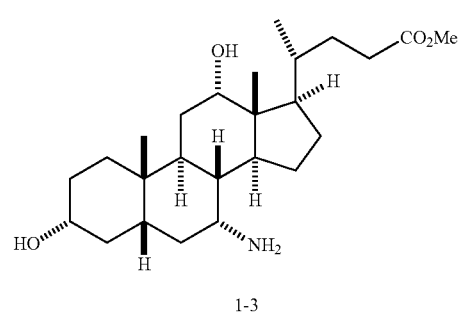

A solution of Cpd.1-2 (5.00 g, 12.3 mmol, 1.00 eq) in MeOH (50.0 mL) was added NH$_4$OAc (9.48 g, 122 mmol, 10.0 eq) and stirred at 40° C. for 16 h. NaBH$_3$CN (772 mg, 12.3 mmol, 1.00 eq) was added to the mixture at 0° C. and stirred at 25° C. for 3 h. Cpd.1-3 was detected on LCMS (ET26515-11-P1A1). The reaction was concentrated in vacuum. The residue was slurried with DCM (10.0 mL). The mixture was filtered; the filter cake was washed with DCM (10.0 mL). The filtrate was concentrate and purified by prep-HPLC (column: Agela DuraShell C18 250*50 mm*10 um; mobile phase: [water (0.1% TFA)-ACN]; B %: 15%-45%, 23 min) to obtain Cpd.1-3 (0.50 g, 1.13 mmol, 9.1% yield, 95% purity) as white solid. $^1$H NMR: (400 MHz, CDCl$_3$) δ 4.04 (brs, 1H), 3.66 (s, 3H), 3.51 (brs, 1H), 2.61-1.00 (m, 24H), 0.99-0.81 (m, 6H), 0.69 (s, 3H). LCMS: ET26515-11-P1a1, t=1.356 min, MS cal.: 421.3, [M+23]$^+$=445.3

General Procedure for Preparation of Compound (I-1)

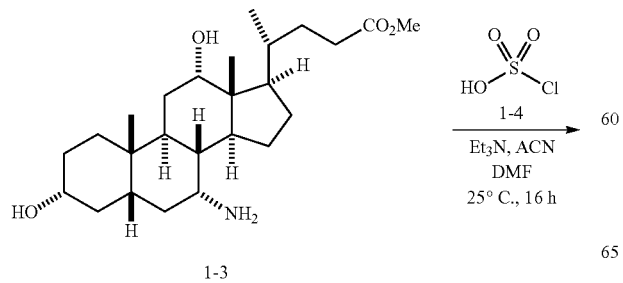

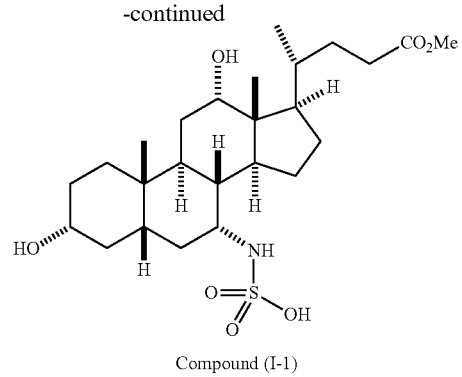

A solution of Cpd.1-3 (0.6 g, 1.42 mmol, 1.00 eq) and Et$_3$N (720 mg, 7.12 mmol, 990 uL, 5.00 eq) in DMF (15.0 mL) was added a solution of sulfurochloridic acid (198 mg, 1.71 mmol, 113 uL, 1.20 eq) in ACN (6.00 mL) at 0° C. under N$_2$. The reaction was stirred at 25° C. for 16 h. Cpd.(I-1) was detected on LCMS (et26314-42-P1B2). The reaction was quenched the reaction with EtOH (5.00 ml) then purified by prep-HPLC (column: Welch Xtimate C18 250*50 mm*10 um; mobile phase: [water (0.05% ammonia hydroxide v/v)-ACN]; B %: 5%-40%, 20 min) to obtain Cpd.(I-1) (0.3 g, 598 umol, 42.0% yield) as yellow solid. $^1$H NMR: (400 MHz, DMSO-d$_6$) δ 4.35 (brs, 1H), 4.23 (d, J=5.6 Hz, 1H), 3.72 (brs, 1H), 3.09 (s, 3H), 3.2$_3$2.98 (m, 5H), 2.40-1.20 (m, 22H), 1.16 (t, J=7.2 Hz, 6H), 0.96-0.25 (m, 8H), 0.58 (s, 3H). LCMS: ET26314-42-P1B2, t=1.106 min, MS cal.: 501.3, [M−1]$^-$=500.3

General Procedure for Preparation of Compound 1

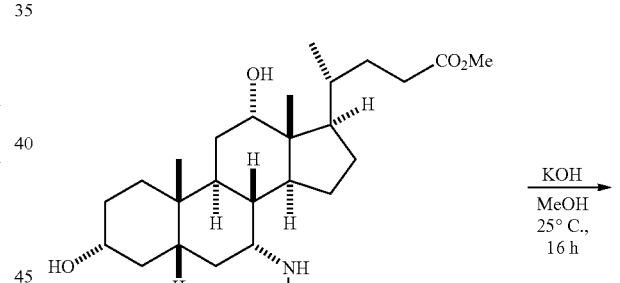

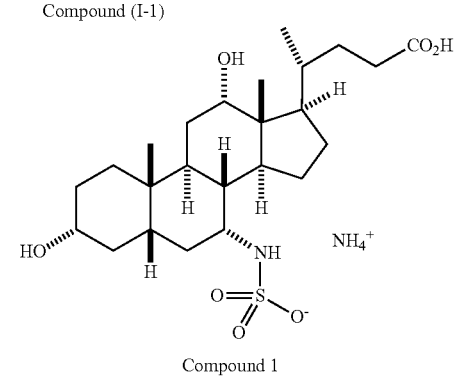

A solution of Cpd.(I-1) (0.15 g, 299 umol, 1.00 eq) in EtOH (1.00 mL) and THF (0.50 mL) was added a solution of KOH (33.5 mg, 598 umol, 2.00 eq) in H$_2$O (1.00 mL) and stir the result mixture at 25° C. for 4 h. LCMS shows the reaction complete. The reaction was filtered and purified by prep-HPLC (column: Waters Xbridge BEH C18 100*30 mm*10 um; mobile phase: [water (0.04% NH₃H₂O)-ACN]; B %: 1%-50%, 10 min) to obtain Compound 1 1 (50 mg, 93.2 umol, 31.2% yield, 90.8% purity) as white solid. $^1$H NMR: (400 MHz, MeOD-$d_4$) δ 3.97 (s, 1H), 3.4₃3.35 (m, 2H), 2.28-2.16 (m, 3H), 2.15-2.00 (m, 3H), 1.95-1.73 (m, 3H), 1.65-1.53 (m, 3H), 1.47-1.21 (m, 5H), 1.15-1.04 (m, 5H), 0.96 (s, 3H), 0.75 (s, 3H). LCMS: ET26314-44-P1A2, t=0.971 min, MS cal.: 487.3, [M−1]⁻=486.3 QC-LCMS: ET26314-44-P1A2, t=1.875 min, MS cal.: 487.3, [M−1]⁺=486.2

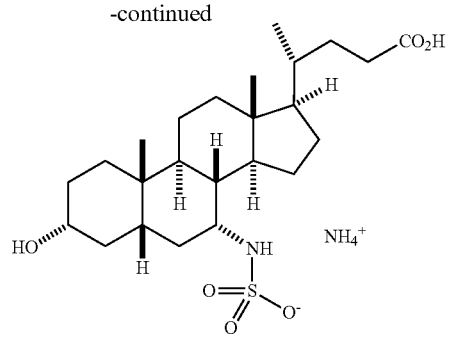

Compound 2

General Procedure for Preparation of Cpd.2-2

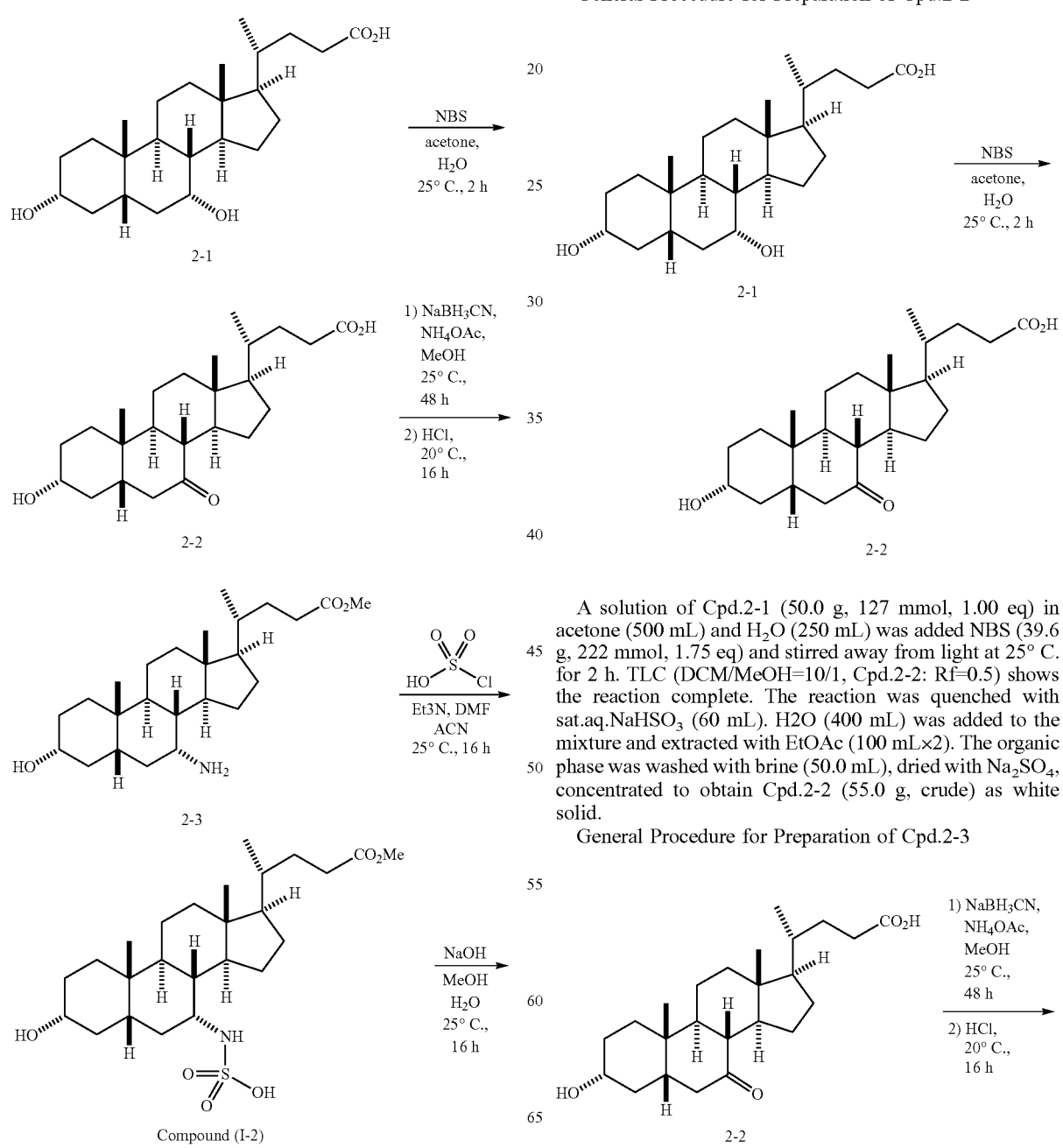

A solution of Cpd.2-1 (50.0 g, 127 mmol, 1.00 eq) in acetone (500 mL) and H₂O (250 mL) was added NBS (39.6 g, 222 mmol, 1.75 eq) and stirred away from light at 25° C. for 2 h. TLC (DCM/MeOH=10/1, Cpd.2-2: Rf=0.5) shows the reaction complete. The reaction was quenched with sat.aq.NaHSO₃ (60 mL). H2O (400 mL) was added to the mixture and extracted with EtOAc (100 mL×2). The organic phase was washed with brine (50.0 mL), dried with Na₂SO₄, concentrated to obtain Cpd.2-2 (55.0 g, crude) as white solid.

General Procedure for Preparation of Cpd.2-3

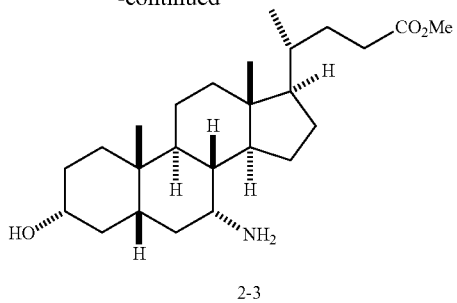

2-3

A mixture of Cpd.2-2 (5.00 g, 12.8 mmol, 1.00 eq) and NH₄OAc (9.87 g, 128 mmol, 10.0 eq) in MeOH (350 mL) was added NaBH₃CN (804 mg, 12.8 mmol, 1.00 eq) at 25° C. and stir at 25° C. for 48 h.-50% Cpd.2-2 remained on TLC. HCl (12 M, 1.06 mL, 1.00 eq) was added dropwise to the above mixture to adjust pH<2, then the mixture was stir at 20° C. for 16 h. LCMS (ET26515-₃P1A) showed Cpd.2-3 was detected. The reaction was concentrated in vacuo. The residue was purified by column chromatography (SiO₂, DCM/MeOH=100/1 to 20/1) to obtain Cpd.2-3 (1.50 g, 2.96 mmol, 23.1% yield, 80.0% purity) as yellow solid. LCMS: t=1.127 min, MS cal.: 405.3, [M+1]⁺=406.3

General Procedure for Preparation of Cpd.(I-2)

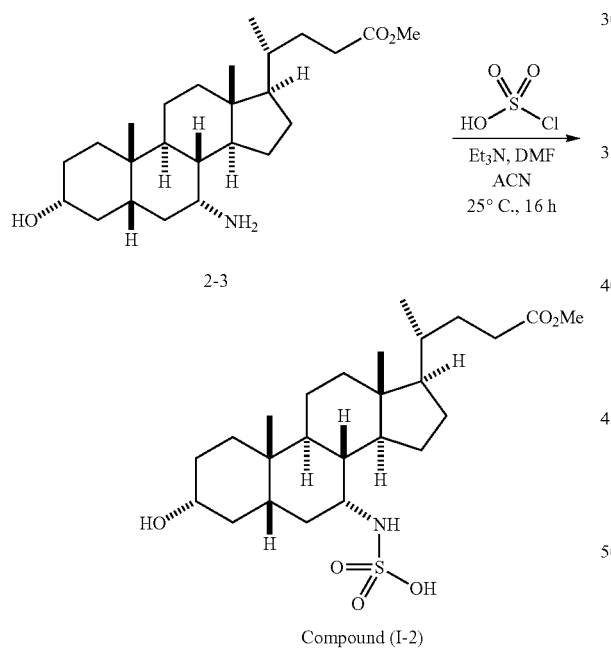

A solution of Cpd.2-3 (0.90 g, 2.22 mmol, 1.00 eq) in DMF (22.5 mL) was added Et₃N (673 mg, 6.66 mmol, 926 uL, 3.00 eq) and a solution of sulfurochloridic acid (374 mg, 3.22 mmol, 214 uL, 1.45 eq) in ACN (9.00 mL), the mixture was stirred at 25° C. for 16 h. LCMS (ET26515-25-P1A) showed Cpd.(I-2) was detected. H₂O (10.0 mL) was added to quenched the reaction and the mixture was concentrated in vacuo. The residue was purified the crude by pre-HPLC (column: Waters Xbridge BEH C18 100*30 mm*10 um; mobile phase: [water (0.04% NH₃H₂O)-ACN]; B %: 15%-45%, 10 min) to obtain Cpd.(I-2) (0.35 g, 720 umol, 32.4% yield) as white solid. ¹H NMR: ET26515-14-P1H (400 MHz, DMSO-d₆) δ 7.22 (brs, 2H), 4.36 (d, J=4.4 Hz, 1H), 3.56 (s, 3H), 3.2₃3.04 (m, 5H), 2.3₃1.29 (m, 17H), 1.21-1.03 (m, 8H), 0.94-0.76 (m, 8H), 0.59 (s, 3H). LCMS: ET26515-25-P1A, t=1.201 min, MS cal.: 485.3, [M−1]⁻=484.4

General Procedure for Preparation of Compound 2

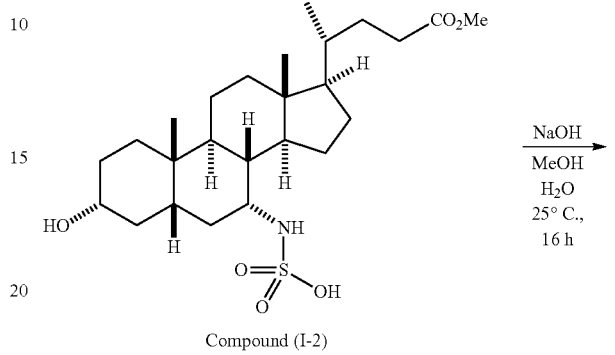

Compound (I-2)

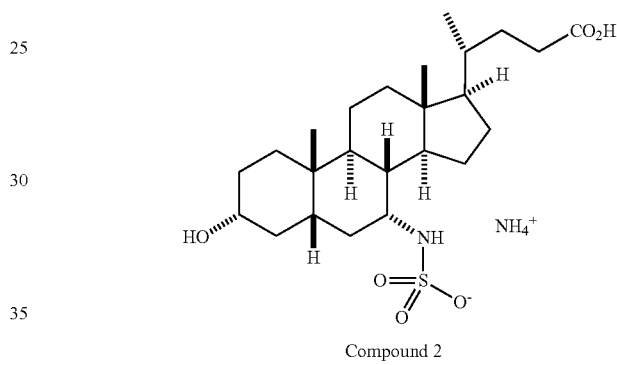

Compound 2

A solution of Cpd.(I-2) (0.35 g, 7.20 umol, 1.00 eq in MeOH (10.0 m an 2 (10 mL) was added NaOH (86.4 mg, 2.16 mmol, 3.00 eq) at 25° C. The mixture was stirred at 25° C. for 16 h. LCMS (ET26515-32-P1A) showed Target 2 was detected. The reaction was concentrated in vacuo. The residue was purified the crude by pre-HPLC (column: Waters Xbridge BEH C18 100*30 mm*10 um; mobile phase: [water (0.04% NH₃H₂O)-ACN]; B %: 1%-40%, 10 min) to obtain Target 2 (60.0 mg, 127 umol, 17.6% yield, 100% purity) as white solid. ¹H NMR: ET26515-32-p1A (400 MHz, MeOD-d₄) S 3.40 (s, 1H), 2.31-2.15 (m, 3H), 2.11-0.97 (m, 24H), 0.96-0.91 (m, 6H), 0.71 (s, 3H). LCMS: t=1.031 min, MS cal.: 471.3, [M−1]=470.3

Compound 3

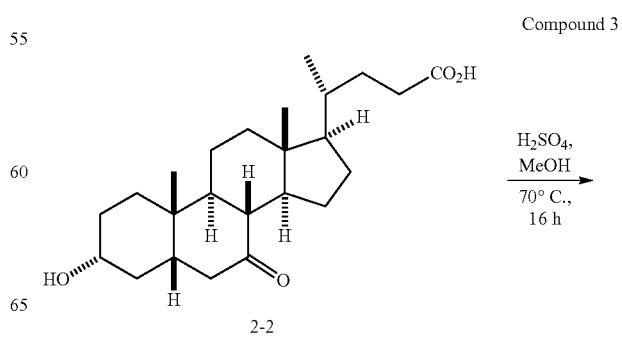

2-2

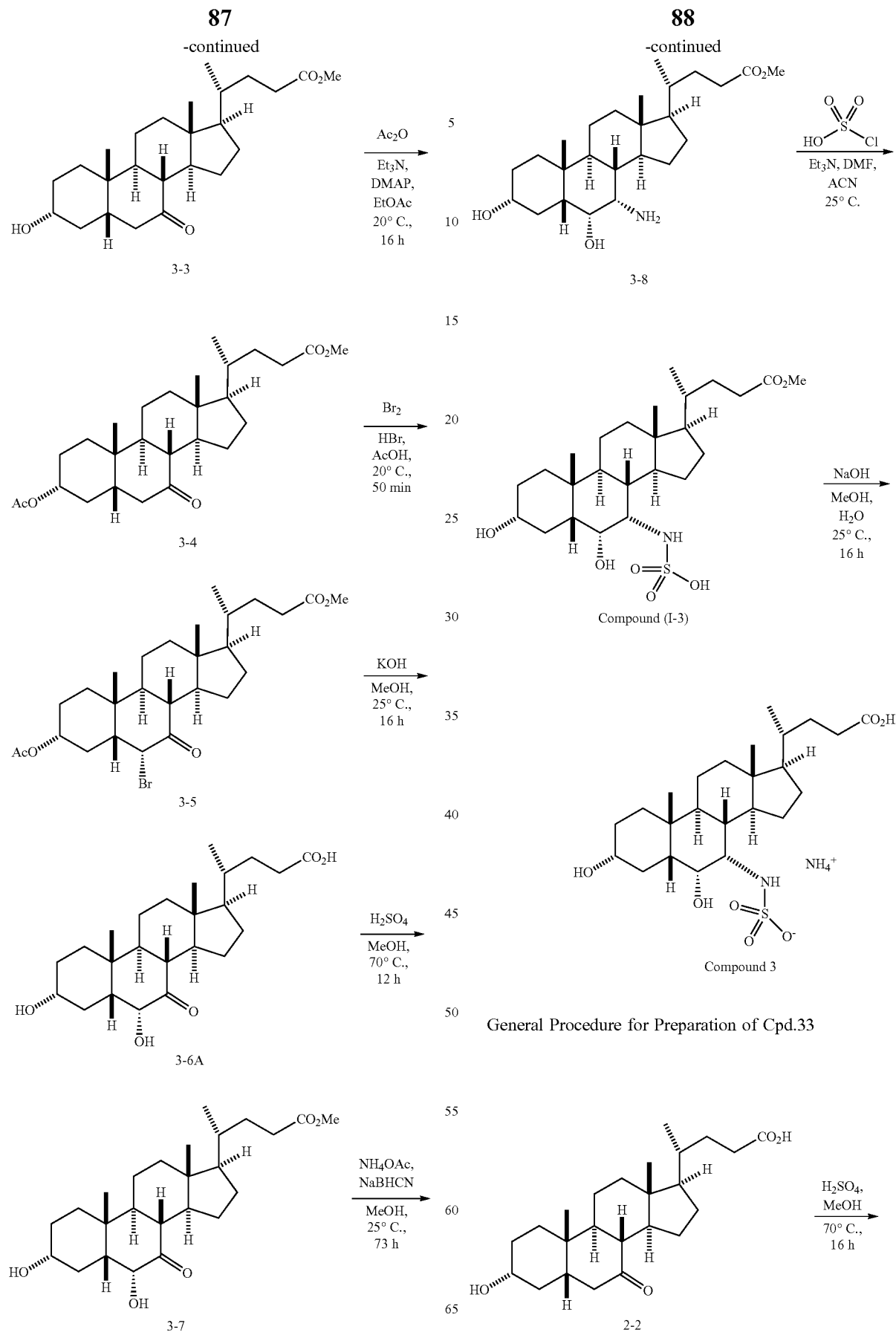

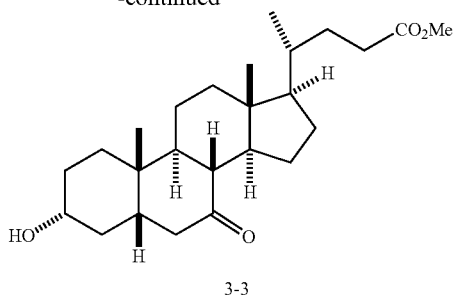

3-3

A solution of Cpd.2-2 (55.0 g, 140 mmol, 1.00 eq) in MeOH (275 mL) was added Drop-wise H$_2$SO$_4$ (16.5 g, 168 mmol, 9.01 mL, 1.20 eq) and stirred at at 70° C. for 16 h. TLC (Petroleum ether/EtOAc=0/1, Cpd.33: Rf=0.28) showed the reaction was complete, some new spots formed. The reaction solution was poured into NaHCO$_3$ (100 mL) and brine (300 mL) and the mixture was extracted with EtOAc (100 ml×3). The combined organic phase was dried over with Na$_2$SO$_4$, filtered and the filtrate was concentrated in vacuo. The residue was purified by column chromatography (SiO$_2$, Petroleum ether/EtOAc=1/1) to obtain Cpd.33 (28.1 g, 69.5 mmol, 49.3% yield) as yellow solid. $^1$H NMR: (400 MHz, CDCl$_3$) δ 3.67 (s, 3H), 3.65-3.49 (m, 1H), 2.88-2.83 (m, 1H), 2.41-2.32 (m, 2H), 2.28-2.14 (m, 2H), 2.02-1.62 (m, 10H), 1.61-1.17 (m, 16H), 1.17-1.05 (m, 3H), 0.93 (d, J=6.4 Hz, 3H), 0.65 (s, 3H).

General Procedure for Preparation of Cpd.$_3$4

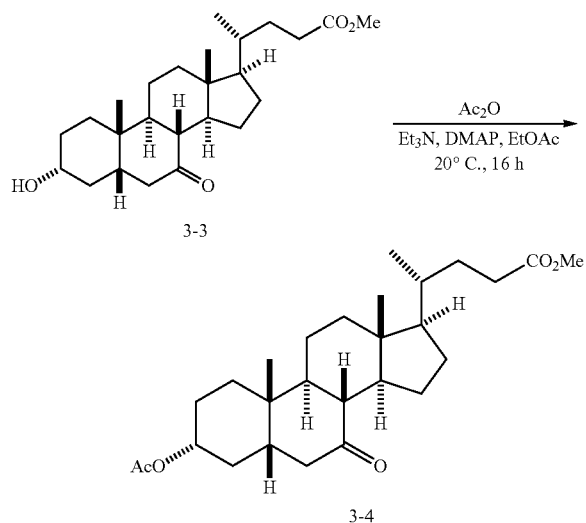

A solution of Cpd.33 (25.0 g, 61.7 mmol, 1.00 eq) in EtOAc (500 mL) was added Et$_3$N (12.5 g, 123 mmol, 17.2 mL, 2.00 eq), DMAP (619 mg, 5.07 mmol, 0.082 eq), followed by Ac$_2$O (12.6 g, 123 mmol, 11.5 mL, 2.00 eq). The reaction was stirred the reaction at 20° C. for 16 h. TLC (Petroleum ether/EtOAc=5/1, Rf=0.45) showed the reaction was completed. H$_2$O (100 ml) was added to the reaction solution. The mixture was extracted with EtOAc (80 ml×3). The combined organic phase was washed with HCl (0.5M, 120 ml), brine (120 ml), dried with anhydrous Na2SO$_4$, filtered and the filtrate was concentrated to obtain Cpd.34 (27.1 g, crude) as white solid. $^1$H NMR: (400 MHz, CDCl$_3$) δ 4.7$_3$4.66 (m, 1H), 3.68 (s, 3H), 2.89-2.85 (m, 1H), 2.40-2.15 (m, 4H), 2.05-1.89 (m, 7H), 1.85-1.68 (m, 5H), 1.52-1.03 (m, 15H), 0.93 (d, J=6.4 Hz, 3H), 0.66 (s, 3H).

General Procedure for Preparation of Cpd. 3-5

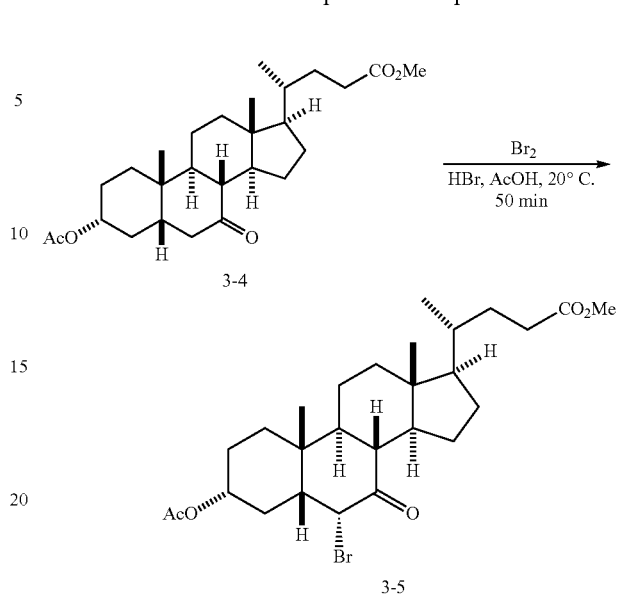

A solution of Cpd. 3-4 (15.0 g, 33.5 mmol, 1.00 eq) in AcOH (150 mL) was added a solution of Br$_2$ (6.44 g, 40.3 mmol, 2.08 mL, 1.20 eq) in AcOH (49.5 mL) at 20° C. Then HBr (4.5 mL) was added to the above mixture and stir for 5 minutes. The solution was allowed to stir at 20° C. for 45 minutes. TLC (Petroleum ether/EtOAc=5/1, Cpd. 3-5: Rf=0.21) showed the reaction was complete. The reaction was poured into water, filter, and filter cake was dissolved in EtOAc (300 mL) and dried over Na$_2$SO$_4$ and concentrated. The residue was purified by column chromatography (SiO$_2$, Petroleum ether/EtOAc=5/1) to obtain Cpd. 3-5 (14.5 g, 24.8 mmol, 73.9% yield, 90.0% purity) as yellow solid. $^1$H NMR: (400 MHz, CDCl$_3$) δ 5.18 (d, J=6.4 Hz, 1H), 4.75-4.25 (m, 1H), 3.67 (s, 3H), 2.47 (t, J=11.2 Hz, 1H), 2.24-2.15 (m, 5H), 2.10-1.92 (m, 5H), 1.54-0.62 (m, 18H), 0.66 (s, 3H).

General Procedure for Preparation of Cpd.3-6A

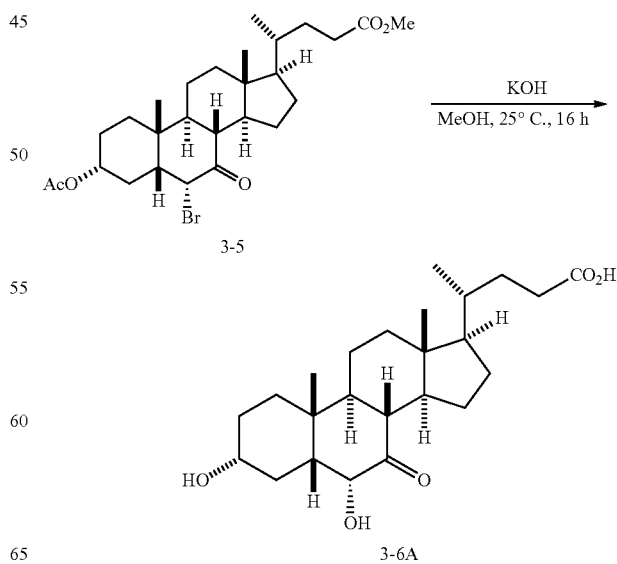

A solution of Cpd. 3-5 (19.0 g, 36.1 mmol, 1.00 eq) in MeOH (285 mL) was added a solution of KOH (146 mg, 209 umol, 349 mL, 8% purity) in MeOH drop wise over 30 mins. The mixture was stirred at 25° C. for 16 h. LCMS (ET26315-1₃P1A1) showed Cpd. 3-5 consumed and Cpd. 3-6A formed. The reaction was concentrated in vacuo. The residue was added water (500 mL), con.H₂SO₄ to pH=2-3. The mixture was extracted with EtOAc (150 mL×3). The combined the organic layer was washed with brine, dried over with Na₂SO₄ and concentrated to obtain Cpd. 3-6A (21.0 g, crude) as light yellow solid LCMS: t=0.923 min, MS cal.: 406.3, [M−1]⁻=405.3

General Procedure for Preparation of Cpd. 3-7

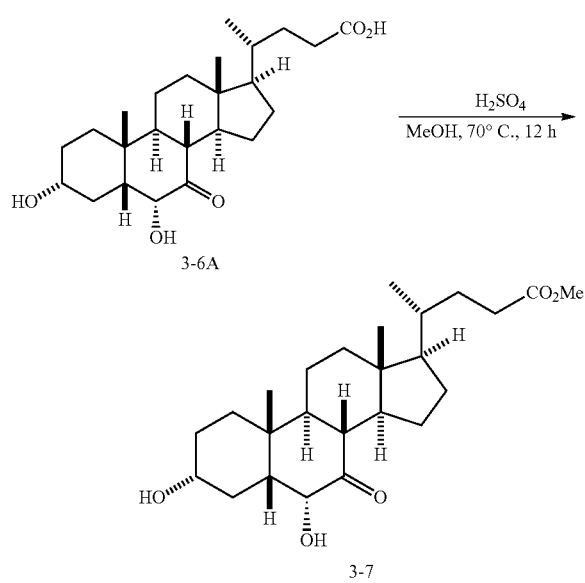

A solution of Cpd. 3-6A (17.0 g, 41.8 mmol, 1.00 eq) in MeOH (510 mL) was added H₂SO₄ (12.3 g, 125 mmol, 6.69 mL, 3.00 eq) dropwise and stirred at 70° C. for 12 h. TLC (Petroleum ether/EtOAc=5/1, Cpd. 3-7: Rf=0.5) showed Cpd. 3-6A was consumed and the reaction was completed. The reaction was concentrated in vacuo to remove the MeOH. The residue was purified by column chromatography (SiO₂, Petroleum ether/Ethyl acetate=10/1 to 0/1) to obtain Cpd. 3-7 (6.90 g, 16.4 mmol, 39.2% yield) as brown oil. ¹H NMR: (400 MHz, CDCl₃) δ 4.52 (t, J=6.4 Hz, 1H), 3.67 (s, 3H), 3.64-3.54 (m, 3H), 3.42 (d, J=4.8 Hz, 1H), 2.46-2.30 (m, 2H), 2.29-2.10 (m, 3H), 2.031.90 (m, 3H), 1.89-1.69 (m, 3H), 1.55-1.23 (m, 9H), 1.21 (s, 3H), 1.20-1.15 (m, 2H), 0.93 (d, J=6.4 Hz, 3H), 0.67 (s, 3H).

General Procedure for Preparation of Cpd. 3-8

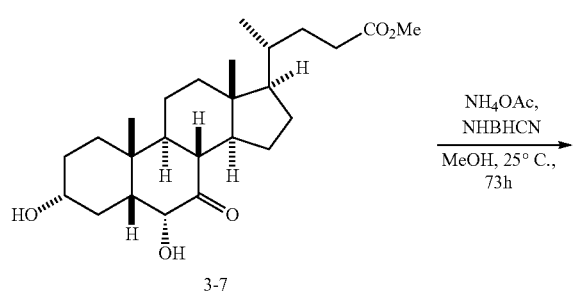

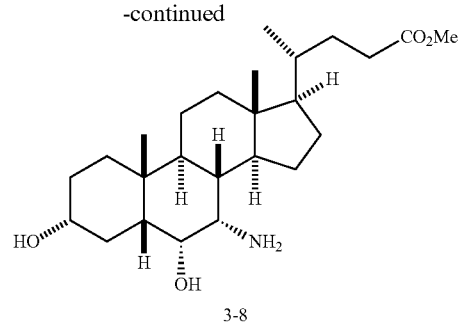

A solution of Cpd.3-7 (5.50 g, 13.0 mmol, 1.00 eq) in MeOH (30.0 mL) was added NH₄OAc (10.0 g, 130 mmol, 10.0 eq) and MgSO₄ (1.89 g, 15.6 mmol, 1.20 eq) and stir at 25° C. for 1 h. Then NaBH₃CN (986 mg, 15.6 mmol, 1.20 eq) was added to the mixture and stir at 25° C. for 72 h. LCMS (ET26315-22-P1L2) showed Cpd. 3-7 consumed and Cpd. 3-8 formed. The reaction was filtered and the filtrate was concentrated. The residue was added water (20.0 mL) and EtOAc (50.0 mL×5). The mixture was extracted with EtOAc (50.0 mL×3). The combined organic phase was washed with brine (100 mL×2) and dried over with Na₂SO₄ and concentrated. The residue was purified by prep-HPLC (column: Phenomenex luna C18 250*150 mm*15 um; mobile phase: [water (0.1% TFA)-ACN]; B %: 10%-45%, 25 min) to obtain Cpd. 3-8 (3.00 g, 7.12 mmol, 54.4% yield) as white solid. LCMS: ET26315-22-P1L2, t=1.929 min, MS cal.: 421.3, [M+1]⁺=422.2

General Procedure for Preparation of Cpd. (I-3)

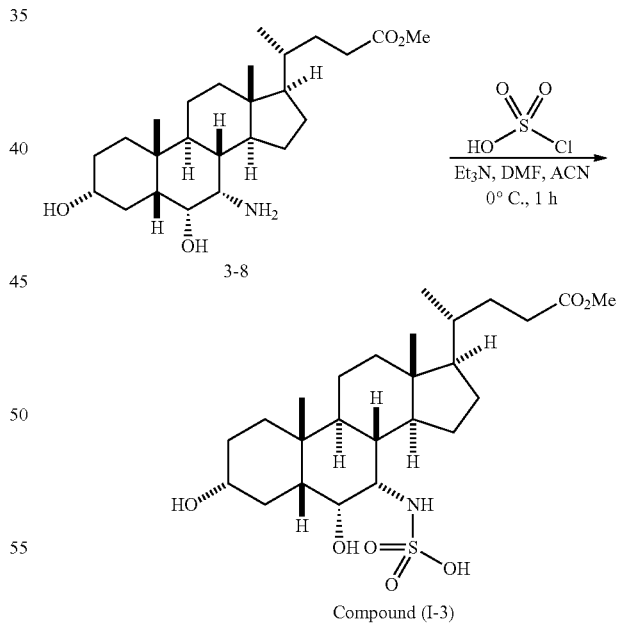

A solution of Cpd. 3-8 (1.00 g, 2.37 mmol, 1.00 eq) and Et₃N (2.40 g, 23.7 mmol, 3.30 mL, 10.0 eq) in DMF (20.0 mL) was added a solution of sulfurochloridic acid (1.00 g, 8.58 mmol, 571.43 uL, 3.62 eq) in ACN (45 mL) at to 0° C. under N₂. The reaction was stirred at 0° C. for 1 h. 40% Cpd. (I-3) was detected on LCMS (et26314-77-p1a2). The reaction was concentrated at 25° C. to remove CH₃CN. The residue was purified the residue by prep-HPLC (column:

Phenomenex luna C18 250*150 mm*15 um; mobile phase: [water (0.1% TFA)-ACN]; B %: 10%-35%, 25 min) to obtain Cpd. (I-3) (0.30 g, 598 umol, 25.2% yield) as white solid. ¹H NMR: (400 MHz, DMSO-d₆) δ 7.25 (brs, 2H), 5.78 (d, J=6.8 Hz, 1H), 4.38 (d, J=4.0 Hz, 1H), 3.82 (d, J=6.4 Hz, 1H), 3.61-3.51 (m, 4H), 3.40-3.31 (m, 1H), 3.17-3.05 (m, 3H), 2.36-2.27 (m, 1H), 2.24-2.12 (m, 2H), 1.95-1.03 (m, 23H), 0.92-0.43 (m, 7H), 0.59 (s, 3H). LCMS: ET26314-77-P1A2, t=1.135 min, MS cal.: 501.3, [M−1]⁻= 500.3

General Procedure for Preparation of Compound 3

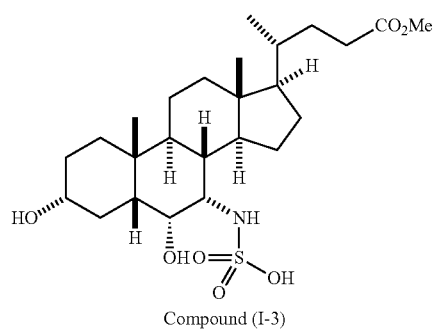

Compound (I-3)

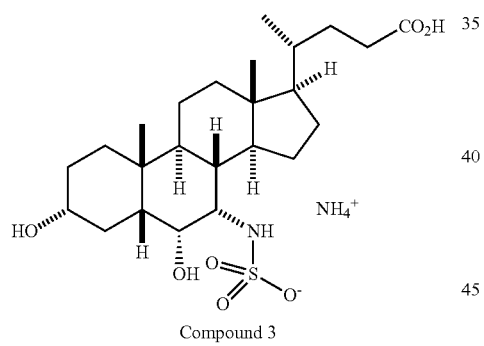

Compound 3

A solution of Cpd. (I-3) (300 mg, 598 umol, 1.00 eq) in MeOH (1.2 mL) was added a solution of NaOH (59.8 mg, 1.49 mmol, 2.50 eq) in H₂O (1.20 mL) and the reaction was stirred at 25° C. for 16 h. LCMS (et26314-84-p1a1) showed the reaction was completed. The reaction was concentrated at 30° C. to remove MeOH. The residue was purified by prep-HPLC (column: Waters Xbridge BEH C18 100*30 mm*10 um; mobile phase: [water (0.04% NH₃H₂O)-ACN]; B %: 1%-25%, 12 min) to obtain Compound 3 (76.0 mg, 150 umol, 25.1% yield, 100% purity) as white solid. ¹H NMR: (400 MHz, DMSO-d₆) δ 5.80 (d, J=6.8 Hz, 1H), 4.40 (d, J=4.0 Hz, 1H), 3.86-3.58 (m, 1H), 3.52-3.33 (m, 4H), 3.16-3.08 (m, 1H), 2.50-1.77 (m, 6H), 1.76-0.95 (m, 18H), 0.91-0.77 (m, 8H), 0.60 (s, 3H). QC-LCMS: ET26314-84-P1C1, t=2.046 min, MS cal.: 487.3, [M−1]⁻=486.2.

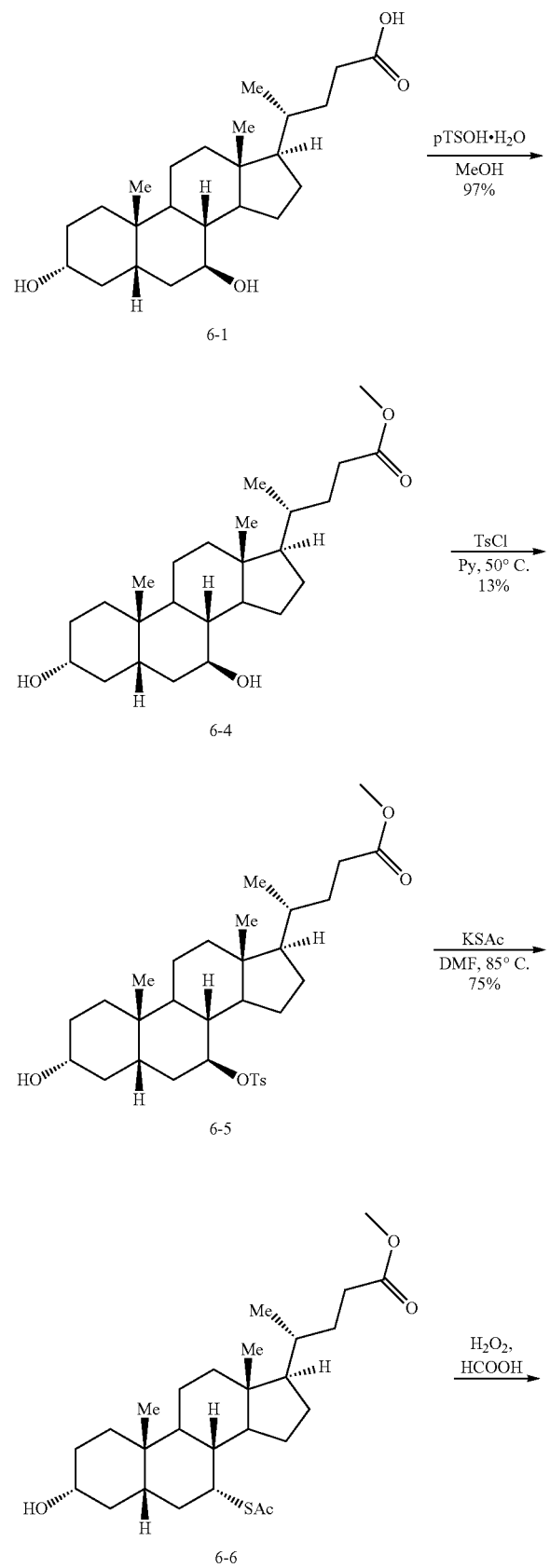

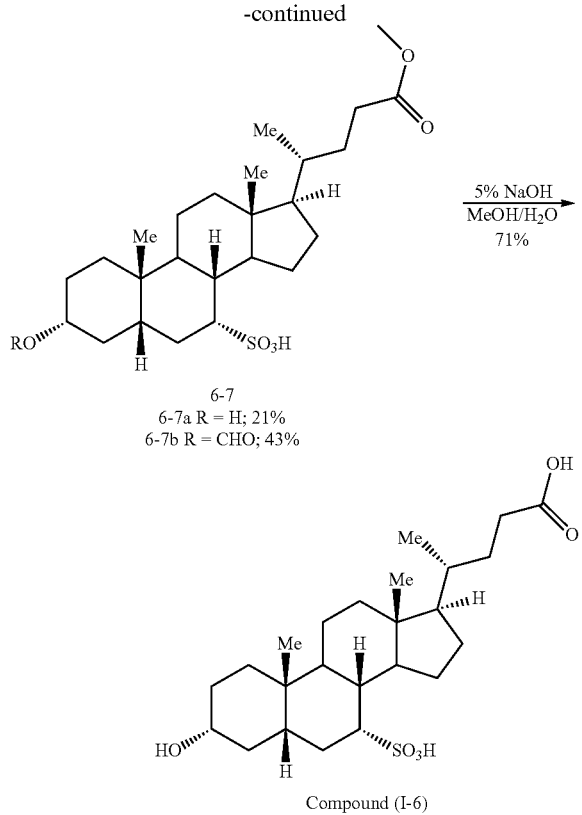

6-7
6-7a R = H; 21%
6-7b R = CHO; 43%

Compound (I-6)

General Method

All oxygen and/or moisture sensitive reactions were carried out under $N_2$ atmosphere. All reagents and solvents were purchased from commercial vendors and used as received. $^1$H NMR spectra were recorded on a 400 MHz spectrometer. HPLC conditions for all LCMS reported: Column: Waters Acquity UPLC CSH C18, 1.8 μm, 2.1×30 mm at 40° C.; Gradient: 5% to 100% B in 2.0 minutes; hold 100% B for 0.7 minute; 0.9 mL/min. Eluent A: Milli-Q H2O+10 mM ammonium formate pH: 3.8; Eluent B: Acetonitrile. LCMS conditions for compound (6-7a) reported: Column: CSH C18, 3.5 μm, 4.6×30 mm at 40° C.; Gradient: Iso 5% B for 0.2 min, 5% to 100% B in 1.8 minutes; hold 100% B for 1 minute; Flow: 3 mL/min. Eluent A: Milli-Q H2O+10 mM Ammonium Formate pH: 3.8 (Am.F.); Eluent B: acetonitrile (no additive).

Experimental (4R)-methyl 4-((3R,5S,7S,8R,10S,13R,17R)-3,7-dihydroxy-10,13-dimethylhexadecahydro-1H-cyclopenta[a]phenanthren-17-yl)pentanoate (6-4)

4-methylbenzenesulfonic acid (877 mg, 5.10 mmol) was added to a solution of ursodeoxycholic acid (1) (20.0 g, 50.9 mmol) in $CH_3OH$ (400 mL) and the reaction mixture was refluxed at 65° C. and stirred for 2.5 h. The mixture was then cooled to room temperature and volatiles were removed under reduced pressure. The residue was dissolved in $CHCl_3$ (300 mL) and washed with an aqueous solution of $K_2CO_3$ (1.00 M, 3×100 mL). The organic phase was dried ($Na_2SO_4$) and concentrated under reduced pressure to give the title compound as a solid (20.1 g, 97% yield). $^1$H NMR (400 MHz, $CDCl_3$) δ 3.66 (s, 3H), 3.63-3.54 (m, 2H), 2.35 (ddd, J=15.3, 10.2, 5.1 Hz, 1H), 2.27-2.17 (m, 1H), 1.99 (dt, J=12.5, 3.2 Hz, 1H), 1.93-1.56 (m, 8H), 1.52-1.12 (m, 13H), 1.11-0.97 (m, 2H), 0.94 (s, 3H), 0.92 (d, J=6.4 Hz, 3H), 0.67 (s, 3H); LCMS (Am formate) $R_t$=1.40 min; MS cal.: 406.60; mass found: [M+NH$_4$]$^+$: 424.5

(4R)-methyl 4-((3R,5S,7S,8R,10S,13R,17R)-3-hydroxy-10,13-dimethyl-7-(tosyloxy) hexadecahydro-1H-cyclopenta[a]phenanthren-17-yl)pentanoate (6-5)

4-methylbenzenesulfonyl chloride (4.22 g, 22.1 mmol) was added to a solution of (4R)-methyl 4-[(3R,5S,7S,8R,10S,13R,17R)-3,7-dihydroxy-10,13-dimethyl-2,3,4,5,6,7,8,9,11,12,14,15,16,17-tetradecahydro-1H-cyclopenta[a]phenanthren-17-yl]pentanoate (6-4) (6.00 g, 14.8 mmol) in pyridine (72.0 mL) and the mixture was heated at 50° C. and stirred for 4 h. The mixture was then cooled to rt and the pyridine was removed under reduced pressure. The mixture was diluted with aqueous HCl (1.00 M, 130 mL) and EtOAc (150 mL). The organic and aqueous layers were separated and the organic layer was washed with aqueous HCl (1.00 M, 2×100 mL). The combined aqueous layers were extracted with EtOAc (2×75.0 mL). The combined organic layers were dried ($Na_2SO_4$) and concentrated under reduced pressure. The residue was purified by silica gel chromatography (120 g, EtOAc/hexanes, 15-100%) to give the title compound as an oil (1.08 g, 13% yield). $^1$H NMR (400 MHz, $CDCl_3$) δ 7.74 (d, J=8.2 Hz, 2H), 7.29 (d, J=8.1 Hz, 2H), 4.63 (td, J=11.2, 5.0 Hz, 1H), 3.64 (s, 3H), 3.49 (ddd, J=14.7, 10.0, 4.8 Hz, 1H), 2.42 (s, 3H), 2.32 (ddd, J=14.8, 10.0, 4.7 Hz, 1H), 2.18 (ddd, J=15.5, 9.1, 6.6 Hz, 1H), 1.94 (d, J=12.5 Hz, 1H), 1.89-1.45 (m, 13H), 1.45-1.16 (m, 5H), 1.10 (td, J=12.7, 3.4 Hz, 1H), 1.05-0.91 (m, 2H), 0.90-0.78 (m, 8H), 0.60 (s, 3H); LCMS (Am formate) $R_t$=1.05 min; MS cal.: 560.78; mass found: [M+NH$_4$]$^+$: 578.7.

(4R)-methyl 4-((3R,5S,7R,8R,10S,13R,17R)-7-(acetylthio)-3-hydroxy-10,13-dimethylhexa deca-hydro-1H-cyclopenta[a]phenanthren-17-yl)pentanoate (6-6)

Potassium thioacetate (699 mg, 6.12 mmol) was added to a DMF (5.00 mL) solution of (4R)-methyl 4-[(3R,5S,7S,8R,10S,13R,17R)-3-hydroxy-10,13-dimethyl-7-(p-tolylsulfonyloxy)-2,3,4,5,6,7,8,9,11,12,14,15,16,17-tetradecahydro-1H-cyclopenta[a]phenanthren-17-yl]pentanoate (6-5) (520 mg, 0.927 mmol). The mixture turned green instantly and was heated at 85° C. and stirred for 3 h. The reaction mixture was cooled to room temperature and diluted with water (30.0 mL) and EtOAc (20.0 mL). The aqueous and organic layers were separated and the aqueous layer was washed with EtOAc (3×15.0 mL). The combined organic layers were washed with water (3×15.0 mL), brine (1×20.0 mL), dried ($Na_2SO_4$) and concentrated under reduced pressure. The residue was purified by silica gel chromatography (60.0 g, EtOAc/Hexanes, 0-100%) to give the title compound as a foamy solid (324 mg, 75% yield). $^1$H NMR (400 MHz, $CDCl_3$) δ 3.85 (td, J=5.0, 1.8 Hz, 1H), 3.66 (s, 3H), 3.54-3.44 (m, 1H), 2.41-2.30 (m, 2H), 2.32 (s, 3H), 2.26-2.17 (m, 1H), 2.10-2.00 (m, 1H), 1.98-1.92 (m, 1H), 1.89-1.72 (m, 5H), 1.70-1.59 (m, 2H), 1.58-1.53 (m, 1H), 1.48-1.20 (m, 8H), 1.18-1.07 (m, 2H), 1.01 (ddd, J=6.7, 5.7, 3.0 Hz, 1H), 0.95 (s, 3H), 0.91 (d, J=6.4 Hz, 3H), 0.64 (s, 3H); LCMS (Am formate) $R_t$=1.71 min; MS cal.: 464.296; mass found: [M+NH$_4$]$^+$: 482.3.

(3R,5S,7R,8R,10S,13R,17R)-3-hydroxy-17-((R)-5-methoxy-5-oxopentan-2-yl)-10,13-dimethylhexadecahydro-1H-cyclopenta[a]phenanthrene-7-sulfonic acid (6-7a) and (3R,5S,7R,8R,10S,13R,17R)-3-(formyloxy)-17-((R)-5-methoxy-5-oxopentan-2-yl)-10,13-dimethylhexadecahydro-1H-cyclopenta[a]phenanthrene-7-sulfonic acid (6-7b)

(4R)-Methyl 4-[(3R,5S,7R,8R,10S,13R,17R)-7-acetylsulfanyl-3-hydroxy-10,13-dimethyl-2,3,4,5,6,7,8,9,11,12,14,15,16,17-tetradecahydro-1H-cyclopenta[a]phenanthren-17-yl]pentanoate (6-6) (600 mg, 1.29 mmol) was taken up in formic acid (6.00 mL) and cooled to 0° C. Hydrogen peroxide (42.6 mmol, 1.32 mL, 30% wt. in $H_2O$) was added to the mixture dropwise over 5 min. The reaction was stirred at 0° C. for 30 min and then at room temperature for 2 h. Volatiles were removed under reduced pressure. The residue was purified by silica gel chromatography (60 g, MeOH/EtOAc, 0-35%) to obtain (6-7a) as an oil (130 mg, 21%). $^1$H NMR (400 MHz, $CDCl_3$) δ 3.63 (s, 3H), 3.49-3.40 (m, 1H), 3.11-3.04 (m, 1H), 2.35 (m, 5H), 2.25-2.00 (m, 7H), 1.94-1.69 (m, 6H), 1.60 (br s, 2H), 1.43-1.06 (m, 10H), 0.92 (s, 3H), 0.89 (d, J=6.4 Hz, 3H), 0.59 (s, 3H); LCMS (Am formate) Rt=1.54 min; MS cal.: 470.662; mass found: $[M+NH_4]^+$: 488.3.

(3R,5S,7R,8R,10S,13R,17R)-3-(formyloxy)-17-((R)-5-methoxy-5-oxopentan-2-yl)-10,13-dimethylhexadecahydro-1H-cyclopenta[a]phenanthrene-7-sulfonic acid (6-7b) was also isolated as an oil (280 mg, 43%). $^1$H NMR (400 MHz, $CDCl_3$) δ 8.05 (s, 1H), 4.65 (s, 1H), 3.65 (s, 3H), 3.14-3.02 (m, 1H), 2.75-2.62 (m, 1H), 2.49-2.14 (m, 8H), 1.97-1.65 (m, 10H), 1.40 (m, 4H), 1.24-1.17 (m, 2H), 1.08-1.01 (m, 1H), 0.96 (s, 3H), 0.91 (d, J=4.8 Hz, 3H), 0.60 (s, 3H); LCMS (Am formate) $R_t$=1.23 min; MS cal.: 498.265; mass found: $[M+NH_4]^+$: 516.6.

(4R)-4-((3R,5S,7R,8R,10S,13R,17R)-3-hydroxy-10,13-dimethyl-7-sulfohexadecahydro-1H-cyclopenta[a]phenanthren-17-yl)pentanoic acid (Compound (I-6))

A solution of NaOH in MeOH (5%, 16.0 mL) and $H_2O$ (3.20 mL) was added to (3R,5S,7R,8R,10S,13R,17R)-3-(formyloxy)-17-((R)-5-methoxy-5-oxopentan-2-yl)-10,13-dimethylhexadecahydro-1H-cyclopenta[a]phenanthrene-7-sulfonic acid (110 mg, 0.220 mmol). The mixture was refluxed for 18 h. The resulting solution was cooled to 0° C. and acidified with aqueous HCl (6 N) until pH=1. The resulting solid was filtered, washed with cold water (3×10.0 mL), EtOAc (2×5.00 mL), $CH_2Cl_2$ (2×5.00 mL) and cold $CHCl_3$ (2×5.00 mL). The solid was dissolved in 30% MeOH/$CHCl_3$ and volatiles were evaporated under reduced pressure. The residue was lyophilized and the resulting solid was triturated with $CH_3CN$ to give the title compound as a white solid (72 mg, 71% yield). $^1$H NMR (400 MHz, MeOD) δ 3.43-3.33 (m, 1H), 3.11-3.04 (m, 1H), 2.66-2.53 (m, 2H), 2.49-2.40 (m, 1H), 2.33 (ddd, J=15.2, 9.9, 5.2 Hz, 1H), 2.28-2.11 (m, 3H), 2.00-1.75 (m, 6H), 1.62 (ddd, J=21.8, 10.7, 6.7 Hz, 2H), 1.51-1.42 (m, 2H), 1.41-1.24 (m, 6H), 1.20 (dd, J=18.7, 9.2 Hz, 1H), 1.05-0.92 (m, 2H), 0.98 (s, 3H), 0.97 (d, J=6.5 Hz, 3H), 0.68 (s, 3H), $^{13}$C NMR (100 MHz, MeOD) δ 176.54, 73.08, 61.20, 56.34, 51.26, 44.06, 42.99, 39.82, 39.64, 38.61, 36.96, 36.86, 36.71, 32.28, 32.11, 31.76, 31.64, 31.32, 29.15, 26.36, 22.98, 21.81, 18.93, 11.96; LCMS (Am formate) $R_t$=0.98 min; MS cal.: 456.255; mass found: $[M+NH4]^+$: 474.5.

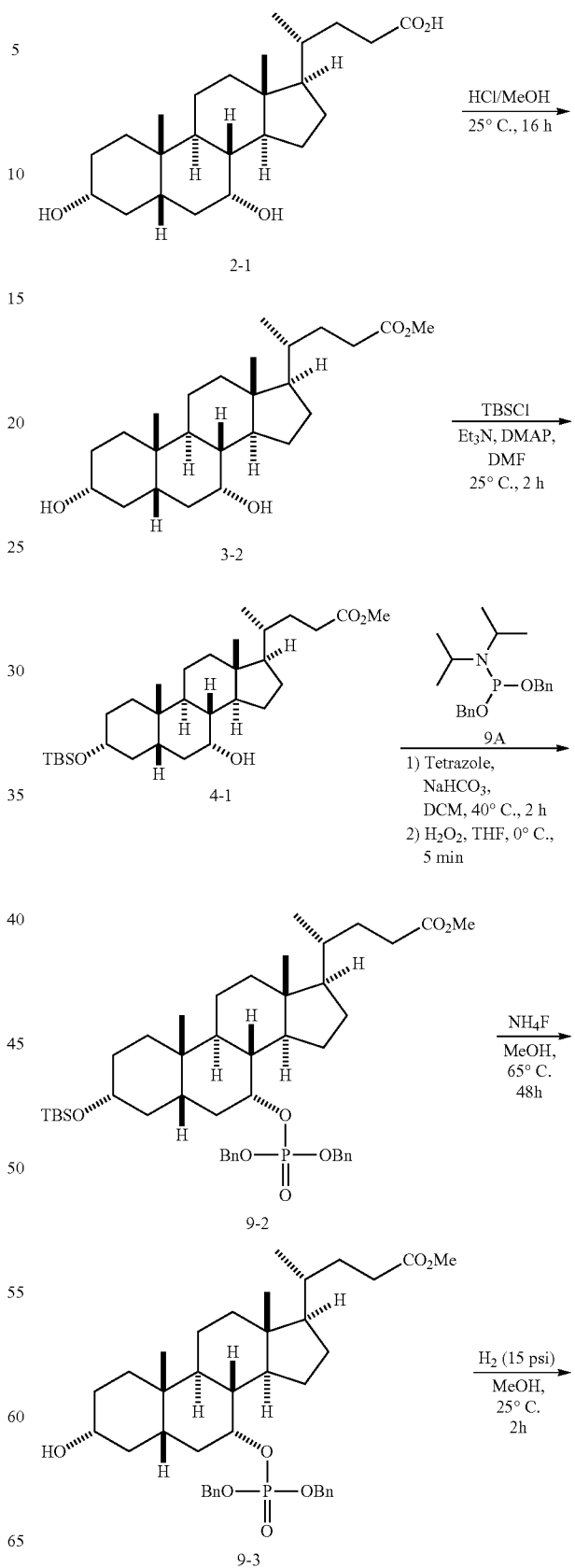

Compound 9

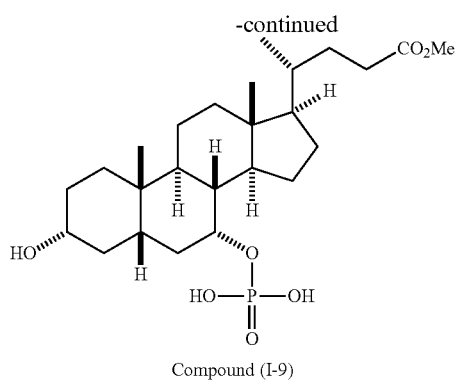

Compound (I-9)

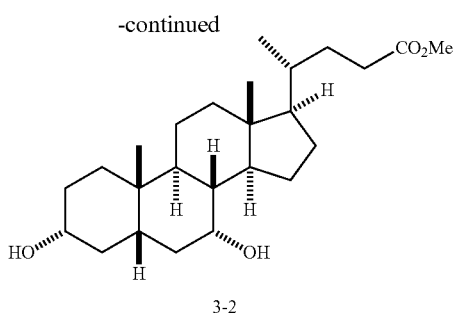

3-2

A solution of Cpd. 3-2 (100 g, 254 mmol, 1.00 eq) in MeOH (600 mL) was added HCl (60.0 mL) at 0° C. and the result mixture was stirred at 25° C. for 16 h. TLC (Petroleum ether/EtOAc=0/1) showed the reaction was completed. The reaction was concentrated, the residue was added sat-.NaHCO$_3$ (1.00 L), extracted with EtOAc (300 mL×3). The combined organic phase was washed with brine (500 mL), dried with Na$_2$SO$_4$ and concentrated to obtain Cpd. 3-2 (70.0 g, 172 mmol, 67.5% yield) as colorless oil. $^1$H NMR: ET26314-1-p1b1 (400 MHz, MeOD-d$_4$) δ 3.81-3.75 (m, 1H), 3.64 (s, 3H), 3.40-3.27 (m, 1H), 2.39-2.15 (m, 3H), 2.01-1.05 (m, 23H), 0.95-0.85 (m, 6H), 0.686 (s, 3H).

General Procedure for Preparation of Cpd.4-1

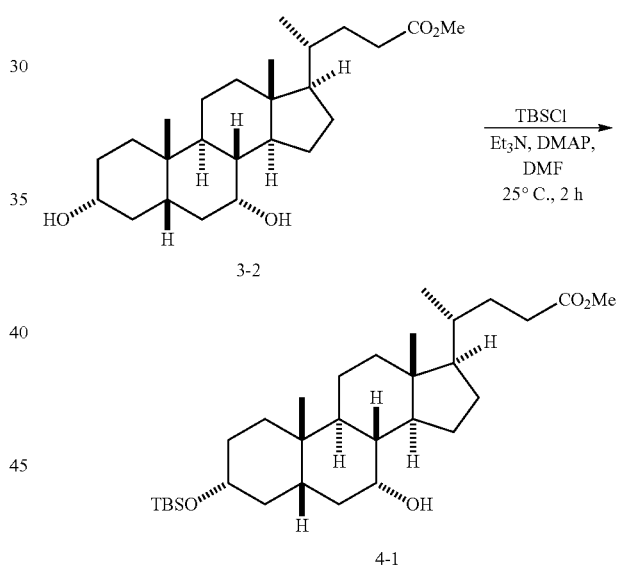

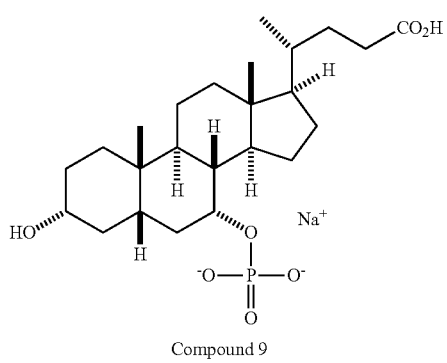

Compound 9

A solution of Cpd. (I-3) (300 mg, 598 umol, 1.00 eq) in MeOH (1.2 mL) was added a solution of NaOH (59.8 mg, 1.49 mmol, 2.50 eq) in H$_2$O (1.20 mL) and the reaction was stirred at 25° C. for 16 h. LCMS (et26314-84-p1a1) showed the reaction was completed. The reaction was concentrated at 30° C. to remove MeOH. The residue was purified by prep-HPLC (column: Waters Xbridge BEH C18 100*30 mm*10 um; mobile phase: [water (0.04% NH$_3$H$_2$O)-can]; B %: 1%-25%, 12 min) to obtain Target 3 (76.0 mg, 150 umol, 25.1% yield, 100% purity) as white solid. $^1$H NMR: (400 MHz, DMSO-d$_6$) δ 5.80 (d, J=6.8 Hz, 1H), 4.40 (d, J=4.0 Hz, 1H), 3.86-3.58 (m, 1H), 3.52-3.33 (m, 4H), 3.16-3.08 (m, 1H), 2.50-1.77 (m, 6H), 1.76-0.95 (m, 18H), 0.91-0.77 (m, 8H), 0.60 (s, 3H). LCMS: ET26314-84-P1A1, t=0.936 min, MS cal.: 487.3, [M−1]$^-$=486.2 QC-LCMS: ET26314-84-P1C1, t=2.046 min, MS cal.: 487.3, [M−1]$^-$=486.2.

General Procedure for Preparation of Cpd. 3-2

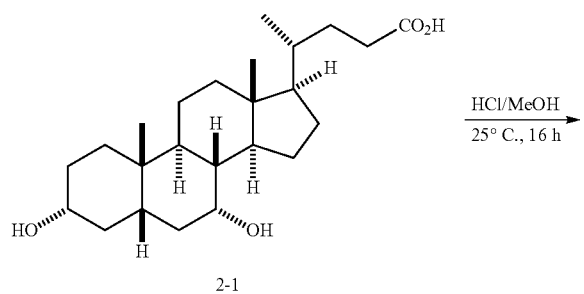

2-1

A solution of Cpd. 3-2 (50.0 g, 122 mmol, 1.00 eq), DMAP (777 mg, 6.37 mmol, 5.18e-2 eq) and Et$_3$N (37.7 g, 373 mmol, 51.9 mL, 3.04 eq) in DMF (220 mL) was added TBSCl (36.6 g, 243 mmol, 29.8 mL, 1.98 eq) at 0° C. and the reaction was stirred at 25° C. for 2 h. TLC (Petroleum ether/EtOAc=5/1) showed the reaction was completed. H$_2$O (1.00 L) was added to the reaction, the reaction was extracted with EtOAc (200 mL×2). The combined organic phase was washed with brine (300 mL), dried with Na$_2$SO$_4$ and concentrated. The residue was purified by column chromatography on silica gel (Petroleum ether/EtOAc=10/1) to obtain Cpd.4-1 (45.0 g, 86.4 mmol, 70.2% yield) as white solid. $^1$H NMR: (400 MHz, CDCl$_3$) δ 3.82-3.77 (m, 1H), 3.62 (s, 3H), 3.42-3.37 (m, 1H), 2.28-2.12 (m, 1H), 2.11-2.05 (m, 2H), 1.96-1.65 (m, 6H), 1.62-1.02 (m, 18H), 0.88 (d, J=6.4 Hz, 3H), 0.83 (s, 9H), 0.68 (s, 3H), 0.00 (s, 6H).

General Procedure for Preparation of Cpd.9-2

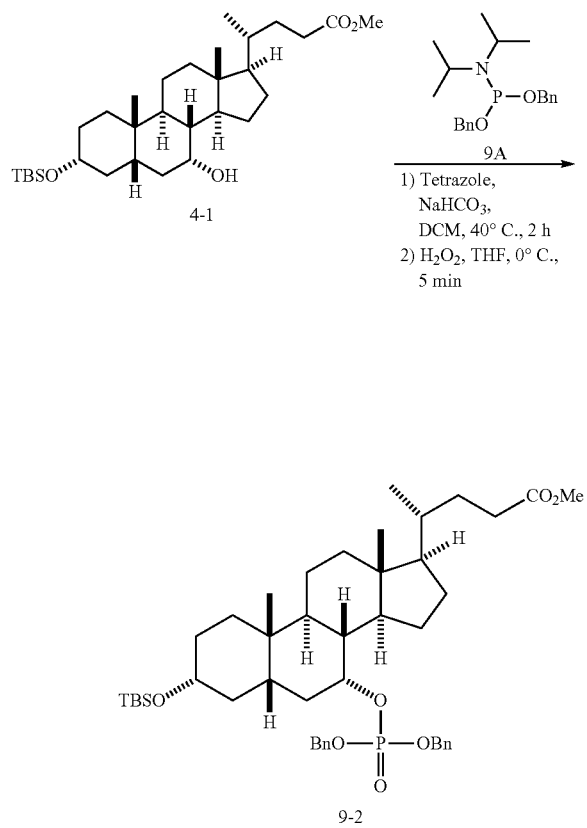

4-1

9A
1) Tetrazole, NaHCO₃, DCM, 40° C., 2 h
2) H₂O₂, THF, 0° C., 5 min 9-2

A solution of Cpd.4-1 (2.00 g, 3.84 mmol, 1.00 eq), NaHCO₃ (1.71 g, 20.3 mmol, 5.30 eq) and 2H-tetrazole (0.45 M, 17.9 mL, 2.1 eq) in DCM (20.0 mL) was added Cpd.9A (6.63 g, 19.2 mmol, 6.44 mL, 5.00 eq) at 25° C. under N₂ and the reaction was stirred at 40° C. for 2 h. TLC (Petroleum ether/EtOAc=5/1, new spot: Rf=0.7) showed Cpd.4-1 was consumed. The reaction was cooled to 0° C., THF (20 mL) was added, follow by H₂O₂ (870 mg, 7.68 mmol, 737 uL, 30% purity, 2.00 eq) and the reaction was stirred at 0° C. for 5 min. TLC (Petroleum ether/EtOAc=5/1, Cpd.9-2: Rf=0.1) showed the reaction was completed. The reaction was poured into aq.Na₂S₂O₃ (20.0 mL), extract with EtOAc (20.0 mL×3). The combined organic phase was washed with brine (20.0 mL), dried with Na₂SO₄ and concentrated. The residue was purified by column chromatography on silica gel (Petroleum ether/EtOAc=5/1) to obtain crude Cpd.9-2 (5 g). The crude was slurry with MeOH (10.0 mL) for 10 min, filtered and the filter cake was concentrated to obtain Cpd.9-2 (1.45 g, 1.86 mmol, 48.3% yield) as white solid. ¹H NMR: (400 MHz, MeOD-d₄) δ 7.34-7.24 (m, 10H), 5.01 (dd, J₁=8.0 Hz, J₂=30.8 Hz, 4H), 4.56-4.54 (m, 1H), 3.65 (s, 3H), 3.43₃.40 (m, 1H), 2.36-2.24 (m, 1H), 2.2₃2.05 (m, 2H), 1.86-1.55 (m, 9H), 1.5₃1.05 (m, 10H), 1.01-0.76 (m, 20H), 0.56 (s, 3H), 0.00 (d, J=7.6 Hz, 6H).

General Procedure for Preparation of Cpd.9-3

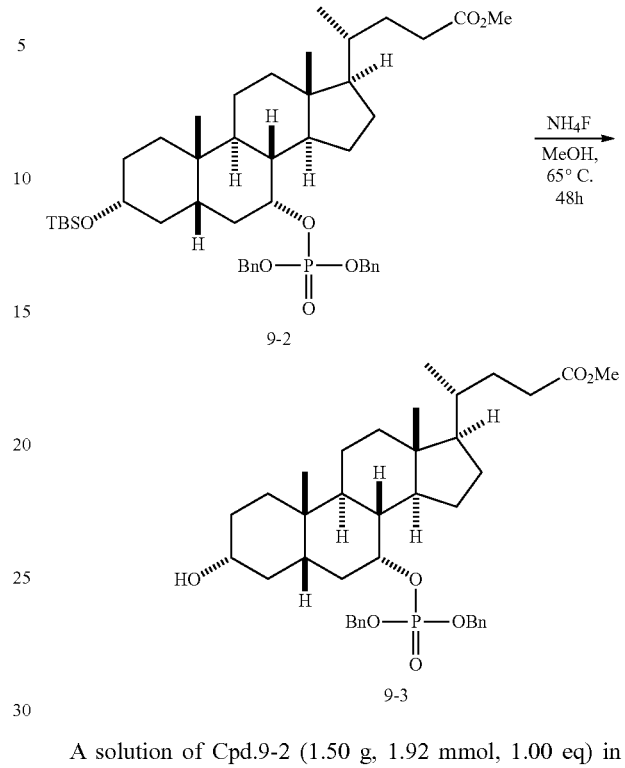

NH₄F
MeOH, 65° C. 48h 9-2

9-3

A solution of Cpd.9-2 (1.50 g, 1.92 mmol, 1.00 eq) in MeOH (15 mL) and THF (10 mL) was added NH₄F (356 mg, 9.61 mmol, 5.00 eq) and stirred at 50° C. for 12 h. LCMS (ET26315-9-P1A) showed Cpd.9-2 consumed and Cpd.9-3 formed. The reaction was concentrated in vacuo to remove MeOH and THF. Water (5.00 ml) was added to the residue, extracted with EtOAc (15.0 mL×3). The combined organic phase was washed with brine (10.0 mL×3), dried with Na₂SO₄ and concentrated. The residue was purified by column chromatography (SiO₂, Petroleum ether/ EtOAc=10/1 to 0/1) to obtain Cpd.9-3 (0.60 g, 901 umol, 46.8% yield) as white solid. ¹H NMR: ET26315-9-P1A (400 MHz, CDCl₃) δ 7.40-731 (m, 10H), 5.11-5.00 (m, 4H), 4.59-4.57 (m, 1H), 3.68 (s, 3H), 3.44-3.39 (m, 1H), 2.38-2.17 (m, 2H), 2.05-1.66 (m, 14H), 1.54-1.19 (m, 11H), 1.10-0.97 (m, 4H), 0.94-0.89 (m, 6H), 0.61 (s, 3H). LCMS: ET26315-9-P1A, t=1.477 min, MS cal.: 666.3, [M+23]⁺= 689.4.

General Procedure for Preparation of Cpd. (I-9)

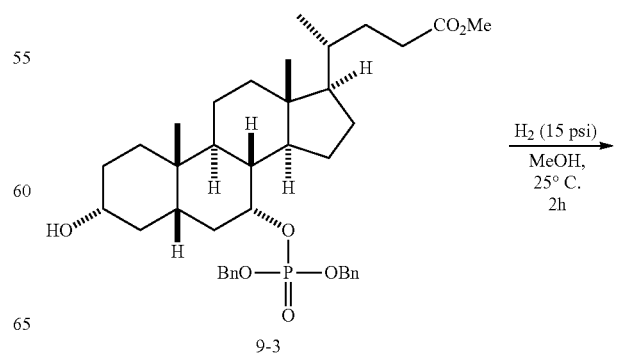

9-3

H₂ (15 psi)
MeOH, 25° C. 2h

-continued

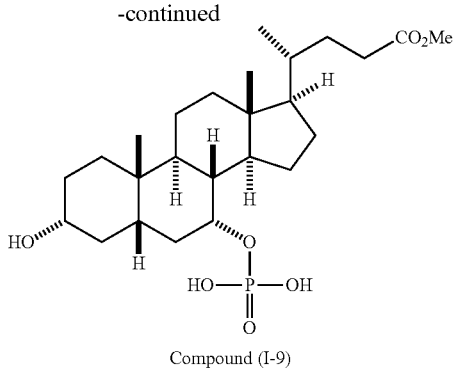

Compound (I-9)

A solution of Cpd.9-3 (0.40 g, 599 umol, 1.00 eq) in MeOH (5.00 mL) was added Pd/C (59.9 umol, 0.1 eq). Degas with $H_2$ three times, then the reaction was stirred at 25° C. under a balloon of $H_2$ for 2 h. LCMS (ET26515-12-P1A) showed Cpd.9-3 consumed and Cpd. (I-9) formed. The reaction was filtered to remove the Pd/C, concentrate to obtain Cpd. (I-9) (0.30 g, crude) as white solid, used to next step without purification. LCMS: ET26515-12-P1A, t=1.254 min, MS cal.: 486.3, [M−1]⁻=485.3.

General Procedure for Preparation of Compound 9

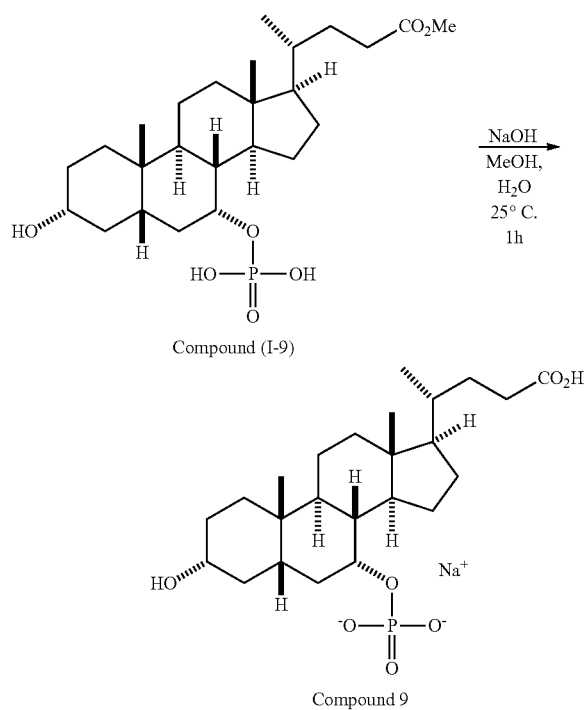

A solution of Cpd. (I-9) (0.30 g, 616 umol, 1.00 eq) in MeOH (5.00 mL) was added a solution of NaOH (49.3 mg, 1.23 mmol, 2.00 eq) in $H_2O$ (5 mL) at 25° C. and stirred at 25° C. for 1 h. LCMS showed Cpd. (I-9) consumed and Compound 9 formed. The reaction was purified the residue by prep-HPLC column: Waters Xbridge BEH C18 100*30 mm*10 um; mobile phase: [water (0.04% $NH_3H_2O$+10 mM $NH_4HCO_3$)-ACN]; B %: 1%-30%, 9 min to obtain Compound 9 (0.04 g, 95.2 umol, 15.4% yield) as white solid. $^1H$ NMR: ET26315-14-P1H3 (400 MHz, $CDCl_3$) δ 4.27 (s, 1H), 3.47-3.42 (m, 1H), 2.22-2.06 (m, 3H), 1.94-1.10 (m, 22H), 1.0₃0.88 (m, 8H), 0.62 (s, 3H). LCMS: ET26315-14-P1B, t=0.899 min, MS cal.: 470.2, [M+1]⁺=471.3. QC-LCMS: ET26315-14-P1B1, t=2.049 min, MS cal.: 470.2, [M+1]⁺=471.2 Example 5. In-vitro studies with Compounds 1, 2, 3, 6, and 9.

The ability of synthetic derivatives of CA7S to activate TGR5 and induce GLP-1 secretion was tested in vitro. 10 mM stock solutions of compounds were made in DMSO and diluted in DMSO for every assay.

Figure 28A:
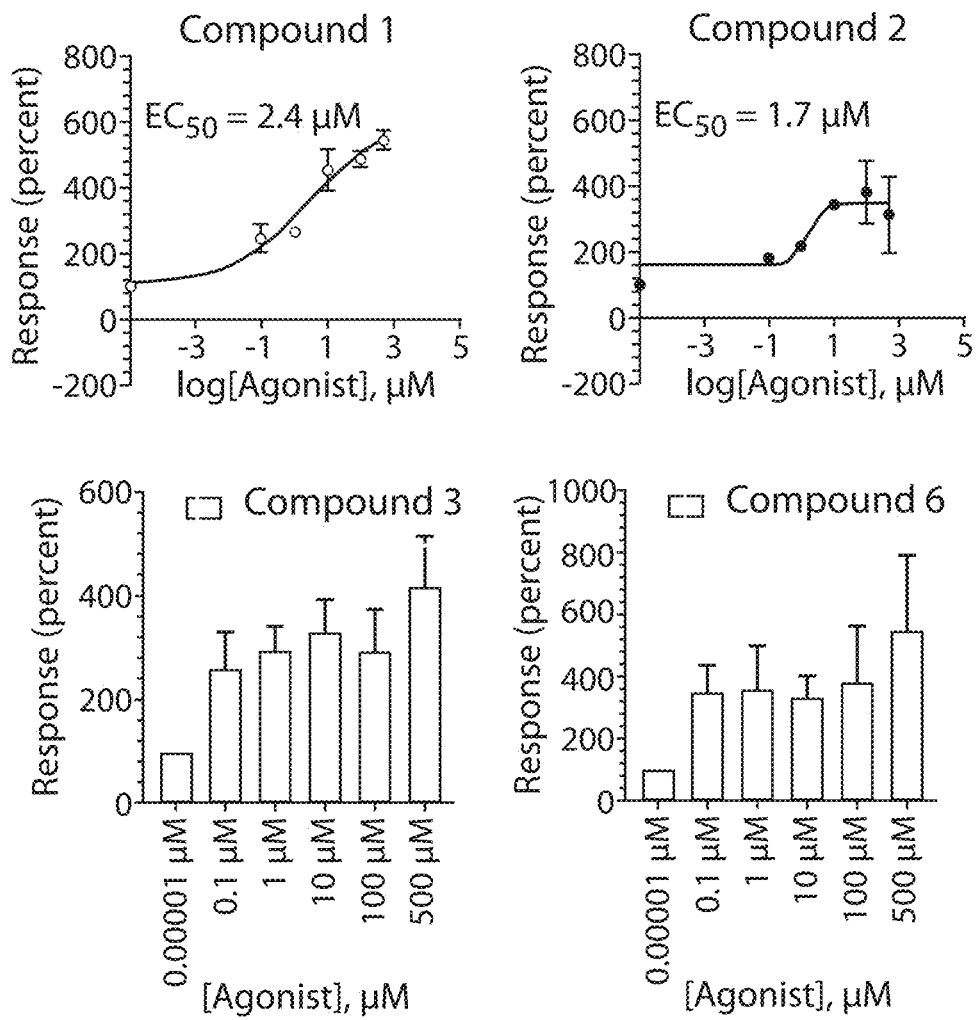
FIG. 28A shows dose response curves or concentration-dependent activation of human TGR5 in HEK293T cells overexpressing human TGR5 for indicated compounds (3 biological replicates per condition). All data are presented as mean±SEM.

Human TGR5 was overexpressed in HEK93T cells along with a luciferase-based TGR5 reporter plasmid. Cells were then incubated with different concentrations of compounds overnight, and TGR5 activation was measured as a luminescence readout. Compounds 1, 2, 3, and 6 induced TGR5 activation in a dose-dependent manner. $EC_{50}$ values were obtained for Compound 1 of $EC_{50}$=2.4 μM and Compound 2 of $EC_{50}$=1.7 μM (FIG. 28A).

Figure 28B:
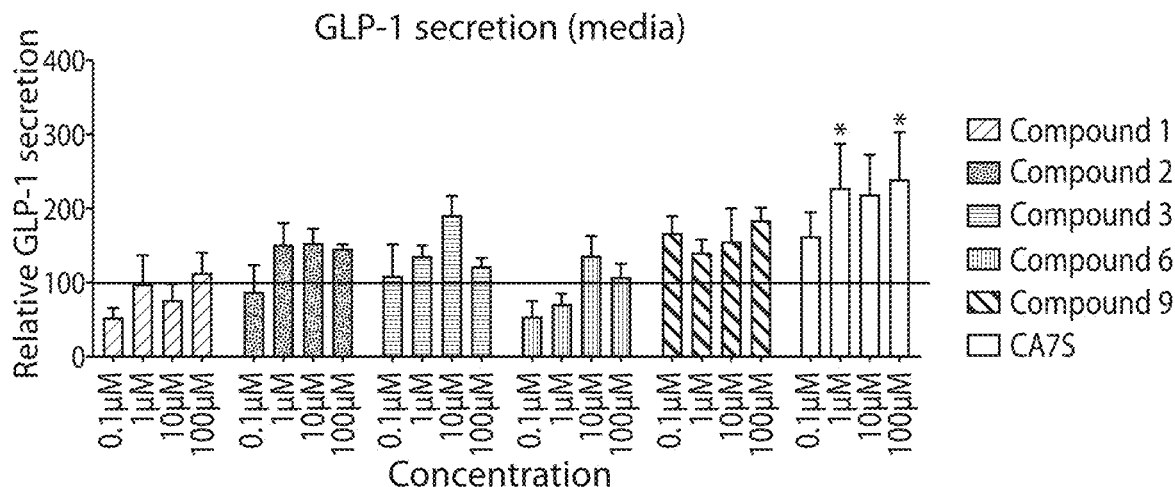
FIG. 28B shows GLP-1 synthesis and secretion induced by synthetic derivatives in NCI-H716 cells compared to DMSO control. Data represented as % GLP-1 secretion=total GLP-1 secreted (media)/(total GLP-1 secreted (media)+total GLP-1 in cell lysates)*100. Also shown is the GLP-1 secretion (total): Compound-induced synthesis and secretion of GLP-1 in NCI-H716 cells compared to DMSO control. Data represented as total GLP-1 levels=total GLP-1 secreted (media)+total GLP-1 in cell lysates). 3 biological replicates per condition, *$p<0.05$, **$p<0.01$, one-way ANOVA followed by Dunnett's multiple comparisons test. All data are presented as mean±SEM.
Figure 28B:
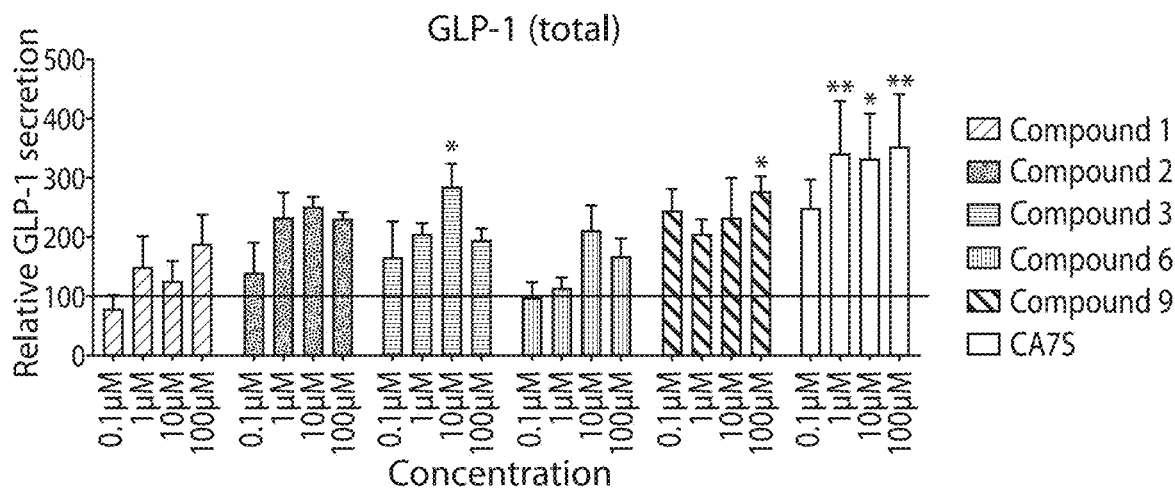

GLP-1 synthesis and secretion were measured in matrigel-polarized NCI-H716 cells. CA7S was included as a positive control. Compounds 1, 2, 3, 6, and 9 increased total GLP-1, indicating that these compounds induced GLP-1 synthesis. Compounds 2, 3, and 9 induced GLP-1 secretion. (FIG. 28B)

Figure 28C:
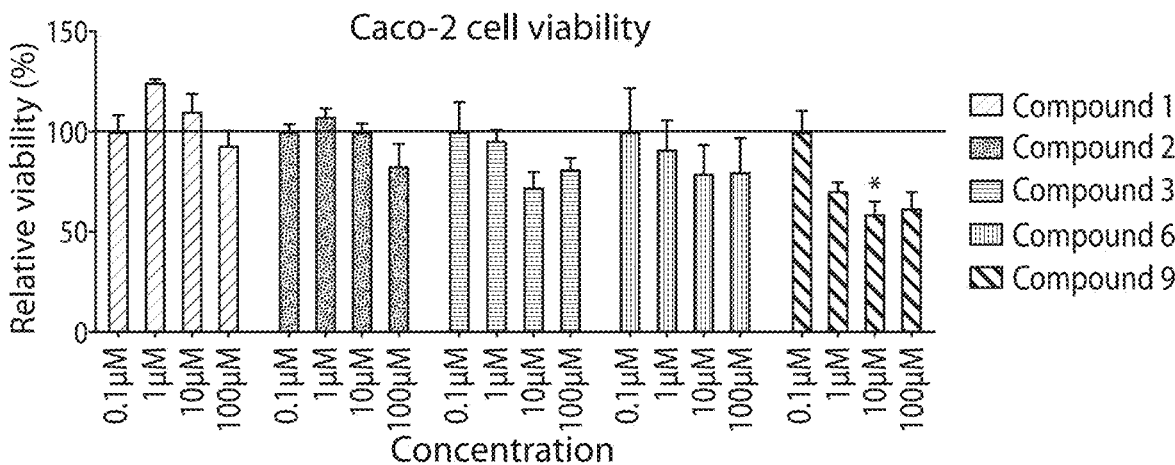
FIG. 28C shows the percentage cell viability upon treatment of Caco-2 cells with compounds in vitro. 3 biological replicates per condition, *$p<0.05$, one-way ANOVA followed by Dunnett's multiple comparisons test. All data are presented as mean±SEM.

Compounds were also tested for toxicity using Caco-2 cells, a human intestinal epithelial cancer cell line. Caco-2 cells were incubated with compounds for 16 hours and cell death was determined using a luminescence assay measuring ATP levels as a readout for cell viability. Compounds 1, 2, 3, and 6 were relatively non-toxic to Caco-2 cells up to a concentration of 100 μM (FIG. 28C).

In summary, the class of compounds with N-linked sulfamates (Compounds 1, 2, and 3) activate TGR5, induce GLP-1 synthesis and secretion, and have low toxicity to human intestinal epithelial Caco-2 cells. The S-linked sulfonate compound Compound 6 also activated TGR5, induced an increase in GLP-1 synthesis and secretion.

Cell culture. NCI-H716 cells and Caco-2 cells were obtained from American Type Culture Collection (Manassas, Va.). HEK-293T cells were a kind gift from the Blacklow lab (BCMP, HMS). Caco-2 and HEK-293T cells were maintained in Minimum Essential Medium (MEM) with GlutaMAX and Earle's Salts (Gibco, Life Technologies, UK). NCI-H716 cells were maintained in RPMI 1640 with L-glutamine (GenClone, San Diego, Calif.). All cell culture media were supplemented with 10% fetal bovine serum (FBS), 100 units/ml penicillin, and 100 μg/ml streptomycin (GenClone). Cells were grown in FBS- and antibiotic-supplemented 'complete' media at 37° C. in an atmosphere of 5% $CO_2$.

Treatment with compounds. NCI-H716 cells were seeded in cell culture plates coated with Matrigel (Corning, N.Y. Cat. No. 356234) diluted in Hank's Balanced Salt Solution (HBSS, Gibco) according to manufacturer's instructions. The cells were allowed to grow for 2 days in complete RPMI media. On the day of the treatment, cells were rinsed gently with low serum (0.5% FBS) RPMI 1640 medium without antibiotics. Compounds were diluted in dimethyl sulfoxide (DMSO, VWR International) and added to cells in the low serum media (0.5% FBS, RPMI 1640) without antibiotics. The concentration of DMSO was kept constant throughout the treatments and used as a negative control. Cells were incubated at 37° C. in an atmosphere of 5% $CO_2$ for 2 hours. After the incubation period, cell culture media was collected in Eppendorf tubes containing 1% trifluoroacetic acid (TFA, Sigma) in sterile purified water (GenClone) to make a final TFA concentration of 0.1% and frozen at −80° C. for further GLP-1 measurements. Cells on cell culture plates were placed on ice and gently washed with PBS (GenClone). Cells used for GLP-1 measurements were treated with ice-cold cell lysis solution of 1% TFA, 1N hydrochloric acid, 5% formic acid, and 1% NaCl (all from Sigma), scraped off of the Matrigel coating, and collected in 96-well plates for peptide purification. Lysates were stored at −80° C. for further analysis.

GLP-1 measurement. Total GLP-1 peptide measurements were performed using the GLP-1 EIA Kit (Sigma, Cat. No. RAB0201) according to manufacturer's instructions. Cell culture media and cell lysates were subjected to peptide purification using Sep Pak C18 Classic columns (Waters Corporation, Milford, Mass.). The column was pretreated with a solution of 0.1% TFA in 80% isopropyl alcohol (EMD Millipore) and equilibrated with 0.1% TFA in water. Cell culture media and cell lysates were loaded onto the column and washed with 0.1% TFA in 80% isopropyl alcohol. The peptides were eluted in 0.1% TFA in water. The eluate was concentrated by drying under vacuum and resuspended in 0.1% TFA in water. 0.1% TFA in water was used as 'blank' for cell culture media and purified cell lysate ELISAs. Excess samples were stored at −80° C. for later analyses. Total GLP-1 amounts in the cell culture media (secreted) and cell lysates were calculated using a standard curve provided in the EIA kit.

Plasmids and transient transfections. Human TGR5 was cloned using cDNA from human Caco-2 cells as template and a forward primer with an EcoRIrestriction-site (5'-CGGAATTCGCACTTGGTCCTTGTGCTCT-3') and a reverse primer with a XhoI-site (5'-GTCTCGAGTTAGTT-CAAGTCCAGGTCGA-3'). The PCR product was cloned into the pCDNA 3.1+plasmid (Promega Corporation, Madison, Wis.) and transfected at a concentration of 0.4 µg/ml of media. For luciferase reporter assays for TGR5 activation, the pGL4.29[luc2P/CRE/Hygro] plasmid (Promega Corporation), and the pGL4.74[hRluc/CMV] plasmid (Promega Corporation) were used at concentration of 2 µg/ml and 0.05 µg/ml of media respectively. All plasmids were transfected using Opti-MEM (Gibco) and Lipofectamine 2000 (Invitrogen, Life Technologies, Grand Island, N.Y., USA) according to manufacturer's instructions. Plasmid transfection were performed in antibiotic-free media (MEM for HEK293T and RPMI for Matrigel-attached NCI-H716 cells) with 10% FBS. After overnight incubation, compounds were added in complete media and incubated overnight. Cells were harvested the next day for luciferase assay.

Luciferase reporter assay. Luminescence was measured using the Dual-Luciferase Reporter Assay System (Promega Corporation) according to manufacturer's instructions. Cells were washed gently with PBS and lysed in PLB from the kit. Matrigel-attached cells were scraped in PLB. Luminescence was measured using the SpectraMax M5 plate reader (Molecular Devices, San Jose, Calif.) at the ICCB-Longwood Screening Facility at Harvard Medical School. Luminescence was normalized to *Renilla* luciferase activity and percentage relative luminescence was calculated compared to DMSO control.

Cell viability assay. Caco-2 cells were treated with compounds diluted in DMSO in complete MEM media. The concentration of DMSO was kept constant and used as a negative control. Cells were incubated with compounds overnight at 37° C. in an atmosphere of 5% $CO_2$. The next day, cell viability was measured using CellTiter-Glo Luminescent Cell Viability Assay from Promega Corporation according to manufacturer's instructions. Luminescence was measured using the SpectraMax M5 plate reader (Molecular Devices, San Jose, Calif.) at the ICCB-Longwood Screening Facility at Harvard Medical School. Luminescence was normalized to DMSO control and percentage relative luminescence was calculated compared to DMSO control.

EQUIVALENTS AND SCOPE

The singular terms "a," "an," and "the" include plural referents unless context clearly indicates otherwise. Similarly, the word "or" is intended to include "and" unless the context clearly indicates otherwise. Although methods and materials similar or equivalent to those provided herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims.

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating diabetes, obesity, or an inflammatory disease in a subject, the method comprising administering to a subject in need thereof a compound of Formula (I):

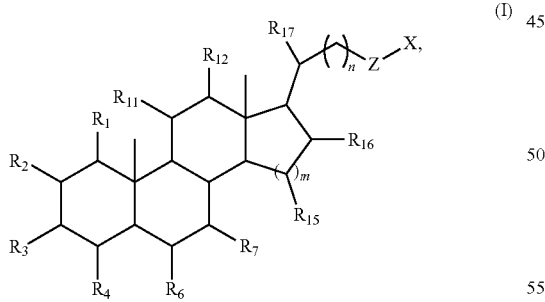

wherein:
n is 1, 2, 3, 4, 5, 6, 7, 8, 9, or 10;
m is 1;
Z is —C(O)—, —C(O)O—, —C(O)NR$_{18}$- or —CH$_2$-;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, CN, —CHO, —CO$_2$H, —CO$_2$R$_{18}$, —NO$_2$, —ONO$_2$, —SO$_2$Cl, —SO$_3$, —OSO$_3$, —NR$_{18}$SO$_3$, —PO$_3{}^{2-}$, —OPO$_3{}^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, -NHC(O)NHNH$_2$, or a polar amino acid;
each R$_1$, R$_2$, R$_4$, R$_{11}$, R$_{15}$, R$_{16}$, and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, CN, —CHO, —CO$_2$H, —CO$_2$R$_{18}$, —NO$_2$, —ONO$_2$, —SO$_2$Cl, —SO$_3{}^-$, —OSO$_3{}^-$, —NR$_{18}$SO$_3$, —PO$_3{}^{2-}$, —OPO$_3{}^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, or -NHC(O)NHNH$_2$;
each R$_3$, R$_6$, and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3$, —OSO$_3$, —NR$_{18}$SO$_3$, —PO$_3{}^{2-}$, —OPO$_3{}^{2-}$, —OSO$_2$R$_{18}$, —OSO$_2$N(R$^{18}$)$_2$, —NR$_{18}$SO$_2$R$_{18}$,—SO$_2$N(R$^{18}$)$_2$, -NHNH$_2$, —ONH$_2$, or -NHC(O)NHNH$_2$;
R$_7$ is —C(R$^{18}$)$_2$SO$_3$H, —C(R$^{18}$)$_2$SO$_3$, —SO$_2$N(R$^{18}$)$_2$, —OSO$_2$N(R$^{18}$)$_2$, —NR$_{18}$SO$_3$H, or —NR$_{18}$SO$_3$;
each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
or a pharmaceutically acceptable salt thereof.

2. The method of claim 1, wherein $R_7$ is —$C(R^{18})_2SO_3H$, —$C(R_{18})_2SO_3^{31}$, —$NR_{18}SO_3^{31}$, —$OSO_2N(R^{18})_2$, or —$SO_2N(R^{18})_2$, —$SO_3^{31}$, —$SO_3H$, or —$SR_{18}$.

3. A compound of Formula (I):

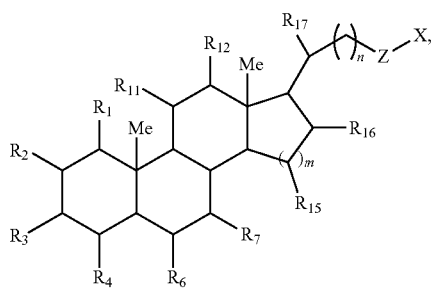

(I)

wherein:
n is 1, 2, 3, 4, 5, 6, 7, 8, 9, or 10;
m is 1;
Z is —C(O)—, —C(O)O—, —C(O)NR$_{18}$-, or —CH$_2$-;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3$, —OSO$_3$, —NR$_{18}$SO$_3$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, -NHC(O)NHNH$_2$, or a polar amino acid;
each R$_1$, R$_2$, R$_4$, R$_{11}$, R$_{15}$, R$_{16}$, and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3^-$, —OSO$_3$, —NR$_{18}$SO$_3$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, or -NHC(O)NHNH$_2$;
each R$_3$, R$_6$, and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3$, —OSO$_3$, —NR$_{18}$SO$_3$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, or -NHC(O)NHNH$_2$;
R$_7$ is —C(R$^{18}$)$_2$SO$_3$H, —C(R$^{18}$)$_2$SO$_3$, —SO$_2$N(R$^{18}$)$_2$, —OSO$_2$N(R$^{18}$)$_2$, —NR$_{18}$SO$_3$H, or —NR$_{18}$SO$_3$;
each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
or a pharmaceutically acceptable salt thereof.

4. The compound of claim 3, wherein the compound is of any one of the Formulae (II)-(XV):

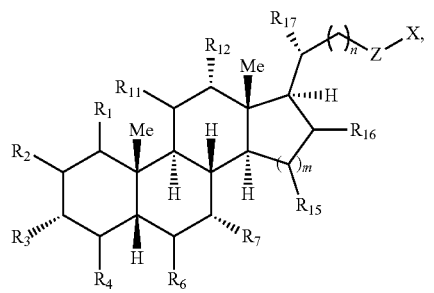

(II)

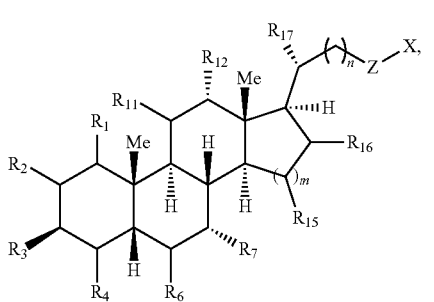

(III)

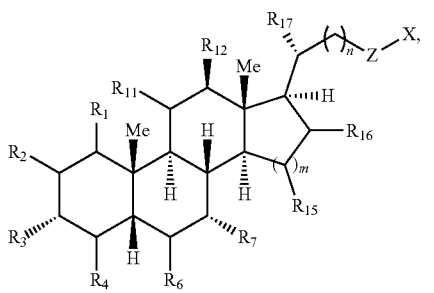

(IV)

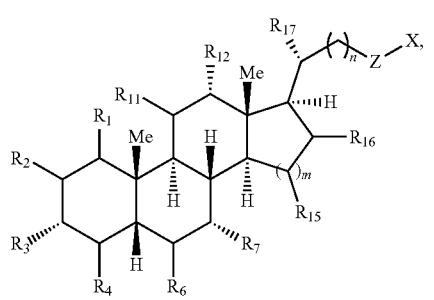

(V)

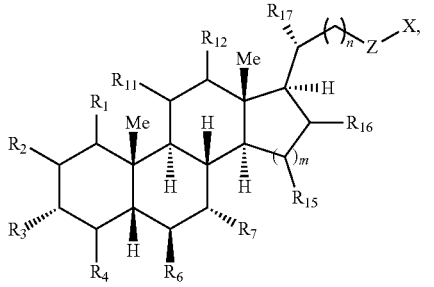

(VI)

(VII)
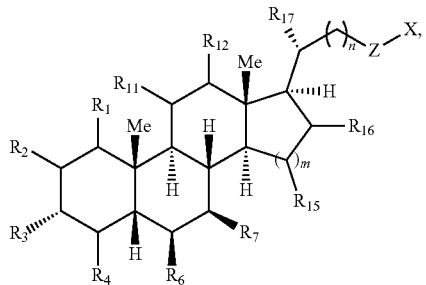

(VIII)
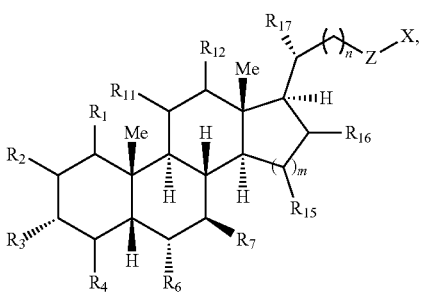

(IX)
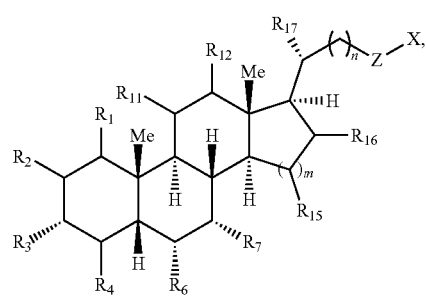

(X)
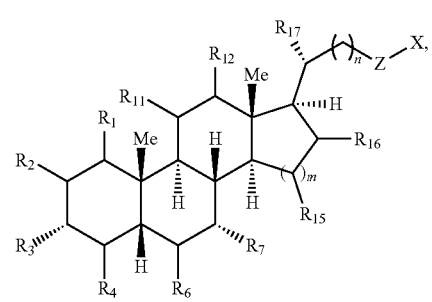

(XI)
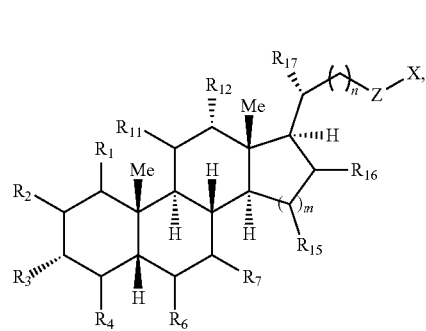

(XII)
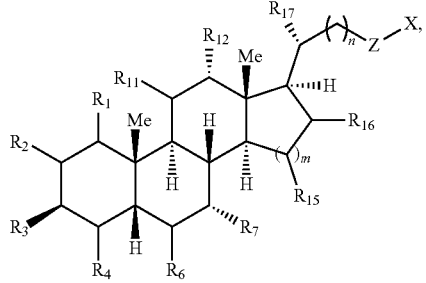

(XIII)
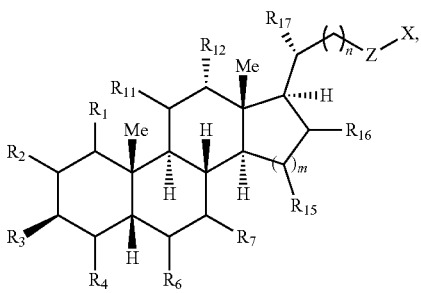

(XIV)
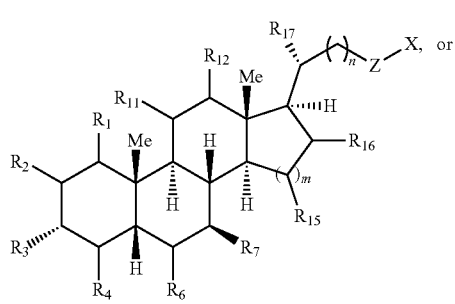

(XV)
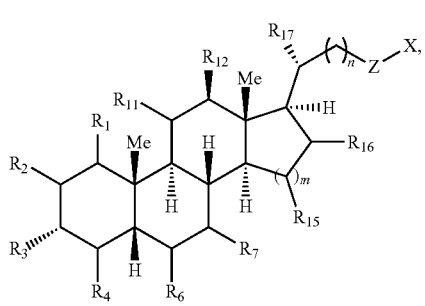

or a pharmaceutically acceptable salt thereof.

5. The compound of claim 3, wherein $R_1$, $R_2$, $R_4$, $R_{15}$, and $R_{16}$ are H.

6. The compound of claim 3, wherein $R_{17}$ is $C_1$-$C_6$ alkyl.

7. The compound of claim 6, wherein $R_{17}$ is unsubstituted methyl.

8. The compound of claim 3, wherein n is 2.

9. The compound of claim 3, wherein at least one of $R_3$, $R_6$, and $R_{12}$ is $-OSO_3^-$, $-NR_{18}SO_3^-$, or $-OPO_3^{2-}$.

10. The compound of claim 3, wherein at least one of $R_6$ and $R_{12}$ is $-OSO_3$, $-NR_{18}SO_3^-$, or $-OPO_3^{2-}$.

11. The compound of claim 3, wherein $R_6$ is $-OSO_3$, $-NR_{18}SO_3^-$, or $-OPO_3^{2-}$.

12. The compound of claim 11, wherein $R_{12}$ is independently $-OSO_3^-$.

13. The compound of claim 3, wherein $R_6$ is $-OSO_3^-$).

14. The compound of claim 3, wherein $R_3$, $R_6$, and $R_{12}$ are independently H, -OH, $-OSO_3$, $-NR_{18}SO_3^-$, or —OPO$_3^{2-}$, provided that at least one of R$_3$, R$_6$, R$_7$, and R$_{12}$ is —OSO$_3^-$, —NR$_{18}$SO$_3$, or —OPO$_3^{2-}$.

15. The compound of claim 3, wherein the compound is of the formula:

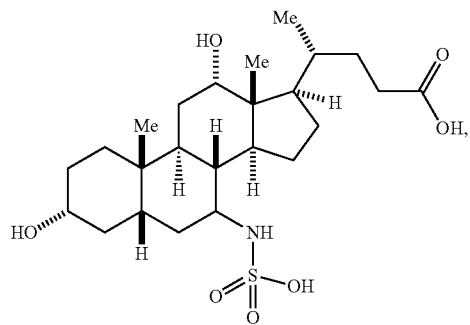

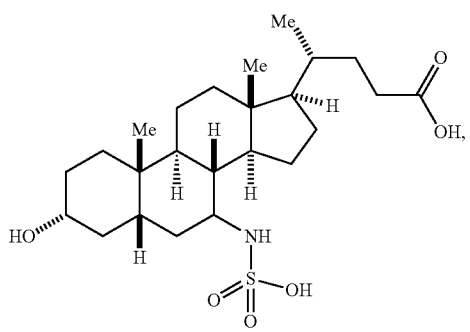

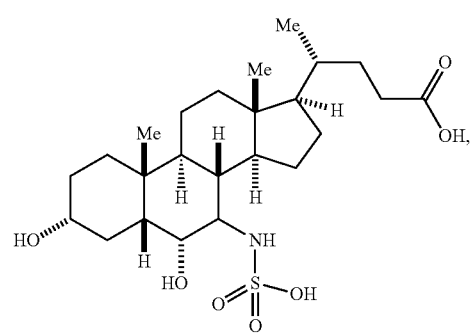

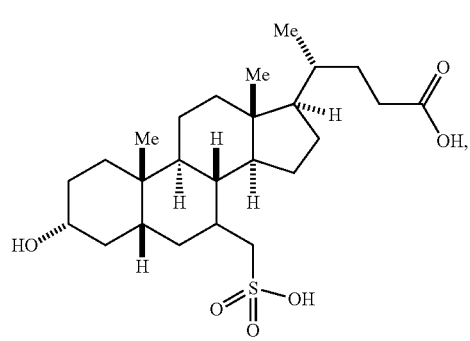

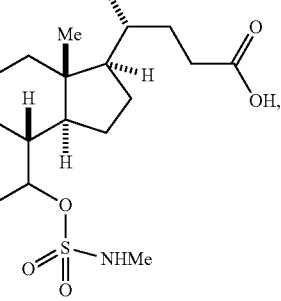

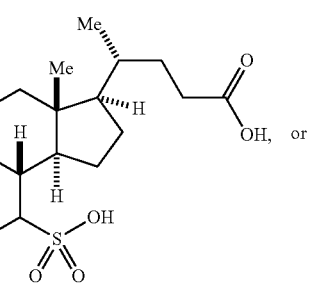

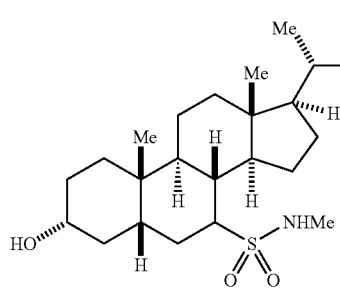

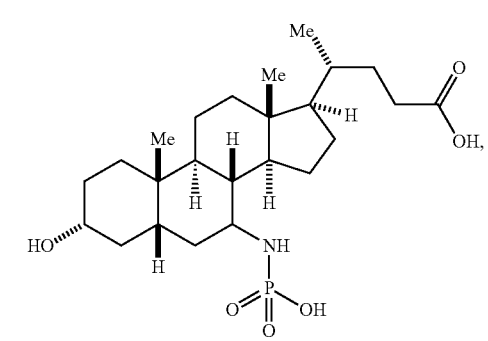

or a pharmaceutically acceptable salt thereof.

16. A pharmaceutically acceptable salt of the compound of claim 15.

17. The pharmaceutically acceptable salt of claim 16, wherein the pharmaceutically acceptable salt is an ammonium salt or a sodium salt.

18. A pharmaceutical composition comprising a compound of Formula (I) and a pharmaceutically acceptable carrier or excipient, wherein compound of Formula (I) has the structure:

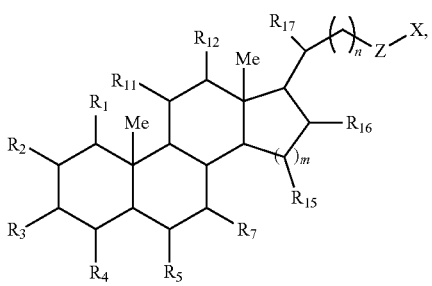

(I)

wherein:
n is 1, 2, 3, 4, 5, 6, 7, 8, 9, or 10;
m is 1;
Z is —C(O)—, —C(O)O—, —C(O)NR$_{18}$-, or —CH$_2$-;
X is H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3^-$, —OSO$_3$, —NR$_{18}$SO$_3$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, -NHC(O)NHNH$_2$, or a polar amino acid;
each R$_1$, R$_2$, R$_3$, R$_4$, R$_{11}$, R$_{15}$, R$_{16}$, and R$_{17}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3^-$, —OSO$_3^-$, —NR$_{18}$SO$_3^-$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, or -NHC(O)NHNH$_2$,
each R$_3$, R$_6$, and R$_{12}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$_{18}$, —N(R$_{18}$)$_2$, —SR$_{18}$, halogen, —CN, —CHO, —CO$_2$H, —CO$_2$R$_{18}$, —NO$_2$, —ONO$_2$, —SO$_2$Cl, —SO$_3$, —OSO$_3$, —NR$_{18}$SO$_3$, —PO$_3^{2-}$, —OPO$_3^{2-}$, —OSO$_2$R$_{18}$, —OSO$_2$N(R$^{18}$)$_2$, —NR$_{18}$SO$_2$R$_{18}$, —SO$_2$N(R$^{18}$)$_2$, -NHNH$_2$, —ONH$_2$, or -NHC(O)NHNH$_2$;
R$_7$ is —C(R$^{18}$)$_2$SO$_3$H, —C(R$^{18}$)$_2$SO$_3$, —SO$_2$N(R$^{18}$)$_2$, —OSO$_2$N(R$^{18}$)$_2$, —NR$_{18}$SO$_3$H, or —NR$_{18}$SO$_3$;
each R$_{18}$ is independently H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
or a pharmaceutically acceptable salt thereof.

19. The compound of claim 18, wherein R$^7$ is —C(R$^{18}$)$_2$SO$_3$H, —C(R$^{18}$)$_2$SO$_3^{31}$, —OSO$_2$N(R$^{18}$)$_2$, or —SO$_2$N(R$^{18}$)$_2$.

* * * * *

SEQUENCE LISTING

<160> NUMBER OF SEQ ID NOS: 3

<210> SEQ ID NO 1
<211> LENGTH: 1743
<212> TYPE: DNA
<213> ORGANISM: Homo sapiens

<400> SEQUENCE: 1

```
ctttccgcct agtgagaggc ggtccgattt ggcccttggg gagtgtccgt cgcgttgatc      60
tgatggattc acgtacacaa caccacattc tatgagattt tgcaggcaaa agtccacaag     120
ctcgatatat gggacacctg caccggcatt ggatttggcc ccgcaacatc ttaaaggaag     180
caggctgtga gccaagggga aggcagagga cagaaatgaa tgtgtttcca ggctttcctg     240
gtggtttatg gcattctcca aactcctatg caagggctat tcctgaccaa gaagatctaa     300
agagaacgtc tctgaaatca agtccggatg aagaattaag agaaaaaaag tgaatatggt     360
ttttgctcac agaatggata acagcaagcc acatttgatt attcctacac ttctggtgcc     420
cctccaaaac cgcagctgca ctgaaacagc cacacctctg ccaagccaat acctgatgga     480
attaagtgag gagcacagtt ggatgagcaa ccaaacagac cttcactatg tgctgaaacc     540
cggggaagtg gccacagcca gcatcttctt tgggattctg tggttgtttt ctatcttcgg     600
caattccctg gtttgtttgg tcatccatag gagtaggagg actcagtcta ccaccaacta     660
ctttgtggtc tccatggcat gtgctgacct tctcatcagc gttgccagca cgcctttcgt     720
cctgctccag ttcaccactg gaaggtggac gctgggtagt gcaacgtgca aggttgtgcg     780
atattttcaa tatctcactc caggtgtcca gatctacgtt ctcctctcca tctgcataga     840
ccggttctac accatcgtct atcctctgag cttcaaggtg tccagagaaa aagccaagaa     900
aatgattgcg gcatcgtgga tctttgatgc aggctttgtg accctgtgc tcttttctc      960 tggctccaac tgggacagtc attgtaacta tttcctcccc tcctcttggg aaggcactgc    1020
ctacactgtc atccacttct tggtgggctt tgtgattcca tctgtcctca taattttatt    1080
ttaccaaaag gtcataaaat atatttggag aataggcaca gatggccgaa cggtgaggag    1140
gacaatgaac attgtccctc ggacaaaagt gaaaactatc aagatgttcc tcattttaaa    1200
```

```
tctgttgttt ttgctctcct ggctgccttt tcatgtagct cagctatggc accccatga      1260 acaagactat aagaaaagtt cccttgtttt cacagctatc acatggatat cctttagttc      1320
ttcagcctct aaacctactc tgtattcaat ttataatgcc aattttcgga gagggatgaa      1380
agagactttt tgcatgtcct ctatgaaatg ttaccgaagc aatgcctata ctatcacaac      1440
aagttcaagg atggccaaaa aaactacgt tggcatttca gaaatccctt ccatggccaa       1500
aactattacc aaagactcga tctatgactc atttgacaga gaagccaagg aaaaaaagct      1560
tgcttggccc attaactcaa atccaccaaa tacttttgtc taagttctca ttctttcaat      1620
tgttatgcac cagagattaa aaagctttaa ctataaaaac agaagctatt tacatatttg      1680
ttttcactca actttccaag ggaaatgttt tattttgtaa aatgcattca tttgtttact      1740
gta                                                                    1743
```

<210> SEQ ID NO 2
<211> LENGTH: 415
<212> TYPE: PRT
<213> ORGANISM: Homo sapiens

<400> SEQUENCE: 2

```
Met Val Phe Ala His Arg Met Asp Asn Ser Lys Pro His Leu Ile Ile
1               5                   10                  15

Pro Thr Leu Leu Val Pro Leu Gln Asn Arg Ser Cys Thr Glu Thr Ala
            20                  25                  30

Thr Pro Leu Pro Ser Gln Tyr Leu Met Glu Leu Ser Glu His Ser
        35                  40                  45

Trp Met Ser Asn Gln Thr Asp Leu His Tyr Val Leu Lys Pro Gly Glu
    50                  55                  60

Val Ala Thr Ala Ser Ile Phe Phe Gly Ile Leu Trp Leu Phe Ser Ile
65                  70                  75                  80

Phe Gly Asn Ser Leu Val Cys Leu Val Ile His Arg Ser Arg Arg Thr
                85                  90                  95

Gln Ser Thr Thr Asn Tyr Phe Val Ser Met Ala Cys Ala Asp Leu
            100                 105                 110

Leu Ile Ser Val Ala Ser Thr Pro Phe Val Leu Gln Phe Thr Thr
            115                 120                 125

Gly Arg Trp Thr Leu Gly Ser Ala Thr Cys Lys Val Val Arg Tyr Phe
130                 135                 140

Gln Tyr Leu Thr Pro Gly Val Gln Ile Tyr Val Leu Leu Ser Ile Cys
145                 150                 155                 160

Ile Asp Arg Phe Tyr Thr Ile Val Tyr Pro Leu Ser Phe Lys Val Ser
                165                 170                 175

Arg Glu Lys Ala Lys Lys Met Ile Ala Ala Ser Trp Ile Phe Asp Ala
            180                 185                 190

Gly Phe Val Thr Pro Val Leu Phe Phe Tyr Gly Ser Asn Trp Asp Ser
        195                 200                 205

His Cys Asn Tyr Phe Leu Pro Ser Ser Trp Glu Gly Thr Ala Tyr Thr
    210                 215                 220

Val Ile His Phe Leu Val Gly Phe Val Ile Pro Ser Val Leu Ile Ile
225                 230                 235                 240

Leu Phe Tyr Gln Lys Val Ile Lys Tyr Ile Trp Arg Ile Gly Thr Asp
                245                 250                 255

Gly Arg Thr Val Arg Arg Thr Met Asn Ile Val Pro Thr Lys Val
            260                 265                 270
```

```
Lys Thr Ile Lys Met Phe Leu Ile Leu Asn Leu Leu Phe Leu Leu Ser
        275                 280                 285

Trp Leu Pro Phe His Val Ala Gln Leu Trp His Pro His Glu Gln Asp
        290                 295                 300

Tyr Lys Lys Ser Ser Leu Val Phe Thr Ala Ile Thr Trp Ile Ser Phe
305                 310                 315                 320

Ser Ser Ser Ala Ser Lys Pro Thr Leu Tyr Ser Ile Tyr Asn Ala Asn
                325                 330                 335

Phe Arg Arg Gly Met Lys Glu Thr Phe Cys Met Ser Ser Met Lys Cys
                340                 345                 350

Tyr Arg Ser Asn Ala Tyr Thr Ile Thr Thr Ser Ser Arg Met Ala Lys
        355                 360                 365

Lys Asn Tyr Val Gly Ile Ser Glu Ile Pro Ser Met Ala Lys Thr Ile
        370                 375                 380

Thr Lys Asp Ser Ile Tyr Asp Ser Phe Asp Arg Glu Ala Lys Glu Lys
385                 390                 395                 400

Lys Leu Ala Trp Pro Ile Asn Ser Asn Pro Pro Asn Thr Phe Val
                405                 410                 415

<210> SEQ ID NO 3
<211> LENGTH: 30
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
                20                  25                  30
```